(12) United States Patent
Macdonald et al.

(10) Patent No.: US 11,612,151 B2
(45) Date of Patent: *Mar. 28, 2023

(54) HUMANIZED LIGHT CHAIN MICE

(71) Applicant: Regeneron Pharmaceuticals, Inc., Tarrytown, NY (US)

(72) Inventors: Lynn Macdonald, Harrison, NY (US); Cagan Gurer, Chappaqua, NY (US); Karolina A. Hosiawa, Yorktown Heights, NY (US); Sean Stevens, Del Mar, CA (US); Andrew J. Murphy, Croton-on-Hudson, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 500 days.

This patent is subject to a terminal disclaimer.

(21) Appl. No.: 16/729,852

(22) Filed: Dec. 30, 2019

(65) Prior Publication Data

US 2020/0221676 A1 Jul. 16, 2020

Related U.S. Application Data

(60) Continuation of application No. 15/585,023, filed on May 2, 2017, now Pat. No. 10,561,124, which is a division of application No. 13/716,238, filed on Dec. 17, 2012, now Pat. No. 9,706,759.

(60) Provisional application No. 61/578,097, filed on Dec. 20, 2011.

(51) Int. Cl.
*A01K 67/027* (2006.01)
*C07K 16/46* (2006.01)
*C12N 9/64* (2006.01)
*C07K 16/28* (2006.01)

(52) U.S. Cl.
CPC ...... *A01K 67/0278* (2013.01); *C07K 16/2866* (2013.01); *C07K 16/462* (2013.01); *C12N 9/6489* (2013.01); *A01K 2217/072* (2013.01); *A01K 2217/15* (2013.01); *A01K 2227/105* (2013.01); *A01K 2267/01* (2013.01); *C12N 2800/204* (2013.01); *C12N 2800/30* (2013.01)

(58) Field of Classification Search
CPC .................................................. A01K 67/0278
See application file for complete search history.

(56) References Cited

U.S. PATENT DOCUMENTS

| | | | |
|---|---|---|---|
| 5,545,806 A | 8/1996 | Lonberg et al. |
| 5,545,807 A | 8/1996 | Surani et al. |
| 5,658,727 A | 8/1997 | Barbas et al. |
| 5,942,435 A | 8/1999 | Wheeler |
| 6,162,963 A | 12/2000 | Kucherlapati et al. |
| 6,461,818 B1 | 10/2002 | Bradley et al. |
| 6,586,251 B2 | 7/2003 | Economides et al. |
| 6,596,541 B2 | 7/2003 | Murphy et al. |
| 6,632,976 B1 | 10/2003 | Tomizuka et al. |
| 6,657,103 B1 | 12/2003 | Kucherlapati et al. |
| 6,673,986 B1 | 1/2004 | Kucherlapati et al. |
| 6,774,279 B2 | 8/2004 | Dymecki |
| 6,998,514 B2 | 2/2006 | Bruggemann |
| 7,105,348 B2 | 9/2006 | Murphy et al. |
| 7,183,076 B2 | 2/2007 | Arathoon et al. |
| 7,435,871 B2 | 10/2008 | Green et al. |
| 7,501,552 B2 | 3/2009 | Lonberg et al. |
| 7,582,298 B2 | 9/2009 | Stevens et al. |
| 7,605,237 B2 | 10/2009 | Stevens et al. |
| 7,910,798 B2 | 3/2011 | Tanamachi et al. |
| 7,932,431 B2 | 4/2011 | Bruggemann |
| 8,158,419 B2 | 4/2012 | Lonberg et al. |
| 8,502,018 B2 | 8/2013 | Murphy et al. |
| 8,642,835 B2 | 2/2014 | MacDonald et al. |
| 8,697,940 B2 | 4/2014 | Macdonald et al. |
| 9,006,511 B2 | 4/2015 | Macdonald et al. |
| 9,012,717 B2 | 4/2015 | Macdonald et al. |
| 9,029,628 B2 | 5/2015 | Macdonald et al. |
| 9,035,128 B2 | 5/2015 | MacDonald et al. |
| 9,066,502 B2 | 6/2015 | Macdonald et al. |
| 9,150,662 B2 | 10/2015 | Macdonald et al. |
| 9,163,092 B2 | 10/2015 | Macdonald et al. |
| 9,206,261 B2 | 12/2015 | Macdonald et al. |
| 9,206,262 B2 | 12/2015 | Macdonald et al. |
| 9,206,263 B2 | 12/2015 | Macdonald et al. |
| 9,226,484 B2 | 1/2016 | Macdonald et al. |
| 9,334,333 B2 | 5/2016 | Macdonald et al. |
| 9,394,373 B2 | 7/2016 | Macdonald et al. |
| 9,399,683 B2 | 7/2016 | Macdonald et al. |
| 9,540,452 B2 | 1/2017 | Macdonald et al. |
| 9,622,459 B2 | 4/2017 | Macdonald et al. |
| 9,706,759 B2 | 7/2017 | Macdonald et al. |
| 9,844,212 B2 | 12/2017 | Macdonald et al. |
| 9,850,462 B2 | 12/2017 | Macdonald et al. |
| 9,932,408 B2 | 4/2018 | Macdonald et al. |
| 9,944,716 B2 | 4/2018 | Macdonald et al. |
| 10,072,095 B2 | 9/2018 | Macdonald et al. |
| 10,266,803 B2 | 4/2019 | Macdonald et al. |
| 10,561,124 B2 | 2/2020 | Macdonald et al. |
| 10,577,430 B2 | 3/2020 | Macdonald et al. |
| 10,694,725 B2 | 6/2020 | Macdonald et al. |

(Continued)

FOREIGN PATENT DOCUMENTS

| | | |
|---|---|---|
| CN | 1203922 A | 1/1999 |
| CN | 1605628 A | 4/2005 |
| CN | 101002549 A | 7/2007 |
| CN | 101501073 A | 8/2009 |
| CN | 101657535 A | 2/2010 |

(Continued)

OTHER PUBLICATIONS

Janssens et al. (2006, PNAS, vol. 103(41), pp. 15130-15135). (Year: 2006).*

(Continued)

*Primary Examiner* — Ram R Shukla
*Assistant Examiner* — David A Montanari
(74) *Attorney, Agent, or Firm* — Choate, Hall & Stewart LLP; Brenda Herschbach Jarrell; Michael L. Vetter

(57) ABSTRACT

Non-human animals, tissues, cells, and genetic material are provided that comprise a modification of an endogenous non-human heavy chain immunoglobulin sequence and that comprise an ADAM6 activity functional in a mouse, wherein the non-human animals express a human immunoglobulin heavy chain variable domain and a cognate human immunoglobulin λ light chain variable domain.

21 Claims, 63 Drawing Sheets

Specification includes a Sequence Listing.

(56) References Cited

U.S. PATENT DOCUMENTS

| | | |
|---|---|---|
| 2002/0026036 A1 | 2/2002 | Shitara et al. |
| 2002/0088016 A1 | 7/2002 | Bruggemann |
| 2002/0106628 A1 | 8/2002 | Economides et al. |
| 2002/0106629 A1 | 8/2002 | Murphy et al. |
| 2003/0108925 A1 | 6/2003 | Dix et al. |
| 2003/0109021 A1 | 6/2003 | Wu et al. |
| 2003/0217171 A1 | 11/2003 | Von Stuermer et al. |
| 2003/0217373 A1 | 11/2003 | Green et al. |
| 2004/0018626 A1 | 1/2004 | Murphy et al. |
| 2005/0060763 A1 | 3/2005 | Bruggeman et al. |
| 2006/0015957 A1 | 1/2006 | Lonberg et al. |
| 2006/0015958 A1 | 1/2006 | Kuroiwa et al. |
| 2006/0026696 A1 | 2/2006 | Buelow et al. |
| 2006/0083747 A1 | 4/2006 | Winter et al. |
| 2006/0106203 A1 | 5/2006 | Winter et al. |
| 2006/0199204 A1 | 9/2006 | Dix et al. |
| 2006/0257406 A1 | 11/2006 | Winter et al. |
| 2006/0280734 A1 | 12/2006 | Winter et al. |
| 2007/0280945 A1 | 12/2007 | Stevens et al. |
| 2008/0196922 A1 | 8/2008 | Van Marion et al. |
| 2008/0267982 A1 | 10/2008 | Kiselev et al. |
| 2009/0258392 A1 | 10/2009 | Gallo et al. |
| 2009/0271880 A1 | 10/2009 | Grosveld et al. |
| 2010/0069614 A1 | 3/2010 | Houtzager et al. |
| 2010/0146647 A1 | 6/2010 | Logtenberg et al. |
| 2011/0138489 A1 | 6/2011 | Tanamachi et al. |
| 2011/0145937 A1 | 6/2011 | MacDonald et al. |
| 2011/0195454 A1 | 8/2011 | Mcwhirter et al. |
| 2011/0236378 A1 | 9/2011 | Green et al. |
| 2011/0283376 A1 | 11/2011 | Murphy et al. |
| 2011/0314563 A1 | 12/2011 | Craig et al. |
| 2012/0021409 A1 | 1/2012 | McWhirter et al. |
| 2012/0047585 A1 | 2/2012 | Rohrer et al. |
| 2012/0070861 A1 | 3/2012 | Macdonald et al. |
| 2012/0073004 A1 | 3/2012 | MacDonald et al. |
| 2012/0096572 A1 | 4/2012 | Macdonald et al. |
| 2012/0167237 A1 | 6/2012 | Bradley et al. |
| 2012/0204278 A1 | 8/2012 | Bradley et al. |
| 2012/0272344 A1 | 10/2012 | Tanamachi et al. |
| 2012/0322108 A1 | 12/2012 | Macdonald et al. |
| 2013/0096287 A1 | 4/2013 | Macdonald et al. |
| 2013/0198879 A1 | 8/2013 | McWhirter et al. |
| 2013/0243759 A1 | 9/2013 | Friedrich et al. |
| 2013/0243773 A1 | 9/2013 | Van Berkel et al. |
| 2013/0263292 A1 | 10/2013 | Liang et al. |
| 2013/0263293 A1 | 10/2013 | Bradley et al. |
| 2013/0318643 A1 | 11/2013 | Bradley et al. |
| 2013/0323235 A1 | 12/2013 | Craig et al. |
| 2013/0323790 A1 | 12/2013 | Macdonald et al. |
| 2013/0326647 A1 | 12/2013 | Macdonald et al. |
| 2014/0137275 A1 | 5/2014 | Macdonald et al. |
| 2014/0213773 A1 | 7/2014 | Macdonald et al. |
| 2014/0283150 A1 | 9/2014 | Bradley et al. |
| 2015/0089680 A1 | 3/2015 | Macdonald et al. |
| 2015/0173331 A1 | 6/2015 | Macdonald et al. |
| 2015/0173332 A1 | 6/2015 | Macdonald et al. |
| 2015/0176002 A1 | 6/2015 | Macdonald et al. |
| 2015/0201589 A1 | 7/2015 | Macdonald et al. |
| 2015/0210776 A1 | 7/2015 | Macdonald et al. |
| 2015/0246976 A1 | 9/2015 | Macdonald et al. |
| 2015/0246977 A1 | 9/2015 | Macdonald et al. |
| 2015/0250152 A1 | 9/2015 | Jakobovits et al. |
| 2015/0320023 A1 | 11/2015 | Macdonald et al. |
| 2015/0351371 A1 | 12/2015 | Macdonald et al. |
| 2016/0057979 A1 | 3/2016 | Macdonald et al. |
| 2016/0060359 A1 | 3/2016 | Macdonald et al. |
| 2017/0107484 A1 | 4/2017 | Macdonald et al. |
| 2017/0258059 A1 | 9/2017 | Macdonald et al. |
| 2017/0332609 A1 | 11/2017 | Macdonald et al. |
| 2018/0064078 A1 | 3/2018 | Macdonald et al. |
| 2018/0345760 A1 | 12/2018 | Macdonald et al. |
| 2018/0346598 A1 | 12/2018 | Macdonald et al. |
| 2018/0346599 A1 | 12/2018 | Macdonald et al. |
| 2018/0362663 A1 | 12/2018 | Macdonald et al. |
| 2019/0153384 A1 | 5/2019 | Macdonald et al. |
| 2019/0203171 A1 | 7/2019 | Macdonald et al. |
| 2020/0221675 A1 | 7/2020 | Macdonald et al. |

FOREIGN PATENT DOCUMENTS

| | | |
|---|---|---|
| EA | 010469 | 8/2008 |
| EA | 010506 B1 | 10/2008 |
| EP | 1970448 A1 | 9/2008 |
| JP | H04500911 A | 2/1992 |
| JP | 2005510253 A | 4/2005 |
| JP | 2005/224242 A | 8/2005 |
| JP | 2005-230020 A | 9/2005 |
| KR | 1993-7002999 | 11/1993 |
| KR | 10-2003-0074634 A | 9/2003 |
| KR | 10-2005-0042792 A | 5/2005 |
| KR | 2011-0125208 A | 11/2011 |
| RU | 2151612 C1 | 6/2000 |
| RU | 2264413 C2 | 11/2005 |
| RU | 010506 U1 | 10/2008 |
| TW | 201030143 A | 8/2010 |
| WO | WO-90/04036 A1 | 4/1990 |
| WO | WO-91/00906 A1 | 1/1991 |
| WO | WO-98/24893 A2 | 6/1998 |
| WO | WO-00/26373 A1 | 5/2000 |
| WO | WO-00/073323 A2 | 12/2000 |
| WO | WO-02/46237 A2 | 6/2002 |
| WO | WO-02/50120 A2 | 6/2002 |
| WO | WO-0243478 A2 | 6/2002 |
| WO | WO-02/066630 A1 | 8/2002 |
| WO | WO-2003/002609 A2 | 1/2003 |
| WO | WO-03/047336 A2 | 6/2003 |
| WO | WO-2004/049794 A2 | 6/2004 |
| WO | WO-2004/058820 A2 | 7/2004 |
| WO | WO-2004/058822 A2 | 7/2004 |
| WO | WO-2005/028510 A2 | 3/2005 |
| WO | WO-2007/003323 A1 | 1/2007 |
| WO | WO-2007/096779 A2 | 8/2007 |
| WO | WO-2007/117410 A2 | 10/2007 |
| WO | WO-2008/015418 A2 | 2/2008 |
| WO | WO-2008/054606 A2 | 5/2008 |
| WO | WO-2008/076379 A2 | 6/2008 |
| WO | WO-2009/097006 A2 | 8/2009 |
| WO | WO-2009/143472 A2 | 11/2009 |
| WO | WO-201 0/039900 A2 | 4/2010 |
| WO | WO-2010/070263 A1 | 6/2010 |
| WO | WO-2011/004192 A1 | 1/2011 |
| WO | WO-2011/072204 A1 | 6/2011 |
| WO | WO-2011/158009 A1 | 12/2011 |
| WO | WO-2011/163311 A1 | 12/2011 |
| WO | WO-2011/163314 A1 | 12/2011 |
| WO | WO-2012/018764 A1 | 2/2012 |
| WO | WO-2012/063048 A1 | 5/2012 |
| WO | WO-2012/141798 A1 | 10/2012 |
| WO | WO-2013/022782 A1 | 2/2013 |
| WO | WO-2013/041844 A2 | 3/2013 |
| WO | WO-2013/041845 A2 | 3/2013 |
| WO | WO-2013/041846 A2 | 3/2013 |
| WO | WO-2013/045916 A1 | 4/2013 |
| WO | WO-2013/061078 A1 | 5/2013 |
| WO | WO-2013/061098 A2 | 5/2013 |
| WO | WO-2013/079953 A1 | 6/2013 |
| WO | WO-2013/096142 A1 | 6/2013 |
| WO | WO-2013/116609 A1 | 8/2013 |

OTHER PUBLICATIONS

Adams, D.J. et al., A genome-wide, end-sequenced 129Sv BAC library resource for targeting vector construction, Genomics, 86(6):753-758 (2005).

Adderson, E.E. et al., Restricted Ig H Chain V Gene Usage in the Human Antibody Response to Haemophilus influenzae TYPE b Capsular Polysaccharide, The Journal of Immunology, 147:1667-1674 (1991).

Adderson, E.E. et al., Restricted Immunoglobulin VH Usage and VDJ Combinations in the Human Response to Haemophilus influenzae Type b Capsular Polysaccharide, Journal of Clinical Investigation, 91:2734-2743 (1993).

(56) References Cited

OTHER PUBLICATIONS

Alfandari, D. et al., Xenopus ADAM 13 is a metalloprotease required for cranial neural crest-cell migration, Current Biology, 11:918-930 (2001).
Amit, M. and Itskovitz-Eldor, J., Embryonic Stem Cells: Isolation, Characterization and Culture, Adv Biochem Engin/Biotechnol, 114:173-184 (2009).
Appeal by Opponent for EP 12716101.6, 14 pages (Jun. 20, 2016).
Astellas Negotiates $295M License Extension to Regeneron's VelocImmune mAb Platform, GEN News Highlights, Jul. 28, 2010.
Austin, C. et al., The Knockout Mouse Project, Nat. Genet., 36(9):921-924 (2004).
Bando, Y. et al., Characterization of VH gene expressed in PBL from children with atopic diseases: detection of homologous VH1-69 derived transcripts from three unrelated patients, Immunology Letters, 94:99-106 (2004).
Baseggio, L. et al., CD5 expression identifies a subset of splenic marginal zone lymphomas with higher lymphocytosis: a clinicopathological, cytogenetic and molecular study of 24 cases, Haematologica, 95(4):604-612 (2010).
Bates, J.G. et al., Chromosomal position of a VH gene segment determines its activation and inactivation as a substrate for V(D)J recombination, Journal of Experimental Medicine, 204(13):3247-3256 (2007).
Berberian, L. et al., A VH Clonal Deficit in Human Immunodeficiency Virus-Positive Individuals Reflects a B-Cell Maturational Arrest, Blood, 78(1):175-179 (1991).
Blobel, Carl P., ADAMS: Key Components in EGFR Signalling and Development, Nature Reviews, Molecular Cell Biology, 6:32-43 (2005).
Borghei, A. et al., Targeted Disruption of Tyrosylprotein Sulfotransferase-2, an Enzyme That Catalyzes Post-translational Protein Tyrosine O-Sulfation, Causes Male Infertility, The Journal of Biological Chemistry, 281(14):9423-9431 (2006).
Brevini, T. A. et al., No shortcuts to pig embryonic stem cells, Theriogenology 74(4):544-550 (2010).
Brezinschek, H.P. et al., Analysis of the Heavy Chain Repertoire of Human Peripheral B Cells Using Single-Cell Polymerase Chain Reaction, Journal of Immunology, 155:190-202 (1995).
Brouwers, B. et al., Unexpected Phenotypes in Mouse Models Carrying the Human Growth Hormone Minigene to Enhance Transgene Expression, Journal of Steroids & Hormonal Science, 6(2): 2 pages (2015).
Bruggemann, M. and Neuberger, M., Strategies for expressing human antibody repertoires in transgenic mice, Review Immunology Today, 192(17):391-397 (1996).
Bruggemann, M. et al., A repertoire of monoclonal antibodies with human heavy chains from transgenic mice, Proceedings of the National of Academy of Science USA, 86:6709-6713 (1989).
Bruggemann, M., Human Antibody Expression in Transgenic Mice, Archivum Immunologiae et Therapiae Experimentalis, 49:203-208 (2001).
Butler, J.E., Immunoglobulin diversity, B-cell and antibody repertoire development in large farm animals, Rev. Sci. Tech. Off. Int. Epiz., 17(1):43-70 (1998).
Canadian Office Action for Application No. 2,820,824, 3 pages, dated Aug. 5, 2014.
Carbonari, M, et al., Hepatitis C Virus Drives the Unconstrained Monoclonal Expansion of VH1-69-Expressing Memory B Cells in Type II Cryoglobulinemia: A Model of Infection-Driven Lymphomagenesis, The Journal of Immunology, 174:6532-6539 (2005).
Carson, S. and Wu, G.E., A linkage map of the mouse immunoglobulin lambda light chain locus, Immunogenetics, 29(3):173-9 (1989).
Cavelier P. et al., B lineage-restricted rearrangement of a human Ig kappa transgene, Eur J Immunol. 27(7):1626-31 (1997).
Chan, C.H. et al., VH1-69 gene is preferentially used by hepatitis C virus-associated B cell lymphomas and by normal B cells responding to the E2 viral antigen, Blood, 97(4):1023-1026 (2001).
Chang, S.P. et al., Immunologic memory to phosphocholine. IV. Hybridomas representative of Group I (T15-like) and Group II (non-T15-like) antibodies utilize distinct VH genes, J. Immunol., 132(3):1550-5 (1984).
Charles, E.D. et al., A flow cytometry-based strategy to identify and express IgM from VH1-69+ clonal peripheral B cells, Journal of Immunological Methods, 363:210-220 (2011).
Cheval, L. et al., Of Mice and Men: Divergence of Gene Expression Patterns in Kidney, PLoS One, 7(10):e46876—12 pages (2012).
Cho, C. et al., Analysis of Mouse Fertilin in Wild-Type and Fertilin ß-/- Sperm: Evidence for C-terminal Modification, αl ß Dimerization, and Lack of Essential Role of Fertilin α in Sperm-Egg Fusion, Developmental Biology, 222:289-295 (2000).
Cho, C. et al., Fertilization Defects in Sperm from Mice Lacking Fertilin ß, Science, 281:1857-1859 (1998).
Cho, Chunghee, Mammalian ADAMS with Testis-Specific or -Predominant Expression, The ADAM Family of Proteases, 239-259 (2005).
Cho, Chunghee, Testicular and epididymal ADAMS: expression and function during fertilization, Nat. Rev. Urol., 9:550-560 (2012).
Choi, H. et al., Identification and characterization of promoter and regulatory regions for mouse Adam2 gene expression, Mol Biol Rep, 40:787-796 (2013).
Choi, I. et al., Characterization and comparative genomic analysis of intronless Adams with testicular gene expression, Genomics, 83(4):636-46 (2004).
Choi, K. et al., Expression of the metabotropic glutamate receptor 5 (mGluR5) induces melanoma in transgenic mice, PNAS, 108(37):15219-15224 (2011).
Clark, J. and Whitelaw, B., A future for transgenic livestock, National Reviews Genetics, 4(10):825-833 (2003).
Cocea, L. et al., A targeted deletion of a region upstream from the Jkappa cluster impairs kappa chain rearrangement in cis in mice and in the 103/bcl2 cell line, J Exp Med. 189(9):1443-50 (1999).
Combriato et al., Regulation of Human Igl Light Chain Gene Expression, The Journal of Immunology, 168: 1259-1266 (2002).
Communication in Cases for which No Other Form is Applicable for PCT/US2012/026416, 9 pages (dated Jun. 7, 2013).
Communication In Cases For Which No Other Form Is Applicable for PCT/US2012/069981, 18 pages (dated Jul. 3, 2013).
Communication pursuant to Article 114(2) EPC, dated Jun. 21, 2013.
Communication Relating to the Results of the Partial International Search for PCT/US2013/029624 (9 pages), dated May 17, 2013.
Davidkova, G. et al., Selective Usage of VH Genes in Adult Human B Lymphocyte Repertoires, Scandinavian Journal of Immunology, 45:62-73 (1997).
De Genst, E. et al., Antibody repertoire development in camelids, Development & Comparative Immunology, 30:187-198 (2006).
De Wildt, R. et al., Analysis of heavy and light chain pairings indicates that receptor editing shapes the human antibody repertoire, J. Mol. Biol., 285(3):895-901 (1999).
Declaration of Dr. Glenn Friedrich, 4 page (Mar. 3, 2016).
Declaration of Dr. Jürgen Roes, Ph.D., 14 pages (Jul. 19, 2014).
Declaration of Dr. Kosuke Yusa and associated Annexes, 7 pages (Oct. 2, 2017).
Declaration of E-Chiang Lee, Ph.D., 8 pages (Jun. 20, 2016).
Declaration of Hui Liu, Ph.D., 4 pages (Jun. 20, 2016).
Declaration of Meng (Amy) Li, Ph.D., 4 pages (Jun. 20, 2016).
Declaration of Prof. Allan Bradley, Ph.D., 37 pages (Jun. 20, 2016).
Declaration of Wei Wang, Ph.D., 8 pages (Jun. 20, 2016).
Dudley, D.D. et al., Mechanism and control of V(D)J recombination versus class switch recombination: similarities and differences, Adv. Immunol., 86:43-112 (2005).
Edwards D.R. et al., The ADAM metalloproteinases, Molecular Aspects of Medicine, 29(5):258-89 (2008).
Enever, C. et al., Next generation immunotherapeutics—honing the magic bullet, Current Opinion in Biotechnology, 20(4):405-11 (2009).
Ensembl database entries for the heavy and light chain immunoglobulin loci, as submitted in EP 2550363 on Oct. 16, 2017, 3 pages.
European Examination Report for EP 14154967.5, dated Sep. 9, 2014, 4 pages.

(56) References Cited

OTHER PUBLICATIONS

European Office Action for 12 716 101.6-1410, 5 pages, dated Jun. 17, 2014.
European Search Report for EP12195716,15 pages (dated Feb. 4, 2013).
Extended European Search Report for 12192727.1, 8 pages (dated Mar. 7, 2013).
Extended European Search Report for 14154918.8, 8 pages (dated Aug. 27, 2014).
Extended European Search Report for 14176593.3, 10 pages (dated Nov. 19, 2014).
Farner, N. et al., Molecular Mechanisms and Selection Influence the Generation ofthe Human VλJλ Repertoire, The Journal of Immunology, 162:2137-2145 (1999).
Featherstone, K. et al., The mouse immunoglobulin heavy chain V-D intergenic sequence contains insulators that may regulate ordered V(D)J recombination, J. Biol. Chem. 285(13): 9327-9338 (2010).
Gallo et al., US 20090258392 A1, Oct. 15, 2009—Seq Id No. 112 alignment with Seq Id No. 100 of 13166200.
Gama Sosa, M.A. et al., Animal transgenesis: an overview, Brain Structure & Function, 214(2-3):91-109 (2010).
Gaultier, A. et al., ADAM13 Disintegrin and Cysteine-rich Domains Bind to the Second Heparin-binding Domain of Fibronectin, The Journal of Biological Chemistry, 277(26):23336-23344 (2002).
GenBank accession No. NT_114985, p. 1, first referenced Dec. 1, 2005, last updated Feb. 9, 2015.
Giallourakis, C.C. et al., Elements between the IgH variable (V) and diversity (D) clusters influence antisense transcription and lineage-specific V(D)K recombination, PNAS, 107(51):22207-22212 (2010).
Glassey, B. and Civetta, A., Positive Selection at Reproductive ADAM Genes with Potential Intercellular Binding Activity, Molecular Biology and Evolution, 21(5):851-859 (2004).
Goni, F. et al., Sequence similarities and cross-idiotypic specificity of L chains among human monoclonal IgM kappa with anti-gamma-globulin activity, The Journal Immunology, 135(6):4073-9 (1985).
Gorman, et al., The LGK 3' Enhancer Influences the Ratio of LGK Versus LGL B Lymphocytes, Immunity, 5(3): 241-252(1996).
Gorman, J.R. et al., The Ig(kappa) enhancer influences the ratio of Ig (kappa) versus Ig(lambda) B lymphocytes, Immunity 5(3):241-252 (1996).
Grawunder, U. et al., Induction of sterile transcription from the kappa L chain gene locus in V(D)J recombinase-deficient progenitor B cells, International Immunology 7(12):1915-1925 (1995).
Green, L. et al., Antigen-specific human monoclonal antibodies from mice engineered with human Ig heavy and light chain YACs, Nature Genetics, 7(1):13-21 (1994).
Hagaman, J. et al., Angiotensin-covering enzyme and male fertility, Proc. Natl. Acad. Sci. USA, 95:2552-2557 (1998).
Han, C. et al., Comprehensive analysis of reproductive ADAMs: relationship of ADAM4 and ADAM6; with an ADAM complex required for fertilization in mice, Biology of Reproduction, 80(5):1001-8 (2009).
Han, C. et al., Impaired sperm aggregation in Adam2 and Adam3 null mice, Fertility and Sterility, 93(8):2754-2756 (2010).
Hatton, K. and Schildkraut, C., The Mouse Innunoglobulin Kappa Light-Chain Genes Are Located in Early- and Late-Replicating Regions of Chromosome 6, Molecular and Cellular Biology, 10(8):4314-4323 (1990).
Hendricks J. et al., Organization ofthe variable region of the immunoglobulin heavy-chain gene locus of the rat, Immunogenetics,62(7):479-86 (2010).
Hoiruchi, K. and Blobel, C. Studies From ADAM Knockout Mice, The ADAM Family of Proteases, 29-64 (2005).
Huang, C. and Stoller, B.D., A Majority of Ig H Chain cDNA of Normal Human Adult Blood Lymphocytes Resembles cDNA for Fegal Ig and Natural Autoantibodies, The Journal of Immunology, 151(10):5290-5300 (1993).
Huovila, A. et al., ADAMs and cell fusion, Current Opinion in Cell Biology, 8:692-699 (1996).
Hussack, G. et al., "A VL single-domain antibody library shows a high-propensity to yield non-aggregating binders," Protein Engineering, Design & Selection, 25(6):313-318 (2012).
Ikawa, M. et al., Calsperin Is a Testis-specific Chaperone Required for Sperm Fertility, The Journal of Biological Chemistry, 286(7):5639-5646 (2011).
Ill, C.R. et al., Design and construction of a hybrid immunoglobulin domain with properties of both heavy and light chain variable regions, Protein Engineering, 10(8):949-57 (1997).
Immler, S. et al., By Hook or by Crook? Morphometry, Competition and Cooperation in Rodent Sperm, PLoS ONE, Issue 1(e170) 5 pages (2007).
Immler, Simone, Sperm competition and sperm cooperation: the potential role of diploid and haploid expression, Reproduction, 135:275-283 (2008).
Interlocutory decision in Opposition proceedings (Art. 101(3)(a) and 106(2) EPC) for EP12716101.6, 36 pages (May 26, 2017).
International Search Report and Written Opinion for PCT/US2011/046196, 13 pages (dated Oct. 17, 2011).
International Search Report and Written Opinion for PCT/US2013/024295, 12 pages (dated Apr. 24, 2013).
International Search Report for PCT/US2011/041366, 5 pages (dated Sep. 22, 2011).
International Search Report for PCT/US2011/041370, 5 pages (dated Sep. 22, 2011).
International Search Report for PCT/US2012/026416, 4 pages (dated Jun. 25, 2012).
International Search Report for PCT/US2012/060487, 7 pages (dated Feb. 1, 2013).
International Search Report for PCT/US2012/069981, 5 pages (dated Mar. 20, 2013).
International Search Report for PCT/US2013/029624, 9 pages (dated Aug. 2, 2013).
Jakobovits, A., Production of fully human antibodies by transgenic mice, Current Opinion in Biotechnology, 6:561-566 (1995).
Janeway, C.A., et al., Immunobiology: The Immune System in Health and Disease, 5th Edition, Chapter 9, New York, Garland Science, 2 pages (2001).
Janssens, R. et al., "Generation of heavy-chain-only antibodies in mice," Proceedings of the National Academy of Sciences, 103(41):15130-15135 (2006).
Johnson, T.A. et al., Ig VH1 Genes Expressed in B Cell Chronic Lymphocytic Leukemia Exhibit Distinctive Molecular Features, The Journal of Immunology, 158:235-246 (1997).
Johnston, C. et al., Complete Sequence Assembly and Characterization ofthe C57BL/6 Mouse Ig Heavy Chain V Region, The Journal of Immunology, 176:4221-4234 (2006).
Kaartinen, M. et al., Combinatorial association of V genes: one VH gene codes for three non-cross-reactive monoclonal antibodies each specific for a different antigen (phoxazolone, NP or gat), Molecular Immunology, 25(9):859-65 (1988).
Kabat, E.A., and Wu, T.T., Identical V region amino acid sequences and segments of sequences in antibodies of different specificities. Relative contributions of VH and VL genes, minigenes, and complementarity-determining regions to binding of antibody-combining sites, J. Immunol., 147(5):1709-19 (1991).
Kantor, A.B. et al., An Unbiased Analysis of VH-D-JH Sequences from B-1a, B-1b, and Conventional B Cells, The Journal of Immunology, 158:1175-1186 (1997).
Kaushik, A. et al., Novel insight into antibody diversification from cattle, Veterinary Immunology and Immunopathology 87(3-4):347-350 (2002).
Kim T. et al., Expression and relationship of male reproductive ADAMs in mouse, Biology of Reproduction, 74(4):744-50 (2006).
Kim, E. et al., Differential localization of ADAM1a and ADAM1b in the endoplasmic reticulum of testicular germ cells and on the surface of epididymal sperm, Biochemical and Biophysical Research Communications, 304:313-309 (2003).
Kim, E. et al., Mouse Sperm Lacking ADAM1b/ADAM2 Fertilin Can Fuse with the Egg Plasma Membrane and Effect Fertilization, The Journal of Biological Chemistry, 281(9):5634-5639 (2006).

(56) References Cited

OTHER PUBLICATIONS

Kim, E. et al., Synthesis, Processing, and Subcellular Localization of Mouse ADAM3 during Spermatogenesis and Epididymal Sperm Transport, Journal of Reproduction and Development, 50(5):571-578 (2004).
Kingzette, M. et al., Trans-chromosomal recombination within the Ig heavy chain switch region in B lymphocytes, Proceedings of the National Academy of Sciences of the USA, 95(20):11840-11845 (1998).
Klebig, M. L., Ectopic Expression of the Agouti Gene in Transgenic Mice Causes Obesity, Features of Type II Diabetes, and Yellow Fur, Proc. Natl. Acad. Sci. USA, vol. 92, pp. 4728-4732, (1995).
Kong et al., Transgene expression is associated with copy number and cytomegalovirus promoter methylation in transgenic pigs, PLoS One 4(8):1-10 (2009).
Krutskikh, A. et al., Epididymal protein Rnase10 is required for post-testicular sperm maturation and male fertility, The FASEB Journal, 26(10):4198-4209 (2012).
Kunert, R. et al., Characterization of Molecular Features, Antigen-Binding, and in Vitro Properties of IgG and IgM Variants of 4E10, an Anti-HIV Type 1 Neutralizing Monoclonal Antibody, Aids Research and Human Retroviruses, 20(7):755-762 (2004).
Kuroiwa, Y. et al., Sequential targeting of the genes encoding immunoglobulin-μ and prion protein in cattle, Nature Genetics, 36:775-780 (2004).
Lavial, F. and Pain B., Chicken embryonic stem cells as a non-mammalian embryonic stem cell model, Develop. Growth Diff. 52(1):101-114 (2010).
Leclercq, L., et al., A novel germ-line JK transcript starting immediately upstream of JK1, Nucleic Acids Research 17(17):6809-6819 (1989).
Lee, E. et al., Complete humanization of the mouse immunoglobulin loci enables efficient therapeutic antibody discovery, Nature Biotechnology, 32:4:356, 12 pages (2014).
Lefranc, M-P. and Lefranc, G., Immunoglobulin Lambda (IGL) Genes of Human and Mouse, Molecular Biology of B Cells, London: Elsevier Academic Press, Eds. Honjo, T. et al., Chapter 4, pp. 37-59 (2004).
Lefranc, M.P., Nomeclature of the human immunoglobulin lambda (IGL) genes, Experimental and clinical immunogenetics, S. Karger Basel C.H.,18(4):242-254 (2001).
Lefranc, M.P., Nomenclature of the Human Immunoglobulin Genes Current Protocols in Immunology, Supplement 40:A.1P.1-A.1P.37 (2000).
Leitzgen, K. et al., Assembly of immunoglobulin Light Chains as a Prerequisite for Secretion, Journal of Biological Chemistry, 272(5):3117-3123 (1997).
Lin, P. et al., Research of Immune Globulin in Mice, Guangzhou Medical Journal, 01:49-50 (1990).
Linder, B. et al., Delayed Translation and Posttranslational Processing of Cyritestin, an Integral Transmembrane Protein of the Mouse Acrosome, Experimental Cell Research, 221:66-72 (1995).
Liu, Y. et al., Primary Genetic Investigation of a Hyperlipidemia Model: Molecular Characteristics and Variants of the Apolipoprotein E Gene in Mongolian Gerbil, Biomed Research International, 2014: 9 pages (2014).
Lonberg, N., Human antibodies from transgenic animals, Nature Biotechnology, 23(9):1117-1125 (2005).
Long, J. et al., Phylogenetic and molecular evolution of the ADAM (A Disintegrin And Metalloprotease) gene family from Xenopus tropicalis, to Mus musculus, Rattus norvegicus, and *Homo sapiens*, Gene, 507:36-43 (2012).
Lovell-Badge, Robin, Many ways to pluripotency, Nature Biotechnology, 25:1114-1116 (2007).
Macdonald, L. et al., Velocigene Technology Extended to Humanization of Several Megabases of Complex Gene Loci, First International MUGEN Conference of Animal Models for Human Immunological Disease, Sep. 10-13, 2006—Athens, Greece, Abstract 21 and Poster, 2 pages (2006).
Mageed, R.A. et al., Rearrangement of the human heavy chain variable region gene V3-23 in transgenic mice generates antibodies reactive with a range of antigens on the basis of VHCDR3 and residues intrinsic to the heavy chain variable region, Clinical and Experimental Immunology, 123(1):1-8 (2001).
Mahmoud, T.L. et al., Limiting CDR-H3 Diversity Abrogates the Antibody Response to the Bacterial Polysaccharide x 1 →3 Dextran, The Journal of Immunology, 187:879-886 (2011).
Mahmoudi, M. et al., V region gene analysis of human IgM hybridoma monoclonal anti-Sm antibodies, Lupus, 6:578-589 (1997).
Manis, J. P. et al., Mechanism and control of Icass-switch recombination, Trends in immunology, 23:1:31-39 (2002).
Marasca, R. et al., Immunoglobulin Gene Mutations and Frequent Use of VH1-69 and VH4-34 Segments in Hepatitis C Virus-Positive and Hepatitis C Virus-Negative Nodal Marginal Zone B-Cell Lymphoma, American Journal of Pathology, 159(1):253-261 (2001).
Marcello, M. et al., Lack of tyrosylprotein sulfotransferase-2 activity results in altered sperm-egg interactions and loss of ADAM3 and ADAM6 in epididymal sperm, J Biol Chem, 286(15):13060-13070 (2011).
Mar. 3, 2016 Letter from H. Van Per Hoff, Opposition against EP 2550363 (2 pages).
Martin, D.J., and Van Ness, B.G. Identification of a Germ Line Transcript from the Unrearranged Kappa Gene in Human B Cells, Molecular and Cellular Biology 9(10)4560-4562 (1989).
Martin, D.J., and Van Ness, B.G. Initiation and Processing of Two Kappa Immunoglobulin Germ Line Transcripts in Mouse B cells, Molecular and Cellular Biology 10(5):1950-1958 (1990).
Mcgoldrick, P. et al., Roden models of amyotrophic lateral sclerosis, Biochimica et Biophysica Acta, 1832:1421-1436 (2013).
Mei, S.et al., Vasoactive intestinal peptide hydrolysis by antibody light chains, The Journal of Biological Chemistry, 266(24):15571-4 (1991).
Melton, David W., Chapter 8: Gene-Targeting Strategies, Methods in Molecular Biology, Transgenesis Techniques, 2nd Edition, Principles and Protocols, 180:19 pages (2002).
Miklos, J.A. et al., Salivary gland mucosa-associated lymphoid tissue lymphoma immunoglobulin VH genes show frequent use of V1-69 with distinctive CDR3 features, Blood, 95:3878-3884 (2000).
Mills, F. et al., Enhancer complexes located downstream of both human immunoglobulin Calpha genes, Journal of Experimental Medicine,186(6):845-58 (1997).
Minutes of the taking of evidence by hearing of witnesses recorded in the oral proceedings before the Opposition Division for EP12716101. 6, 25 pages (May 26, 2017).
Montaño, R.F. and Morrison, S.L. , Influence of the Isotype of the Light Chain on the Properties of IgG, Journal of Immunology, 168:224-231 (2002).
Moore, H. et al., Exceptional sperm cooperation in the wood mouse, Nature, 418:174-177 (2002).
Moran N., Mouse platforms jostle for slice of humanized antibody market, Nature Biotechnology, 31(4): 267-268, (2013).
Morrison, S.L. et al., Variable region domain exchange influences the functional properties of IgG, Journal of Immunology, 160(6):2802-8 (1999).
Mortari, F. et al., Human Cord Blood Antibody Repertoire, The Journal of Immunology, 150(4):1348-1357 (1993).
Muller, S. et al., B-Cell Abnormalities in AIDS: Stable and Clonally-Restricted Antibody Response in HIV-1 Infection, Scandinavian Journal of Immunology, 38:327-334 (1993).
Murphy, A., Declaration Under 37 C.F.R. §1.132, 4 pages (2014).
Murphy, Andrew, Chapter 8: Veloclmmune: Immunoglobulin Variable Region Humanized Mice, Recombinant Antibodies for Immunotherapy, Part III, 14 pages (2009).
Murphy, D., BAC-based Modifications of the Mouse Genome: The Big and the Backward, Wellcome Trust Advanced Course: Genetic Manipulation of ES Cells, 58 pages (2009).
Murphy, K., The Generation of Lymphocyte Antigen Receptors, Janeway's Immunobiology, 8th Edition, New York: Garland Science, Chapters, Sections 5-1 to 5-4, pp. 158-162 (2012).
Murphy, Kenneth. *Janeway's Immunobiology* 8th Edition. New York: Garland Science, 2012. Printed in USA. Chapter 5, Sections 5-1 to 5-4, pp. 157-162.

(56) References Cited

OTHER PUBLICATIONS

Murphy, L. and Silha, J., Unexpected and unexplained phenotypes in transgenic models, Growth Horm IGF Res., 10(5):233-235 (2000).
Muñoz, M. et al., Conventional pluripotency markers are unspecific for bovine embryonic-derived cell-lines, Theriogenology 69(9):1159-1164 (2008).
Nagle (2007) Regeneron helps make Sanofi VelocImmune to its "weak pipeline", <http://www.outsourcing-pharma.com/Preclinical-Research/Regeneron-helps-make-Sanofi-VelocImmune-to-its-weak-pipeline>—Published Dec. 3, 2007.
Nagle, Mike, Regeneron helps make Sanofi VelocImmune to its 'weak' pipeline, Breaking News on Contract Research, Manufacturing & Clinical Trials, 2 pages (2007).
Nakanishi, T. et al., Selective Passage Through the Uterotubal Junction of Sperm from a Mixed Population Produced by Chimeras of Calmegin-Knockout and Wild-Type Male Mice, Biology of Reproduction, 71:959-965 (2004).
News In Brief Article (2007) Big Pharma vies for mice, *Nature Biotechnology* 2007, 25(6): 613—Published Jun. 2007.
Nicholson, I.C. et al., Antibody Repertoires of Four- and Five-Feature Translocus Mice Carrying Human Immunoglobulin Heavy Chain and kappa and lambda light chain Yeast Artificial Chromosomes. Journal of Immunology 163(12):6898-6906 (1999).
Niemann, H. et al., Transgenic farm animals: present and future, Review of Science Technology, 24(1):285-298 (2005).
Nishimura, H. et al., Analysis of Loss of Adhesive Function in Sperm Lacking Cyritestin or Fertilin ß, Developmental Biology, 233:204-213 (2001).
Nishimura, H. et al., Identification of an ADAM2-ADAM3 Complex on the Surface of Mouse Testicular Germ Cells and Cauda Epididymal Sperm, The Journal of Biological Chemistry, 282(24):17900-17907 (2007).
Nishimura, H. et al., Possible Function ofthe ADAM1a/ADAM2 Fertilin Complex in the Appearance of ADAM3 on the Sperm Surface, The Journal of Biological Chemistry, 279(33):34957-34962 (2004).
Nitschke, L. et al., Deletion ofthe DQ52 element within the Ig heavy chain locus leads to a selective reduction in VDJ recombination and altered D gene usage, Journal of Immunology, 166(4):2540-52 (2001).
Notice of Opposition to a European Patent for EP2550363, 28 pages (Dec. 10, 2014).
Oberdoerffer, P. et al., Unidirectional Cre-mediated genetic inversion in mice using the mutant loxP pair lox66/lox71, Nucleic Acids Research, 31(22)(e140):1-7 (2003).
Office Action for U.S. Appl. No. 13/716,238, 7 pages (dated Jan. 4, 2016).
Office Action for U.S. Appl. No. 13/951,996, 7 pages (dated Dec. 17, 2015).
Office Action for U.S. Appl. No. 14/137,902, 23 pages (dated Oct. 30, 2015).
Office Action for U.S. Appl. No. 14/818,162, 30 pages (dated Dec. 11, 2015).
Opinion & Order between Regeneron Pharmaceuticals, Inc. and Merus B.V., 114 pages (Nov. 2, 2015).
Opponent Final Submissions for EP2550363,15 pages (Jan. 27, 2017).
Paris, D.B. and Stout, T.A, Equine embryos and embryonic stem cells: defining reliable markers of pluripotency, Theriogenology 74(4):516-524 (2010).
Parng, C.L. et al., Gene conversion contributes to Ig light chain diversity in cattle, The Journal of Immunology 157(12):5478-5486 (1996).
Pasqualini, R. and Arap, W., Hybridoma-free generation of monoclonal antibodies, Proceedings of the National Academy of Sciences USA, 101(1):257-259 (2004).
Patentee Final Submissions for EP12716101.6, 4 pages (Jan. 27, 2017).
Pereira, B. et al., Cardiolipin binding a light chain from lupus-prone mice, Biochemistry, 37(5):1430-7 (1998).

Perez, M. et al., Primary cutaneous B-cell Lymphoma is associated with somatically hypermutated immunoglobulin variable genes and frequent use of VH1-69 and VH4-59 segments, British Journal of Dermatopathology, 162:611-618 (2010).
Peterson, Norman C., Advances in Monoclonal Antibody Technology: Genetic Engineering of Mice, Cells, and Immunoglobulins, ILAR Journal, 46(3):314-319 (2005).
Petitte, J.N. et al., Avian pluripotent stem cells, Mech. of Develop. 121(9):1159-1168 (2004).
Pettersson, S. et al., A second B cell-specific enhancer 3' of the immunoglobulin heavy-chain locus, Nature, 344(6262):165-168 (1990).
Pizzari, T. and Foster, K., Sperm Sociality: Cooperation, Altruism, and Spite, PLoS Biology, 6(5)(e130):0925-0931 (2008).
Popov, et al., A Human Immunoglobulin I locus is Similarly Well Expressed in Mice and Humans, J. Exp. Med., 189(10):1611-1619(1999).
Pos, W. et al., VH1-69 germline encoded antibodies directed towards ADAMTS13 in patients with acquired thrombotic thrombocytopenic purpura, Journal of Thrombosis and Haemostatis, 7:421-428 (2008).
Poueymirou, W. et al., F0 generation mice fully derived from gene-targeted embryonic stem cells allowing immediate phenotypic analyses, Nature Biotechnology, 25(1):91-99 (2007).
Preliminary Opinion of Opposition Division on EP 2550363, 24 pages, Jul. 29, 2016.
Primakoff, P. and Myles, D., The ADAM gene family: surface proteins with adhesion and protease activity, Trends Genet, 16(2):83-87 (2000).
Provision of the minutes in accordance with Rule 124(4) EPC for EP1276101.6, 62 pages (May 26, 2017).
Qi, N.R. et al., A new transgenic rat model of hepatic steatosis and the metabolic syndrome, Hypertension, 45(5):1004-1011. (2005).
Ramírez-Solis, R. et al., Chromosome engineering in mice, Nature, 378(6558):720-724 (1995).
Ravetch, J.V. et al., "Structure ofthe human immunoglobulin mu locus: characterization of embryonic and rearranged J and D genes," Cell, 27:583-591 (1981).
Ray Lambert et al,, Breeding Strategies for Maintaining Colonies of Laboratory Mice, A Jackson Laboratory Resource Manual, pp. 1-29 (2007).
Ray, P. et al., Ectopic expression of a c-kitW42 minigene in transgenic mice: recapitulation of W phenotypes and evidence for c-kit function in melanoblast progenitors, Genes Development, 5(12A):2265-2273 (1991).
Reply to Third Party Observations on EP2501817, (May 20, 2013).
Response to Summons to attend Oral Proceedings for EP255036, 1 page (Feb. 28, 2017).
Ristevski, Sika, Making better transgenic models: conditional, temporal, and spatial approaches, Molecular Biotechnology, 29(2):153-163 (2005).
Rocca-Serra, J. et al., Two monoclonal antibodies against different antigens using the same VH germ-line gene, Nature, 304(5924):353-5 (1983).
Rodríguez, C.I., et al., High-efficiency deleter mice show that FLPe is an alternative to Cre-loxP, Nat. Genet., 25(2):139-40 (2000).
Roebroek, A. et al., Chapter 10: Knockin Approaches, Methods in Molecular Biology, Transgenic Mouse Methods and Protocols, 209:16 pages (2003).
Rojas, G. et al., Phage antibody fragments library combining a single human light chain variable region with immune mouse heavy chain variable regions, Journal of Biotechnology, 94(3):287-298 (2002).
Roychaudhuri, R. et al., ADAM9 Is a Novel Product of Polymorphonuclear Neutrophils: Regulation of Expression and Contributions to Extracellular Matrix Protein Degradation during Acute Lung Injury, The Journal of Immunology, 193:2469-2482 (2014).
Rudikoff, S. et al., Single amino acid substitution altering antigen-binding specificity, Immunology, 79:1979-1983 (1982).
Sapparapu, G. et al., Antigen-specific proteolysis by hybrid antibodies containing promiscuous proteolytic light chains paired with an antigen-binding heavy chain, The Journal of Biological Chemistry, 284(36):24622-33 (2009).

(56) References Cited

OTHER PUBLICATIONS

Sasso E.H. et al., A Fetally Expressed Immunoglobulin VH1 Gene Belongs to a Complex Set of Alleles, Journal of Clinical Investigation, 91:2358-2367 (1993).
Sasso E.H. et al., Expression ofthe Immunoglobulin VH Gene 51p1 is Proportional to its Germline Gene Copy Number Journal of Clinical Investigation, 97(9):2074-2080 (1996).
Sasso, E.H. et al., Prevalence and Polymorphism of Human VH3 Genes, The Journal of Immunology, 145(8):2751-2757 (1990).
Schelonka, R.L. et al., A Single DH Gene Segment Creates Its Own Unique CDR-H3 Repertoire and Is Sufficient for B Cell Development and Immune Function, The Journal of Immunology, 175:6624-6632 (2005).
Schlissel, M.S., and Baltimore, D., Activation of Immunoglobulin Kappa Gene Rearrangement Correlates with Induction of Germline Kappa Gene Transcription, Cell, 58:1001-1007(1989).
Schulze, M. et al., Derivation, Maintenance, and Characterization of Rat Embryonic Stem Cells In Vitro, Methods in Molecular Biology, 329:45-58 (2006).
Schwartz, D. and Cantor, C., Separation of Yeast Chromosome-Sized DNAs by Pulsed Field Gradient Gel Electrophoresis, Cell, 37:67-75 (1984).
Scott, C.T., Mice with a human touch, Nature Biotechnology, 25(10):1075-1077 (2007).
Seals D.F. and Courtneidge S.A., The ADAMs family of metalloproteases: multidomain; proteins with multiple functions, Genes and Development, 17(1):7-30 (2003).
Second Declaration of Meng (Amy) Li, Ph.D., 14 pages (Sep. 15, 2016).
Sen, R. and Baltimore, D., Multiple nuclear factors interact with the immunoglobulin enhancer sequences, Cell, 46(5):705-716 (1986).
Shamsadin, R. et al., Male Mice Deficient for Germ-Cell Cyritestin Are Infertile, Biology of Reproduction, 61:1445-1451 (1999).
Shmerling et al., Strong and ubiquitous expression of transgenes targeted into the β-actinlocus by Cre/lox cassette replacement, Genesis 42(5):229-235 (2005).
Sibilia, J. et al., Structural Analysis of Human Antibodies to Proteinase 3 from Patients with Wegener Granulomatosis, The Journal of Immunology, 159:712-719 (1997).
Sigmund, Curt D., Viewpoint: Are Studies in Genetically Altered Mice Out of Control?, Arterioscler Thromb Vase Biol, 20(6):1425-1429 (2000).
Simon, T. and Rajewsky, K., Antibody domain mutants demonstrate autonomy ofthe antigen binding site, EMBO J., 9(4):1051-6 (1990).
Smith, Kevin R., Gene transfer in higher animals: theoretical considerations and key concepts, Journal of Biotechnology, 99(1):1-22 (2002).
Solomon, A. et al., Light chain-associated amyloid deposits comprised of a novel kappa constant domain, The Proceedings ofthe National Academy of Sciences of the United States of America, 95(16):9547-51 (1998).
Song, M.K. et al., Light chain of natural antibody plays a dominant role in protein antigen binding. Biochemical Biophysical Research Communications, 268(2):390-4 (2000).
Sorrell, D. and Kolb, A., Chapter XI: Targeted Modification of Mammalian Genomes, Focus on Genome Research, 6 pages (2004).
Souroujon, M.C. et al., Polymorphisms in Human H Chain V Region Genes from the VHIII Gene Family, The Journal fo Immunology, 143(2):706-711 (1989).
Stamatopoulos, K., Follicular lymphoma immunoglobulin kappa light chains are affected by the antigen selection process, but to a lesser degree than their partner heavy chains, British Journal of Haematology, 96(1):132-46 (1997).
Statement of Relatedness for U.S. Appl. No. 13/951,996, ADAM6 Patents, 2 pages (Oct. 2, 2015).
Statement of Relatedness for U.S. Appl. No. 13/951,996, Lambda Light Chain Patents, 2 pages (Oct. 2, 2015).

Stevens, S. et al., VelocImmune: Humanization of Immunoglobulin Loc Using Velocigene Technology, First International MUGEN Conference of Animal Models for Human Immunological Disease, Sep. 10-13, 2006—Athens, Greece, Abstract 4 and Poster, 2 pages (2006).
Storb, U. et al., Transgenic Mice with μ and κ Genes Encoding Antiphosphorycholine Antibodies, J. Exp Med, 164:627-64 (1986).
Suarez, Susan S., Sperm Transport and Motility in the Mouse Oviduct: Observations in Situ, Biology of Reproduction, 36:203-210 (1987).
Sui, J. et al., Structural and functional bases for broad-spectrum neutralization of avian and human influenza A viruses, Nature Structural and Molecular Biology, 16(3):265-273 (2009).
Sun, M. et al., Antigen recognition by an antibody light chain, The Journal of Biological Chemistry, 269(1):734-8 (1994).
Supplemental Examination Certificate for U.S. Appl. No. 96/000,136, 6 pages (Feb. 2, 2016).
Suzuki, I. et al., Representation of Rearranged VH Gene Segments in the Human Adult Antibody Repertoire, The Journal of Immunology, 154:3902-3911 (1995).
Swanson, W. and Vacquier, V., The Rapid Evolution of Reproductive Proteins, Nature Reviews, Genetics, 3:137-144 (2002).
Taki, S. et al., Targeted Insertion of a Variable Region Gene into the Immunoglobulin Heavy Chain Locus, Science, 262:1268-1271 (1993).
Taylor, L.D. et al., A Transgenic Mouse that Expresses a Diversity of Human Sequence Heavy and Light Chain Immunoglobulins, Nucleic Acid Research, 20(23):6287-6295 (1992).
Third Party Observation for EP11728508.0, 6 pgs (Dec. 3, 2012).
Third Party Observation for PCT/US2012/069981, 4 pages (Jul. 3, 2013).
Third Party Observation in EP11728509.8, 7 pages (Dec. 4, 2012).
Third Party Observations in EP11728509, dated Dec. 4, 2012.
Third Party Observations on EP2501817, (Feb. 28, 2013).
Third Party Observations on European Patent Application No. 12192727.1, 17 pages (Jun. 18, 2013).
Third Party Observations on European Patent Application No. 12192727.1, 3 pages (Feb. 25, 2014).
Third Party Observations on European Patent Application No. 12192727.1, 5 pages (Nov. 17, 2014).
Third Party Observations on European Patent Application No. 12192727.1, 7 pages (Apr. 8, 2015).
Third Party Observations on European Patent Application No. 12192727.1, 9 pages (Aug. 11, 2015).
Third Party Observations on European Patent Application No. 12716101.6, 4 pages (Feb. 25, 2014).
Third Party Observations on European Patent Application No. 12716101.6, 4 pages (Jul. 31, 2014).
Third Party Observations on European Patent Application No. 12716101.6, 4 pages (Sep. 4, 2013).
Third Party Observations on European Patent Application No. 12716101.6, 5 pages (Jun. 27, 2014).
Third Party Observations on European Patent Application No. 12809955.3, 3 pages (Aug. 6, 2015).
Third Party Observations on European Patent Application No. 12809955.3, 4 pages (Jun. 24, 2014).
Third Party Observations on European Patent Application No. 14154918.8, 5 pages (Nov. 26, 2014).
Third Party Observations on European Patent Application No. 14154918.8, 7 pages (Apr. 14, 2015).
Third Party Observations on European Patent Application No. 14154967.5, 5 pages (Nov. 18, 2014).
Third Party Observations on European Patent Application No. 14154967.5, 7 pages (Apr. 23, 2015).
Third Party Observations on European Patent Application Nos. 12192727.1, 14154918.8, 14154967.5, 14176593.3 and 12809955.3, 3 pages (Nov. 12, 2015).
Third Party Observations on U.S. Appl. No. 13/890,519, 27 pages (Oct. 23, 2013).
Timetable for Mouse ES Cells course at Wellcome Trust Sanger Institute Oct. 26, 2009—Nov. 8, 2009 (black and white).
Timetable for Mouse ES Cells course at Wellcome Trust Sanger Institute Oct. 26, 2009—Nov. 8, 2009 (greyscale).

(56) References Cited

OTHER PUBLICATIONS

Tokuhiro, K. et al., Protein disulfide isomerase homolog PDILT is required for quality control of sperm membrane protein ADAM3 and male fertility, PNAS, 109(10):3850-3855 (2012).
Torres and Kuhn, Laboratory Protocols for Conditional Gene Targeting, 37-40 (1997).
Tsybovsky, Y.I. et al., Folding and stability of chimeric immunofusion VL-barstar, Biochemistry (Moscow), 69(9):939-948 (2004).
Tuaillon, N. et al., Human immunoglobulin heavy-chain minilocus recombination in transgenic mice: Gene-segment use in u and y transcripts, Proceeding of the National Academy of Science USA, 90:3720-3724 (1993).
Tuaillon, N., Repertoire analysis in human immunoglobulin heavy chain minilocus transgenic, [mu]MT/[mu]MT mice, Molecular Immunology, 37(5):221-231 (2000).
Valenzuela, D. et al., High-throughput engineering of the mouse genome coupled with high-resolution expression analysis, Nature Biotechnology, 21(6):652-659 (2003).
Van Den Beucken, T. et al., Building novel binding ligands to B7.1 and B7.2 based on human; antibody single variable light chain domains, Journal of Molecular Biology, 310(3):591-601 (2001).
Van Ness, B.G. et al., Transcription of the unrearranged mouse C kappa locus: sequence of the initiation region and comparison of activity with a rearranged V kappa-C kappa gene, Cell 27:593-602 (1981).
Verkoczy, L. et al., Autoreactivity in an HIV-1 broadly reactive neutralizing antibody variable region heavy chain induces immunologic tolerance, Proc. Natl. Acad. Sci. U.S.A., 107(1): 181-6(2010).
Wagner S.D. et al., The diversity of antigen-specific monoclonal antibodies from transgenic mice bearing human immunoglobulin gene miniloci, Eur J Immunol. 24(11):2672-81 (1994).
Wagner, S.D. et al., Antibodies generated from human immunoglobulin miniloci in transgenic mice, Nucleic Acids Research, 22(8):1389-1393 (1994).
Wallace, H.A. et al., Manipulating the mouse genome to engineer precise functional syntenic replacements with human sequence, Cell, 128(1):197-209 (2007).
Wang, T.T. and Palese, P., Universal epitopes of influenza virus hemagglutinins?, Nature Structural & Molecular Biology, 16(3):233-234 (2009).
Watson, J. and Crick, F., Molekulyarnaya biotekhnologiya. Printsipy i primeneniye, Moscow Mir., 45-47 (2002).
White, Judith M., ADAMS: modulators of cell-cell and cell-matrix interactions, Current Opinion in Cell Biology, 15:598-606 (2003).
Williams, S.C. et al., Sequence Evolution of the Human Germline V lambda Repertoire, J. Mol. Biol. 264(2):220-232 (1996).
Wolfsberg, T. et al., ADAM, a Widely Distributed and Developmentally Regulated Gene Family Encoding Membrane Proteins with A Disintegrin And Metalloprotease Domain, Developmental Biology, 169:378-383 (1995).
Written Opinion for PCT/US2011/041366, 10 pages (dated Sep. 22, 2011).
Written Opinion for PCT/US2011/041370, 9 pages (dated Sep. 22, 2011).
Written Opinion for PCT/US2012/026416 (8 pages), dated Jun. 25, 2012.
Written Opinion for PCT/US2012/060487, 5 pages (dated Feb. 1, 2013).
Written Opinion for PCT/US2012/069981 (8 pages) dated Mar. 20, 2013.
Written Opinion for PCT/US2013/029624, 12 pages (dated Aug. 2, 2013).
Written Opinion for PCT/US2014/026040 dated Jul. 29, 2014 (8 pages).
Xu, J.L. and Davis, M.M., Diversity in the CDR3 region of VH is sufficient for most antibody specificities, Immunity 13(1):37-45 (2000).
Yamada, M. et al., Preferential Utilization of Specific Immunoglobulin Heavy Chain Diversity and Joining Segments in Adult Human Peripheral Blood B Lymphocytes, Journal of Experimental Medicine, 173:395-407 (1991).
Yamaguchi, R. et al., Aberrant Distribution of ADAM3 in Sperm from Both Angiotensin-Converting Enzyme (Ace)- and Calmegin (Clgn)-Deficient Mice, Biology of Reproduction, 75:760-766 (2006).
Yamaguchi, R. et al., Disruption of ADAM3 Impairs the Migration of Sperm into Oviduct in Mouse, Biology of Reproduction, 81:142-146 (2009).
Yamaguchi, R. et al., Mice expressing aberrant sperm-specific protein PMIS2 produce normal-looking but fertilization-incompetent spermatozoa, MBoC, 23:2671-2679 (2012).
Yantha, J. et al., Unexpected Acceleration of Type 1 Diabetes by Transgenic Expression of B7-H1 in NOD Mouse Peri-Islet Glia, Diabetes, 59:2588-2596 (2010).
Zachau, H. G., Immunoglobulin k Genes of Human and Mouse, Molecular Biology of B Cells, London: Elsevier Academic Press, Eds. Honjo, T. et al., Chapter 3, pp. 27-36 (2003).
Zhang, Y. et al., A new logic for DNA engineering using recombination in *Escherichia coli*, Nature Genetics, 20:123-128 (1998).
Zheng, B. et al., Engineering mouse chromosomes with Cre-loxP: range, efficiency, and somatic applications. Molecular and Cellular Biology, 20(2):648-655 (2000).
Zhu, G. et al., Testase 1 (ADAM 24) a plasma membrane-anchored sperm protease implicated in sperm function during epididymal maturation or fertilization, Journal of Cell Science, 114:1787-1794 (2001).
Zou, Y. et al., Cre-loxP-mediated gene replacement: a mouse strain producing humanized antibodies, Current Biology, 4:1099-1103 (1994).
European Search Report for EP12195716, 15 pages (dated Jan. 29, 2013).
Glassy, M. et al., Final Oral Progamme, The Twelfth International Conference on Human Antibodies & Hybridomas, 4 pages (May 10-12, 2006).
Glassy, M. et al., Second Circular and Provisional Conference Program, The Twelfth International Conference on Human Antibodies & Hybridomas, 8 pages (May 10-12, 2006).
Glik, B. Molecular Biotechnology, Moscow. Mir., pp. 211-212, 429-433 (2002).
Hirohata, S. et al., Chromosomal Assignment of Two ADAM Genes, TACE (ADAM17) and MLTNB (ADAM 19), to Human Chromosomes 2 and 5, Respectively, and of Mltnb to Mouse Chromosome 11, Genomics, 54:178-179 (1998).
Ignatovich, O. et al., Dominance of Intrinsic Genetic Factors in Shaping the Human Immunoglobulin Vλ Repertoire, J. Mol. Biol., 294:457-465 (1999).
Ignatovich, O. et al., The Creation of Diversity in the Human Immunoglobulin Vλ Repertoire, J. Mol. Biol., 268:69-77 (1997).
Janssens, R. et al., Generation of heavy-chain-only antibodies in mice, Proc Natl Acad Sci USA, 103(41):15130-5 (2006).
Karow, Margaret, Making the VelocImmune mouse using Velocigene technology [abstract], Session 5: Molecular biology—II, Human Antibodies, 15:19-28 (2006).
Murphy, Andrew, Making the VelocImmune Mouse Using VelociGene Technology, Human Antibodies & Hybridomas, 31 pages (May 10-12, 2006).
Patent Prosecution History of U.S. Appl. No. 13/166,200, filed Jun. 22, 2011.
Popov, A. et al., Assembly and extension of yeast artificial chromosomes to build up a large locus, Gene, 177:195-201 (1996).
Poueymirou, W.T. et al., F0 generation mice fully derived from gene-targeted embryonic stem cells allowing immediate phenotypic analyses, Nat Biotechnol, 25(1):91-9 (2007).
Valenzuela, D.M., et al., High-throughput engineering of the mouse genome coupled with high-resolution expression analysis, Nat Biotechnol, 21(6):652-9 (2003).
Veronina, V. et al., Deletion of Adam6 in Mus musculus leads to male subfertility and deficits in sperm ascent into the oviduct, Biology of Reproduction, 100(3):686-696 (2019).
Chirino, A. et al., Minimizing the immunogenicity of protein therapeutics, DDT, 9(2):82-90 (2004).

(56) References Cited

OTHER PUBLICATIONS

Stevens, S., Human antibody discovery VelocImmune—a novel platform, Asia Focus, Christian Conference of Asia, Thailand, 8:72-74 (2008).

Xu, Y. et al., Deletion of the Igκ Light Chain Intronic Enhancer/Matrix Attachment Region Impairs but Does Not Abolish VκJκ Rearrangment, Immunity, pp. 377-385 (1996).

* cited by examiner

|  | | A | B | C | D | E | F | G | H |
|---|---|---|---|---|---|---|---|---|---|
| Parental ES | Theoretical copy number | 2 | 2 | 2 | 2 | 2 | 2 | 0 | 0 |
| | Observed copy number | 1.9 | 1.8 | 2.1 | 1.8 | 1.9 | 1.8 | <0.01 | <0.04 |
| Modified ES | Theoretical copy number | 2 | 2 | 1 | 1 | 2 | 2 | 1 | 1 |
| | Observed copy number | 1.9 | 2.4 | 1.0 | 1.0 | 2.0 | 1.9 | + | + |

FIG. 3B

|  | copy number | D | H |
|---|---|---|---|
| WT Mice | Theoretical | 2 | 0 |
| | Observed 1 | 1.71 | <0.01 |
| | Observed 2 | 2.07 | <0.01 |
| | Observed 3 | 2.16 | <0.01 |
| | Observed 4 | 1.88 | <0.01 |
| Het Mice | Theoretical | 1 | 1 |
| | Observed 1 | 1.22 | 1.04 |
| | Observed 2 | 0.94 | 1.02 |
| | Observed 3 | 0.85 | 0.95 |
| | Observed 4 | 1.02 | 1.00 |
| Homo Mice | Theoretical | 0 | 2 |
| | Observed 1 | <0.01 | 2.37 |
| | Observed 2 | <0.01 | 2.22 |
| | Observed 3 | <0.01 | 2.43 |
| | Observed 4 | <0.01 | 1.93 |

FIG. 3C

| 3'$V_H$ | N | $D_H$ | N | 5' $J_H$ |
|---|---|---|---|---|
| | | ($D_H$ 1-26) GGTATAGTGGGAGCTACTAC | | |
| (3-72) GCTAG | | TAGTGGGgCCTAC | AGGC | CTTTTGATATC(3) |
| (3-9) GCAAAAG | CCCAGGGG | AGTGGGAGCTACTAC | ACCT | ATGCTTTTGATATC(3) |
| (3-7) GCGAGAGA | G | GGTATAGTGGGAaCTACT | GAGG | ACTTTGAtTAC(4) |
| (4-59) GCGAGAG | GGAC | AGTGGGAGC | CCT | CTTTGACTAC(4) |
| (3-23) GCGAAAA | CC | TAGTGGGAGCTACT | C | CTGGTTCGACCCC(5) |
| | | ($D_H$ 1-7) GGTATAACTGGAACTAC | | |
| (4-34) GCGAGAGG | AGGAG | GGTATAACTGGAACT | CGA | ATGCTTTTGATATC(3) |
| (1-2) GCGAGAG | GA | TATAACTGGA | | ACTACTTTGACTAC(4) |
| (3-23) GCGAAAGA | | GTATAACTGGAACCAC | TGG | TACTTTGACTAC(4) |
| (3-7) GCGAGAGA | G | ATAACTGGAAC | CCC | CTTTGACTAC(4) |
| (4-59) GCGAG | GGGA | TATAACTGGAACT | TTTCTTTT | TTTGACTAC(4) |
| (4-39) GCGAGA | GG | TAACTGGAACT | CTCTGGG | CTTTGACTAC(4) |
| | | ($D_H$ 3-10) GTATTACTATGGTTCGGGGAGTTATTATAAC | | |
| (3-30) GCGA | AAAGGGC | TACTATGGTTCGGGGAG | CTC | TTGACTAC(4) |
| (1-2) GCGAGAGA | | TATTACTATGGTTCGGGGAGTTATTATAAC | GAAGGT | CTACGGTATGGACGTC(6) |
| | | ($D_H$ 6-6) GAGTATAGCAGCTCGTCC | | |
| (1-2) GCGAGAGA | | GTATAGCAG | | CTTTGACTAC(4) |
| (3-48) GCGAGA | GA | GAGTATAGCAGCTCGT | TG | TGACTAC(4) |
| (3-13) GCAAGAGA | GG | ATAGgAGCTCGcCCC | CTCGGG | TACTTGACTAC(4) |
| | | ($D_H$ 7-27) CTAACTGGGGA | | |
| (3-7) GCGAGAGA | TCT | TGGGGA | AGG | CTAC(4) |
| (3-15) ACCAC | CCA | TAACTGGGGA | GGG | TTTGACTAC(4) |
| (3-48) GCGAGA | GATA | GGGGA | | CCg(5) |

FIG. 7A

| 3'Vκ | | N | 5' Jκ |
|---|---|---|---|
| (1-6) | CAACAGAGTTAtAGTACCCCTCC | GGA | GACG(1) |
| (1-9) | CAACAGCTTAATAGTTACCCTC | | GGACG(1) |
| (1-9) | CAACAGCTTAATAGTTACC | | ATTCACT(3) |
| (1-9) | CAACAtTTAATAGTTACCC | | GCTCACT(4) |
| (3-15) | CAGCAGTATAATAACTGGCCTC | | TCACT(4) |
| (1-17) | CTACAGCATAATAGTTACCC | | GTGGACG(1) |
| (1-17) | CTACAGCATAATAGTTACCCTC | | GGACG(1) |
| (3-20) | CAGCAGTATGGTAGCTCACCTC | | GGACG(1) |
| (2-30) | ATGCAAGGTACACACTGGCC | | GTGGACG(1) |
| (2-30) | ATGCAAGGTtCACACTGGCC | | GTACACT(2) |
| (2-30) | ATGCAAGGTACACACTGGCC | | GCTCACT(4) |
| (1-33) | CAACAGTATGATAATCTCCCTCC | | CACT(3) |
| (1-33) | CAACAGTATGATAATCTCCC | | ATTCACT(3) |
| (1-33) | CAACAGTATGATAATCTCCC | CG | TCACT(4) |
| (1-33) | CAACAGTATGATAATCTCCC | | GATCACC(5) |
| (1-37) | CAACGGAtTTACAATGCC | GA | CACC(5) |
| (1-39) | CAACAGAGTTACAGTACCCCC | CA | TGTACACT(2) |
| (1-39) | CAACAGAGTTACAGTACCCCTC | | TCACT(4) |
| (1-39) | CAACAGAGTTACAGTACtCCTCC | | CACT(4) |

FIG. 7B

|      | 3' Human Vλ | Human Jλ1 | 5' Mouse Cκ |
|------|-------------|-----------|-------------|
| A6   | GCAACAATT   | tcGTCTTCGGAACTGGGACCAAGGTCACCGTCCTAG | GGGCTGATGCTGCACCAACTGTATCCATCTTC |
| B6   | GCAACAATT   | ATGTCTTCGGAACTGGGACCAAGGTCACCGTCCTAG | GGGCTGATGCTGCACCAACTGTATCCATCTTC |
| F6   | GCAACAATT   | ATGTCTTCGGAACTGGGACCAAGGTCACCGTCCTAG | GGGCTGATGCTGCACCAACTGTATCCATCTTC |
| B7   | GCAACAATT   | ATGTCTTCGGAACTGGGACCAAGGTCACCGTCCTAG | GGGCTGATGCTGCACCAACTGTATCCATCTTC |
| E7   | GCAACAAT    | GTCTTCGGAACTGGGACCAAGGTCACCGTCCTAG   | GGGCTGATGCTGCACCAACTGTATCCATCTTC |
| F7   | GCAACAATT   | ATGTCTTCGGAACTGGGACCAAGGTCACCGTCCTAG | GGGCTGATGCTGCACCAACTGTATCCATCTTC |
| C8   | GCAACAATT   | ATGTCTTCGGAACTGGGACCAAGGTCACCGTCCTAG | GGGCTGATGCTGCACCAACTGTATCCATCTTC |
| E12  | GCAACAATTT  | gTGTCTTCGGAACTGGGACCAAGGTCACCGTCCTAG | GGGCTGATGCTGCACCAACTGTATCCATCTTC |
| 1-4  | CAAGTCGGTT  | TATGTCTTCGGAACTGGGACCAAGGTCACCGTCCTAG | GGGCTGATGCTGCACCAACTGTATCCATCTTC |
| 1-20 | TGAGTGCT    | gctttTTtgGAACTGGGACCAAGGTCACCGTCCTAG | GGGCTGATGCTGCACCAACTGTATCCATCTTC |
| 3B43 | TGAGTGCg    | TATGTCTTCGGAACTGGGACCAAGGTCACCGTCCTAG | GGGCTGATGCTGCACCAACTGTATCCATCTTC |
| 5-8  | CTGAATGGT   | CATGTCTTCGGAACTGGGACCAAGGTCACCGTCCTAG | GGGCTGATGCTGCACCAACTGTATCCATCTTC |
| 5-19 | AGTGGTAAT   | TATGTCTTCGGAACTGGGACCAAGGTCACCGTCCTAG | GGGCTGATGCTGCACCAACTGTATCCATCTTC |
| 1010 | AGTGGTGCT   | TATGTCTTCGGAACTGGGACCAAGGTCACCGTCCTAG | GGGCTGATGCTGCACCAACTGTATCCATCTTC |
| 11A1 | AGCAGCGCT   | TATGTCTTCGGAACTGGGACCAAGGTCACCGTCCTAG | GGGCTGATGCTGCACCAACTGTATCCATCTTC |
| 7A8  | GGTGGTGCT   | TATGTCTTCGGAACTGGGACCAAGGTCACCGTCCTAG | GGGCTGATGCTGCACCAACTGTATCCATCTTC |
| 3A3  | AGTAGCACT   | TATGTCTTCGGAACTGGGACCAAGGTCACCGTCCTAG | GGGCTGATGCTGCACCAACTGTATCCATC    |
| 2-7  | AGCAGCACT   | TATGTCTTCGGAACTGGGACCAAGGTCACCgCCTgg | GGGCTGATGCTGCACCA                |
| FWR4 |             | F G T G T K V T V L G                | A D A A P T V S I F              |

FIG. 29

|  | 3' Human Vλ | Human Jλ | 5' Mouse Cκ |
|---|---|---|---|
| 5-2 | CAGCCTGAGTGGTTC | TGTGTTCGGAGGAGGCACCCGGCTGACCGCCCTCG | GGGCTGATGCTGCACCAACTGTATCCATC |
| 2-5 | CAGCCTGAGTGGTT | ATGTCTTCGGAGGAACTGGGACACCCAGTCACCGTCCTAG | GGGCTGATGCTGCACCAACTGTATCCATC |
| 1-3 | CAGCCTGAATGGT | GCTGTGTTCGGAGGAGGCACCCAGCTGACCGTCCTCG | GGGCTGATGCTGCACCAACTGTATCCATC |
| 4B-1 | CAGCCTGAGTGGTC | GGGTGTTCGGCGGAGGGACCAAGCTGACCGTCCTAG | GGGCTGATGCTGCACCAACTGTATCCATC |
| 3B-5 | CAGCAGCACTGC | TGTGTTCGGAGGAGGCACCCAGCTGACCGTCCTCG | GGGCTGATGCTGCACCAACTGTATCCATC |
| 7A-1 | CAGCAGTGGTAAT | GCTGTGTTCGGAGGAGGCACCCAGCTGACCGCCCTCG | GGGCTGATGCTGCACCAACTGTATCCATC |
| 5-1 | CAGCAGTGGTAATCATAG | GGTGTTCGGCGGAGGGACCAAGCTGACCGTCCTAG | GGGCTGATGCTGCACCAACTGTATCCATC |
| 4A-1 | CAGCCTGAGTGGTT | ATGTCTTCGGAACTGGGACCAAGGTCACCGTCCTAG | GGGCTGATGCTGCACCAACTGTATCCATC |
| 11A-1 | CAGCAGCGCT | GTGGTATTCGGCGGAGGGACCAAGCTGACCGTCCTAG | GGGCTGATGCTGCACCAACTGTATCCATC |
| 5-7 | CTACTATGGTGGTGCTC | GGGTGTTCGGCGGAGGGACCAAGCTGACCGTCCTAG | GGGCTGATGCTGCACCAACTGTATCCATC |
| 5-4 | CTCCTATAGTGGTGCTCGa | GTATTCGGCGGAGGGACCAAGCTGACCGTCCTAG | GGGCTGATGCTGCACCAACTGTATCCATC |
| 2-3 | GAGCAACTTCGTGT | CTGTGTTCGGAGGAGGCACCCAGCTGACCGCCCTCG | GGATTGATGCTGCACCAACTGTATCCATC |
| FWR4 |  | F  G  G  G  T  K  L  T  V  L  G | A  D  A  A  P  T  V  S  I |

FIG. 30

|  | 3' Human Vλ | Human Jλ1 | 5' Mouse Cλ2 |
|---|---|---|---|
| 2D1 | GCAGGCAGCAACAATTTa | aGTCTTCGGAACTGGGACCAAGGTCACCGTCCTAG | GTCAGCCCAAGTCCACTCCCACTCTC |
| 2D9 | GACAGCAGTGGTAATCAT | TATGTCTTCGGAACTGGGACCAAGGTCACCGTCCTAG | GTCAGCCCAAGTCCACTCCCACTCTC |
| 3E15 | GACAGCAGCACTGCc | GTCTTCGGAACTGGGACCAAGGTCACCGTCCTAG | GTCAGCCCAAGTCCACTCCCACTCTC |
| FWR4 |  | F G T K V T V L G | Q P K S T P T L |

FIG. 31

SEQUENCE LISTING

```
<160> NUMBER OF SEQ ID NOS: 163

<210> SEQ ID NO 1
<211> LENGTH: 754
<212> TYPE: PRT
<213> ORGANISM: Mus musculus

<400> SEQUENCE: 1

Met Leu Ser Leu Thr Trp Gly Met Arg Leu Val Glu Arg Pro Val Val
1               5                   10                  15

Pro Arg Val Leu Leu Leu Leu Phe Ala Leu Trp Leu Leu Leu Leu Val
            20                  25                  30

Pro Val Trp Cys Ser Gln Gly His Pro Thr Trp Arg Tyr Ile Ser Ser
        35                  40                  45

Glu Val Val Ile Pro Arg Lys Glu Ile Tyr His Thr Lys Gly Leu Gln
    50                  55                  60

Ala Gln Arg Leu Leu Ser Tyr Ser Leu Arg Phe Arg Gly Gln Arg His
65                  70                  75                  80

Ile Ile His Leu Arg Arg Lys Thr Leu Ile Trp Pro Arg His Leu Leu
                85                  90                  95

Leu Thr Thr Gln Asp Asp Gln Gly Ala Leu Gln Met Glu Tyr Pro Phe
            100                 105                 110

Phe Pro Val Asp Cys Tyr Tyr Ile Gly Tyr Leu Glu Gly Ile Leu Gln
        115                 120                 125

Ser Met Val Thr Val Asp Thr Cys Tyr Gly Gly Leu Ser Gly Val Ile
    130                 135                 140

Lys Leu Asp Asn Leu Thr Tyr Glu Ile Lys Pro Leu Asn Asp Ser Gln
145                 150                 155                 160

Ser Phe Glu His Leu Val Ser Gln Ile Val Ser Glu Ser Asp Asp Thr
                165                 170                 175

Gly Pro Met Asn Ala Trp Lys His Trp Ser His Asn Thr Gly Ser Pro
            180                 185                 190

Ser Ser Arg Leu Glu Tyr Ala Asp Gly Ala Pro Arg Leu Ser Ser Lys
        195                 200                 205
```

```
Asn Tyr Ala Thr His Pro Ala Ala Ile Lys Gly His Phe Gln Ala Thr
210                 215                 220
His Ser Val Tyr Ser Ala Ser Gly Gly Asp Lys Leu Ser Ser Thr Val
225                 230                 235                 240
Glu Tyr Leu Phe Lys Val Ile Ser Leu Met Asp Thr Tyr Leu Thr Asn
                245                 250                 255
Leu His Met Arg Tyr Tyr Val Phe Leu Met Thr Val Tyr Thr Glu Ala
                260                 265                 270
Asp Pro Phe Ser Gln Asp Phe Arg Val Pro Gly Gly Gln Ala His Thr
            275                 280                 285
Phe Tyr Glu Arg Val Phe Tyr Ala His Phe Arg Pro Asp Ala Gly Ala
290                 295                 300
Ile Ile Asn Lys Asn Ser Pro Gly Asp Asp Ala Val Asn Pro Ala Glu
305                 310                 315                 320
Arg Ser Ile Cys Ser Pro Ser Ala Leu Ile Cys Leu Gly Gln His Gly
                325                 330                 335
Arg Asn Pro Leu Phe Leu Ser Ile Ile Thr Asn Arg Val Gly Arg
            340                 345                 350
Ser Leu Gly Leu Lys His Asp Glu Gly Tyr Cys Ile Cys Gln Arg Arg
                355                 360                 365
Asn Thr Cys Ile Met Phe Lys Asn Pro Gln Leu Thr Asp Ala Phe Ser
370                 375                 380
Asn Cys Ser Leu Ala Glu Ile Ser Asn Ile Leu Asn Thr Pro Asp Leu
385                 390                 395                 400
Met Pro Cys Leu Phe Tyr Asp Arg His Val Tyr Tyr Asn Thr Ser Leu
                405                 410                 415
Thr Tyr Lys Phe Cys Gly Asn Phe Lys Val Asp Asn Asn Glu Gln Cys
                420                 425                 430
Asp Cys Gly Ser Gln Lys Ala Cys Tyr Ser Asp Pro Cys Cys Gly Asn
            435                 440                 445
Asp Cys Arg Leu Thr Pro Gly Ser Ile Cys Asp Lys Glu Leu Cys Cys
450                 455                 460
Ala Asn Cys Thr Tyr Ser Pro Ser Gly Thr Leu Cys Arg Pro Ile Gln
465                 470                 475                 480
Asn Ile Cys Asp Leu Pro Glu Tyr Cys Ser Gly Ser Lys Phe Ile Cys
                485                 490                 495
Pro Asp Asp Thr Tyr Leu Gln Asp Gly Thr Pro Cys Ser Glu Glu Gly
                500                 505                 510
Tyr Cys Tyr Lys Gly Asn Cys Thr Asp Arg Asn Ile Gln Cys Met Glu
            515                 520                 525
Ile Phe Gly Val Ser Ala Lys Asn Ala Asn Ile Lys Cys Tyr Asp Ile
530                 535                 540
Asn Lys Gln Arg Phe Arg Phe Gly His Cys Thr Arg Ala Glu Glu Ser
545                 550                 555                 560
Leu Thr Phe Asn Ala Cys Ala Asp Gln Asp Lys Leu Cys Gly Arg Leu
                565                 570                 575
Gln Cys Thr Asn Val Thr Asn Leu Pro Phe Leu Gln Glu His Val Ser
            580                 585                 590
Phe His Gln Ser Val Ile Ser Gly Val Thr Cys Phe Gly Leu Asp Glu
            595                 600                 605
His Arg Gly Thr Glu Thr Ala Asp Ala Gly Leu Val Arg His Gly Thr
610                 615                 620
```

```
Pro Cys Ser Arg Gly Lys Phe Cys Asp Arg Gly Ala Cys Asn Gly Ser
625                 630                 635                 640

Leu Ser Arg Leu Gly Tyr Asp Cys Thr Pro Glu Lys Cys Asn Phe Arg
            645                 650                 655

Gly Val Cys Asn Asn Arg Arg Asn Cys His Cys His Phe Gly Trp Ser
        660                 665                 670

Pro Pro Lys Cys Lys Glu Glu Gly His Ser Gly Ser Ile Asp Ser Gly
    675                 680                 685

Ser Pro Pro Val Gln Arg Arg Ile Ile Lys Gln Asn Leu Glu Pro Val
690                 695                 700

Val Tyr Leu Arg Ile Leu Phe Gly Arg Ile Tyr Phe Leu Phe Val Ala
705                 710                 715                 720

Leu Leu Phe Gly Ile Ala Thr Arg Val Gly Val Thr Lys Ile Phe Arg
            725                 730                 735

Phe Glu Asp Leu Gln Ala Ala Leu Arg Ser Trp Gln Glu Gln Ala Lys
                740                 745                 750

Asp Lys

<210> SEQ ID NO 2
<211> LENGTH: 756
<212> TYPE: PRT
<213> ORGANISM: Mus musculus

<400> SEQUENCE: 2

Met Leu Ser Leu Thr Trp Gly Met Arg Leu Val Glu Arg Pro Val Val
1               5                   10                  15

Pro Arg Val Leu Leu Leu Phe Ala Leu Trp Leu Leu Leu Leu Leu Val
                20                  25                  30

Pro Val Trp Cys Ser Gln Gly His Pro Thr Trp Arg Tyr Ile Ser Ser
            35                  40                  45

Glu Val Val Ile Pro Arg Lys Glu Ile Tyr His Thr Lys Gly Leu Gln
        50                  55                  60

Ala Gln Arg Leu Leu Ser Tyr Ser Leu His Phe Arg Gly Gln Arg His
65                  70                  75                  80

Ile Ile His Leu Arg Arg Lys Thr Leu Ile Trp Pro Arg His Leu Leu
                85                  90                  95

Leu Thr Thr Gln Asp Asp Gln Gly Ala Leu Gln Met Asp Tyr Pro Phe
                100                 105                 110

Phe Pro Val Asp Cys Tyr Tyr Ile Gly Tyr Leu Glu Gly Ile Pro Gln
            115                 120                 125

Ser Met Val Thr Val Asp Thr Cys Tyr Gly Gly Leu Ser Gly Val Met
130                 135                 140

Lys Leu Asp Asp Leu Thr Tyr Glu Ile Lys Pro Leu Asn Asp Ser Gln
145                 150                 155                 160

Ser Phe Glu His Leu Val Ser Gln Ile Val Ser Glu Ser Asp Asp Thr
                165                 170                 175

Gly Pro Met Asn Ala Trp Lys His Trp Ser His Asn Thr Gly Ser Pro
            180                 185                 190

Ser Ser Arg Leu Glu Tyr Ala Asp Gly Ala Pro Arg Ile Ser Ser Lys
        195                 200                 205

Asn Tyr Ala Thr His Pro Ala Ala Ile Lys Gly His Phe Gln Ala Thr
210                 215                 220

Asn Ser Val Tyr Asn Ser Ala Ala Gly Asp Lys Leu Ser Ser Thr Val
225                 230                 235                 240
```

```
Gly Tyr Leu Phe Gln Val Ile Ser Leu Met Asp Thr Tyr Leu Thr Asn
                    245                 250                 255

Leu His Met Arg Tyr Tyr Val Phe Leu Met Thr Val Tyr Thr Asn Ser
            260                 265                 270

Asp Pro Phe Arg Leu Glu Phe Ala Val Pro Gly Gly Ser Ala Tyr Asn
        275                 280                 285

Tyr Tyr Val Ser Val Phe Tyr Asn Lys Phe Lys Pro Asp Ala Gly Val
    290                 295                 300

Leu Leu Asn Lys Tyr Gly Pro Gln Asp Asn Gln Val Asn Pro Ala Glu
305                 310                 315                 320

Arg Ser Ile Cys Ser Ser Leu Ala Leu Ile Cys Ile Gly Lys Tyr Asp
                325                 330                 335

Arg Asn Pro Leu Phe Leu Ser Pro Ile Ile Thr Asn Arg Val Gly Arg
            340                 345                 350

Ser Leu Gly Leu Lys Tyr Asp Glu Gly Tyr Cys Val Cys Gln Arg Arg
        355                 360                 365

Asn Thr Cys Ile Met Phe Arg His Pro Gln Leu Thr Asp Ala Phe Ser
    370                 375                 380

Asn Cys Ser Leu Ala Glu Ile Ser Asn Ile Leu Asn Thr Pro Gly Leu
385                 390                 395                 400

Met Pro Cys Leu Phe Tyr Asp Arg His Val Tyr Tyr Asn Thr Ser Leu
                405                 410                 415

Thr Tyr Lys Phe Cys Gly Asn Phe Lys Val Asp Asn Asp Glu Gln Cys
            420                 425                 430

Asp Cys Gly Ser Gln Lys Ala Cys Tyr Ser Asp Pro Cys Cys Gly Asn
        435                 440                 445

Asp Cys Arg Leu Thr Pro Gly Ser Ile Cys Asp Lys Glu Leu Cys Cys
    450                 455                 460

Ala Asn Cys Thr Tyr Ser Pro Ser Gly Thr Leu Cys Arg Pro Ile Gln
465                 470                 475                 480

Asn Ile Cys Asp Leu Pro Glu Tyr Cys Asn Gly Thr Lys Tyr Ile Cys
                485                 490                 495

Pro Asp Asp Thr Tyr Leu Gln Asp Gly Thr Pro Cys Ser Glu Asp Gly
            500                 505                 510

Tyr Cys Tyr Lys Gly Asn Cys Thr Asp Arg Asn Ile Gln Cys Met Glu
        515                 520                 525

Ile Phe Gly Val Ser Ala Lys Asn Ala Asn Ile Lys Cys Tyr Asp Ile
    530                 535                 540

Asn Lys Gln Arg Phe Arg Phe Gly His Cys Thr Arg Ala Glu Glu Ser
545                 550                 555                 560

Leu Thr Phe Asn Ala Cys Ala Asp Gln Asp Lys Leu Cys Gly Arg Leu
                565                 570                 575

Gln Cys Thr Asn Val Thr Asn Leu Pro Tyr Leu Gln Glu His Val Ser
            580                 585                 590

Phe His Gln Ser Ile Ile Ser Gly Phe Thr Cys Phe Gly Leu Asp Glu
        595                 600                 605

His Arg Gly Thr Glu Thr Thr Asp Ala Gly Met Val Arg His Gly Thr
    610                 615                 620

Pro Cys Ser Lys Ser Lys Phe Cys Asp Gln Gly Ala Cys Ser Gly Ser
625                 630                 635                 640

Leu Ser His Leu Gly Tyr Asp Cys Thr Pro Glu Lys Cys Ser Phe Arg
                645                 650                 655
```

```
Gly Val Cys Asn Asn His Arg Asn Cys His Cys His Phe Gly Trp Lys
            660                 665                 670

Pro Pro Glu Cys Lys Glu Glu Gly Leu Ser Gly Ile Asp Ser Gly
        675                 680                 685

Ser Pro Pro Val Gln Arg His Thr Ile Lys Gln Lys Gln Glu Pro Val
    690                 695                 700

Val Tyr Leu Arg Ile Leu Phe Gly Arg Ile Tyr Phe Leu Phe Val Ala
705                 710                 715                 720

Leu Leu Phe Gly Ile Ala Thr Arg Val Gly Val Thr Lys Ile Phe Arg
                725                 730                 735

Phe Glu Asp Leu Gln Ala Thr Leu Arg Ser Gly Gln Gly Pro Ala Arg
            740                 745                 750

Asp Lys Pro Lys
        755

<210> SEQ ID NO 3
<211> LENGTH: 13894
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3
gtcctaaggt agcgagggat gacagattct ctgttcagtg cactcagggt ctgcctccac      60
gagaatcacc atgcccttc tcaagactgt gttctgtgca gtgccctgtc agtggaaatc     120
tggagagcat gcttccatga gcttgtgagt agtatatcta gtaagccatg gctttgtgtt    180
aatggtgatg ttctacatac cagttctctg cttaataat gaggtgatga ttctatgttc     240
ctgtaacgct tcctcaactg gtcctaagt ctttcttcac tccatctatt cctctaagga     300
atgatcctga aaatcccatc acaaactata ggagatggga accatcaaaa aacacagtga    360
caaagaggtg ggaacgcatc agggttcagg aaccatattt taaaaagata tcgtaaataa    420
cttcttaaaa gagatataga caaatctcca ttaatacgga gaccagaggc ctaaggctaa    480
gaaccaatgg tggctcaagg tctcctgcta cccgaggagc aaacgtagag cagtttctaa    540
tgatttattt aaaatataga atcaaaagta ccagtttgca attttgaaag atttatttca    600
gcaatgcaac aacatcaggt ggtgccgagt ccaacacgtc ttatgtccca tgatataaac    660
aaaggccatc cagaactgtg gactggagtt ctaccttgtc ccctaatgac attcagattt    720 ttttccatt ctctttatct tagaggagac aggggggctaa ctcatttac ttgtcctttg     780 cttgttcttg ccaagaacgt aaagcagctt gcaagtcttc aaacctaaat atcttagtaa    840
ctcctacacg agtggcaatg ccaaagagca gtgcaacaaa gaggaagtaa atacgaccaa    900
agagtattct taaatacact actggctcta ggttctgttt tattatgcgc ctttgaaccg    960 gagggaccc actgtctatg ctcccactgt gtccctcttc tttgcacttt ggagggctcc   1020
aaccaaaatg gcaatggcaa ttccgacgat tgttacacac tcctctgaaa ttgcatttt   1080 ctggggtgca gtcataaccc aaacgagata aacttccatt gcaagctcct cgatcacaga   1140 acttaccct tgaacacggg gtaccatgtc tcaccaatcc agcatctgct gtttctgtcc    1200
cacgatgttc atcaagccca agcaggtaa ccccagagat aaccgattga tggaatgaaa    1260
catgttcttg caaaaatgga agattggtga cattggtaca ctgcaacctt ccacacagct   1320
tgtcctgatc agcacaagca ttgaatgtga ggctttcttc tgctctagta caatgcccaa   1380
atcgaaaccg ttgtttgttg atgtcatagc acttaatatt agcattctta gcacttacac   1440
```

```
caaagatttc catgcattgt atgttgcgat cagtgcagtt acctttatag cagtaaccct    1500
cttctgagca tggtgtccca tcttgcagat aagtgtcatc tgggcaaatg aacttagagc    1560
cactacagta ctctggaaga tcacatatgt tctggatagg tctgcagagt gtcccagaag    1620
gactgtaagt gcaatttgca cagcataatt ctttatcaca aatgctacca ggtgttaacc    1680
tgcaatcatt tccacagcag ggatctgaat aacatgcctt ttgggagcca cagtcacact    1740
gctcattgtt atctactttg aagttttcca caaaacttata agtcaatgat gtattataat    1800
aaacatgacg gtcatagaaa agacatggca tcagatcagg agtattaagt atgttgctta   1860
tctctgcaag ggaacaattg ctgaaagcat ctgttaattg aggattttttg aacatgatgc   1920 aggtgttcct tctctggcag atacagtacc cctcatcatg ttttaggcct aaactccttc    1980
caacacgatt ggttattata atagataaaa ataaaggatt tcgaccatgt tgaccaagac    2040
aaattagggc tgagggagaa catatactcc tctcagctgg attaacagca tcatctcctg    2100
gcgaattctt gttaattata gctcctgcat caggcctaaa atgagcataa aatactctct    2160
catagaaagt atgagcctgc cctcctggaa ctcgaaaatc ttgtgaaaat ggatcagcct    2220
cggtatacac agtcatgaga aagacatagt accgcatatg aagattggtc agataggtgt    2280 ccattaaaact aatgacttta aacaaatact caacagtaga tgaaagtttg tcacctccag   2340
aagcactata tacagaatgg gttgcttgaa agtggccttt tatagcagct ggatgtgtag    2400
cgtaattctt actagatagt ctgggagctc catctgcata ttccaatctg gaggagggag   2460
aacctgtatt atggctccag tgcttccatg cattcatagg ccctgtgtca tcagactcag    2520
atactatctg agaaacaagg tgttcaaagc tctgtgaatc attgaggggt ttgatttcat    2580
aggtaaggtt atccaacttt atgacccctg acaggcccccc ataacaagta tccacagtga   2640
ccatggattg caggatcccc tccaggtagc caatatagta acaatctaca ggaaaaaagg    2700
ggtactccat ctgtaaggct ccttggtcat cttgagttgt cagcaacaag tgtctgggcc    2760
aaatgagtgt ctttctccgc aagtggatga tatgtctctg gccccgaaaa cgcaagctat    2820
acgagagcag tctttgtgct tgaagtcctt tggtatggta gatctccttc cgaggaataa    2880
ccacctccga tgagatgtaa cgccaagtgg gatggccttg agaacaccag actggaacca    2940
ggaggagcag ccagagtgca aatagcaaga ggaggaccct ggggaccaca ggtctttcca    3000
ctagcctcat gccccaggtc agagataaca tcctgggtgg agctaactcc ctctgctgtg    3060
gccactgcct ggtctagaaa atactgacag aggactaaaa acctcctcag gctcccaacc    3120
taagtggtta cccagacaac tggagttagg taacagtcac tgggtgtggc aggaattgag    3180
tctgaatgtg ttagctgagg ttgaggttaa atattgtcaa aagggatgtc tataaatgtg    3240
cctggacaag aaaagtcaga agcagcaagg agtgtctctg acaggctcaa tcctttcttt    3300
tctttttttg aagttcaaaa tatcatttcc acgtgaatgt atttggttcc cagtgtgact    3360
ctgggtctct ttctaggagt caatatttct ttatatcttg gctcatgttt ttcacagttg    3420
ttctaacttc ttgttttgtt ttgtttgttt gtttgtttga agttagaag taaatactgt    3480 ctatattagc cttttagcta taaatgattg ttttttatttc ttctaatcat gttttgtttg    3540
agttttggtt aaactattta caaatgagtt tttttttttcc ttttgggtgt tgctcgaaag    3600
tttggagctt tctgttaata ttgtgttgtt gtttctccaa tattattaga cctgagaatt    3660
ctacctgggt acctgtgaac tccagaattt ttaaaaattc catctcttgg gaacattatc    3720
tctgaccccg tctgaggccg aagtggctgt ccccctccaa cctttagtat ctttctttcc    3780
tgactattgg gatttcttca agcaatcagg ctgatgggtt ctcagcagtg agaccagtag    3840
```

```
actgtcggta tgaacgtcga agagtctgcc acacactccg ggttcatcaa cagtgctttc    3900
gcgtctctta cttttgtaga aggaaatgca gcctctgagt tttctccaag aaatcattga    3960
tgaaagggtg aaaagatggg tatcacccgg agttcatgac aagccctggc tcagacacgt    4020
gagcaaggtc tacagcccca agataggct gccctgcaac atgtatttat aagataggag    4080
aaaaaaatgg gtagttggag ggttgatcaa cttacttcct ctcaaacata tatatctcat    4140
ctaagtgtgc aggggaaaac tctgtagaac tactgggata cctgctcacc cccaggagcc    4200
tcatgaataa gtctctgctt ctgccttgta gccatgagca ttactgcacc tgataccct    4260 gcagcttcct agggaagagg gaggaagtga cttggcccct gtctggttaa ggtaagagga    4320
gataaatccc ttctcattga ttagggtgag aggggtcatg tgctctatca ttggtgaccc    4380
agttgggaca tgggtttata ccaaagtcat cactctgagg ttctgtgtac caccaggctg    4440
aactcccata tcctacatgg acataggaca acaccaagca gaaggaggtt ttaggactaa    4500
actgaaggac agagatgcgg tttctaaaca actaggagt gccagggcca gcctctctaa    4560
ccactatagg acactgtgga gtctggttac aaagagagat tactcaaggt ccttagcact    4620
gattacagag catatctcag atgccttctg ctgaccagat gtatctttgc ataatctgcc    4680
tatccagatt cagaaaattg atgccacata gccaagtgga ctttcaggaa cagacgattt    4740
aaaaacaggc agagagatgt gagagaaagg agaaggagag agagaaggga gagggagaga    4800
agagagaggg agacggagaa ggaaagaggg agaaggagaa ggagagaagg ggcatggaca    4860
gagggaggga cagaaggaga gaggagatag agagggggat aaggaagaag ggagggaggg    4920
agagagagag aaggctaagt cttccatac ctgggtccca atacctctta taacccaagc    4980
acatggtttc acatatcaca atgcggttgg gatatagata actgtaaata cttgtgaaaa    5040
taatggggct gagatctggg gttttcatga tagtttcaaa gtcaccgtac tgactaaaac    5100
cttccactgg cccatctcca gcttcctaat ctgagggtat caaatttccc actaagtgtg    5160
tttagaaaga tctccaccct tttgcccttg tcttccagtg ccccacctac gttctggtct    5220
cccacatctg atgtcttctc agtgattctg gccctgcctg ctccacagct acaaacccct    5280
tcctataatg agctctgtgc tgagccatca tcctgaatca atccacctta agcagatgtt    5340
ttgcttattt ttcctgtgtc catactacag aggaaaggta ggcatgtaga agctgaagca    5400
tctcacctca ttccaagcac cctcagtctc taaatgtgcc cccttgtttc cagaagtgca    5460
acctcaagca tcttttattc attcatctta gagggccaca tgtgctgtag tgttataaga    5520
tgaaatttaa agcattaatt attcctaaca agccaattaa acaagccaaa acattcatc    5580 agtcattccc atggaacctc tgaagcatct tcctgctcta accttgggtt ttccagggct    5640
gctctgggat cacaggagct gtcctgtcta ccagccatat aaaggcagac ctatcagaat    5700
tacaccagac ttctcaccat agactataaa agccagaata tcctggacag atgttataca    5760
gaaactaaga gaacacaaat gccagcccag gctactatac ccagcaaaac tctcaattac    5820
catcgatgaa gaaaccaaga tattccatta caagtccaaa tttacacaat atcttttccat    5880 aaatccagcc ctacaaagga tagcagatgg aaaactccaa cacaggtagg aaaactacac    5940
cctagaaaga gcactaaagt aatcatcttt caacacactc aaaagaagat aaccacacaa    6000
acataattcc acctctaaca acaaaaataa agtaggcaac aatcactatt ccttaatatc    6060
tcttttaaca tcaatggact caattctcca ataaaaagac atagactaac agactgaata    6120
cataaacagg acacagcatt tgctgcata aagcaaacac agcgttactt ttttttttct    6180
aaatgacatt ttttattaga tattgtcttt attgacattt caaatgttat cccctttcct    6240
```

```
ggtttaccct ctgaaatccc ctatctcctc ccctccccc tgctcaccaa tccacccact    6300
cccacttcca ggccctggca atccctata tttgggcata gagccttcac aggaccaagg    6360
tactctcctt gcattgatga ccaactagtc cattctctgc tacaaatgca gctagatcta    6420
tgagtcccac catgttttct tttgttggtg gtttcatgcc agggagctct tggagtactg    6480
attggttcat attgttgttc tccctatggg gttacaaaac ccttcaactt cttgggtcct    6540
ttctctggct gcctcattgg ggaccttgtg cgaagtccaa tggatgactg tgagcatcca    6600
cttctgtatt tgccaggcac tggcagagcc tctcagaaga cagctatatc aagatcctgg    6660
cagcaagctc ttgttggtat ccacaaaagt gtctggtggt tgtctatggg atggatcccc    6720
aaaggggcag tctctggatg gtcattcctt cagtctctgt tccacacttt gtctctttaa    6780
ctccttccat gactatttta ttcctccctc taagaaggac cgaagtattc atactttggt    6840
cttccttctt gaaattcatg tgttttgtga attgtatctt tgatattccg aacttctggg    6900
ctaatatcca cttatcagtg agtgaatatc atgtgtgttc ttatgtgatt gagttacctc    6960
actcaggatg atatcctcca gaaccatcca tttgtctaag aatttaatga attcattgtt    7020
tttaatagct gaggagtact ccattgtgta aatgtaccac attttctgta cccattgttc    7080
tcttgaggga catctgggtt cttaaagct tctggacatt aaatataagg ctgctatgga    7140
aatagtggag aatgtgtcct tattacatgt tggagcatct tctgggtata tgcccaggag    7200
tgctattgct ggatcctctg atagtactat gtccaatttt ctgaggaact gccaaactga    7260
tttacagagt ggttgtacca gcttgcaatt ccaccagcaa tggagaaatg ttcccttcc    7320 tccacatcct caccaacatc tgctgtcacc tcaatttgtt cttagtgatt cagcaggtg    7380 tgaggtggaa atcagggtt gtttggcatt tccctgatga ctagtgatat tgaaaaaaat    7440
tttaagtgtt tctcagccat tcagtattct tcagttgaga attcactgtt tagctctgta    7500
ctcaggtttt tttaataggg ttatttggtt ttctggagtc taacgtcttg aattcttct    7560 atatattgga tattagcct ctgtcatatt taggattggt aaagatcttt cccaatatgt    7620
tggctgcctt tttgtgtcct ttgccttaca gaaccttttt aattttatga ggtcccattt    7680
gctaattctt cattttacag cacaagccat tggtgttctg ttcaaaaatc tttccccctg    7740
aaccctatct tcgaggatct tccccacttt ctcctctata agtttcagtg tctctattat    7800
tgtgctgagg ggtaccgaag ttcctattcc gaagttccta ttctctagaa agtataggaa    7860
cttccctagg gtttaaaccc gcggtggagc tctgatgtgg gaacgcttca gtgttcagga    7920
accatatgat ttatttaaaa tatagaatca aaagtaccaa tttgcagttt tgaaagattt    7980
attccagtgt aagcattagc aatgcaccaa catcaggtga tttctgaatc caacacgtct    8040
tatgtcctca tgatattaaa aaaaaaaaaa ggccatccag aactgtgaac ttgagttcta    8100
ccttgttccc tactgacatt cagattttct tttttgcatt ctctttatct tacaggagac    8160
aggaggggag ggctaactca ttttactttg gcttgtccct tgctggtcct tgcccagaac    8220
gtaaagtagc ttgcaagtct tcaaatctaa aaatcttagt aactcctaca cgagtggcaa    8280
tgccaaagag cagtgcaaca aagaggaagt aaatacgacc aaagagtatt cttaaataca    8340
ccactggctc ttgttttgt tttattgtgt gcctttgaac tggaggggac ccactgtcta    8400
tgctcccact tagtccctct tctttgcact ctggaggctt ccaaccaaaa tgacaatggc    8460
aattccgatg attgttacac actcctctaa aactgcattt ttctggggtg cagtcataac    8520
ccaaatgaga taaacttcca ctgcaagctc cttgatcaca gaacttactt ttggagcagg    8580
gggtaccatg tctcaccatt ccagcatctg ttgtttctgt cccacgatgt tcatcaagcc    8640
```

```
caaagcaggt aaacccagag ataatcgatt gatggaatga aacatgttct tgcaaatatg    8700
gaagattggt gacattggta cactgcaacc ttccacacag cttgtcctga tcagcacaag    8760
cattgaatgt gaggctttct tctgctctag tacaatgccc aaatcgaaac cgttgtttgt    8820
tgatgtcata gcacttaata ttagcattct tagcacttac accaaagatt ccatgcatt    8880 gtatgttgcg atcagtgcag ttacctttat agcagtaacc atcttctgag catggtgtcc    8940
catcttgcag ataagtgtca tctgggcaaa tgtatttagt cccattacag tactctggaa    9000
gatcacatat gttctggata ggtctgcaga gtgtcccaga aggactgtaa gtgcaatttg    9060
cacagcataa ttctttatca caaatgctac caggtgttaa cctgcaatca tttccacagc    9120
agggatctga ataacatgcc ttttgggagc cacagtcaca ctgctcatcg ttatctactt    9180
tgaagtttcc acaaaactta taagtcaatg atgtattata ataaacatga cggtcataga    9240
aaagacatgg catcagacca ggagtattaa gtatgttgct tatctctgca agggaacaat    9300
tgctgaaagc atctgttaat tgaggatgtc tgaacataat gcaggtgttc cttctctggc    9360
agacacagta cccctcatca tattttaagc ctaaactcct tccaacacga ttggttatta    9420
taggagataa aaataaagga tttcgatcat atttaccaat acaaattagg gctaaggaag    9480
aacatatact cctctcagct ggattaacct ggttatcttg tgcccatac ttattaagta    9540 aaactcctgc atcaggctta aatttattat aaaagactga cacatagtaa ttataagccg    9600
accctcctgg aactgcaaac tcaagtcgaa atggatcaga attggtgtac acagtcatga    9660
gaaagacata gtaccgcata tgaagattgg tcagataggt gtccattaaa ctaatgactt    9720
gaaacaaata cccaacagta gatgaaagtt tgtcacctgc agcagaatta tatacagaat    9780
tggttgcttg aaagtggcct tttatagcag ctggatgtgt agcgtagttc ttactagata    9840
ttctgggagc tccatctgca tattccaatc tggaggaggg agaacctgta ttatggctcc    9900
agtgcttcca tgcattcata ggccctgtgt catcagactc agatactatc tgagaaacaa    9960
ggtgttcaaa gctctgtgaa tcattgaggg gtttgatttc ataggtaagg tcatctaact   10020
tcatgacccc tgacaggccc ccataacaag tatccacagt gaccatggat tgtgggatcc   10080
cctccaggta gccaatatag taacaatcta caggaaaaaa ggggtaatcc atctgtaagg   10140
ctccttggtc atcttgagtt gtcagcaaca agtgtctggg ccaaatgagt gtctttctcc   10200
gcaggtggat gatatgtctc tggccccgaa aatgcaagct atatgagagc agtctttgtg   10260
cttgaagtcc tttggtatgg tagatctcct tccgaggaat aaccacctcc gatgagatgt   10320
aacgccaagt aggatggcct tgagaacacc agactggaac caggaggagc agccagagtg   10380
caaatagcaa gaggaggacc ctggggacca caggtctttc cactagcctc atgccccagg   10440
tcagagataa catcctgggt ggagctaaat ccctctgctg tggccactgc ctggtctaga   10500
aaatactgac agaggactaa aaacctcctc aggctcccaa cctaagtggt tacccagaca   10560
actggagtta ggtaacagtc actgggtgtg gcaggaattg agtctgaatg tgttagctga   10620
ggttgaggtt aaatattgtc aaaagggatg tctataaatg tgcctggaca agaaaagtca   10680
gaagcagcaa ggagtgtctc tgacaggctc aatcctttct tttctttttt tgaagttcaa   10740
aatatcattt ccacgtgaat gtatttggtt cccagtgtga ctctgggtct ctttctagga   10800
gtcaatattt ctttatatct tggctcatgt ttctcacagt tgttctaatt tcttgttttg   10860
ttttgtttgt ttgtttgaac gttagtagta aatactgtct atattagcct tttagctata   10920
aatgattgtt tttatttctt ctaatcatat tttgtttgag ttttggttaa actatttaca   10980
aatgagtttt ttttttttcc ttttgggtgt tgctcgaaag tttggagctt tctgttaata   11040
```

```
ttgtgttgtt attttttccaa tattattaga cctgagaatt ctatctgggt acctgtgaac   11100
tctagaattt ttaaaaattc catctcttgg gaacattacc tctgaccccg tctgaggccg   11160
aagtggctgt ccccctccaa cctttagtat ctttctttcc tgactattgg gatttcttca   11220
agcaatcagg ctgatgggtt ctcagcagtg agaccagtag actgccggta tgaacgtcga   11280
agagactgcc acacactcca ggttcatcaa cagtgctttc gcgtctctta cttttgtaga   11340
aggaaaagca gcctctgagt tatctccaag aaatcattaa tgaaagagtt aaaagatggg   11400
tatcacccgg agttcatgac aagccctggc tcagacacgt gagcaaggtc tacagcccca   11460
aagataggct gccctgcaac atgtatttat aagatagaag aaaaaaatgg gtggttggag   11520
ggttgatcaa cttacttcct ctcaaacata tatatctcat ctaagtgtgc aggggaaaac   11580
tctgtaggac tactgggatt gttattatca ttattattat tattattatt attattatta   11640
ttattattat tattaactta aggcatttta ttagatattt tcttcattta gttttcaaat   11700
gttatcccccg gaacctccta tactctctcc ctgccctgct ccccaaccca cccactccta   11760
catcctggcc ctggcattcc cctatactgt ggcagatgat cttcgtaaga ccaagagcct   11820
ttcctcccat tgatggccta ctaggctatc ctctttttaca tatgcaacta gagtcacagc   11880
tctggggagg tattgcttag ttcatattgt ttttcctcct atagggttgc agatcccttt   11940
agctccttgg gtactttctc tagctcctcc attgggggcc ctgtgttcca tccaatagat   12000
gactgtgagc atccacttct gtatttgcca ggtattggca tggatcttac tgcaccttct   12060
gaactctcta agcagctttc ctggtcacct ccaggagcct catgaataag tctctgcttc   12120
cccccttgtgg ctatgagcat tactgcacct gatacaccct gcagcttcct agggaagagg   12180
gaggaagtgg cttggcccct gtctggttaa ggtaagagga gataaatccc ttctcatgaa   12240
ttagggtgag aagggtcatg tgctctatca ttggtgacca acttggggac atgggcttat   12300
acagtcatca ctctgaggct ctgtgtacca ccagactgaa ctcccatatc ctacatgcac   12360
ataggacaac accaagtaga aggaggtttt aggactaaac tgaaggacag agatgggggtt   12420
tctaaacaac tagggagtgc cagggccagc ctctctaacc actataggac actatggagt   12480
ctggttacaa agagagatta ctcaaggtcc ttagcactga ttacagagca tatctcagat   12540
gccttctgct gaccagatgt atctttgcat aatctgccta tccagattca gaaaattgat   12600
gccacatagc caagtggact ttcaggaaca gacgatttaa aaacaggcag agagatgtga   12660
gagaaaggag aaggagagag agaagggaga gggagagaag agagagggag acggagaagg   12720
aaagagggag aaggagaagg agagaagggg catggacaga gggagggaca gaaggagaga   12780
ggagatagag aggggataa ggaagaaagg agggagggag agagagagaa ggctaagtct   12840
ttccatacct gggtcccaat acctcttata acccaagcac atggtttcag atatcacaat   12900
gcggttggga tatagataac tgtaaatact tgtgaaaata atggggctga gatctggggt   12960
tttcatgata gtttcaaagt cactgtactg actaaaacct tccactggcc catctccagc   13020
ttgttaatct gagggtatca aatttcccac taagtgtgtt tagaaagatc tccacctttt   13080
tgccctagtc ttccagtgcc ccacctacgt tctggtctcc cacatctgat gtcttctcag   13140
tgattctggc cctgcctgct ccacagctac aaacccccttc ctataatgag ctctgtgctg   13200
agccatcatc ctgaatcaat ccaccttaag cagatgtttt gcttattttt cctgtgtcca   13260
tactacagag gaagggtagg catgtagaag ctgaggcatc tcatctcact ctaagcaccc   13320
tcagtctcta aatgtgcccc tttgtttcca gcagttcagc ctcaagcatc ttttattcac   13380
tcgtcttaga gggacacatg tgctgtagtg ttataagatg aaatttaaag cattagttat   13440
```

```
tcccaacaag ccaattaaac aagccaaaaa cattcatcag tcattcccat ggaacctctg    13500
aagcatcttc ctgctctaac cttgagtttc ctagggctgc tgtgggatca caggagctgt    13560
cctgtttacc agcctatcct gtcccacggg attcagttat tagtgggtgc gaggggggacc   13620 gcaaacctgg aagaaaatgg gattggaaga gaaaagagaa acgaagacca agtagatctt    13680
ttcctatcaa ggtcttcgtt tattaggctg aggtgcctgg tgtaaagcat gcatcgcggg    13740
gaataggaag gggtcgaggg ggaattttac aaagaacaaa gaagcgggca tctgctgaca    13800
tgagggccga agtcaggctc caggcagcgg gagctccacc gcggtggcgc catttcatta    13860
cctctttctc cgcacccgac atagataaag ctta                                13894

<210> SEQ ID NO 4
<211> LENGTH: 251
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4
ccagcttcat tagtaatcgt tcatctgtgg taaaaaggca ggatttgaag cgatggaaga     60
tgggagtacg gggcgttgga agacaaagtg ccacacagcg cagccttcgt ctagaccccc    120
gggctaacta taacggtcct aaggtagcga ggggatgaca gattctctgt tcagtgcact    180
cagggtctgc ctccacgaga atcaccatgc cctttctcaa gactgtgttc tgtgcagtgc    240
cctgtcagtg g                                                         251

<210> SEQ ID NO 5
<211> LENGTH: 245
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5
aggggtcgag ggggaatttt acaaagaaca aagaagcggg catctgctga catgagggcc     60
gaagtcaggc tccaggcagc gggagctcca ccgcggtggc gccatttcat tacctctttc    120
tccgcacccg acatagataa agcttatccc ccaccaagca aatcccccta cctgggccg    180 agcttcccgt atgtgggaaa atgaatccct gaggtcgatt gctgcatgca atgaaattca    240
actag                                                                245

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
caggtacagc tgcagcagtc a                                               21

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 7
ggagatggca caggtgagtg a                                              21

<210> SEQ ID NO 8
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
tccaggactg gtgaagc                                                   17

<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
tagtcccagt gatgagaaag agat                                           24

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
gagaacacag aagtggatga gatc                                           24

<210> SEQ ID NO 11
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
tgagtccagt ccaggga                                                   17

<210> SEQ ID NO 12
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
aaaaattgag tgtgaatgga taagagtg                                       28

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 13
aaccctggtc agaaactgcc a                                            21

<210> SEQ ID NO 14
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
agagaaacag tggatacgt                                               19

<210> SEQ ID NO 15
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
aactacgcac agaagttcca gg                                           22

<210> SEQ ID NO 16
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
gctcgtggat ttgtccgc                                                18

<210> SEQ ID NO 17
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
cagagtcacg attacc                                                  16

<210> SEQ ID NO 18
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
tgagcagcac cctcacgtt                                               19

<210> SEQ ID NO 19
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide -continued

<400> SEQUENCE: 19
gtggcctcac aggtatagct gtt                                               23

<210> SEQ ID NO 20
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
accaaggacg agtatgaa                                                     18

<210> SEQ ID NO 21
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
gctagtagtg gggcctacag gcctttgat atc                                     33

<210> SEQ ID NO 22
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
gcaaaagccc aggggagtgg gagctactac acctatgctt ttgatatc                    48

<210> SEQ ID NO 23
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
gcgagagagg gtatagtggg aactactgag gactttgatt ac                          42

<210> SEQ ID NO 24
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
gcgagaggga cagtgggagc cctctttgac tac                                    33

<210> SEQ ID NO 25
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
gcgaaaccta gtgggagcta ctcctggttc gacccc                                   36

<210> SEQ ID NO 26
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
gcgagaggag gagggtataa ctggaactcg aatgcttttg atatc                         45

<210> SEQ ID NO 27
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
gcgagaggat ataactggaa ctactttgac tac                                      33

<210> SEQ ID NO 28
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
gcgaaagagt ataactggaa ccactggtac tttgactac                                39

<210> SEQ ID NO 29
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
gcgagagaga taactggaac cccctttgac tac                                      33

<210> SEQ ID NO 30
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
gcgaggggat ataactggaa cttttctttt tttgactac                                39

<210> SEQ ID NO 31
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
gcgagaggta actggaactc tctgggcttt gactac                                   36

<210> SEQ ID NO 32
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
gcgaaaaggg ctactatggt tcggggagct cttgactac                                39

<210> SEQ ID NO 33
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
gcgagagata ttactatggt tcggggagtt attataacga aggtctacgg tatggacgtc         60

<210> SEQ ID NO 34
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
gcgagagagt atagcagctt tgactac                                             27

<210> SEQ ID NO 35
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
gcgagagaga gtatagcagc tcgttgtgac tac                                      33

<210> SEQ ID NO 36
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
gcaagagagg ataggagctc gcccctcggg tactttgact ac                            42

<210> SEQ ID NO 37
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
gcgagagatc ttggggaagg ctac                                                  24

<210> SEQ ID NO 38
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
accacccata actggggagg gtttgactac                                            30

<210> SEQ ID NO 39
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
gcgagagata ggggaccg                                                         18

<210> SEQ ID NO 40
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
caacagagtt atagtacccc tccggagacg                                            30

<210> SEQ ID NO 41
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
caacagctta atagttaccc tcggacg                                               27

<210> SEQ ID NO 42
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
caacagctta atagttacca ttcact                                                26

<210> SEQ ID NO 43
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43 caacattta atagttaccc gctcact                                                27

<210> SEQ ID NO 44
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
cagcagtata ataactggcc tctcact                                               27

<210> SEQ ID NO 45
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
ctacagcata atagttaccc gtggacg                                               27

<210> SEQ ID NO 46
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
ctacagcata atagttaccc tcggacg                                               27

<210> SEQ ID NO 47
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
cagcagtatg gtagctcacc tcggacg                                               27

<210> SEQ ID NO 48
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
atgcaaggta cacactggcc gtggacg                                               27

<210> SEQ ID NO 49
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 49
atgcaaggtt cacactggcc gtacact                                         27

<210> SEQ ID NO 50
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
atgcaaggta cacactggcc gctcact                                         27

<210> SEQ ID NO 51
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
caacagtatg ataatctccc tcccact                                         27

<210> SEQ ID NO 52
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
caacagtatg ataatctccc attcact                                         27

<210> SEQ ID NO 53
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
caacagtatg ataatctccc cgtcact                                         27

<210> SEQ ID NO 54
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
caacagtatg ataatctccc gatcacc                                         27

<210> SEQ ID NO 55
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 55
caacggattt acaatgccga cacc                                              24

<210> SEQ ID NO 56
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
caacagagtt acagtacccc catgtacact                                        30

<210> SEQ ID NO 57
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
caacagagtt acagtacccc tctcact                                           27

<210> SEQ ID NO 58
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58
caacagagtt acagtactcc tcccact                                           27

<210> SEQ ID NO 59
<211> LENGTH: 219
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 59
actttcagaa tgttcttgaa cagtctctga gaaacacgga agacggccgc ataacttcgt       60
atagtataca ttatacgaag ttattctaga ccccgggct cgataactat aacggtccta       120
aggtagcgac tcgagataac ttcgtataat gtatgctata cgaagttatc catggtaagc     180
ttacgtggca tacagtgtca gattttctgt ttatcaagc                             219

<210> SEQ ID NO 60
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60
agctgaatgg aaacaaggca a                                                 21

```
<210> SEQ ID NO 61
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61
ggagacaatg ccccagtga                                                  19

<210> SEQ ID NO 62
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62
tcccataggg ctaggatttc c                                               21

<210> SEQ ID NO 63
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
tcccctcaca ctgttcccc                                                  19

<210> SEQ ID NO 64
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64
ggtggagagg ctattcggc                                                  19

<210> SEQ ID NO 65
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
gaacacggcg gcatcag                                                    17

<210> SEQ ID NO 66
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66
tcaacctttc ccagcctgtc t                                               21
```

```
<210> SEQ ID NO 67
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67
ccccagagag agaaaacaga tttt                                              24

<210> SEQ ID NO 68
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 68
ccctggtgaa gcatgtttgc                                                   20

<210> SEQ ID NO 69
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 69
tgtggcctgt ctgccttacg                                                   20

<210> SEQ ID NO 70
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 70
cacacctaga ccccggaagt c                                                 21

<210> SEQ ID NO 71
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 71
tcgctttgcc agttgattct c                                                 21

<210> SEQ ID NO 72
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 72
tgcggccgat cttagcc                                                      17
```

<210> SEQ ID NO 73
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 73
ttgaccgatt ccttgcgg                                              18

<210> SEQ ID NO 74
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 74
gcaaacaaaa accactggcc                                            20

<210> SEQ ID NO 75
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 75
ggccacattc catgggttc                                             19

<210> SEQ ID NO 76
<211> LENGTH: 22
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 76
ccatgactgg gcctctgtag ac                                         22

<210> SEQ ID NO 77
<211> LENGTH: 25
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 77
caagtcaggg tgctaatgct gtatc                                      25

<210> SEQ ID NO 78
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 78
cacagcttgt gcagcctcc                                             19

<210> SEQ ID NO 79
<211> LENGTH: 22
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 79
gggcactgga tacgatgtat gg                                      22

<210> SEQ ID NO 80
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 80
tcataggtag gtctcagttt g                                       21

<210> SEQ ID NO 81
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 81
tgatctgcgc tgtttcatcc t                                       21

<210> SEQ ID NO 82
<211> LENGTH: 31
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 82
tgacatgaac catctgtttc tctctcgaca a                            31

<210> SEQ ID NO 83
<211> LENGTH: 29
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 83
agagacgctc cgaggtcaag gtgctctag                               29

<210> SEQ ID NO 84
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 84
tgggcacaac agacaatcgg ctg                                     23

<210> SEQ ID NO 85
<211> LENGTH: 16
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 85
accctctgct gtccct                                                    16

<210> SEQ ID NO 86
<211> LENGTH: 26
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 86
ccaagcagga ggtgctcagt tcccaa                                         26

<210> SEQ ID NO 87
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 87
tccacactgt cggctgggag ctca                                           24

<210> SEQ ID NO 88
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 88
acgagcgggt tcggcccatt c                                              21

<210> SEQ ID NO 89
<211> LENGTH: 37
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 89
ctgttcctct aaaactggac tccacagtaa atggaaa                             37

<210> SEQ ID NO 90
<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 90
tgccgcttat acaacactgc catctgc                                        27

<210> SEQ ID NO 91
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 91
agaagaagcc tgtactacag catccgtttt acagtca                        37

<210> SEQ ID NO 92
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 92
gggctacttg aggaccttgc t                                         21

<210> SEQ ID NO 93
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 93
gacagccctt acagagtttg gaa                                       23

<210> SEQ ID NO 94
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 94
aagaccagga gctctgccta agt                                       23

<210> SEQ ID NO 95
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 95
cccatcacga actgaagttg ag                                        22

<210> SEQ ID NO 96
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 96
cagggcctcc atcccaggca                                           20

```
<210> SEQ ID NO 97
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 97
ccccagtgtg tgaatcactc taccctcc                                            28

<210> SEQ ID NO 98
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 98
cctctcctcc tcaccctcct                                                     20

<210> SEQ ID NO 99
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 99
atgrccdgst yyyctctcct                                                     20

<210> SEQ ID NO 100
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 100
ctcctcactc agggcaca                                                       18

<210> SEQ ID NO 101
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 101
atggcctggg ctctgctsct                                                     20

<210> SEQ ID NO 102
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 102
atggcctgga ycsctctcc                                                      19
```

```
<210> SEQ ID NO 103
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 103
tcaccatggc ytggrycycm ytc                                            23

<210> SEQ ID NO 104
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 104
tcaccatggc ctgggtctcc tt                                             22

<210> SEQ ID NO 105
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 105
tcaccatggc ctggamtcyt ct                                             22

<210> SEQ ID NO 106
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 106
tcaccatggc ctgggctcca ctactt                                         26

<210> SEQ ID NO 107
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 107
tcaccatggc ctggactcct                                                20

<210> SEQ ID NO 108
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 108
tcaccatggc ctggatgatg ctt                                            23
```

```
<210> SEQ ID NO 109
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 109
taaatatggc ctgggctcct ct                                              22

<210> SEQ ID NO 110
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 110
tcaccatgcc ctgggctctg ct                                              22

<210> SEQ ID NO 111
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 111
tcaccatggc cctgactcct ct                                              22

<210> SEQ ID NO 112
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 112
cccaagctta ctggatggtg ggaagatgga                                      30

<210> SEQ ID NO 113
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 113
gtaaaacgac ggccag                                                     16

<210> SEQ ID NO 114
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 114
caggaaacag ctatgac                                                    17
```

```
<210> SEQ ID NO 115
<211> LENGTH: 440
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 115
gggcctgggc tctgctgctc ctcaccctcc tcactcaggg cacagggtcc tgggcccagt      60
ctgccctgac tcagcctccc tccgcgtccg ggtctcctgg acagtcagtc accatctcct     120
gcactggaac cagcagtgac gttggtggtt ataactatgt ctcctggtac caacagcacc     180
caggcaaagc ccccaaactc atgatttatg aggtcagtaa gcggccctca ggggtccctg     240
atcgcttctc tggctccaag tctggcaaca cggcctccct gaccgtctct gggctccagg     300
ctgaggatga ggctgattat tactgcagct catatgcagg cagcaacaat ttcgtcttcg     360
gaactgggac caaggtcacc gtcctagggg ctgatgctgc accaactgta tccatcttcc     420
caccatccag taagcttggg                                                 440

<210> SEQ ID NO 116
<211> LENGTH: 441
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 116
atggcctggg ctctgctgct cctcaccctc ctcactcagg gcacagggtc ctgggcccag      60
tctgccctga ctcagcctcc ctccgcgtcc gggtctcctg gacagtcagt caccatctcc     120
tgcactggaa ccagcagtga cgttggtggt tataactatg tctcctggta ccaacagcac     180
ccaggcaaag cccccaaact catgatttat gaggtcacta gcggccctca gggggtccct     240
gatcgcttct ctggctccaa gtctggcaac acggcctccc tgaccgtctc tgggctccag     300
gctgaggatg aggctgatta ttactgcagc tcatatgcag gcagcaacaa ttatgtcttc     360
ggaactggga ccaaggtcac cgtcctaggg gctgatgctg caccaactgt atccatcttc     420
ccaccatcca gtaagcttgg g                                               441

<210> SEQ ID NO 117
<211> LENGTH: 441
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 117
atggcctggg ctctgctgct cctcaccctc ctcactcagg gcacagggtc ctgggcccag      60
tctgccctga ctcagcctcc ctccgcgtcc gggtctcctg gacagtcagt caccatctcc     120
tgcactggaa ccagcagtga cgttggtggt tataactatg tctcctggta ccaacagcac     180
ccaggcaaag cccccaaact catgatttat gaggtcagta gcggccctca gggggtccct     240
gatcgcttct ctggctccaa gtctggcaac acggcctccc tgaccgtctc tgggctccag     300
gctgaggatg aggctgatta ttactgcagc tcatatgcag gcagcaacaa ttatgtcttc     360
ggaactggga ccaaggtcac cgtcctaggg gctgatgctg caccaactgt atccatcttc     420
ccaccatcca gtaagcttgg g                                               441
```

```
<210> SEQ ID NO 118
<211> LENGTH: 438
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 118
atggcctggg ctctgctcct caccctcctc actcagggca cagggtcctg ggcccagtct      60
gccctgactc agcctccctc cgcgtccggg tctcctggac agtcagtcac catctcctgc     120
actggaacca gcagtgacgt tggtggttat aactatgtct cctggtacca acagcaccca     180
ggcaaagccc ccaaactcat gatttatgag gtcagtaagc ggccctcagg ggtccctgat     240
cgcttctctg gctccaagtc tggcaacacg gcctccctga ccgtctctgg gctccaggct     300
gaggatgagg ctgattatta ctgcagctca tatgcaggca gcaacaatta tgtcttcgga     360
actgggacca aggtcaccgt cctaggggct gatgctgcac caactgtatc catcttccca     420
ccatccagta agcttggg                                                    438

<210> SEQ ID NO 119
<211> LENGTH: 438
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 119
atggcctggg ctctgctgct cctcaccctc ctcactcagg gcacagggtc ctgggcccag      60
tctgccctga ctcagcctcc ctccgcgtcc gggtctcctg gacagtcagt caccatctcc     120
tgcactggaa ccagcagtga cgttggtggt tataactatg tctcctggta ccaacagcac     180
ccaggcaaag cccccaaact catgatttat gaggtcagta agcggccctc aggggtccct     240
gatcgcttct ctggctccaa gtctggcaac acggcctccc tgaccgtctc tgggctccag     300
gctgaggatg aggctgatta ttactgcagc tcatatgcag gcagcaacaa tgtcttcgga     360
actgggacca aggtcaccgt cctaggggct gatgctgcac caactgtatc catcttccca     420
ccatccagta agcttggg                                                    438

<210> SEQ ID NO 120
<211> LENGTH: 441
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 120
atggcctggg ctctgctcct cctcaccctc ctcactcagg gcacagggtc ctgggcccag      60
tctgccctga ctcagcctcc ctccgcgtcc gggtctcctg gacagtcagt caccatctcc     120
tgcactggaa ccagcagtga cgttggtggt tataactatg tctcctggta ccaacagcac     180
ccaggcaaag cccccaaact catgatttat gaggtcagta agcggccctc aggggtccct     240
gatcgcttct ctggctccaa gtctggcaac acggcctccc tgaccgtctc tgggctccag     300
gctgaggatg aggctgatta ttactgcagc tcatatgcag gcagcaacaa ttatgtcttc     360
ggaactggga ccaaggtcac cgtcctaggg gctgatgctg caccaactgt atccatcttc     420
ccaccatcca gtaagcttgg g                                                441
```

<210> SEQ ID NO 121
<211> LENGTH: 442
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 121

```
atggcctggg ctctgctgct cctcaccctc ctcactcagg gcacagggtc ctgggcccag      60
tctgccctga ctcagcctcc ctccgcgtcc gggtctcctg gacagtcagt caccatctcc     120
tgcactggaa ccagcagtga cgttggtggt tataactatg tctcctggta ccaacagcac     180
ccaggcaaag cccccaaact catgatttat gaggtcagta agcggccctc aggggtccct     240
gatcgcttct ctggctccaa gtctggcaac acggcctccc tgaccgtctc tgggctccag     300
gctgaggatg aggctgatta ttactgcagc tcatatgcag cagcaacaa tttatgtctt      360
cggaactggg accaaggtca ccgtcctagg gctgatgct gcaccaactg tatccatctt      420
cccaccatcc agtaagcttg gg                                               442
```

<210> SEQ ID NO 122
<211> LENGTH: 428
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 122

```
ccttcatttt ctccacaggt ctctgtgctc tgcctgtgct gactcagccc ccgtctgcat      60
ctgccttgct gggagcctcg atcaagctca cctgcaccct aagcagtgag cacagcacct     120
acaccatcga atggtatcaa cagagaccag ggaggtcccc ccagtatata atgaaggtta     180
agagtgatgg cagccacagc aagggggacg ggatccccga tcgcttcatg ggctccagtt     240
ctggggctga ccgctaccte accttctcca acctccagtc tgacgatgag gctgagtatc     300
actgtggaga gagccacacg attgatggcc aagtcggttg tgtcttcgga actgggacca     360
aggtcaccgt cctaggggct gatgctgcac caactgtatc catcttccca ccatcagta      420
agcttggg                                                               428
```

<210> SEQ ID NO 123
<211> LENGTH: 441
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 123

```
atgacctgct cccctctcct cctcacccctt ctcattcact gcacagggtc ctgggcccag     60
tctgtgttga cgcagccgcc ctcagtgtct gcggccccag gacagaaggt caccatctcc    120
tgctctggaa gcagctccaa cattgggaat aattatgtat cctggtacca gcagctccca    180
ggaacagccc ccaaactcct catttatgac aataataagc gaccctcagg gattcctgac    240
cgattctctg gctccaagtc tggcacgtca gccaccctgg gcatcaccgg actccagact    300
ggggacgagg ccgattatta ctgcggaaca tgggatagca gcctgagtgc ttatgtcttc    360
ggaactggga ccaaggtcac cgtcctaggg gctgatgctg caccaactgt atccatcttc    420
ccaccatcca gtgagcagtt a                                              441
```

```
<210> SEQ ID NO 124
<211> LENGTH: 441
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 124
atgacctgct cccctctcct cctcacccett ctcattcact gcacagggtc ctgggcccag      60
tctgtgttga cgcagccgcc ctcagtgtct gcggccccag acagaaggt caccatctcc      120 tgctctggaa gcagctccaa cattgggaat aattatgtat cctggtacca gcagctccca      180
ggaacagccc ccaaactcct catttatgac aataataagc gaccctcagg gattcctgac      240
cgattctctg gctccaagtc tggcacgtca gccaccctgg catcaccgg actccagact      300 ggggacgagg ccgattatta ctgcggaaca tgggatagca gcctgagtgc ggctttttt      360 ggaactggga ccaaggtcac cgtcctaggg gctgatgctg caccaactgt atccatcttc      420
ccaccatcca gtgagcagtt a                                                 441

<210> SEQ ID NO 125
<211> LENGTH: 345
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 125
cccgggcaga gggtcaccat ctcttgttct ggaagcagct ccaacatcgg aagtaatact      60
gtaaactggt accagcagct cccaggaacg gcccccaaac tcctcatcta tagtaataat      120
cagcggccct caggggtccc tgaccgattc tctggctcca agtctggcac ctcagcctcc      180
ctggccatca gtgggctcca gtctgaggat gaggctgatt attactgtgc agcatgggat      240
gacagcctga tggttatgt cttcggaact gggaccaagg tcaccgtcct aggggctgat      300
gctgcaccaa ctgtatccat cttcccacca tccagtgagc agtta                      345

<210> SEQ ID NO 126
<211> LENGTH: 432
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 126
atggcctgga cccctctcct gctcccccte ctcactttct gcacagtctc tgaggcctcc      60
tatgagctga cacagccacc ctcggtgtca gtgtccccag acaaacggc caggatcacc      120 tgctctggag atgcattgcc aaaaaaatat gcttattggt accagcagaa gtcaggccag      180
gcccctgtgc tggtcatcta tgaggacagc aaacgaccct ccgggatccc tgagagattc      240
tctggctcca gctcagggac aatggccacc ttgactatca gtggggccca ggtggaggat      300
gaagctgact actactgtta ctcaacagac tacagtggta atcatgtctt cggaactggg      360
accaaggtca ccgtcctagg ggctgatgct gcaccaactg tatccatctt cccaccatcc      420
agtgagcagt ta                                                           432
```

<210> SEQ ID NO 127
<211> LENGTH: 426
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 127

```
atggcctgga ctcctctctt tctgttcctc ctcacttgct gcccagggtc caattcccag      60
gctgtggtga ctcaggagcc ctcactgact gtgtccccag agggacagt cactctcacc     120
tgtggctcca gcactggagc tgtcaccagt ggtcattatc cctactgtt ccagcagaag     180
cctggccaag cccccaggac actgatttat gatacaagca caaacactc ctggacacct     240
gcccggttct caggctccct ccttggggc aaagctgccc tgaccctttc gggtgcgcag     300
cctgaggatg aggctgagta ttactgcttg ctctcctata gtggtgctta tgtcttcgga     360
actgggacca aggtcaccgt cctaggggct gatgctgcac caactgtatc catcttccca     420
ccatcc                                                               426
```

<210> SEQ ID NO 128
<211> LENGTH: 331
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 128

```
agtggtcctg ggacagacgg ccaggattac ctgtggggga acaacattg gaagtaaaaa      60
tgtgcactgg taccagcaga agccaggcca ggccctgtg ctggtcatct atagggataa     120
caaccggccc tctgggatcc ctgagcgatt ctctggctcc aactcgggga cacggccac     180
cctgaccatc agcagagccc aagcggggga tgaggctgac tattactgtc aggtgtggga     240
cagcagcact tatgtcttcg gaactgggac caaggtcacc gtcctagggg ctgatgctgc     300
accaactgta tccatcttcc caccatccag t                                   331
```

<210> SEQ ID NO 129
<211> LENGTH: 417
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 129

```
actcctctcc tcctcctgtt cctctctcac tgcacaggtt ccctctcgca ggctgtgctg      60
actcagccgt cttccctctc tgcatctcct ggagcatcag ccagtctcac ctgcaccttg     120
cgcagtggca tcaatgttgg tacctacagg atatactggt accagcagaa gccagggagt     180
cctccccagt atcctgag gtacaaatca gactcagata agcagcaggg ctctggagtc     240
cccagccgct tctctggatc caaagatgct tcggccaatg cagggatttt actcatctct     300
gggctccagt ctgaggatga ggctgactat tactgtatga tttggcacag cagcgcttat     360
gtcttcggaa ctgggaccaa ggtcaccgtc ctaggggctg atgctgcacc aactgta       417
```

<210> SEQ ID NO 130
<211> LENGTH: 393
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 130

| | | | | | |
|---|---|---|---|---|---|
| tttctgttcc | tcctcacttg | ctgcccaggg | tccaattctc | agactgtggt | gactcaggag | 60 |
| ccctcactga | ctgtgtcccc | aggagggaca | gtcactctca | cctgtgcttc | cagcactgga | 120 |
| gcagtcacca | gtggttacta | tccaaactgg | ttccagcaga | aacctggaca | agcacccagg | 180 |
| gcactgattt | atagtacaag | caacaaacgc | tcctggaccc | ctgcccggtt | ctcaggctcc | 240 |
| ctccttgggg | gcaaagctgc | cctgacactg | tcaggtgtgc | agcctgagga | cgaggctgag | 300 |
| tattactgcc | tgctctacta | tggtggtgct | tatgtcttcg | gaactgggac | caaggtcacc | 360 |
| gtcctagggg | ctgatgctgc | accaactgta | tcc | | | 393 |

<210> SEQ ID NO 131
<211> LENGTH: 417
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 131

| | | | | | |
|---|---|---|---|---|---|
| atggcctggg | ctctgctgct | cctcactctc | ctcactcagg | acacagggtc | ctgggcccag | 60 |
| tctgccctga | ctcagcctgc | ctccgtgtct | gggtctcctg | gacagtcgat | caccatctcc | 120 |
| tgcactggaa | ccagcagtga | tgttgggagt | tataaccttg | tctcctggta | ccaacagcac | 180 |
| ccaggcaaag | cccccaaact | catgatttat | gagggcagta | agcggccctc | aggggtttct | 240 |
| aatcgcttct | ctggctccaa | gtctggcaac | acggcctccc | tgacaatctc | tgggctccag | 300 |
| gctgaggacg | aggctgatta | ttactgctgc | tcatatgcag | gtagtagcac | ttatgtcttc | 360 |
| ggaactggga | ccaaggtcac | cgtcctaggg | gctgatgctg | caccaactgt | atccatc | 417 |

<210> SEQ ID NO 132
<211> LENGTH: 348
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 132

| | | | | | |
|---|---|---|---|---|---|
| cagtctgccc | tgactcagcc | tgcctccgtg | tctgggtctc | ctggacagtc | gatcaccatc | 60 |
| tcctgcactg | gaaccagcag | tgacgttggt | ggttataact | atgtctcctg | gtaccaacag | 120 |
| cacccaggca | agcccccaa | actcatgatt | tatgaggtca | gtaatcggcc | ctcaggggtt | 180 |
| tctaatcgct | tctctggctc | caagtctggc | aacacggcct | ccctgaccat | ctctgggctc | 240 |
| caggctgagg | acgaggctga | ttattactgc | agctcatata | caagcagcag | cacttatgtc | 300 |
| ttcggaactg | ggaccaaggt | caccggcctg | ggggctgatg | ctgcacca | | 348 |

<210> SEQ ID NO 133
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 133
aacaaccgag ctccaggtgt      20

<210> SEQ ID NO 134
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 134
agggcagcct tgtctccaa      19

<210> SEQ ID NO 135
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 135
cctgccagat tctcaggctc      20

<210> SEQ ID NO 136
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 136
catcacaggg gcacagactg      20

<210> SEQ ID NO 137
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 137
gatttgctga gggcagggt      19

<210> SEQ ID NO 138
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 138 cccccaagtct gatccttcct t      21

<210> SEQ ID NO 139
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 139
gctgaccaac gatcgcctaa 20

<210> SEQ ID NO 140
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 140
taagcgccac actgcacct 19

<210> SEQ ID NO 141
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 141
cctgccagat tctcaggctc cctg 24

<210> SEQ ID NO 142
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 142
ctgattggag acaaggctgc cct 23

<210> SEQ ID NO 143
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 143
ccttcatact cttgcatcct cccttctcca 30

<210> SEQ ID NO 144
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 144
ttccttctct tctgtgactc aattatttgt ggaca 35

<210> SEQ ID NO 145
<211> LENGTH: 159
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 145

```
tctggcacct cagcctccct ggccatcact gggctccagg ctgaggatga ggctgattat    60
tactgccagt cctatgacag cagcctgagt ggttctgtgt tcggaggagg cacccggctg   120
accgccctcg gggctgatgc tgcaccaact gtatccatc                          159
```

<210> SEQ ID NO 146
<211> LENGTH: 159
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 146

```
tctggcacct cagcctccct ggccatcact gggctccagg ctgaggatga ggctgattat    60
tactgccagt cctatgacag cagcctgagt ggttatgtct tcggaactgg gaccaaggtc   120
accgtcctag gggctgatgc tgcaccaact gtatccatc                          159
```

<210> SEQ ID NO 147
<211> LENGTH: 159
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 147

```
tctggcacct cagcctccct ggccatcagt gggctccagt ctgaggatga ggctgattat    60
tactgtgcag catgggatga cagcctgaat ggtgctgtgt tcggaggagg cacccagctg   120
accgccctcg gggctgatgc tgcaccaact gtatccatc                          159
```

<210> SEQ ID NO 148
<211> LENGTH: 159
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 148

```
tctggcacct cagcctccct ggccatcagt gggctccggt ccgaggatga ggctgattat    60
tactgtgcag catgggatga cagcctgagt ggtcgggtgt tcggcggagg gaccaagctg   120
accgtcctag gggctgatgc tgcaccaact gtatccatc                          159
```

<210> SEQ ID NO 149
<211> LENGTH: 153
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 149

```
tcggggaaca cggccaccct gaccatcagc agagcccaag ccggggatga ggctgactat    60
tactgtcagg tgtgggacag cagcactgct gtgttcggag gaggcaccca gctgaccgcc   120
ctcggggctg atgctgcacc aactgtatcc atc                                153
```

<210> SEQ ID NO 150
<211> LENGTH: 156
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 150
tcagggacaa tggccaccett gactatcagt ggggcccagg tggaggatga agctgactac    60
tactgttact caacagacag cagtggtaat gctgtgttcg gaggaggcac ccagctgacc   120
gccctcgggg ctgatgctgc accaactgta tccatc                             156

<210> SEQ ID NO 151
<211> LENGTH: 159
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 151
tcagggacaa tggccaccett gactatcagt ggggcccagg tggaggatga agctgactac    60
tactgttact caacagacag cagtggtaat cataggtgt tcggcggagg gaccaagctg    120
accgtcctag gggctgatgc tgcaccaact gtatccatc                           159

<210> SEQ ID NO 152
<211> LENGTH: 159
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 152
tctggcacct cagcctccct ggccatcact gggctccagg ctgaggatga ggctgattat    60
tactgccagt cctatgacag cagcctgagt ggttatgtct tcggaactgg gaccaaggtc   120
accgtcctag gggctgatgc tgcaccaact gtatccatc                           159

<210> SEQ ID NO 153
<211> LENGTH: 159
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 153
gatgcttcgg ccaatgcagg gattttactc atctctgggc tccagtctga ggatgaggct    60
gactattact gtatgatttg gcacagcagc gctgtggtat tcggcggagg gaccaagctg   120
accgtcctag gggctgatgc tgcaccaact gtatccatc                           159

<210> SEQ ID NO 154
<211> LENGTH: 153
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 154

| cttgggggca aagctgccct gacactgtca ggtgtgcagc ctgaggacga ggctgagtat | 60 |
| tactgcctgc tctactatgg tggtgctcgg gtgttcggcg agggaccaa gctgaccgtc | 120 |
| ctagggctg atgctgcacc aactgtatcc atc | 153 |

<210> SEQ ID NO 155
<211> LENGTH: 153
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 155

| cttgggggca aagctgccct gacccttcg ggtgcgcagc ctgaggatga ggctgagtat | 60 |
| tactgcttgc tctcctatag tggtgctcga gtattcggcg agggaccaa gctgaccgtc | 120 |
| ctagggctg atgctgcacc aactgtatcc atc | 153 |

<210> SEQ ID NO 156
<211> LENGTH: 165
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 156

| tcaggcctga atcggtacct gaccatcaag aacatccagg aagaggatga gagtgactac | 60 |
| cactgtgggg cagaccatgg cagtgggagc aacttcgtgt ctgtgttcgg aggaggcacc | 120 |
| cagctgaccg ccctcggggc tgatgctgca ccaactgtat ccatc | 165 |

<210> SEQ ID NO 157
<211> LENGTH: 164
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 157

| tctggcacgt cagccaccct gggcatcacc ggactccaga ctggggacga ggccgattat | 60 |
| tactgcggaa catgggatag cagcctgagt gctggccccg ggtgttcggc ggagggacca | 120 |
| agctgaccgt cctagggct gatgctgcac caactgtatc catc | 164 |

<210> SEQ ID NO 158
<211> LENGTH: 22800
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 158

| aagctctaaa actacaaaact gctgaaagat ctaatgacta ggacagccta gtaattttca | 60 |
| taggggcata aatgtgaaac gccttgtgca tcgtagaaga aagcagaaga gaaagcattc | 120 |
| ccaatttctt aactgccttt tacctatatt aatcagtaat atactggctt ttacctctgt | 180 |
| taatcataat aaacaaattc tcaataaatt ttatcgatac tcttcaatgc ctgctcagca | 240 |
| acattttccg aaggcagctc aagatattaa ataactcata agggccaacc tcctattgca | 300 |

-continued

```
gcattctttg ggatttaacc agtttcccaa gactcttttc acaatgttaa gatgttagaa        360
atagatccaa aactaggtga tatatcccct agtaaaactg tgaggtcaaa cttgtctggc        420
taatgcttcc atttaaaaat ttctctttct tgatccttca ttgtatgtac acaataaatc        480
aggggaaaac tttaactgag tgaatcaaag tattctcatt attataatag gagcttcaca        540
cacacacaaa aaaatcaatt ctattactct cagcctcagt tcctaaagcc aagttaaagt        600
cctgttctaa gatcattgtt gcatgaccat atgtattcca ggtctaatct aaactgtgga        660
taaatcccag caggacatta gagattttttg tgagagtaag catataggat tcagggttta      720
tgagctttag atttttcttg tcaaaatgaa tgagagttgc catatctaaa aattattccc        780
agataaataa aattcactac ctagaattaa tttatgcata taagtagaaa tgctatctcc        840 cttttttacca tccaaagtgg aaagcctcat ggaactagaa attaatatta gaaaatcag        900 ttaataaaag tatgtcattt catcaattca ataagttata atagcaaaaa accataataa      960
attatcactt aaatgtcaat acatttataa actatggtac ataaatagga tattgaatag      1020
ccattgatgc tcctgatgaa aattagcagg cagtgataaa tgataaatat gaagcacatg      1080
tcaataaata aaataagttt tatgtaattt aggagaaaat ggtgataatg acacaaaatg      1140
tgaattatgg atgcatctat aaaattcttt gtacatttgt gaattgtaaa tatttatctt      1200
agagacatta ttactttgta tatgttccat ttgctcacct atatgtccca gtctccttac      1260
aaatgctatg gccaaagaaa taggcataca tacatccttt gcaggctgag gcaggaaaaa      1320
gatcttacgg aattttccag tctatccttt atctgtataa gcaacttaag aggccatgtg      1380
ctccaaatgt gcaaataca agatggtaga gcctctgtct gcctggatcc ttgagtggct      1440
gcatggagca gagcaccttt ctggccctgg tgaagattgt agcatgagca agatataagc      1500
atttgttgga gctaggccat gagatttggg gcagtggtat aacctaccct attatggaaa      1560
atataaatac acaaaacaga aaagagagag agaagtgaga gaagactgtg agagaagtgc      1620
atgagagaag actgtgtttt gttcatttcc tataatccta tatcaccatg ggatcctgtg      1680
ccttctggtg atcaaactaa tgttctacag ctccaaagaa gaatgctcgc taacgtctc      1740 cattccaatg acctagagac taaaagccaa aaagaacctt agaaattatc tattgcattc      1800
tttgatgtaa ggaaatatct tagagggcac agatagaaat atcttaaccc aggtcactta      1860
gttcgtggca gagctgaggc taaaaccagg ccttttgact cctaattttg tgctcttac       1920 accttctcac atcacttctc caacccaaag tctagcagaa aaggctaaaa taagatatat      1980
gcatagattt gctattataa gtccatgtac ttcctcagac gctttaagat ggggcttctc      2040
atggttcaca ataagcagca gagggaagtg aataactatc ttcgtctccc ctactgctat      2100
ttgtgcagtt tgaagcttat ctcttaaatc atgttttctt ctcgtagtaa atactacaac      2160
ttgtgccttt tatgtgtgta taaattttaa tataattttt ttccatgaac cattcaagta      2220
aaatggacac tccaaaaaga tgttcaataa ggttacatgg cttcacattg cccctctac      2280 accatcttgt ggagctacac attcacctca cccaaatttg agaaaataa tcaagaaaat      2340 gactctcact agcagtgaga ccaagtccat aagcactaat gtcatcagtg cacactgcag      2400
cctcatgctg ccaagcatgt tttgggcgta tccctggact ggtttggtga catgatcaaa      2460
ggtacatttt ccacctgcat agccccatcc tggatctata gccttccttg tgtctttgtg      2520
aacaacctag tgtgaactca agtatgaga cagatctcaa ttaatttaga aagtttattt      2580
tcccaagatt aaggacaagc ccatgataaa gcctccagag gtcctgatat atgtgcccaa      2640
gggggtcggg gcacagcttg gtgttataca ttttagggag acaagaaaca tcaatcgata      2700
```

```
tgtagaagat gtgcatcgct ttggtctgga aaggtgtgac aactcaaggc agggaagggg      2760
gcttcctgct gggggttgcat tgttttgagt ctctgatcag cctttcacat gtgaaaggca    2820
ggtagagaaa tagtcattta tgccttagtc tggcttattg aaacagtagg gcagaagaag    2880
cattgcatat gcatttgtct gaagtgaaca gagggatgac tttgagctct gtcctttctt    2940
tgtccacaag gaattacctt gtgggcaaat tgtgagggag gtatgtagct tttttttctt    3000
tgtagctatc ttatttagga ataaaatggg aggcaggttt gcctgatgca attcccagct    3060
tgactttccc ttttggctta gtgatttttg gggtcctgag gtttattttt tctttcacat    3120
tagtataact acttttcttt ttctaattcc ttttctactt gtatgtgtta cagctgactt    3180
atgttacttg caaaaagaat tctgactaat gcaccatctg actagaaggc agggttcttc    3240
gatgataacg aatcctccag aatctagtaa acagaattgc ctgaaaaaga ggtgggtgtc    3300
ttcttgggga atttctcatg gcaatgaatg gcaactggcc aaaggattta tgaccagact    3360
gagctctctt ttatctattc tgttactcac caagacctat tagggtttgt gctccacagg    3420
gacactggtt tctaagttct agggttaaac agtccactcc caggcccacc acaccatacc    3480
ctcctgacat ctggtgaaca gcaataaaat tgtttcttat tctgaaaatc ctccaatact    3540
tccaccatcc ccaaaaatgc agtggaggag gagagaaaat gaattgttcc attagagaac    3600
acaatatcca ttatattatt cttggccttt gagatacctt acaaaacaaa tacaaaaaaa    3660
gtcccaattt aacatctttt aataatcttt acaaaacaga acacatctcc tttcttgata    3720
atagtcaaga ggctcagtgg caactgtggt gaaaagtgtc agattctggt catgtttcaa    3780
aggtagaaaa aatagaattt gttaacatat tggatgtgag gcgtgggaga aacgtgaaat    3840
caaggtggtt gcaagtgttt aacctgagca actagagaat ttgaaggac attttctgag    3900 atggggaagg caggcgggaa tcagggatta gagttgaaca tattagacat ttgagatgcc    3960
tgctagacct ctaattggca atatcccttg gacaggtgga tgaatatgcg tgattctgga    4020
gttcgggaaa tagtccgggt ggagatgcaa atttgggaaa cagggcgagg ttactagcaa    4080
tgagttaaat caatgaaggc aggctgggac ctggcaggta acccaacaag tagaggtcga    4140
agagatgaga agaaaacagc acaggagact tagaagcagt ggtcaggagg aaggagttga    4200
accaagaaag tgatgtccca gagccaacaa aataaggatt tcttttctgt ttacaaatgt    4260
aaaattaaaa ggtttaataa aaagaaaatt tacttttatg gttggttgtt attaagtggt    4320
ccaaacactg tctcctattt gtagaatcag aactctctca tggcagtaga aaatttggaa    4380
agttactttt taaaaggtgt gtgcactgct gcccttttgct ggtcaagttt atgcactgca    4440
aattccaagg acgattgctc gtcagctttt ctcctttaaa atagctcagg ctgtacaagc    4500
tagaaagaac ctcgcaagat attccttcca acatttgcat ttgacttatg ggaagtgcag    4560
gttcagccag aaaagttgtg tgcaaggccg tttatgtaag tttatcagac ctgattctta    4620
cggctcttcc cattgttcg agcctccctt ccattcactt cccgctcata cgcgaccaag    4680
tataggacag gagtagttat tctgcacttt atagcagctc cactgtctgg cactctgatg    4740
ttctttaatt acaagcttta tgacagtgat tctcaacctg ctccactgcc tccacctagt    4800
ggcagaaaga agaaaatgtg tgtaactcgg gagtctctgg tctgaaagct ccggggtatc    4860
atttcttcaa agtcttgagc ttgttttttgt ttgtatttat ttatttattt gttttagaga    4920
caaggtctcg cactgcactc cagcctggga gacagagcga gacaattcag gatctatcta    4980
gtgaataaag agatatcagt aatgactgtt ttatattgtg gctgtagcgc attcgaggga    5040
taattcgatt ctgttctgct ttcgaatgca tggctcactg taacctccaa ctcccgggct    5100
```

```
caagcgatcc tcctacctca gcttctccag tagttgagct tgatttattt taaagtttca   5160
taaaattttg gcatttcttt ccacaatatg gccatgtgtg ctttactata aatattttc   5220
atcacaaaat ttacatcgct ggaaatcccc ataagccagt ttgagaaaca aacccaaga   5280
aagcagaaca gactcaaatt atcccttaaa tccccttaa ccacaaatat aaaacagtcc   5340
gtgactgggc gtgttggctt acacctgtaa tcccagcact ttgggaggcc aaggcgggtg   5400
gattacttga gctcaggagt tcaagaccag cctggccaac atggtgaaac cccgtcccta   5460
ttaaaaatac aaaattattc aggagttgtg gcaggcagtt gtaatcccag ctacttggga   5520
ggctgaggca ggagaatcac ttgaacccag gaggtggagg ttgtagtgag ccaagattgt   5580
gccagtgcac tccagcctgg gcaacagagc gagacttcca tcttaaaaaa aaaaaattaa   5640
gtaaataaaa tataaaaaaa taaagcagtc cctattgata tctctttatt cactaaatca   5700
acctggaatt gacctgaatt ctgatttttt tttcatcatg gattttttgc attaattttg   5760
attgtttaaa tattgcatta aaatattatt tatcttgact actgagtttg cgggacctcc   5820
ttaaaattta tgaccaaggc aatgcctcac tcactcgcct taccataatc tgggccacat   5880
atcaggggct ccaatagcaa gcaacatgac ttttgaacag ctaagacttc tctcttcact   5940
gtgaagacca gatgggccct gcaaacagtg taacctctac atgaaaatgc acgagattcc   6000
aactacaacc aggcacaaaa gactctgatg gtgaagtccc agccctccaa gtcccaactt   6060
cctgaaggga aagagcaccc caagttctga ccagaggcca gagtcataac gaagatggaa   6120
tgtgagcttg acatagaagg ggtggtagca cctggctcag taatgaagag gctttcggtc   6180
ctgaaggaag agctcagcac attcaaagat tagaagggag gtcccagtca taggagcagg   6240
gaaggagaga aggcccaata agaaacacag acaggaggga ggggtcaggg caagatcata   6300
ctggaaacaa ctagagagct aataaaagtc acagtgccca gtccccacat ggaccagact   6360
cttcggaatc tctaggcatc aatttgggca ccagtagttt tcaaagttct ccagaagatt   6420
ctatgcacac cagccaaggg tgggaaccac aggtgttggc ctaggatca tgacaatgag   6480
tttctaagtg caataagaaa cctccagaga gtttaagcag gggaataatt tgatttgttt   6540
cttgtttgtg attttaaag atcagtctgg ttactgtgtg taagacaata atccagaaaa   6600
tctgttgctc atgaaccaca tatctgtaaa tttgcttccc ctgtaactgg atctaaccaa   6660
caaaaattag tacttactaa gaaattacat gcccagggac tatgctaagt aattcataaa   6720
cactatttta tttactcctc acagcaagtt tataagagaa acgttattat ttccacatttt   6780
cggatgagaa atttgaggct tggggaaagt taagtaattt acctaatgtc acacccagtt   6840
cataagatgc agagttaaga ttctaattct gtgtctaagt tgatgctcca tcaaacacac   6900
cacgcctcca actaggaagc aacatgctgg ccagaggatg ctgtcatcaa gtttacagaa   6960
tggttagatt tctaggcaca gatgaataaa tcaacatgtt ggtttgcaat agaatgaatc   7020
tatccagctc tgaatttgca tccaagggtt tgtgagcaca caagtctaaa agtgtggcct   7080
cagctctgct aacttcatca aggtgaatac ctaggaggcc accctctgag accaccagat   7140
ggacagtcca ccatctgttt acagatggta aagccacata ccagctttgc catctgatgt   7200
tctctattca cattcaacat ttatacaaga aatagtcata tggatccttt tcaatagaca   7260
gtactgggga aattgaattg ccatatgcag aagaatggaa ctagacctct atctctcacc   7320
aaatacaaaa gttaactcaa gacagattaa agacttacat ataagacctg taactacaaa   7380
aacactagaa gaaaacctag ggaaaatgct tctggaatta atctaggtga agaactcagg   7440
actaagatat caaaagcaca agcaccaaaa caaaaataga caaacaggac ttaattaaac   7500
```

-continued

```
tagaacgctt ctgaacagca agagaaataa tcaatagagt gaacagataa tctgcagaat    7560
gggtgaaaat atttgcaaac tatgcatcct acagggaaat aatgtccaga atttagaagg    7620
aactcaaaca attcaacaac aacagcaaaa taaccccacc aaaaaagtgg gcaaaggaca    7680
tgaatagaca tttttcaaaa gaaggtatat gatatggttt ggctctgtgt ctccacccag    7740
atctcacctt aaattgtaat aatcccaca tatcatggga gagacccggt gggaggtaat    7800
tgaatcatgg gggcaggttt gtcccatgct gttctcatga tactgaataa gtcctatgag    7860
atctgatgat tttataaagg ggagttcccc tgcacacact ctcttgcctg cctccatgta    7920
atatgtgcct ttgcttctcc tttgccttct gccatgattg tgaggcctct ccagccatat    7980
ggaactgagt caattaaacc actttttctt tgtaaattac ccaatcttgg gtatgtcttt    8040
attagcagca taagaacaga ctaatacagt gtacaaatgg ccaagaagcg tacaaaaaac    8100
aaaatgctca aatcactaat cactagagaa tcgcaagtta aaaccacaat gagatattat    8160
cttacagcag tcagaatgcc tattattaaa acaccaaaaa ataacatgtt ggcaaggatg    8220
cagagaaaag ggaatactta cacattatta gtgggaatgt aaactagtac agcttctgtg    8280
gaaaacacta tggagatttc tcaaagaact agaaatagaa ctaccatgtg gttcagcaat    8340
accacaactg ggtatctacc caagggaaa taaattatta tataaaaaag atatctgcac    8400
tcacttgttt attgcagcac tattcacaat agcaaagata tggaatcaac ccaagtgtcc    8460
atcaacagat gattggataa agaaaacgtg gtgtgtgtgt gtgtgtgtgt gtgtgtgtat    8520
acacatacca caatgaaata ctattcagct ataagaaaaa gaatgaaatc atgtcttttg    8580
cagcaatgtg gttggaactg gaggccatta tcttaagtgg ataattcaaa aacagaaggt    8640
caaatgtcac atgttctcac ttataagtgg gagctaaatg atgtgtacac atggacatag    8700
agtgtggtat gataaacact ggagattgag atgggtggaa gggtggaagg aggttgagtg    8760
atgagaaaat actaaatgga tacaatatac atgattcagg cgatagatac actaaaagcc    8820
cagacttcac cactacacag tatagctatg tagcaaaatt gcacctgtat tgcttaaatt    8880
tatacaagta aaaaaagat cgtacgaatt ctgttttta ttctctatga aattactact    8940
gagagtatta tccaatgccg tttctatgca gtgcccccaa tattatccat ttagcagctc    9000
ctatgcaatg ccccaagata gaaattgtct tcaacttta tcccaggaaa accttcagtc    9060
acacgtagaa actagaaatt tttcccctag atgaaagtta tgtaacataa cacattatct    9120
tcatttagtc ggtttccaag aagctcagaa ccagatttta tgttcaatca aaaactgctt    9180
attttaagtg aggtttactg aggtataaat tacaataaaa gccaccttt cgtgtatatt    9240 tctataagtt ttggcaaatg catagctgtg taaccacaac cacattcaag ataggaca     9300 agtccctcat cctttaaagt tccttatgc cccttcctc accccagccc ttggcaacca    9360 ctggttttg tctgatccaa tcgtttgcct cttcctgaat gtcatgtaaa tagagccatg    9420
caatgtgaag cctttgagt ctggctttgt tcacttgttc acttaggaga atgcatttga    9480
gattcatctt tgctgtttcg tgtagcacta gttcactgtc tattgttgag tagtattcca    9540
ttgtgtggat atgccacaga ttgtttatct agttaacaat ttaaagccat tggtcatttt    9600 ctaatttta gctgctaaga ataaagttgc tgtaagcttt ccaatgcagg ttttttgtgtg    9660 aactcaggat ttcatttcgc ttgggtaaat tcctagcttt gggactgctg agtcatctgg    9720
taggtgtatg ttgaactta taagaaactg ccaaactgtt ttccaaagtt gctgtgctct    9780
tttgcactcc catcagcagt gaatgagggt tccacttgct cgagcctagt attttaactt    9840
cactatatac cttctttgat gacatatcct ttcaaatttt tggtcaagtt tttattgggg    9900
```

```
tgttgttact atggactgtg agagttcttt gtatattctg catatgattt tttctcaca    9960
tttgtgtttt atgaatatgt tctcccaatg tgtggcgcct tttatttct taacgtgcca   10020
tgtgaagagc agaagtttaa tttatgatg tccaaattat cttttttct tttcttttt    10080
agatcaaaat aggggtctat tttgattacc actgttattt tatctccatt tgattttcga  10140
tttttatttt tattttcta atttcattgt aaattttaa ttaaacccaa atattctagg    10200
ggaaagaggc aagataaaaa tagtctaact tgggcataaa ttttagagtc atattctctt  10260
gccgagaaag gaaactagct ctcttacatt gattgtttaa tttcagacgt cactacttta  10320
tgaggatgcc caaattatgg gctttaaaaa atatatatcc aaacaggggt tcagaaagaa  10380
taactaattt gtccacaaca acacaaaaaa tgattccacc ataagtttgc ccagtgacag  10440
ggtctatatt attttctata tatcaaattc tacaactggt tcttaaagct actgtacata  10500
acctaagtta aaatattagg tattagttga taagacattt tatcatctat gaaatgttgc  10560
ctgttgtcat agttagagaa tcttttaaaa tatggagcta ttttcataga ttaaactatg  10620
ccagttaaaa gttgggtaaa aagaactaca gaataatatt tatgtttatc gtgtaaggtt  10680
ttaaagcaaa ctccaagtca ttttcatcaa tgaaatcaat aaggttttgc aaatatatat  10740
gtatgaaaat actgatttaa aatgcaaata aggggagagt ttgagagaga gagagagacc  10800
aaatgatttt ataattctag taagtttata ggtttatggg ttttttacgt acttttctac  10860
ccaacttgtc tataagactt taatgaatca cttagaattt ttaaataat ttattattac   10920
tctgtacctg ttctttactc tgcaaatctt accttgccct tttgtctaaa agcaataaaa  10980
tctgacctgg tttatatcgt atcattgatt ttgttactta gcaagcacag tgatccatta  11040
ggcctatgta ggctcatggt ttatacaaca ctgccatctg ctgacagagt gtgacagtca  11100
cagtcagcaa cacgagacca ctttattttc atttttagtg tttatagaaa tatgaatata  11160
cacaaatagt ataatgaacc ctaagcttca caaattaaca ttttgctaat cttgtttcaa  11220
ctaccgcctc cccctcatc caattactct gttctctcac ctcctcacac acagacactg   11280
gcagtatttt tcagccaatc attaatacgt tgccaactga taaggacttt taaaaaacaa  11340
ccaccattcc attatgattc ccagcataat tgagagtaat tccctaatat ccaatacccA  11400
ttttctattc caatttcctt gattgtcttt aaactgtttt taccctaagt ttgcttaaat  11460
caaagtccag gtcctgttaa acatatggtt aagttttacc caaacccaaa taataataa   11520
aataaataaa taaataacct attttttcca attccaggga atagtgaaag agggtaaatg  11580
ccattattta gaaacataaa tcacatcata ggactagaat tatcttgaag tcaaaattga  11640
agactgaaaa tggaaaagaa aggtatagac taaacttatt taaaaacttc aatgcagaac  11700
tctaagagaa gatattagaa agttgtacca gcattcatta ttcagtattc atcagtattc  11760
actcagctat atgtagttga aatctaacta gaggagcttg atcagataaa gagatacatt  11820
tttctcacca aggcggactc tggaggcagg tggttcagag ctagacagct gctgcaggac  11880
ccaggtcctt tccctgcctg ctcctccact ctagcttgtg actttcatcc tgcaagatgg  11940
gtgtttctgc caagttccag atagaagaag atagaacaca aaggagaaat aagcagtggt  12000
gcctctgtcc atcaagcaaa attttttccag aaatgcacaa tagatttcag atgatgtctc  12060
aacagtccta actgcaaaga agctgaggaa ttagattttt ggctgggaca ctgttgccct  12120
gtaaaaaat tgggattctg ttattaaaga ataagaggag ggaagaaaga ttgaaaactc    12180
ctatgcaata gtgaaaaaaa taagaaactc aataaaaaag tgggcatacc ttaaaaacag  12240
gcaattcaca acagatgaga ccccaatagc caataaacat ttttaaatgg tcaacctcat  12300
```

```
gagtgatcag aaaacacaaa tatgtatttt aaaccaaaaa taaaatacaa tgtattgacc    12360
atttgagtgg aaaaaaatta aaaagcctga taatatcaag tattggagag gatgtagagt    12420
gaggaaactc catggaggac ctatcattgc aaatgtggga atgaaactta atacacgaat    12480
ttgaggccaa tttgtaaatt gaaaaatgcg cacaccctgc aaccaagtac cccttgcaat    12540 attttttgaaa agacaaaaac gttatgtaaa tggaatcatg caatatgtga cctttatact    12600
cagcataatg cccctcagat ccattgaagt catgtgtatc aacagctcac tattttttt     12660 ttaattttt ttagagacag agtctcactc tgtcacacag ggtggagtgc agtggcgaga     12720
tcataactct ctctagcagc ctcgaactcc tgggctcaag catcctcctg cctcagcctc    12780
ccaagtagct aggactacag gcatgggaca caacacacag ctaattttt taaattttt     12840 ttagagacat ggtctcacta tgttgcctac gctggtctca aactcctagg tcaagcgatt    12900
ctcccacctc tacttcacaa agtgctgtag gtatgtaggt atggattgta ggtatgaacc    12960
accgtgccca actcactact ttttattact aattattcca tgggatggat gtaccgcagt    13020
ttgttttacc attaatctat tgtaggacat ttgactgat tccagttttt ttttaataca    13080
aataaaacca ctatgaatag ttgtgtattg tatacgtttt tgtgctaagt tttcattttt    13140
ctgggataag ttttcatttc tttgggcttt tactgtatcc ttgatattat aatatgttac    13200
atcttcagtt ttattctatt caatatataa tcttttattt tccttgaaat ctcccatgga    13260
ttgtttagaa gtgtgttgtt ttgtttccaa gggtttggca ttttttccat tattttttcta   13320 ttatcgattt ccagtttgat tccaggtggt cagagaacac acttcatgtg atttcagttc    13380
tattaaattt gttgaggttt gttacatggc ccagtatatg gcaattttgg tatatgttcc    13440
atgagcactt gaaaagaatg cgaattctgc tggtgctggt tggagttttc cagcaatgtt    13500
gatttatgat cttactcatt gatggtggtg ttgagtttga tgtgttctta cgatggcagc    13560
tttaacattc ttgtcaggta attctaacgt ctctgtcatg tcagtattag cgcctcttaa    13620
ctgtctcatc aaagctgaga ttttcctggt tcccctggtt cctgttggga tgtgtggttt    13680
tcatttgaaa tctggacttt ggagtattgt gttatgaggc tttggatctc atttaaactc    13740
atctcagcga atttcctctc ttgccactca ggaaggagaa gttgggtgtt tgaatggagc    13800
agagccgtta ctgcctaaga attgttttac tgggcttccc ctttctttct cctttgacta    13860
gagagagcca gcttttttatt agggctttat gttttttctgg gcctgttggt gtttctgggt    13920
tgacaaactt ctccagaacc aagtctggaa tggatgaggc aaaaagaaac cccgtggaat    13980
gcactgctgg gtcgctcctt gggtcccaat gttcctaact ggtctgcctt cttctctcca    14040
gcttccagag tcttcataag tttgctttac gtacaatgtc cggggttttt actttacttg    14100
agagaaatag gtaaaagtaa ttctactcca tctttcagga agcaaaagcc cccttgtgta    14160
tttttttaaa cttcaaaaa caaaacaaaa ggcagctgca acagtaaaga agctagtaac    14220
acccttggtg ggaaattcaa gtccaaatac acatttaag tttggctagc cagtgagaac    14280
atcagaatag ttcaggtttt aaacaaattt atatttatga ttatgcatat actaaaagct    14340
gaaggcatct tatatttact aagcacctat tttgttcttg ttaaaaagac agaattccat    14400
tccctaggaa atttgacctg gcagctggag ctgatccacc tggccactag agcacagagc    14460
agggagagta gtagccctgc cccagccacc cctcaagaca ggattctttc tctgggaact    14520
gtaggtaaca ctaaatcgtt ctggaacaca acaacgaaag aagaaaggaa agagaaagaa    14580
agaaaggaag aaagagagag agaaggaagg aagggaggga gggaaggaag gaaggggaag    14640
ggaagggaat ggaagggaag gaaggaagga aaaggaagga agggagggag agagggagga    14700
```

```
aggaaggaaa ggaaaggaag gaaggaagaa ggaaagaaaa aaagaaagaa agaagaaaga    14760
aagaaagaca agaaagaaag aaagaaagaa agaaagggga aagaaaagaa agaggaaaga    14820
aagagaaaga aagaaaagaa agaaaggaaa gaaagagaaa gaaagaaaaa gaaagagaaa    14880
gaaagagaaa gacaagaaag aaaaaggaaa gaaaagaaag agaaagaaaa gaaagaaagg    14940
aaagaaagag aaagaaagaa aaagaaagaa agaaagaaag aaagagaaag aaagaaagaa    15000
aaagaaagaa agaagaaag aaagaaaaag aaaagaaag gagaaaatga cagcaattac     15060
ttttgcaaca acctaatata agtttttttaa aagttaaata ttctgttcca tgcattgctg   15120
gataccttat aaataacagg gcatcctatg acctgaattt cccaaattat gagttgaggg    15180
tttgaactag ttttaaaaaa caaggaggcc aggcgcactg gctcatgcct gtaatcccag    15240
cactttggga ggctgaggca ggtggatcac gaggtcagga gctcgagacc agccttacca    15300
acatagtgaa acaccgcctc tactaaaaat acaaaaatta gccgggcgtg atggtgcgca    15360
cctgtaatct cagctactca gcaggctgag gcaggagaat cgcttgaacc cagaaggcgg    15420
aggttgcagt gagccaagat cacagcattg cactccagcc tgggcgacag agggagactc    15480
cgtcttcaaa aaaaaaaaaa aagacaagga atctgtaaaa caggcactgg aagtatatgc    15540
acttttattt tcattctatg ctatccgatg cctactgcta tttcccttca tatttaacct    15600
ccaacagctg cattttgctc cctccagacc acctgattgg agctcacgtg ctcccacaca    15660
gtacctccaa ccagagagag tcgagtccca cagaaaggcg taacaatcac cagtaatttt    15720
gcacttattt tacattgtgc cttgatacag agtactcaat gaatgctctt tgaatcatat    15780
ttaataaata tgtgtatttg ggattgtagc atattgcagc tacctggata tataatttaa    15840
ttagaaaaaa aattttgtgt ggctcaatca acaaacgact tttctctctc tctctttctc    15900
tttctccctc tctctctctt tcttctcagt tgatgttgct ggagttcagt gttgtgcaga    15960
tggcagtgac aaatgccatg ggcacatgag atatgataaa aggtccctga agaaggtgga    16020
gaaccagtta tcttatgaaa ttttccagag tgggtactgg atctctcctg tctggcacca    16080
tgctggcctc agcccaaggg gaatttcctt ccagagacag agggcagtga ttgaggtggg    16140
gagacagatc gtaacactga gacttacatg aggacaccaa acagaaaaaa ggtggcaagt    16200
atagaaaatt cttctcttctg gacagtcttc tctgttctaa cttcagcaaa attctccccc    16260
cagtggatgc tattgcacaa ccctacatat gctatgtttt ttcctataca cacttaccta    16320
tgataaaatg cattaattag tcacagtaag aggttaacaa caataactag taataaaata    16380
gaacaattca gtaaaataag agttacttga gcacaaacac taggatatca tgacagtcaa    16440
tctgatgacc aagagggcta ctaagcatct aaacaggagg gtaagtgtag acagcatgga    16500
gacgctggac aaagggatga ttcagtccca ggctggtatg gagcggaagg gcatgatatg    16560
tcatcacgct actaaggcac acaatttaaa atgagtaaat tcttatttct agaaatttct    16620
ttttaatatt ttcagactac agttgcctac aggtaactga aacccagaa agcaaaattg      16680 ttgataagga ggtactactg tacatcgtcc tttgaaccaa ctttatcatt tgctagtata    16740
tacatatata cctacataca tacatataca catcctgca cacacctata tgtatacgta     16800
cacacacaca cacgcacaca cacacactca catctactaa tgttagaata agtttgctaa    16860
ataagatgca caacttgtta atgtcctaca gagcaataaa accataagca ttggggttat    16920
cttttctact agataaaaat ccattatcat tttcataaag ttttctttac attaacatct    16980
aacttttgca atctagtttt taatcatcat aaataggaag caaatgaact gtttctctag    17040
tgaatcaaat atccttgaaa acatacatag tcatcttttt ggtttatttt tattttttaga  17100
```

```
taaattattt aaagttttaa ataatttaac attcacaata gtttgtgact gtatatttg      17160 acttggtcct tcaaacttaa tttgtacttt tatgtatcgt gcttacctca atttttatt      17220 cacttttcct aaactttgct ggattggttt attattttg tctatttctt ttccttctag      17280
tggtttggga gggtttttta aatcccatta ctattgaatg cctattaact tgcccccttt      17340
ttctttcaat ctctattccc acggcctgaa gcatgagggc caagctgtct gtaaccagca      17400
gagagatgac ccaggtgtta ttccactctc cactgtccac ctatcaccat tcccagcccg      17460
atagctctga agtacggctt ttctggggct ctgtgggaa aactagaact ggctgcttca       17520
aggacacctc ctgttttgc aatggaaaaa atgtttctaa attccagttt ctctatgaat       17580
tcaatgacat ggtttaaatc tctgtggtgt tcttcaaagt ttttcttct aataggacct       17640 ctcatgattc tccaaccacg aaataaattc attatcattt ttatatttct tctgtcattg     17700
caaaggaggt tttgaaagag tggaggacgc gctaatgaac tcaaaaatcc acactattcc     17760
ttgtttccat ctgttgttca ttcattgttt ccattggcct gtccgcctcc tatcctcctt    17820
cttagacttg gagctctagc ctcagccagg atagggaaaa gagagatcag actgttactt    17880
tgtctatgta gaaaggaag acataagaaa ctccattttg atctgtatcc tgaacaattg     17940
ttttgccttg agatgctgtt aatctgtaac tttagcccca accttgtgct cacagaaaca    18000
tgtgttgtat ggaatcaaga tttaagggat ctagggctgt gcagaatgtg ccttgttaac    18060
aacatgttta caggcagtat gcttggtaaa agtcatcgcc attctccatt ctcgattaac    18120
taggggcaca gtgcactgcg gaaagccgca gggacctctg cccaggaaaa ctgggtattg    18180
tccaaggttt ctccccactg agacagcctg agatatggcc ttgcgggatg ggaaagatct   18240
gaccgtcccc cagcctgaca cccgtgaagg gtctgcgctg aggaggatta gtaaaagagg   18300
aaggcctctt gcggttgaga taagaggaag ccctctgtct cctgcatgcc cctgggaacg   18360
gcatgtctca gtgtaaaacc tgattgtaca ttcgttctat tctgagatag gagaaaaccg   18420
ctctgtggct ggaggcgaga tatgctggcg gcaatgctgc tctgttgttc tttactacac   18480
tgagatgttt gggtgagaga agcataaatc tggcctacgt gcacatccag gcatagtacc   18540
ttcccttgaa tttacttgtg acacagattc ctttgctcac atgttttctt gctgaccttc    18600
tccccactat caccctgttc tcctgccgca ttccccttgc tgaggtagtg aaaatagtaa    18660
tcaataaata ctgagggaac tcagagaccg gtgccagcgc gggtcctccg tatgctgagt    18720
gacggtccct tgggcccact gttccttctc tatactttgt ctctgtgtct tatttctttt    18780
ctcagtctct cgtcccacct gacgagaaat acccacaggt gtggaggggc tggacaccc     18840 ttcgagccag gattatcagg gcatttgggg gtctgcaaaa ctaagcccca actcatcgat    18900
ttcacaactt catccagagc cagcctgaac agtagttgcc catgatttct atgccttaat    18960
acgagaagag aacatagggg ctgggtgcca agtaggtaga cagggagggc agggaactct    19020
aagacagagc ttgaggggct cattcctctt gcaaaatgaa acaaaaacca cagcactgaa    19080
tatgtaaatc tcggtggctg aaccctcct aggatagtaa gccctgacac aattgctgct     19140
atcttctctt tctctcaagg aagtcaaaaa acacctgcag ccttactgtc cccttggaaa    19200
caagatgaac atctacattt tctaaagtgg gacaagaatc tctgttcata tttatgtccc    19260
atgcatttgc acgtggccgg acaaaggact ttgcttctgc cagcacatct gtcttcagat    19320
atgagaggaa acagacacaa cctgaggcg gcaaagaagc agctcttcct caagtgacct     19380
cctctatctc cctacttcct ggctaatggg gcagccttga tccttgggaa tccaggacag    19440
atatccactc gtgacaaact agctggaaga atgacaacca atcaggttcc aagcaccact    19500
```

```
ggatgtgaac cacagaattt cctcctctcc ttgtggaatg tcagcttacg tctgacaaaa   19560
aatgtaaaac tgagagagtt acaatcttaa ggaggagtca agctaaagca gaaagaatca   19620
cctactctgg actccagcat gactgctgag ctcaaatata tatagagaga gaaagaacca   19680
caaacttgaa gatggatatc agctacagac tttcctgagt caggtaggga aatggccatc   19740
cctcaaacct tgcaaaaggc aaacttatgc cattgtgtcc tctgacatac tgggtgatgt   19800
actgtatgtt actgatgtga ggggaacttc ctaaattggc tagtaaatta tgccaaataa   19860
aaagcaaaaa tgatatttct tgaaatgtta catctgagga acattgctaa ataaatttat   19920
cagtagtttt caggatgatt tatagatgtg cattgaagtg tgtacttgtg ctctctctct   19980
cctctctctc tctcttctc tcctctctct cgctctttct ctccttgccc cctccctcc   20040 ctgactttcc ttcctgtccc ctccacagca gtttatattt ttttttctgat aatctaactt   20100 tgctgagggt tcaatgtaaa gcaccttcag tgatgagtta gttggaatgt tccccaagaa   20160
attctatttc cagcactctt ttacatgaaa tccaagaagc tctcagacta tcttactgac   20220
accttgcctt tcctcaacag atcaatctta tcaatgtcca tcacagatat tttgtagaac   20280
ggtggatcct ggcagagtct cacagatgct tctgagacaa catttgcttt caaaaaatga   20340
accacacaca tcctaaagat ctcagccact tcccatgttt cattttgtgt tacagcaaac   20400
atcacaacaa tcattcctac agatcaccac tgcatgtgat caataaaata gttttttgcaa   20460 caatggtact tatgataatc atcttttatt gtttacaaat actgctttac aatagttatt   20520
cggttgcact gttcatatta gatttccaat tagctcactt aggaacataa gtccctcgaa   20580
cagctcagtc atctttttca ttcctgtttc tatcccctac atctctttcc tttgcagacg   20640
actatctcct acactgaaac aggaaagctt ttaccttttt ggcatgcttg atttaaagat   20700
tatagaaaag tatttgacaa agaaaactca cacatgtgtg tacatatctt ttaaaaagtt   20760
atgtttatgc attgcacagg aatatcgaga atgctaatag gcaatgtcag agtttactgt   20820
ttttcaaaat tagtacagtt ttattatttc taaaaactat aaaatgaata tattcacatc   20880
accatacaga gagtaggag gagatggcat aaagtgtcat tgttcctcct ctgcaatccc   20940
aggagataac taccaagcac aatttatgtc ttttaaaatt cagcccgtat ttatatacat   21000
atatattcaa tgtagatggg atcatgatat ctcaccacac atactcttca gtgacctgca   21060
ttttcacaaa caccttccac gtaactatat agaagtctac gtcttcccct taatgtctgc   21120
tttgtgctac attgtaaagc tctagcacag tttaaccaaa ctcctattaa tgaggatttt   21180 agttatttt cactctttaa acaatatttc catgtgtagt cttatacata cgtctgtaca   21240
cacttatccc agtctaagga gttccttta ccttccccca tcccagcatt ccctgtcacg   21300
cttgttgctt ccgttgagtg actttactcc tggagtataa tctgcgtata gttcagttaa   21360
aaacatggga tctgagttta ggtcacagct ctgccactta ctgccataag ccagttcctt   21420
gacctctctg ccctcaagtt tttgcaccta caaagtaggg gataatatta gttcctagtt   21480
catagagtct tgggaataat taaatgtgat gatccatgta caatgtctgg cacttagtaa   21540
gtgctcaata aatgtcaccc tttatgattg gtattgcgtg tatgtctgca gagaaaatca   21600
ctttgtgtcc cctttaaaaa aggactatgc ccttggtcag ctattttgca cattaaattt   21660
cacttgccaa tattaactct ccacctctaa cttgatccct ctccttcctc atcttctggt   21720
gagaccaaat gctaattctg ctattcaagg caactagcaa agctgccagt gacagaatca   21780
aataaaccta cccctaatct ttagaattgt agttatgatt tctgttgtaa aagttactgt   21840
tgtggcagtc agtattagtc tttggtctat gatagcatct ctgatctatt attgayttc   21900
```

```
aattakgtat tttttttttat ttattctgaa aatgtttgtt aagcatttgc taagtaaaga   21960
tactggackg agcctcccaa atacagggca aataaaacat caaacagctt ataatttaga   22020
agggtagaag agaatctgaa agcaggtaaa aataaacagg cactcggctg ggcgcggtgg   22080
ctcacgcctg taatcccagc actttgggag gccgaggtgg gcggatcacg aggtcaggag   22140
atcgagacca tcctggctaa cacggtgaaa ccccgtctct actaaaaata caaaaaatta   22200
gcgaggcgtg gtggcgggcg cctttagtcc cagctagtcg ggaggctgag gcaggagaat   22260
ggtgtgaacc cgggaggcgg agcttgcagt gagccaagat cgcaccactg cactccagcc   22320
tgggygacag agcgagactc cgtctcaaaa aaaataaata aataaaataa aaaataatta   22380
ggtactctag gcccagtgac ctgtctctgt actctgtaaa ttcaggtcac ctgctcaggg   22440
ctaatctgag agaaggtctc tcttcagttg aattttgaaa gacaattagc agttcacaag   22500
ctaacccagg tggacaaaga tgttcccaag cagagggagt gcttgtgaaa gctggaggcc   22560
atagaaaaac tctaaggagt gtagggaggt gggagtaatg tatggaaggg gtggagatgg   22620
aaggttaaga gagatacaag gctgcaaaaa tggagctgga ctcaaaagaa aatactgaaa   22680
aggtcttcag tgttgttgat gagattacta tggaaacact atggaacact gggactccat   22740
ggcagctcca aagatggcat gcgcctggtc cagctcagta agagctgagc tcttcctgtg   22800
```

<210> SEQ ID NO 159
<211> LENGTH: 154
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 159

```
tctggcaaca cggcctccct gaccgtctct gggctccagg ctgaggatga ggctgattat     60
tactgcagct catatgcagg cagcaacaat ttaagtcttc ggaactggga ccaaggtcac    120
cgtcctaggt cagcccaagt ccactcccac tctc                                154
```

<210> SEQ ID NO 160
<211> LENGTH: 156
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 160

```
tcagggacaa tggccacctt gactatcagt ggggcccagg tggaggatga agctgactac     60
tactgttact caacagacag cagtggtaat cattatgtct cggaactggg accaaggtc     120 accgtcctag gtcagcccaa gtccactccc actctc                              156
```

<210> SEQ ID NO 161
<211> LENGTH: 150
<212> TYPE: DNA
<213> ORGANISM: Artificial Sequence
<220> FEATURE:
<223> OTHER INFORMATION: Description of Artificial Sequence: Synthetic
      polynucleotide

```
<400> SEQUENCE: 161
tctgggaaca cagccactct gaccatcagc gggacccagg ctatggatga ggctgactat      60
tactgtcagg cgtgggacag cagcactgcc gtcttcggaa ctgggaccaa ggtcaccgtc     120
ctaggtcagc ccaagtccac tcccactctc                                      150

<210> SEQ ID NO 162
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 162
aggtggaaac acggtgagag t                                                21

<210> SEQ ID NO 163
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 163
ccactcgggg aaaagttgga a                                                21
```

HUMANIZED LIGHT CHAIN MICE

CROSS-REFERENCE TO RELATED APPLICATIONS

This application is a continuation of U.S. application Ser. No. 15/585,023, filed May 2, 2017, which is a divisional of U.S. application Ser. No. 13/716,238, filed Dec. 17, 2012, which claims the benefit under 35 USC § 119(e) of U.S. Provisional Application Ser. No. 61/578,097, filed Dec. 20, 2011, which applications are hereby incorporated by reference in their entirety.

SEQUENCE LISTING

The instant application contains a Sequence Listing that has been submitted electronically in ASCII format and is hereby incorporated by reference in its entirety. The ASCII copy, created on Jan. 16, 2020, is named 2010794-1955_SL.txt and is 111,334 bytes in size.

FIELD OF INVENTION

Genetically modified non-human fertile animals that express human immunoglobulin λ light chain variable sequences cognate with human heavy chain variable sequences. Genetically modified mice, cells, embryos, and tissues that comprise a nucleic acid sequence encoding an ADAM6a functional in a mouseADAM6 locus are described, wherein the mice, cells, embryos, and tissues comprise human immunoglobulin lambda light chain gene segments that are capable of rearranging to form a functional immunoglobulin light chain variable domain. Modifications include human and/or humanized immunoglobulin loci. Mice that comprise ADAM6 function are described, including mice that comprise an ectopic nucleic acid sequence that encodes an ADAM6 protein. Genetically modified male mice that comprise a genetic modification of an endogenous mouse immunoglobulin $V_H$ region locus, and that further comprise ADAM6 activity are described, including mice that comprise an ectopic nucleic acid sequence that restores fertility to the male mouse.

Genetically modified non-human fertile animals that comprise a deletion or a modification of an endogenous ADAM6 gene or homolog or ortholog thereof, and that comprise a genetic modification that restores ADAM6 (or homolog or ortholog thereof) function in whole or in part, wherein the non-human animals express a human immunoglobulin λ variable sequence in the context of a λ or a κ light chain constant sequence.

BACKGROUND

Pharmaceutical applications for antibodies in the last two decades has fueled a great deal of research into making antibodies that are suitable for use as human therapeutics. Early antibody therapeutics, based on mouse antibodies, were not ideal as human therapeutics because repeatedly administering mouse antibodies to humans results in immunogenicity problems that can confound long-term treatment regimens. Solutions based on humanizing mouse antibodies to make them appear more human and less mouse-like were developed. Methods for expressing human immunoglobulin sequences for use in antibodies followed, mostly based on in vitro expression of human immunoglobulin libraries in phage, bacteria, or yeast. Finally, attempts were made to make useful human antibodies from human lymphoctyes in vitro, in mice engrafted with human hematopoietic cells, and in transchromosomal or transgenic mice with disabled endogenous immunoglobulin loci. In the transgenic mice, it was necessary to disable the endogenous mouse immunoglobulin genes so that the randomly integrated fully human transgenes would function as the source of immunoglobulin sequences expressed in the mouse. Such mice can make human antibodies suitable for use as human therapeutics, but these mice display substantial problems with their immune systems. These problems (1) make the mice impractical for generating a sufficiently diverse antibody repertoire, (2) require the use of extensive re-engineering fixes, (3) provide a suboptimal clonal selection process likely due to incompatibility between human and mouse elements, and (4) render these mice an unreliable source of large and diverse populations of human variable sequences needed to be truly useful for making human therapeutics.

Transgenic mice that contain fully human antibody transgenes contain randomly inserted transgenes that contain unrearranged human immunoglobulin heavy chain variable sequences (V, D, and J sequences) linked to human heavy chain constant sequences, and unrearranged human immunoglobulin light chain variable sequences (V and J) linked to human light chain constant sequences. The mice therefore generate rearranged antibody genes from loci other than endogenous mouse loci, where the rearranged antibody genes are fully human. In general, the mice contain human heavy chain sequences and human κ light chain sequences, although mice with at least some human λ sequences have also been reported. The transgenic mice generally have damaged and nonfunctional endogenous immunoglobulin loci, or knockouts of endogenous immunoglobulin loci, so that the mice are incapable of rearranging human antibody sequences at an endogenous mouse immunoglobulin locus. The vagaries of such transgenic mice render them less than optimal for generating a sufficiently diverse human antibody repertoire in mice, likely due at least in part to a suboptimal clonal selection process that interfaces fully human antibody molecules within an endogenous mouse selection system.

There remains a need in the art for making improved genetically modified non-human animals that are useful in generating immunoglobulin sequences, including human antibody sequences, and that are useful in generating a sufficiently diverse human antibody repertoire. There also remains a need for mice that are capable of rearranging immunoglobulin gene segments to form useful rearranged immunoglobulin genes, including human heavy chain variable domains that are cognate with human λ or human κ variable domains, or that are capable of making proteins from altered immunoglobulin loci, including loci that contain a sufficiently diverse selection of human λ and/or human κ light chain variable sequences. There is a need for non-human animals that can generate antibody variable regions from both human κ and human λ segments, wherein the human κ and human λ segments are cognate with human heavy chain variable domains. There is also a need for increased usage in genetically modified animals of human λ sequences.

SUMMARY OF INVENTION

Genetically modified non-human animals are described that comprise a modification that reduces or eliminates activity of an ADAM6 gene or homolog or ortholog thereof, wherein the modification results in a loss of fertility, and the animals further comprise a sequence that encodes an activity that complements or rescues the lost or reduced ADAM6 activity (or homolog or ortholog activity), and the non-human animals further comprise modifications that enable them to express human immunoglobulin heavy chain variable regions that are cognate with human immunoglobulin λ light chain variable regions. In various aspects, the human immunoglobulin light chain variable regions are expressed fused to λ or κ constant regions.

In various aspects, the sequence that encodes ADAM6 activity is contiguous with a human immunoglobulin sequence. In various aspects, the sequence that encodes ADAM6 activity is contiguous with a non-human immunoglobulin sequence. In various aspects, the sequence is present on the same chromosome as the endogenous non-human immunoglobulin heavy chain locus of the non-human animal. In various aspects, the sequence is present on a different chromosome than the immunoglobulin heavy chain locus of the non-human animal.

Genetically modified non-human animals are described that comprise a modification that maintains activity of an ADAM6 gene or homolog or ortholog thereof, wherein the modification includes insertion of one or more human immunoglobulin heavy chain gene segments upstream of a non-human immunoglobulin heavy chain constant region, and the non-human animals further comprise modifications that enable them to express human immunoglobulin λ light chain variable regions cognate with human immunoglobulin heavy chain variable regions. In various aspects, the human immunoglobulin λ light chain variable regions are expressed fused to λ or κ constant regions.

In various aspects, the insertion of one or more human immunoglobulin heavy chain gene segments is performed 3' or downstream of the ADAM6 gene of the non-human animal. In various aspects, the insertion of one or more human immunoglobulin heavy chain gene segments is performed in a manner such that the ADAM6 gene(s) of the non-human animal are not disrupted, deleted and/or functionally silenced such that the ADAM6 activity of the non-human animal is at the same or comparable level as in a non-human animal that does not contain such an insertion. Exemplary disruptions, deletions and/or functionally silencing modifications include any modifications that result in a reduction, elimination and/or loss of activity of the ADAM6 protein(s) encoded by the ADAM6 gene(s) of the non-human animal.

In one aspect, nucleic acid constructs, cells, embryos, mice, and methods are provided for making mice that comprise a modification that results in a nonfunctional endogenous mouse ADAM6 protein or ADAM6 gene (e.g., a knockout of or a deletion in an endogenous ADAM6 gene), wherein the mice comprise a nucleic acid sequence that encodes an ADAM6 protein or ortholog or homolog or fragment thereof that is functional in a male mouse.

In one aspect, nucleic acid constructs, cells, embryos, mice, and methods are provided for making mice that comprise a modification of an endogenous mouse immunoglobulin locus, wherein the mice comprise an ADAM6 protein or ortholog or homolog or fragment thereof that is functional in a male mouse. In one embodiment, the endogenous mouse immunoglobulin locus is an immunoglobulin heavy chain locus, and the modification reduces or eliminates ADAM6 activity of a cell or tissue of a male mouse.

In one aspect, mice are provided that comprise an ectopic nucleotide sequence encoding a mouse ADAM6 or ortholog or homolog or functional fragment thereof; mice are also provided that comprise an endogenous nucleotide sequence encoding a mouse ADAM6 or ortholog or homolog or fragment thereof, and at least one genetic modification of a heavy chain immunoglobulin locus.

In one aspect, methods are provided for making mice that comprise a modification of an endogenous mouse immunoglobulin locus, wherein the mice comprise an ADAM6 protein or ortholog or homolog or fragment thereof that is functional in a male mouse.

In one aspect, methods are provided for making mice that comprise a genetic modification of a heavy chain immunoglobulin locus, wherein application of the methods result in male mice that comprise a modified heavy chain immunoglobulin locus (or a deletion thereof), and the male mice are capable of generating offspring by mating. In one embodiment, the male mice are capable of producing sperm that can transit from a mouse uterus through a mouse oviduct to fertilize a mouse egg.

In one aspect, methods are provided for making mice that comprise a genetic modification of an immunoglobulin heavy chain locus and an immunoglobulin light chain locus, wherein application of the methods to modify the heavy chain locus result in male mice that exhibit a reduction in fertility, and the mice comprise a genetic modification that restores in whole or in part the reduction in fertility. In various embodiments, the reduction in fertility is characterized by an inability of the sperm of the male mice to migrate from a mouse uterus through a mouse oviduct to fertilize a mouse egg. In various embodiments, the reduction in fertility is characterized by sperm that exhibit an in vivo migration defect. In various embodiments, the genetic modification that restores in whole or in part the reduction in fertility is a nucleic acid sequence encoding a mouse ADAM6 gene or ortholog or homolog or fragment thereof that is functional in a male mouse.

In one embodiment, the genetic modification comprises replacing endogenous immunoglobulin heavy chain variable loci with immunoglobulin heavy chain variable loci of another species (e.g., a non-mouse species). In one embodiment, the genetic modification comprises insertion of orthologous immunoglobulin heavy chain variable loci into endogenous immunoglobulin heavy chain variable loci. In a specific embodiment, the species is human. In one embodiment, the genetic modification comprises deletion of an endogenous immunoglobulin heavy chain variable locus in whole or in part, wherein the deletion results in a loss of endogenous ADAM6 function. In a specific embodiment, the loss of endogenous ADAM6 function is associated with a reduction in fertility in male mice.

In one embodiment, the genetic modification comprises inactivation of an endogenous non-human immunoglobulin heavy chain variable locus in whole or in part, wherein the inactivation does not result in a loss of endogenous ADAM6 function. Inactivation may include replacement or deletion of one or more endogenous non-human gene segments resulting in an endogenous non-human immunoglobulin heavy chain locus that is substantially incapable of rearrangement to encode a heavy chain of an antibody that comprises endogenous non-human gene segments. Inactivation may include other modifications that render the endogenous immunoglobulin heavy chain locus incapable of rearranging to encode the heavy chain of an antibody, wherein the modification does not include replacement or deletion of endogenous gene segments. Exemplary modifications include chromosomal inversions and/or translocations mediated by molecular techniques, e.g., using precise placement of site-specific recombination sites (e.g., Cre-lox technology). Other exemplary modifications include disabling the operable linkage between the non-human immunoglobulin variable gene segments and the non-human immunoglobulin constant regions.

In one embodiment, the genetic modification comprises inserting into the genome of the non-human animal a DNA fragment containing one or more human $V_H$ gene segments, one or more human $D_H$ gene segments and one or more human $J_H$ gene segments of another species (e.g., a non-mouse species) operably linked to one or more constant region sequences (e.g., an IgM and/or an IgG gene). In one embodiment, the DNA fragment is capable of undergoing rearrangement in the genome of the non-human animal to form a sequence that encodes a heavy chain variable domain of an antibody. In one embodiment, the species is human. In one embodiment, the genetic modification comprises insertion of one or more human immunoglobulin heavy chain gene segments downstream or 3' of an endogenous ADAM6 gene of the non-human animal such that ADAM6 activity (e.g. expression and/or function of an encoded protein) is the same or comparable to a non-human animal that does not comprise the insertion.

In one aspect, mice are provided that comprise a modification that reduces or eliminates mouse ADAM6 expression from an endogenous ADAM6 allele such that a male mouse having the modification exhibits a reduced fertility (e.g., a highly reduced ability to generate offspring by mating), or is essentially infertile, due to the reduction or elimination of endogenous ADAM6 function, wherein the mice further comprise an ectopic ADAM6 sequence or homolog or ortholog or functional fragment thereof. In one aspect, the modification that reduces or eliminates mouse ADAM6 expression is a modification (e.g., an insertion, a deletion, a replacement, etc.) in a mouse immunoglobulin locus.

In one embodiment, the reduction or loss of ADAM6 function comprises an inability or substantial inability of the mouse to produce sperm that can travel from a mouse uterus through a mouse oviduct to fertilize a mouse egg. In a specific embodiment, at least about 95%, 96%, 97%, 98%, or 99% of the sperm cells produced in an ejaculate volume of the mouse are incapable of traversing through an oviduct in vivo following copulation and fertilizing a mouse ovum.

In one embodiment, the reduction or loss of ADAM6 function comprises an inability to form or substantial inability to form a complex of ADAM2 and/or ADAM3 and/or ADAM6 on a surface of a sperm cell of the mouse. In one embodiment, the loss of ADAM6 function comprises a substantial inability to fertilize a mouse egg by copulation with a female mouse.

In one aspect, a mouse is provided that lacks a functional endogenous ADAM6 gene, and comprises a protein (or an ectopic nucleotide sequence that encodes a protein) that confers ADAM6 functionality on the mouse. In one embodiment, the mouse is a male mouse and the functionality comprises enhanced fertility as compared with a mouse that lacks a functional endogenous ADAM6 gene.

In one embodiment, the protein is encoded by a genomic sequence located within an immunoglobulin locus in the germline of the mouse. In a specific embodiment, the immunoglobulin locus is a heavy chain locus. In another specific embodiment, the heavy chain locus comprises at least one human $V_H$, at least one human $D_H$ and at least one human $J_H$ gene segment. In one embodiment, the ectopic protein is encoded by a genomic sequence located within a non-immunoglobulin locus in the germline of the mouse. In one embodiment, the non-immunoglobulin locus is a transcriptionally active locus. In a specific embodiment, the transcriptionally active locus is the ROSA26 locus. In a specific embodiment, the transcriptionally active locus is associated with tissue-specific expression. In one embodiment, the tissue-specific expression is present in reproductive tissues. In one embodiment, the protein is encoded by a genomic sequence randomly inserted into the germline of the mouse.

In one embodiment, the mouse comprises a human or chimeric human/mouse or chimeric human/rat light chain (e.g., human variable, mouse or rat constant) and a chimeric human variable/mouse or rat constant heavy chain. In a specific embodiment, the mouse comprises a transgene that comprises a chimeric human variable/rat or mouse constant light chain gene operably linked to a transcriptionally active promoter, e.g., a ROSA26 promoter. In a further specific embodiment, the chimeric human/mouse or rat light chain transgene comprises a rearranged human light chain variable region sequence in the germline of the mouse.

In one embodiment, the ectopic nucleotide sequence is located within an immunoglobulin locus in the germline of the mouse. In a specific embodiment, the immunoglobulin locus is a heavy chain locus. In one embodiment, the heavy chain locus comprises at least one human $V_H$, at least one human $D_H$ and at least one human $J_H$ gene segment. In one embodiment, the ectopic nucleotide sequence is located within a non-immunoglobulin locus in the germline of the mouse. In one embodiment, the non-immunoglobulin locus is a transcriptionally active locus. In a specific embodiment, the transcriptionally active locus is the ROSA26 locus. In one embodiment, the ectopic nucleotide sequence is positioned randomly inserted into the germline of the mouse.

In one aspect, a mouse is provided that lacks a functional endogenous ADAM6 gene, wherein the mouse comprises an ectopic nucleotide sequence that complements the loss of mouse ADAM6 function. In one embodiment, the ectopic nucleotide sequence confers upon the mouse an ability to produce offspring that is comparable to a corresponding wild-type mouse that contains a functional endogenous ADAM6 gene. In one embodiment, the sequence confers upon the mouse an ability to form a complex of ADAM2 and/or ADAM3 and/or ADAM6 on the surface of sperm cell of the mouse. In one embodiment, the sequence confers upon the mouse an ability to travel from a mouse uterus through a mouse oviduct to a mouse ovum to fertilize the ovum.

In one embodiment, the mouse lacking the functional endogenous ADAM6 gene and comprising the ectopic nucleotide sequence produces at least about 50%, 60%, 70%, 80%, or 90% of the number of litters a wild-type mouse of the same age and strain produces in a six-month time period.

In one embodiment, the mouse lacking the functional endogenous ADAM6 gene and comprising the ectopic nucleotide sequence produces at least about 1.5-fold, about 2-fold, about 2.5-fold, about 3-fold, about 4-fold, about 6-fold, about 7-fold, about 8-fold, or about 10-fold or more progeny when bred over a six-month time period than a mouse of the same age and the same or similar strain that lacks the functional endogenous ADAM6 gene and that lacks the ectopic nucleotide sequence that is bred over substantially the same time period and under substantially the same conditions.

In one embodiment, the mouse lacking the functional endogenous ADAM6 gene and comprising the ectopic nucleotide sequence produces an average of at least about 2-fold, 3-fold, or 4-fold higher number of pups per litter in a 4- or 6-month breeding period than a mouse that lacks the functional endogenous ADAM6 gene and that lacks the ectopic nucleotide sequence, and that is bred for the same period of time.

In one embodiment, the mouse lacking the functional endogenous ADAM6 gene and comprising the ectopic nucleotide sequence is a male mouse, and the male mouse produces sperm that when recovered from oviducts at about 5-6 hours post-copulation reflects an oviduct migration that is at least 10-fold, at least 20-fold, at least 30-fold, at least 40-fold, at least 50-fold, at least 60-fold, at least 70-fold, at least 80-fold, at least 90-fold, 100-fold, 110-fold, or 120-fold or higher than a mouse that lacks the functional endogenous ADAM6 gene and that lacks the ectopic nucleotide sequence.

In one embodiment, the mouse lacking the functional endogenous ADAM6 gene and comprising the ectopic nucleotide sequence when copulated with a female mouse generates sperm that is capable of traversing the uterus and entering and traversing the oviduct within about 6 hours at an efficiency that is about equal to sperm from a wild-type mouse.

In one embodiment, the mouse lacking the functional endogenous ADAM6 gene and comprising the ectopic nucleotide sequence produces about 1.5-fold, about 2-fold, about 3-fold, or about 4-fold or more litters in a comparable period of time than a mouse that lacks the functional ADAM6 gene and that lacks the ectopic nucleotide sequence.

In one aspect, a mouse comprising, in its germline, a non-mouse nucleic acid sequence that encodes an immunoglobulin protein is provided, wherein the non-mouse immunoglobulin sequence comprises an insertion of a mouse ADAM6 gene or homolog or ortholog or functional fragment thereof. In one embodiment, the non-mouse immunoglobulin sequence comprises a human immunoglobulin sequence. In one embodiment, the sequence comprises a human immunoglobulin heavy chain sequence. In one embodiment, the sequence comprises a human immunoglobulin light chain sequence. In one embodiment, the sequence comprises one or more V gene segments, one or more D gene segments, and one or more J gene segments; in one embodiment, the sequence comprises one or more V gene segments and one or more J gene segments. In one embodiment, the one or more V, D, and J gene segments, or one or more V and J gene segments, are unrearranged. In one embodiment, the one or more V, D, and J gene segments, or one or more V and J gene segments, are rearranged. In one embodiment, following rearrangement of the one or more V, D, and J gene segments, or one or more V and J gene segments, the mouse comprises in its genome at least one nucleic acid sequence encoding a mouse ADAM6 gene or homolog or ortholog or functional fragment thereof. In one embodiment, following rearrangement the mouse comprises in its genome at least two nucleic acid sequences encoding a mouse ADAM6 gene or homolog or ortholog or functional fragment thereof. In one embodiment, following rearrangement the mouse comprises in its genome at least one nucleic acid sequence encoding a mouse ADAM6 gene or homolog or ortholog or functional fragment thereof. In one embodiment, the mouse comprises the ADAM6 gene or homolog or ortholog or functional fragment thereof in a B cell. In one embodiment, the mouse comprises the ADAM6 gene or homolog or ortholog or functional fragment thereof in a non-B cell.

In one aspect, mice are provided that express a human immunoglobulin heavy chain variable region or functional fragment thereof from an endogenous mouse immunoglobulin heavy chain locus, wherein the mice comprise an ADAM6 activity that is functional in a male mouse.

In one embodiment, the male mice comprise a single unmodified ADAM6 allele or ortholog of homolog or functional fragment thereof at an endogenous ADAM6 locus.

In one embodiment, the male mice comprise an ectopic mouse ADAM6 sequence or homolog or ortholog or functional fragment thereof that encodes a protein that confers ADAM6 function.

In one embodiment, the male mice comprise an ADAM6 sequence or homolog or ortholog or functional fragment thereof at a location in the mouse genome that approximates the location of the endogenous mouse ADAM6 allele, e.g., 3' of a V gene segment sequence and 5' of an initial D gene segment.

In one embodiment, the male mice comprise an ADAM6 sequence or homolog or ortholog or functional fragment thereof flanked upstream, downstream, or upstream and downstream (with respect to the direction of transcription of the ADAM6 sequence) of a nucleic acid sequence encoding an immunoglobulin variable gene segment. In a specific embodiment, the immunoglobulin variable gene segment is a human gene segment. In one embodiment, the immunoglobulin variable gene segment is a human gene segment, and the sequence encoding the mouse ADAM6 or ortholog or homolog or fragment thereof functional in a mouse is between human V gene segments; in one embodiment, the mouse comprises two or more human V gene segments, and the sequence is at a position between the final V gene segment and the penultimate V gene segment; in one embodiment, the sequence is at a position following the final V gene segment and the first D gene segment.

In one embodiment, the male mice comprise an ADAM6 sequence or homolog or ortholog or functional fragment thereof that is located at a position in an endogenous immunoglobulin locus that is the same or substantially the same as in a wild type male mouse. In a specific embodiment, the endogenous locus is incapable of encoding the heavy chain variable region of an antibody, wherein the variable region comprises or is derived from an endogenous non-human gene segment. In a specific embodiment, the endogenous locus is positioned at a location in the genome of the male mouse that renders it incapable of encoding the heavy chain variable region of an antibody. In various embodiments, the male mice comprise an ADAM6 sequence located on the same chromosome as human immunoglobulin gene segments and the ADAM6 sequence encodes a functional ADAM6 protein.

In one aspect, a male mouse is provided that comprises a nonfunctional endogenous ADAM6 gene, or a deletion of an endogenous ADAM6 gene, in its germline; wherein sperm cells of the mouse are capable of transiting an oviduct of a female mouse and fertilizing an egg.

In one aspect, a male mouse is provided that comprises a functional endogenous ADAM6 gene and a modification to an endogenous immunoglobulin heavy chain locus. In one embodiment, the modification is made downstream, or 3', of the endogenous ADAM6 gene. In one embodiment, the modification is a replacement of one or more endogenous immunoglobulin heavy chain gene segments with one or more human immunoglobulin heavy chain gene segments. In one embodiment, the modification is an insertion of one or more human immunoglobulin heavy chain gene segments upstream of an endogenous immunoglobulin heavy chain constant region gene.

In one aspect, mice are provided that comprise a genetic modification that reduces endogenous mouse ADAM6 function, wherein the mouse comprises at least some ADAM6 functionality provided either by an endogenous unmodified allele that is functional in whole or in part (e.g., a heterozygote), or by expression from an ectopic sequence that encodes an ADAM6 or an ortholog or homolog or functional fragment thereof that is functional in a male mouse.

In one embodiment, the mice comprise ADAM6 function sufficient to confer upon male mice the ability to generate offspring by mating, as compared with male mice that lack a functional ADAM6. In one embodiment, the ADAM6 function is conferred by the presence of an ectopic nucleotide sequence that encodes a mouse ADAM6 or a homolog or ortholog or functional fragment thereof. In one embodiment, the ADAM6 function is conferred by an endogenous ADAM6 gene present in an endogenous immunoglobulin locus, wherein the endogenous immunoglobulin locus is incapable of encoding the heavy chain variable region of an antibody. ADAM6 homologs or orthologs or fragments thereof that are functional in a male mouse include those that restore, in whole or in part, the loss of ability to generate offspring observed in a male mouse that lacks sufficient endogenous mouse ADAM6 activity, e.g., the loss in ability observed in an ADAM6 knockout mouse. In this sense ADAM6 knockout mice include mice that comprise an endogenous locus or fragment thereof, but that is not functional, i.e., that does not express ADAM6 (ADAM6a and/or ADAM6b) at all, or that expresses ADAM6 (ADAM6a and/or ADAM6b) at a level that is insufficient to support an essentially normal ability to generate offspring of a wild-type male mouse. The loss of function can be due, e.g., to a modification in a structural gene of the locus (i.e., in an ADAM6a or ADAM6b coding region) or in a regulatory region of the locus (e.g., in a sequence 5' to the ADAM6a gene, or 3' of the ADAM6a or ADAM6b coding region, wherein the sequence controls, in whole or in part, transcription of an ADAM6 gene, expression of an ADAM6 RNA, or expression of an ADAM6 protein). In various embodiments, orthologs or homologs or fragments thereof that are functional in a male mouse are those that enable a sperm of a male mouse (or majority of sperm cells in the ejaculate of a male mouse) to transit a mouse oviduct and fertilize a mouse ovum.

In one embodiment, male mice that express the human immunoglobulin variable region or functional fragment thereof comprise sufficient ADAM6 activity to confer upon the male mice the ability to generate offspring by mating with female mice and, in one embodiment, the male mice exhibit an ability to generate offspring when mating with female mice that is in one embodiment at least 25%, in one embodiment, at least 30%, in one embodiment at least 40%, in one embodiment at least 50%, in one embodiment at least 60%, in one embodiment at least 70%, in one embodiment at least 80%, in one embodiment at least 90%, and in one embodiment about the same as, that of mice with one or two endogenous unmodified ADAM6 alleles.

In one embodiment male mice express sufficient ADAM6 (or an ortholog or homolog or functional fragment thereof) to enable a sperm cell from the male mice to traverse a female mouse oviduct and fertilize a mouse egg.

In one embodiment, the ADAM6 functionality is conferred by a nucleic acid sequence that is contiguous with a mouse chromosomal sequence (e.g., the nucleic acid is randomly integrated into a mouse chromosome; or placed at a specific location, e.g., by targeting the nucleic acid to a specific location, e.g., by site-specific recombinase-mediated (e.g., Cre-mediated) insertion or homologous recombination). In one embodiment, the ADAM6 sequence is present on a nucleic acid that is distinct from a chromosome of the mouse (e.g., the ADAM6 sequence is present on an episome, extrachromosomally, e.g., in an expression construct, a vector, a YAC, a transchromosome, etc.).

In one aspect, genetically modified mice and cells are provided that comprise a modification of an endogenous immunoglobulin heavy chain locus, wherein the mice express at least a portion of an immunoglobulin heavy chain sequence, e.g., at least a portion of a human sequence, wherein the mice comprise an ADAM6 activity that is functional in a male mouse. In one embodiment, the modification reduces or eradicates an ADAM6 activity of the mouse. In one embodiment, the mouse is modified such that both alleles that encode ADAM6 activity are either absent or express an ADAM6 that does not substantially function to support normal mating in a male mouse. In one embodiment, the mouse further comprises an ectopic nucleic acid sequence encoding a mouse ADAM6 or ortholog or homolog or functional fragment thereof. In one embodiment, the modification maintains ADAM6 activity of the mouse and renders an endogenous immunoglobulin heavy chain locus incapable of encoding a heavy chain variable region of an antibody. In a specific embodiment, the modification includes chromosomal inversions and or translocations that render the endogenous immunoglobulin heavy chain variable gene segments incapable of rearranging to encode a heavy chain variable region of antibody that is operably linked to a heavy chain constant region.

In one aspect, genetically modified mice and cells are provided that comprise a modification of an endogenous immunoglobulin heavy chain locus, wherein the modification reduces or eliminates ADAM6 activity expressed from an ADAM6 sequence of the locus, and wherein the mice comprise an ADAM6 protein or ortholog or homolog or functional fragment thereof. In various embodiments, the ADAM6 protein or fragment thereof is encoded by an ectopic ADAM6 sequence. In various embodiments, the ADAM6 protein or fragment thereof is expressed from an endogenous ADAM6 allele. In various embodiments, the mouse comprises a first immunoglobulin heavy chain allele comprises a first modification that reduces or eliminates expression of a functional ADAM6 from the first immunoglobulin heavy chain allele, and the mouse comprises a second immunoglobulin heavy chain allele that comprises a second modification that does not substantially reduce or does not eliminate expression of a functional ADAM6 from the second immunoglobulin heavy chain allele.

In various embodiments, the modification is the insertion of one or more human immunoglobulin heavy chain gene segments upstream, or 5', of an endogenous immunoglobulin heavy chain constant region gene. In various embodiments, the modification maintains the endogenous ADAM6 gene located at the endogenous immunoglobulin heavy chain locus.

In one embodiment, the second modification is located 3' (with respect to the transcriptional directionality of the mouse V gene segment) of a final mouse V gene segment and located 5' (with respect to the transcriptional directionality of the constant sequence) of a mouse (or chimeric human/mouse) immunoglobulin heavy chain constant gene or fragment thereof (e.g., a nucleic acid sequence encoding a human and/or mouse: $C_H1$ and/or hinge and/or $C_H2$ and/or $C_H3$).

In one embodiment, the modification is at a first immunoglobulin heavy chain allele at a first locus that encodes a first ADAM6 allele, and the ADAM6 function results from expression of an endogenous ADAM6 at a second immunoglobulin heavy chain allele at a second locus that encodes a functional ADAM6, wherein the second immunoglobulin heavy chain allele comprises at least one modification of a V, D, and/or J gene segment. In a specific embodiment, the at least one modification of the V, D, and or J gene segment is a deletion, a replacement with a human V, D, and/or J gene segment, a replacement with a camelid V, D, and/or J gene segment, a replacement with a humanized or camelized V, D, and/or J gene segment, a replacement of a heavy chain sequence with a light chain sequence, and a combination thereof. In one embodiment, the at least one modification is the deletion of one or more heavy chain V, D, and/or J gene segments and a replacement with one or more light chain V and/or J gene segments (e.g., a human light chain V and/or J gene segment) at the heavy chain locus.

In one embodiment, the modification is at a first immunoglobulin heavy chain allele at a first locus and a second immunoglobulin heavy chain allele at a second locus, and the ADAM6 function results from expression of an ectopic ADAM6 at a non-immunoglobulin locus in the germline of the mouse. In a specific embodiment, the non-immunoglobulin locus is the ROSA26 locus. In a specific embodiment, the non-immunoglobulin locus is transcriptionally active in reproductive tissue.

In one embodiment, the modification is at a first immunoglobulin heavy chain allele at a first locus and a second immunoglobulin heavy chain allele at a second locus, and the ADAM6 function results from an endogenous ADAM6 gene in the germline of the mouse. In a specific embodiment, the endogenous ADAM6 gene is juxtaposed by mouse immunoglobulin gene segments.

In one embodiment, the modification is at a first immunoglobulin heavy chain allele at a first locus and a second immunoglobulin heavy chain allele at a second locus, and the ADAM6 function results from expression of an ectopic ADAM6 sequence at the first immunoglobulin heavy chain allele. In one embodiment, the modification is at a first immunoglobulin heavy chain allele at a first locus and a second immunoglobulin heavy chain allele at a second locus, and the ADAM6 function or activity results from expression of an ectopic ADAM6 at the second immunoglobulin heavy chain allele.

In one aspect, a mouse comprising a heterozygous or a homozygous knockout of ADAM6 is provided. In one embodiment, the mouse further comprises a modified immunoglobulin sequence that is a human or a humanized immunoglobulin sequence, or a camelid or camelized human or mouse immunoglobulin sequence. In one embodiment, the modified immunoglobulin sequence is present at the endogenous heavy chain immunoglobulin locus. In one embodiment, the modified immunoglobulin sequence comprises a human heavy chain variable gene sequence at an endogenous heavy chain immunoglobulin locus. In one embodiment, the human heavy chain variable gene sequence replaces an endogenous heavy chain variable sequence at the endogenous immunoglobulin heavy chain locus.

In one aspect, a mouse incapable of expressing a functional endogenous mouse ADAM6 from an endogenous mouse ADAM6 locus is provided. In one embodiment, the mouse comprises an ectopic nucleic acid sequence that encodes an ADAM6, or functional fragment thereof, that is functional in the mouse. In a specific embodiment, the ectopic nucleic acid sequence encodes a protein that rescues a loss in the ability to generate offspring exhibited by a male mouse that is homozygous for an ADAM6 knockout. In a specific embodiment, the ectopic nucleic acid sequence encodes a mouse ADAM6 protein.

In one aspect, a mouse is provided that lacks a functional endogenous ADAM6 locus, and that comprises an ectopic nucleic acid sequence that confers upon the mouse ADAM6 function. In one embodiment, the nucleic acid sequence comprises an endogenous mouse ADAM6 sequence or functional fragment thereof. In one embodiment, the endogenous mouse ADAM6 sequence comprises ADAM6a- and ADAM6b-encoding sequence located in a wild-type mouse between the 3'-most mouse immunoglobulin heavy chain V gene segment ($V_H$) and the 5'-most mouse immunoglobulin heavy chain D gene segment ($D_H$).

In one embodiment, the nucleic acid sequence comprises a sequence encoding mouse ADAM6a or functional fragment thereof and/or a sequence encoding mouse ADAM6b or functional fragment thereof, wherein the ADAM6a and/or ADAM6b or functional fragment(s) thereof is operably linked to a promoter. In one embodiment, the promoter is a human promoter. In one embodiment, the promoter is the mouse ADAM6 promoter. In a specific embodiment, the ADAM6 promoter comprises sequence located between the first codon of the first ADAM6 gene closest to the mouse 5'-most $D_H$ gene segment and the recombination signal sequence of the 5'-most $D_H$ gene segment, wherein 5' is indicated with respect to direction of transcription of the mouse immunoglobulin genes. In one embodiment, the promoter is a viral promoter. In a specific embodiment, the viral promoter is a cytomegalovirus (CMV) promoter. In one embodiment, the promoter is a ubiquitin promoter.

In one embodiment, the promoter is an inducible promoter. In one embodiment, the inducible promoter regulates expression in non-reproductive tissues. In one embodiment, the inducible promoter regulates expression in reproductive tissues. In a specific embodiment, the expression of the mouse ADAM6a and/or ADAM6b sequences or functional fragment(s) thereof is developmentally regulated by the inducible promoter in reproductive tissues.

In one embodiment, the mouse ADAM6a and/or ADAM6b are selected from the ADAM6a of SEQ ID NO:1 and/or ADAM6b of sequence SEQ ID NO:2. In one embodiment, the mouse ADAM6 promoter is a promoter of SEQ ID NO:3. In a specific embodiment, the mouse ADAM6 promoter comprises the nucleic acid sequence of SEQ ID NO:3 directly upstream (with respect to the direction of transcription of ADAM6a) of the first codon of ADAM6a and extending to the end of SEQ ID NO:3 upstream of the ADAM6 coding region. In another specific embodiment, the ADAM6 promoter is a fragment extending from within about 5 to about 20 nucleotides upstream of the start codon of ADAM6a to about 0.5 kb, 1 kb, 2 kb, or 3 kb or more upstream of the start codon of ADAM6a.

In one embodiment, the nucleic acid sequence comprises SEQ ID NO:3 or a fragment thereof that when placed into a mouse that is infertile or that has low fertility due to a lack of ADAM6, improves fertility or restores fertility to about a wild-type fertility. In one embodiment, SEQ ID NO:3 or a fragment thereof confers upon a male mouse the ability to produce a sperm cell that is capable of traversing a female mouse oviduct in order to fertilize a mouse egg.

In one embodiment, the nucleic acid sequence is any sequence encoding an ADAM6 gene or homolog or ortholog or functional fragment thereof that when placed into or maintained in a mouse yields a level of fertility that is the same or comparable to a wild-type mouse. An exemplary level of fertility may be demonstrated by the ability of a male mouse to produce a sperm cell that is capable of traversing a female mouse oviduct in order to fertilize a mouse egg.

In one aspect, a mouse is provided that comprises a deletion of an endogenous nucleotide sequence that encodes an ADAM6 protein, a replacement of an endogenous mouse $V_H$ gene segment with a human $V_H$ gene segment, and an ectopic nucleotide sequence that encodes a mouse ADAM6 protein or ortholog or homolog or fragment thereof that is functional in a male mouse.

In one embodiment, the mouse comprises an immunoglobulin heavy chain locus that comprises a deletion of an endogenous immunoglobulin locus nucleotide sequence that comprises an endogenous ADAM6 gene, comprises a nucleotide sequence encoding one or more human immunoglobulin gene segments, and wherein the ectopic nucleotide sequence encoding the mouse ADAM6 protein is within or directly adjacent to the nucleotide sequence encoding the one or more human immunoglobulin gene segments.

In one embodiment, the mouse comprises a replacement of all or substantially all endogenous $V_H$ gene segments with a nucleotide sequence encoding one or more human $V_H$ gene segments, and the ectopic nucleotide sequence encoding the mouse ADAM6 protein is within, or directly adjacent to, the nucleotide sequence encoding the one or more human $V_H$ gene segments. In one embodiment, the mouse further comprises a replacement of one or more endogenous $D_H$ gene segments with one or more human $D_H$ gene segments at the endogenous $D_H$ gene locus. In one embodiment, the mouse further comprises a replacement of one or more endogenous $J_H$ gene segments with one or more human $J_H$ gene segments at the endogenous $J_H$ gene locus. In one embodiment, the mouse comprises a replacement of all or substantially all endogenous $V_H$, $D_H$, and $J_H$ gene segments and a replacement at the endogenous $V_H$, $D_H$, and $J_H$ gene loci with human $V_H$, $D_H$, and $J_H$ gene segments, wherein the mouse comprises an ectopic sequence encoding a mouse ADAM6 protein. In one embodiment, the mouse comprises an insertion of human $V_H$, $D_H$ and $J_H$ gene segments at an endogenous immunoglobulin heavy chain locus, wherein the mouse comprises an ADAM6 gene that is functional in the mouse. In a specific embodiment, the ectopic sequence encoding the mouse ADAM6 protein is placed between the penultimate 3'-most $V_H$ gene segment of the human $V_H$ gene segments present, and the ultimate 3' $V_H$ gene segment of the human $V_H$ gene segments present. In a specific embodiment, the mouse comprises a deletion of all or substantially all mouse $V_H$ gene segments, and a replacement with all or substantially all human $V_H$ gene segments, and the ectopic nucleotide sequence encoding the mouse ADAM6 protein is placed downstream of human gene segment $V_H$1-2 and upstream of human gene segment $V_H$6-1.

In a specific embodiment, the mouse comprises a replacement of all or substantially all endogenous $V_H$ gene segments with a nucleotide sequence encoding one or more human $V_H$ gene segments, and the ectopic nucleotide sequence encoding the mouse ADAM6 protein is within, or directly adjacent to, the nucleotide sequence encoding the one or more human $V_H$ gene segments.

In one embodiment, the ectopic nucleotide sequence that encodes the mouse ADAM6 protein is present on a transgene in the genome of the mouse. In one embodiment, the ectopic nucleotide sequence that encodes the mouse ADAM6 protein is present extrachromosomally in the mouse.

In one aspect, a mouse is provided that comprises a modification of an endogenous immunoglobulin heavy chain locus, wherein the mouse expresses a B cell that comprises a rearranged immunoglobulin sequence operably linked to a heavy chain constant region gene sequence, and the B cell comprises in its genome (e.g., on a B cell chromosome) a gene encoding an ADAM6 or ortholog or homolog or fragment thereof that is functional in a male mouse. In one embodiment, the rearranged immunoglobulin sequence operably linked to the heavy chain constant region gene sequence comprises a human heavy chain V, D, and/or J sequence; a mouse heavy chain V, D, and/or J sequence; a human or mouse light chain V and/or J sequence. In one embodiment, the heavy chain constant region gene sequence comprises a human or a mouse heavy chain sequence selected from the group consisting of a $C_H1$, a hinge, a $C_H2$, a $C_H3$, and a combination thereof.

In one aspect, a mouse is provided that comprises a functionally silenced endogenous immunoglobulin heavy chain variable gene locus, wherein ADAM6 function is maintained in the mouse, and further comprises an insertion of one or more human immunoglobulin gene segments upstream or 5' of one or more mouse heavy chain constant region. In one embodiment, the one or more human immunoglobulin gene segments include one or more human $V_H$ gene segments, one or more human $D_H$ gene segments and one or more human $J_H$ gene segments. In a specific embodiment, the mouse further comprises a functionally silenced endogenous light chain locus, wherein the mouse comprises an ADAM6 activity that is the same or comparable to a wild-type mouse, and further comprises an insertion of one or more human λ light chain gene segments upstream or 5' of a mouse light chain constant region. In one embodiment, the human λ light chain gene segments comprise 12 human Vλ gene segments and one or more human Jλ gene segments. In one embodiment, the human λ light chain gene segments comprise 12 human Vλ gene segments and four human Jλ gene segments. In one embodiment, the human λ light chain gene segments comprise 28 human Vλ gene segments and one or more human Jλ gene segments. In one embodiment, the human λ light chain gene segments comprises 28 human Vλ gene segments and four human Jλ gene segments. In one embodiment, the human λ light chain gene segments comprises 40 human Vλ gene segments and one or more human Jλ gene segments. In one embodiment, the human λ light chain gene segments comprise 40 human Vλ gene segments and four human Jλ gene segments. In various embodiments, the four human Jλ gene segments include Jλ1, Jλ2, Jλ3 and Jλ7. In various embodiments, the mouse light chain constant region is a mouse Cκ or a mouse Cλ.

In one aspect, a genetically modified mouse is provided, wherein the mouse comprises a functionally silenced immunoglobulin light chain gene, and further comprises a replacement of one or more endogenous immunoglobulin heavy chain variable region gene segments with one or more human immunoglobulin heavy chain variable region gene segments, wherein the mouse lacks a functional endogenous ADAM6 locus, and wherein the mouse comprises an ectopic nucleotide sequence that expresses a mouse ADAM6 protein or an ortholog or homolog or fragment thereof that is functional in a male mouse.

In one aspect, a mouse is provided that lacks a functional endogenous mouse ADAM6 locus or sequence and that comprises an ectopic nucleotide sequence encoding a mouse ADAM6 locus or functional fragment of a mouse ADAM6 locus or sequence, wherein the mouse is capable of mating with a mouse of the opposite sex to produce a progeny that comprises the ectopic ADAM6 locus or sequence. In one embodiment, the mouse is male. In one embodiment, the mouse is female.

In one aspect, a genetically modified mouse is provided, wherein the mouse comprises a human immunoglobulin heavy chain variable region gene segment at an endogenous mouse immunoglobulin heavy chain variable region gene locus, the mouse lacks an endogenous functional ADAM6 sequence at the endogenous mouse immunoglobulin heavy chain variable region gene locus, and wherein the mouse comprises an ectopic nucleotide sequence that expresses a mouse ADAM6 protein or an ortholog or homolog or fragment thereof that is functional in a male mouse.

In one embodiment, the ectopic nucleotide sequence that expresses the mouse ADAM6 protein is extrachromosomal. In one embodiment, the ectopic nucleotide sequence that expresses the mouse ADAM6 protein is integrated at one or more loci in a genome of the mouse. In a specific embodiment, the one or more loci include an immunoglobulin locus.

In one aspect, a mouse is provided that expresses an immunoglobulin heavy chain sequence from a modified endogenous mouse immunoglobulin heavy chain locus, wherein the heavy chain is derived from a human V gene segment, a D gene segment, and a J gene segment, wherein the mouse comprises an ADAM6 activity that is functional in the mouse.

In one embodiment, the mouse comprises a plurality of human V gene segments, a plurality of D gene segments, and a plurality of J gene segments. In one embodiment, the D gene segments are human D gene segments. In one embodiment, the J gene segments are human J gene segments. In one embodiment, the mouse further comprises a humanized heavy chain constant region sequence, wherein the humanization comprises replacement of a sequence selected from a $C_H1$, hinge, $C_H2$, $C_H3$, and a combination thereof. In a specific embodiment, the heavy chain is derived from a human V gene segment, a human D gene segment, a human J gene segment, a human $C_H1$ sequence, a human or mouse hinge sequence, a mouse $C_H2$ sequence, and a mouse $C_H3$ sequence. In another specific embodiment, the mouse further comprises a human light chain constant sequence.

In one embodiment, the mouse comprises an ADAM6 gene that is flanked 5' and 3' by endogenous immunoglobulin heavy chain gene segments. In a specific embodiment, the endogenous immunoglobulin heavy chain gene segments are incapable of encoding a heavy chain of an antibody. In a specific embodiment, the ADAM6 gene of the mouse is at a position that is the same as in a wild-type mouse and the endogenous immunoglobulin heavy chain variable gene loci of the mouse are incapable of rearranging to encode a heavy chain of an antibody.

In one embodiment, the V gene segment is flanked 5' (with respect to transcriptional direction of the V gene segment) by a sequence encoding an ADAM6 activity that is functional in the mouse.

In one embodiment, the V gene segment is flanked 3' (with respect to transcriptional direction of the V gene segment) by a sequence encoding an ADAM6 activity that is functional in the mouse.

In one embodiment, the D gene segment is flanked 5' (with respect to transcriptional direction of the D gene segment) by a sequence encoding an ADAM6 activity that is functional in the mouse.

In one embodiment, the ADAM6 activity that is functional in the mouse results from expression of a nucleotide sequence located 5' of the 5'-most D gene segment and 3' of the 3'-most V gene segment (with respect to the direction of transcription of the V gene segment) of the modified endogenous mouse heavy chain immunoglobulin locus.

In one embodiment, the ADAM6 activity that is functional in the mouse results from expression of a nucleotide sequence located between two human V gene segments in the modified endogenous mouse heavy chain immunoglobulin locus. In one embodiment, the two human V gene segments are a human $V_H1$-2 gene segment and a $V_H6$-1 gene segment.

In one embodiment, the nucleotide sequence comprises a sequence selected from a mouse ADAM6b sequence or functional fragment thereof, a mouse ADAM6a sequence or functional fragment thereof, and a combination thereof.

In one embodiment, the nucleotide sequence between the two human V gene segments is placed in opposite transcription orientation with respect to the human V gene segments. In a specific embodiment, nucleotide sequence encodes, from 5' to 3' with respect to the direction of transcription of ADAM6 genes, and ADAM6a sequence followed by an ADAM6b sequence.

In one embodiment, the mouse comprises a replacement of a human ADAM6 pseudogene sequence between human V gene segments $V_H1$-2 and $V_H6$-1 with a mouse ADAM6 sequence or a functional fragment thereof.

In one embodiment, the sequence encoding the ADAM6 activity that is functional in the mouse is a mouse ADAM6 sequence or functional fragment thereof.

In one embodiment, the mouse comprises an endogenous mouse DFL16.1 gene segment (e.g., in a mouse heterozygous for the modified endogenous mouse immunoglobulin heavy chain locus), or a human $D_H1$-1 gene segment. In one embodiment, the D gene segment of the immunoglobulin heavy chain expressed by the mouse is derived from an endogenous mouse DFL16.1 gene segment or a human $D_H1$-1 gene segment.

In one aspect, a mouse is provided that comprises a nucleic acid sequence encoding a mouse ADAM6 (or homolog or ortholog or functional fragment thereof) in a DNA-bearing cell of non-rearranged B cell lineage, but does not comprise the nucleic acid sequence encoding the mouse ADAM6 (or homolog or ortholog or functional fragment thereof) in a B cell that comprise rearranged immunoglobulin loci, wherein the nucleic acid sequence encoding the mouse ADAM6 (or homolog or ortholog or functional fragment thereof) occurs in the genome at a position that is different from a position in which a mouse ADAM6 gene appears in a wild-type mouse. In one embodiment, the nucleic acid sequence encoding the mouse ADAM6 (or homolog or ortholog or functional fragment thereof) is present in all or substantially all DNA-bearing cells that are not of rearranged B cell lineage; in one embodiment, the nucleic acid sequence is present in germline cells of the mouse, but not in a chromosome of a rearranged B cell.

In one aspect, a mouse is provided that comprises a nucleic acid sequence encoding a mouse ADAM6 (or homolog or ortholog or functional fragment thereof) in all or substantially all DNA-bearing cells, including B cells that comprise rearranged immunoglobulin loci, wherein the nucleic acid sequence encoding the mouse ADAM6 (or homolog or ortholog or functional fragment thereof) occurs in the genome at a position that is different from a position in which a mouse ADAM6 gene appears in a wild-type mouse. In one embodiment, the nucleic acid sequence encoding the mouse ADAM6 (or homolog or ortholog or functional fragment thereof) is on a nucleic acid that is contiguous with the rearranged immunoglobulin locus. In one embodiment, the nucleic acid that is contiguous with the rearranged immunoglobulin locus is a chromosome. In one embodiment, the chromosome is a chromosome that is found in a wild-type mouse and the chromosome comprises a modification of a mouse immunoglobulin locus.

In one aspect, a genetically modified mouse is provided, wherein the mouse comprises a B cell that comprises in its genome an ADAM6 sequence or ortholog or homolog thereof. In one embodiment, the ADAM6 sequence or ortholog or homolog thereof is at an immunoglobulin heavy chain locus. In one embodiment, the ADAM6 sequence or ortholog or homolog thereof is at a locus that is not an immunoglobulin locus. In one embodiment, the ADAM6 sequence is on a transgene driven by a heterologous promoter. In a specific embodiment, the heterologous promoter is a non-immunoglobulin promoter. In a specific embodiment, B cell expresses an ADAM6 protein or ortholog or homolog thereof.

In one embodiment, 90% or more of the B cells of the mouse comprise a gene encoding an ADAM6 protein or an ortholog thereof or a homolog thereof or a fragment thereof that is functional in the mouse. In a specific embodiment, the mouse is a male mouse.

In one embodiment, the B cell genome comprises a first allele and a second allele comprising the ADAM6 sequence or ortholog or homolog thereof. In one embodiment, the B cell genome comprises a first allele but not a second allele comprising the ADAM6 sequence or ortholog or homolog thereof.

In one aspect, a mouse is provided that comprises a modification at one or more endogenous immunoglobulin heavy chain alleles, wherein the modification maintains one or more endogenous ADAM6 alleles and the mouse further comprises an insertion of one or more human Vλ gene segments and one or more human Jλ gene segments upstream of a mouse light chain constant region. In various embodiments, the mouse light chain constant region is a mouse Cκ or a mouse Cλ.

In one embodiment, the modification renders the mouse incapable of expressing a functional heavy chain that comprises rearranged endogenous heavy chain gene segments from at least one heavy chain allele and maintains an endogenous ADAM6 allele located within the at least one endogenous immunoglobulin heavy chain allele.

In one embodiment, the mice are incapable of expressing a functional heavy chain that comprises rearranged endogenous heavy chain gene segments from at least one of the endogenous immunoglobulin heavy chain alleles, and the mice express and ADAM6 protein from an endogenous ADAM6 allele. In a specific embodiment, the mice are incapable of expressing a functional heavy chain that comprises rearranged endogenous heavy chain gene segments from two endogenous immunoglobulin heavy chain alleles, and the mice express an ADAM6 protein from one or more endogenous ADAM6 alleles.

In one embodiment, the mice are incapable of expressing a functional heavy chain from each endogenous heavy chain allele, and the mice comprise an functional ADAM6 allele located within 1, 2, 3, 4, 5, 10, 20, 30, 40, 50, 60, 70, 80, 90, 100, 110, or 120 or more Mbp upstream (with respect to the direction of transcription of the mouse heavy chain locus) of a mouse immunoglobulin heavy chain constant region sequence. In a specific embodiment, the functional ADAM6 allele is at the endogenous immunoglobulin heavy chain locus (e.g., in an intergenic V-D region, between two V gene segments, between a V and a D gene segment, between a D and a J gene segment, etc.). In a specific embodiment, the functional ADAM6 allele is located within a 90 to 100 kb intergenic sequence between the final mouse V gene segment and the first mouse D gene segment.

In one aspect, a mouse is provided that comprises a modification at one or more endogenous ADAM6 alleles.

In one embodiment, the modification renders the mouse incapable of expressing a functional ADAM6 protein from at least one of the one or more endogenous ADAM6 alleles. In a specific embodiment, the mouse is incapable of expressing a functional ADAM6 protein from each of the endogenous ADAM6 alleles.

In one embodiment, the mice are incapable of expressing a functional ADAM6 protein from each endogenous ADAM6 allele, and the mice comprise an ectopic ADAM6 sequence.

In one embodiment, the mice are incapable of expressing a functional ADAM6 protein from each endogenous ADAM6 allele, and the mice comprise an ectopic ADAM6 sequence located within 1, 2, 3, 4, 5, 10, 20, 30, 40, 50, 60, 70, 80, 90, 100, 110, or 120 or more kb upstream (with respect to the direction of transcription of the mouse heavy chain locus) of a mouse immunoglobulin heavy chain constant region sequence. In a specific embodiment, the ectopic ADAM6 sequence is at the endogenous heavy chain locus (e.g., in an intergenic V-D region, between two V gene segments, between a V and a D gene segment, between a D and a J gene segment, etc.). In a specific embodiment, the ectopic ADAM6 sequence is located within a 90 to 100 kb intergenic sequence between the final mouse V gene segment and the first mouse D gene segment. In another specific embodiment, the endogenous 90 to 100 kb intergenic V-D sequence is removed, and the ectopic ADAM6 sequence is placed between the final V and the first D gene segment.

In one aspect, an infertile male mouse is provided, wherein the mouse comprises a deletion of two or more endogenous ADAM6 alleles. In one aspect, a female mouse is provided that is a carrier of a male infertility trait, wherein the female mouse comprises in its germline a nonfunctional ADAM6 allele or a knockout of an endogenous ADAM6 allele.

In one aspect, a mouse comprising an endogenous immunoglobulin heavy chain V, D, and or J gene segment that are incapable of rearranging to encode an heavy chain of an antibody is provided, wherein the majority of the B cells of the mouse comprise an functional ADAM6 gene. In various embodiments, the majority of the B cells of the mouse further comprise one or more human Vλ gene segments and one or more human Jλ gene segments upstream of a mouse immunoglobulin light chain constant region. In one embodiment, the mouse immunoglobulin light chain constant region is selected from a mouse Cκ and a mouse Cλ.

In one embodiment, the mouse comprises an intact endogenous immunoglobulin heavy chain V, D, and J gene segments that are incapable of rearranging to encode a functional heavy chain of an antibody. In one embodiment, the mouse comprises at least one and up to 89 V gene segments, at least one and up to 13 D gene segments, at least one and up to four J gene segments, and a combination thereof; wherein the at least one and up to 89 V gene segments, at least one and up to 13 D gene segments, at least one and up to four J gene segments are incapable of rearranging to encode a heavy chain variable region of an antibody. In a specific embodiment, the mouse comprises a functional ADAM6 gene located within the intact endogenous immunoglobulin heavy chain V, D, and J gene segments. In one embodiment, the mouse comprises an endogenous heavy chain locus that includes an endogenous ADAM6 locus, wherein the endogenous heavy chain locus comprises 89 V gene segments, 13 D gene segments, and four J gene segments, wherein the endogenous heavy chain gene segments are incapable of rearranging to encode a heavy chain variable region of an antibody and the ADAM6 locus encodes an ADAM6 protein that is functional in the mouse.

In one aspect, a mouse that lacks an endogenous immunoglobulin heavy chain V, D, and J gene segment is provided, wherein a majority of the B cells of the mouse comprise an ADAM6 sequence or ortholog or homolog thereof. In one embodiment, the majority of the B cells of the mouse express a immunoglobulin light chain comprising a human lambda variable domain and an endogenous immunoglobulin light chain constant region.

In one embodiment, the mouse lacks endogenous immunoglobulin heavy chain gene segments selected from two or more V gene segments, two or more D gene segments, two or more J gene segments, and a combination thereof. In one embodiment, the mouse lacks immunoglobulin heavy chain gene segments selected from at least one and up to 89 V gene segments, at least one and up to 13 D gene segments, at least one and up to four J gene segments, and a combination thereof. In one embodiment, the mouse lacks a genomic DNA fragment from chromosome 12 comprising about three megabases of the endogenous immunoglobulin heavy chain locus. In a specific embodiment, the mouse lacks all functional endogenous heavy chain V, D, and J gene segments. In a specific embodiment, the mouse lacks 89 $V_H$ gene segments, 13 $D_H$ gene segments and four $J_H$ gene segments.

In one aspect, a mouse is provided, wherein the mouse has a genome in the germline comprising a modification of an immunoglobulin heavy chain locus, wherein the modification to the immunoglobulin heavy chain locus comprises the replacement of one or more mouse immunoglobulin variable region sequences with one or more non-mouse immunoglobulin variable region sequences, and wherein the mouse comprises a nucleic acid sequence encoding a mouse ADAM6 protein. In a preferred embodiment, the $D_H$ and $J_H$ sequences and at least 3, at least 10, at least 20, at least 40, at least 60, or at least 80 $V_H$ sequences of the immunoglobulin heavy chain locus are replaced by non-mouse immunoglobulin variable region sequences. In a further preferred embodiment, the $D_H$, $J_H$, and all $V_H$ sequences of the immunoglobulin heavy chain locus are replaced by non-mouse immunoglobulin variable region sequences. The non-mouse immunoglobulin variable region sequences can be non-rearranged. In a preferred embodiment, the non-mouse immunoglobulin variable region sequences comprise complete non-rearranged $D_H$ and $J_H$ regions and at least 3, at least 10, at least 20, at least 40, at least 60, or at least 80 non-rearranged $V_H$ sequences of the non-mouse species. In a further preferred embodiment, the non-mouse immunoglobulin variable region sequences comprise the complete variable region, including all $V_H$, $D_H$, and $J_H$ regions, of the non-mouse species. The non-mouse species can be Homo sapiens and the non-mouse immunoglobulin variable region sequences can be human sequences.

In one aspect, a mouse that expresses an antibody that comprises at least one human variable domain/non-human constant domain immunoglobulin polypeptide is provided, wherein the mouse expresses a mouse ADAM6 protein or ortholog or homolog thereof from a locus other than an immunoglobulin locus.

In one embodiment, the ADAM6 protein or ortholog or homolog thereof is expressed in a B cell of the mouse, wherein the B cell comprises a rearranged immunoglobulin sequence that comprises a human variable sequence and a non-human constant sequence.

In one embodiment, the non-human constant sequence is a rodent sequence. In one embodiment, the rodent is selected from a mouse, a rat, and a hamster.

In one aspect, a method is provided for making an infertile male mouse, comprising rendering an endogenous ADAM6 allele of a donor ES cell nonfunctional (or knocking out said allele), introducing the donor ES cell into a host embryo, gestating the host embryo in a surrogate mother, and allowing the surrogate mother to give birth to progeny derived in whole or in part from the donor ES cell. In one embodiment, the method further comprises breeding progeny to obtain an infertile male mouse.

In one aspect, a method is provided for making a mouse with a genetic modification of interest, wherein the mouse is infertile, the method comprising the steps of (a) making a genetic modification of interest in a genome; (b) modifying the genome to knockout an endogenous ADAM6 allele, or render an endogenous ADAM6 allele nonfunctional; and, (c) employing the genome in making a mouse. In various embodiments, the genome is from an ES cell or used in a nuclear transfer experiment.

In one aspect, a mouse made using a targeting vector, nucleotide construct, or cell as described herein is provided.

In one aspect, a progeny of a mating of a mouse as described herein with a second mouse that is a wild-type mouse or genetically modified is provided.

In one aspect, a method for maintaining a mouse strain is provided, wherein the mouse strain comprises a replacement of a mouse immunoglobulin heavy chain sequence with one or more heterologous immunoglobulin heavy chain sequences. In one embodiment, the one or more heterologous immunoglobulin heavy chain sequences are human immunoglobulin heavy chain sequences.

In one embodiment, the mouse strain comprises a deletion of one or more mouse $V_H$, $D_H$, and/or $J_H$ gene segments. In one embodiment, the mouse further comprises one or more human $V_H$ gene segments, one or more human $D_H$ gene segments, and/or one or more human $J_H$ gene segments. In one embodiment, the mouse comprises at least 3, at least 10, at least 20, at least 40, at least 60, or at least 80 human $V_H$ segments, at least 27 human $D_H$ gene segments, and at least six $J_H$ gene segments. In a specific embodiment, the mouse comprises at least 3, at least 10, at least 20, at least 40, at least 60, or at least 80 human $V_H$ segments, the at least 27 human $D_H$ gene segments, and the at least six $J_H$ gene segments are operably linked to a constant region gene. In one embodiment, the constant region gene is a mouse constant region gene. In one embodiment, the constant region gene comprises a mouse constant region gene sequence selected from a $C_H1$, a hinge, a $C_H2$, a $C_H3$, and/or a $C_H4$ or a combination thereof.

In one embodiment, the method comprises generating a male mouse heterozygous for the replacement of the mouse immunoglobulin heavy chain sequence, and breeding the heterozygous male mouse with a wild-type female mouse or a female mouse that is homozygous or heterozygous for the human heavy chain sequence. In one embodiment, the method comprises maintaining the strain by repeatedly breeding heterozygous males with females that are wild type or homozygous or heterozygous for the human heavy chain sequence.

In one embodiment, the method comprises obtaining cells from male or female mice homozygous or heterozygous for the human heavy chain sequence, and employing those cells as donor cells or nuclei therefrom as donor nuclei, and using the cells or nuclei to make genetically modified animals using host cells and/or gestating the cells and/or nuclei in surrogate mothers.

In one embodiment, only male mice that are heterozygous for the replacement at the heavy chain locus are bred to female mice. In a specific embodiment, the female mice are homozygous, heterozygous, or wild type with respect to a replaced heavy chain locus.

In one embodiment, the mouse further comprises a replacement of λ and/or κ light chain variable sequences at an endogenous immunoglobulin light chain locus with heterologous immunoglobulin light chain sequences. In one embodiment, the heterologous immunoglobulin light chain sequences are human immunoglobulin λ and/or κ light chain variable sequences.

In one embodiment, the mouse further comprises a transgene at a locus other than an endogenous immunoglobulin locus, wherein the transgene comprises a sequence encoding a rearranged or unrearranged heterologous λ or κ light chain sequence (e.g., unrearranged $V_L$ and unrearranged $J_L$, or rearranged VJ) operably linked (for unrearranged) or fused (for rearranged) to an immunoglobulin light chain constant region sequence. In one embodiment, the heterologous λ or κ light chain sequence is human. In one embodiment, the constant region sequence is selected from rodent, human, and non-human primate. In one embodiment, the constant region sequence is selected from mouse, rat, and hamster. In one embodiment, the transgene comprises a non-immunoglobulin promoter that drives expression of the light chain sequences. In a specific embodiment, the promoter is a transcriptionally active promoter. In a specific embodiment, the promoter is a ROSA26 promoter.

In one aspect, a nucleic acid construct is provided, comprising an upstream homology arm and a downstream homology arm, wherein the upstream homology arm comprises a sequence that is identical or substantially identical to a human immunoglobulin heavy chain variable region sequence, the downstream homology arm comprises a sequence that is identical or substantially identical to a human or mouse immunoglobulin variable region sequence, and disposed between the upstream and downstream homology arms is a sequence that comprises a nucleotide sequence encoding a mouse ADAM6 protein. In a specific embodiment, the sequence encoding the mouse ADAM6 gene is operably linked with a mouse promoter with which the mouse ADAM6 is linked in a wild type mouse.

In one aspect, a targeting vector is provided, comprising (a) a nucleotide sequence that is identical or substantially identical to a human variable region gene segment nucleotide sequence; and, (b) a nucleotide sequence encoding a mouse ADAM6 or ortholog or homolog or fragment thereof that is functional in a mouse.

In one embodiment, the targeting vector further comprises a promoter operably linked to the sequence encoding the mouse ADAM6. In a specific embodiment, the promoter is a mouse ADAM6 promoter.

In one aspect, a nucleotide construct for modifying a mouse immunoglobulin heavy chain variable locus is provided, wherein the construct comprises at least one site specific recombinase recognition site and a sequence encoding an ADAM6 protein or ortholog or homolog or fragment thereof that is functional in a mouse.

In one aspect, mouse cells and mouse embryos are provided, including but not limited to ES cells, pluripotent cells, and induced pluripotent cells, that comprise genetic modifications as described herein. Cells that are XX and cells that are XY are provided. Cells that comprise a nucleus containing a modification as described herein are also provided, e.g., a modification introduced into a cell by pronuclear injection. Cells, embryos, and mice that comprise a virally introduced ADAM6 gene are also provided, e.g., cells, embryos, and mice comprising a transduction construct comprising an ADAM6 gene that is functional in the mouse.

In one aspect, a genetically modified mouse cell is provided, wherein the cell lacks a functional endogenous mouse ADAM6 locus, and the cell comprises an ectopic nucleotide sequence that encodes a mouse ADAM6 protein or functional fragment thereof. In one embodiment, the cell further comprises a modification of an endogenous immunoglobulin heavy chain variable gene sequence. In a specific embodiment, the modification of the endogenous immunoglobulin heavy chain variable gene sequence comprises a deletion selected from a deletion of a mouse $V_H$ gene segment, a deletion of a mouse $D_H$ gene segment, a deletion of a mouse $J_H$ gene segment, and a combination thereof. In a specific embodiment, the mouse comprises a replacement of one or more mouse immunoglobulin $V_H$, $D_H$, and/or $J_H$ sequences with a human immunoglobulin sequence. In a specific embodiment, the human immunoglobulin sequence is selected from a human $V_H$, a human $V_L$, a human $D_H$, a human $J_H$, a human $J_L$, and a combination thereof.

In one embodiment, the cell is a totipotent cell, a pluripotent cell, or an induced pluripotent cell. In a specific embodiment, the cell is a mouse ES cell.

In one aspect, a mouse B cell is provided, wherein the mouse B cell comprises a rearranged immunoglobulin heavy chain gene, wherein the B cell comprises on a chromosome of the B cell a nucleic acid sequence encoding an ADAM6 protein or ortholog or homolog or fragment thereof that is functional in a male mouse. In one embodiment, the mouse B cell comprises two alleles of the nucleic acid sequence.

In one embodiment, the nucleic acid sequence is on a nucleic acid molecule (e.g., a B cell chromosome) that is contiguous with the rearranged mouse immunoglobulin heavy chain locus.

In one embodiment, the nucleic acid sequence is on a nucleic acid molecule (e.g., a B cell chromosome) that is distinct from the nucleic acid molecule that comprises the rearranged mouse immunoglobulin heavy chain locus.

In one embodiment, the mouse B cell comprises a rearranged non-mouse immunoglobulin variable gene sequence operably linked to a mouse or human immunoglobulin constant region gene, wherein the B cell comprises a nucleic acid sequence that encodes an ADAM6 protein or ortholog or homolog or fragment thereof that is functional in a male mouse.

In one aspect, a somatic mouse cell is provided, comprising a chromosome that comprises a modified immunoglobulin heavy chain locus, and a nucleic acid sequence encoding a mouse ADAM6 or ortholog or homolog or fragment thereof that is functional in a male mouse. In one embodiment, the nucleic acid sequence is on the same chromosome as the modified immunoglobulin heavy chain locus. In one embodiment, the nucleic acid is on a different chromosome than the modified immunoglobulin heavy chain locus. In one embodiment, the somatic cell comprises a single copy of the nucleic acid sequence. In one embodiment, the somatic cell comprises at least two copies of the nucleic acid sequence. In a specific embodiment, the somatic cell is a B cell. In a specific embodiment, the cell is a germ cell. In a specific embodiment, the cell is a stem cell.

In one aspect, a mouse germ cell is provided, comprising a nucleic acid sequence encoding a mouse ADAM6 (or homolog or ortholog or functional fragment thereof) on a chromosome of the germ cell, wherein the nucleic acid sequence encoding the mouse ADAM6 (or homolog or ortholog or functional fragment thereof) is at a position in the chromosome that is different from a position in a chromosome of a wild-type mouse germ cell. In one embodiment, the nucleic acid sequence is at a mouse immunoglobulin locus. In one embodiment, the nucleic acid sequence is on the same chromosome of the germ cell as a mouse immunoglobulin locus. In one embodiment, the nucleic acid sequence is on a different chromosome of the germ cell than the mouse immunoglobulin locus. In one embodiment, the mouse immunoglobulin locus comprises a replacement of at least one mouse immunoglobulin sequence with at least one non-mouse immunoglobulin sequence. In a specific embodiment, the at least one non-mouse immunoglobulin sequence is a human immunoglobulin sequence.

In one aspect, a pluripotent, induced pluripotent, or totipotent cell derived from a mouse as described herein is provided. In a specific embodiment, the cell is an mouse embryonic stem (ES) cell.

In one aspect, a cell or tissue derived from a mouse as described herein is provided. In one embodiment, the cell or tissue is derived from spleen, lymph node or bone marrow of a mouse as described herein. In one embodiment, the cell is a B cell. In one embodiment the cell is an embryonic stem cell. In one embodiment, the cell is a germ cell.

In one embodiment, the tissue is selected from connective, muscle, nervous and epithelial tissue. In a specific embodiment, the tissue is reproductive tissue.

In one embodiment, the cell and/or tissue derived from a mouse as described herein is isolated for use in one or more ex vivo assays. In various embodiments, the one or more ex vivo assays include measurements of physical, thermal, electrical, mechanical or optical properties, a surgical procedure, measurements of interactions of different tissue types, the development of imaging techniques, or a combination thereof.

In aspect, use of cell or tissue derived from a mouse as described herein to make an antibody is provided. In one aspect, use of a cell or tissue derived from a mouse as described herein to make a hybridoma or quadroma is provided.

In one aspect, a non-human cell comprising a chromosome or fragment thereof of a non-human animal as described herein. In one embodiment, the non-human cell comprises a nucleus of a non-human animal as described herein. In one embodiment, the non-human cell comprises the chromosome or fragment thereof as the result of a nuclear transfer.

In one aspect, a nucleus derived from a mouse as described herein is provided. In one embodiment, the nucleus is from a diploid cell that is not a B cell.

In one aspect, a nucleotide sequence encoding an immunoglobulin variable region made in a mouse as described herein is provided.

In one aspect, an immunoglobulin heavy chain or immunoglobulin light chain variable region amino acid sequence of an antibody made in a mouse as described herein is provided.

In one aspect, an immunoglobulin heavy chain or immunoglobulin light chain variable region nucleotide sequence encoding a variable region of an antibody made in a mouse as described herein is provided.

In one aspect, an antibody or antigen-binding fragment thereof (e.g., Fab, F(ab)$_2$, scFv) made in a mouse as described herein is provided.

In one aspect, a method for making a genetically modified mouse is provided, comprising replacing one or more immunoglobulin heavy chain gene segments upstream (with respect to transcription of the immunoglobulin heavy chain gene segments) of an endogenous ADAM6 locus of the mouse with one or more human immunoglobulin heavy chain gene segments, and replacing one or more immunoglobulin gene segments downstream (with respect to transcription of the immunoglobulin heavy chain gene segments) of the ADAM6 locus of the mouse with one or more human immunoglobulin heavy chain or light chain gene segments. In one embodiment, the one or more human immunoglobulin gene segments replacing one or more endogenous immunoglobulin gene segments upstream of an endogenous ADAM6 locus of the mouse include V gene segments. In one embodiment, the human immunoglobulin gene segments replacing one or more endogenous immunoglobulin gene segments upstream of an endogenous ADAM6 locus of the mouse include V and D gene segments. In one embodiment, the one or more human immunoglobulin gene segments replacing one or more endogenous immunoglobulin gene segments downstream of an endogenous ADAM6 locus of the mouse include J gene segments. In one embodiment, the one or more human immunoglobulin gene segments replacing one or more endogenous immunoglobulin gene segments downstream of an endogenous ADAM6 locus of the mouse include D and J gene segments. In one embodiment, the one or more human immunoglobulin gene segments replacing one or more endogenous immunoglobulin gene segments downstream of an endogenous ADAM6 locus of the mouse include V, D and J gene segments.

In one embodiment, the one or more immunoglobulin heavy chain gene segments upstream and/or downstream of the ADAM6 gene are replaced in a pluripotent, induced pluripotent, or totipotent cell to form a genetically modified progenitor cell; the genetically modified progenitor cell is introduced into a host; and, the host comprising the genetically modified progenitor cell is gestated to form a mouse comprising a genome derived from the genetically modified progenitor cell. In one embodiment, the host is an embryo. In a specific embodiment, the host is selected from a mouse pre-morula (e.g., 8- or 4-cell stage), a tetraploid embryo, an aggregate of embryonic cells, or a blastocyst.

In one aspect, a method for making a genetically modified mouse is provided, comprising replacing a mouse nucleotide sequence that comprises a mouse immunoglobulin gene segment and a mouse ADAM6 (or ortholog or homolog or fragment thereof functional in a male mouse) nucleotide sequence with a sequence comprising a human immunoglobulin gene segment to form a first chimeric locus, then inserting a sequence comprising a mouse ADAM6-encoding sequence (or a sequence encoding an ortholog or homolog or functional fragment thereof) into the sequence comprising the human immunoglobulin gene segment to form a second chimeric locus.

In one embodiment, the second chimeric locus comprises a human immunoglobulin heavy chain variable ($V_H$) gene segment. In one embodiment, the second chimeric locus comprises a human immunoglobulin light chain variable ($V_L$) gene segment. In a specific embodiment, the second chimeric locus comprises a human $V_H$ gene segment or a human $V_L$ gene segment operably linked to a human $D_H$ gene segment and a human $J_H$ gene segment. In a further specific embodiment, the second chimeric locus is operably linked to a third chimeric locus that comprises a human $C_H1$ sequence, or a human $C_H1$ and human hinge sequence, fused with a mouse $C_H2+C_H3$ sequence.

In one aspect, use of a mouse that comprises an ectopic nucleotide sequence comprising a mouse ADAM6 locus or sequence to make a fertile male mouse is provided, wherein the use comprises mating the mouse comprising the ectopic nucleotide sequence that comprises the mouse ADAM6 locus or sequence to a mouse that lacks a functional endogenous mouse ADAM6 locus or sequence, and obtaining a progeny that is a female capable of producing progeny having the ectopic ADAM6 locus or sequence or that is a male that comprises the ectopic ADAM6 locus or sequence, and the male exhibits a fertility that is approximately the same as a fertility exhibited by a wild-type male mouse.

In one aspect, use of a mouse as described herein to make an immunoglobulin variable region nucleotide sequence is provided.

In one aspect, use of a mouse as described herein to make a fully human Fab or a fully human F(ab)$_2$ is provided.

In one aspect, use of a mouse as described herein to make an immortalized cell line is provided.

In one aspect, use of a mouse as described herein to make a hybridoma or quadroma is provided.

In one aspect, use of a mouse as described herein to make a phage library containing human heavy chain variable regions and human light chain variable regions is provided.

In one aspect, use of a mouse as described herein to generate a variable region sequence for making a human antibody is provided, comprising (a) immunizing a mouse as described herein with an antigen of interest, (b) isolating a lymphocyte from the immunized mouse of (a), (c) exposing the lymphocyte to one or more labeled antibodies, (d) identifying a lymphocyte that is capable of binding to the antigen of interest, and (e) amplifying one or more variable region nucleic acid sequence from the lymphocyte thereby generating a variable region sequence.

In one embodiment, the lymphocyte is derived from the spleen of the mouse. In one embodiment, the lymphocyte is derived from a lymph node of the mouse. In one embodiment, the lymphocyte is derived from the bone marrow of the mouse.

In one embodiment, the labeled antibody is a fluorophore-conjugated antibody. In one embodiment, the one or more fluorophore-conjugated antibodies are selected from an IgM, an IgG, and/or a combination thereof.

In one embodiment, the lymphocyte is a B cell.

In one embodiment, the one or more variable region nucleic acid sequence comprises a heavy chain variable region sequence. In one embodiment, the one or more variable region nucleic acid sequence comprises a light chain variable region sequence. In a specific embodiment, the light chain variable region sequence is an immunoglobulin κ light chain variable region sequence. In one embodiment, the one or more variable region nucleic acid sequence comprises a heavy chain and a κ light chain variable region sequence.

In one embodiment, use of a mouse as described herein to generate a heavy and a κ light chain variable region sequence for making a human antibody is provided, comprising (a) immunizing a mouse as described herein with an antigen of interest, (b) isolating the spleen from the immunized mouse of (a), (c) exposing B lymphocytes from the spleen to one or more labeled antibodies, (d) identifying a B lymphocyte of (c) that is capable of binding to the antigen of interest, and (e) amplifying a heavy chain variable region nucleic acid sequence and a κ light chain variable region nucleic acid sequence from the B lymphocyte thereby generating the heavy chain and κ light chain variable region sequences.

In one embodiment, use of a mouse as described herein to generate a heavy and a κ light chain variable region sequence for making a human antibody is provided, comprising (a) immunizing a mouse as described herein with an antigen of interest, (b) isolating one or more lymph nodes from the immunized mouse of (a), (c) exposing B lymphocytes from the one or more lymph nodes to one or more labeled antibodies, (d) identifying a B lymphocyte of (c) that is capable of binding to the antigen of interest, and (e) amplifying a heavy chain variable region nucleic acid sequence and a κ light chain variable region nucleic acid sequence from the B lymphocyte thereby generating the heavy chain and κ light chain variable region sequences.

In one embodiment, use of a mouse as described herein to generate a heavy and a κ light chain variable region sequence for making a human antibody is provided, comprising (a) immunizing a mouse as described herein with an antigen of interest, (b) isolating bone marrow from the immunized mouse of (a), (c) exposing B lymphocytes from the bone marrow to one or more labeled antibodies, (d) identifying a B lymphocyte of (c) that is capable of binding to the antigen of interest, and (e) amplifying a heavy chain variable region nucleic acid sequence and a κ light chain variable region nucleic acid sequence from the B lymphocyte thereby generating the heavy chain and κ light chain variable region sequences. In various embodiments, the one or more labeled antibodies are selected from an IgM, an IgG, and/or a combination thereof.

In various embodiments, use of a mouse as described herein to generate a heavy and κ light chain variable region sequence for making a human antibody is provided, further comprising fusing the amplified heavy and light chain variable region sequences to human heavy and light chain constant region sequences, expressing the fused heavy and light chain sequences in a cell, and recovering the expressed heavy and light chain sequences thereby generating a human antibody.

In various embodiments, the human heavy chain constant regions are selected from IgM, IgD, IgA, IgE and IgG. In various specific embodiments, the IgG is selected from an IgG1, an IgG2, an IgG3 and an IgG4. In various embodiments, the human heavy chain constant region comprises a $C_H1$, a hinge, a $C_H2$, a $C_H3$, a $C_H4$, or a combination thereof. In various embodiments, the light chain constant region is an immunoglobulin κ constant region. In various embodiments, the cell is selected from a HeLa cell, a DU145 cell, a Lncap cell, a MCF-7 cell, a MDA-MB-438 cell, a PC3 cell, a T47D cell, a THP-1 cell, a U87 cell, a SHSY5Y (human neuroblastoma) cell, a Saos-2 cell, a Vero cell, a CHO cell, a GH3 cell, a PC12 cell, a human retinal cell (e.g., a PER.C6™ cell), and a MC3T3 cell. In a specific embodiment, the cell is a CHO cell.

In one aspect, a method for generating a reverse-chimeric rodent-human antibody specific against an antigen of interest is provided, comprising the steps of immunizing a mouse as described herein with the antigen, isolating at least one cell from the mouse producing a reverse-chimeric mouse-human antibody specific against the antigen, culturing at least one cell producing the reverse-chimeric mouse-human antibody specific against the antigen, and obtaining said antibody.

In one embodiment, the reverse-chimeric mouse-human antibody comprises a human heavy chain variable domain fused with a mouse or rat heavy chain constant gene, and a human light chain variable domain fused with a mouse or rat or human light chain constant gene.

In one embodiment, culturing at least one cell producing the reverse-chimeric rodent-human antibody specific against the antigen is performed on at least one hybridoma cell generated from the at least one cell isolated from the mouse.

In one aspect, a method for generating a fully human antibody specific against an antigen of interest is provided, comprising the steps of immunizing a mouse as described herein with the antigen, isolating at least one cell from the mouse producing a reverse-chimeric rodent-human antibody specific against the antigen, generating at least one cell producing a fully human antibody derived from the reverse-chimeric rodent-human antibody specific against the antigen, and culturing at least one cell producing the fully human antibody, and obtaining said fully human antibody.

In various embodiments, the at least one cell isolated from the mouse producing a reverse-chimeric rodent-human antibody specific against the antigen is a splenocyte or a B cell.

In various embodiments, the antibody is a monoclonal antibody.

In various embodiments, immunization with the antigen of interest is carried out with protein, DNA, a combination of DNA and protein, or cells expressing the antigen.

In one aspect, use of a mouse as described herein to make a nucleic acid sequence encoding an immunoglobulin variable region or fragment thereof is provided. In one embodiment, the nucleic acid sequence is used to make a human antibody or antigen-binding fragment thereof. In one embodiment, the mouse is used to make an antigen-binding protein selected from an antibody, a multi-specific antibody (e.g., a bi-specific antibody), an scFv, a bi-specific scFv, a diabody, a triabody, a tetrabody, a V-NAR, a $V_{HH}$, a $V_L$, a F(ab), a F(ab)$_2$, a DVD (i.e., dual variable domain antigen-binding protein), a an SVD (i.e., single variable domain antigen-binding protein), or a bispecific T-cell engager (BiTE).

In one aspect, use of a mouse as described herein to introduce an ectopic ADAM6 sequence into a mouse that lacks a functional endogenous mouse ADAM6 sequence is provided, wherein the use comprises mating a mouse as described herein with the mouse that lacks the functional endogenous mouse ADAM6 sequence.

In one aspect, use of genetic material from a mouse as described herein to make a mouse having an ectopic ADAM6 sequence is provided. In one embodiment, the use comprises nuclear transfer using a nucleus of a cell of a mouse as described herein. In one embodiment, the use comprises cloning a cell of a mouse as described herein to produce an animal derived from the cell. In one embodiment, the use comprises employing a sperm or an egg of a mouse as described herein in a process for making a mouse comprising the ectopic ADAM6 sequence.

In one aspect, a method for making a fertile male mouse comprising a modified immunoglobulin heavy chain locus is provided, comprising fertilizing a first mouse germ cell that comprises a modification of an endogenous immunoglobulin heavy chain locus with a second mouse germ cell that comprises an ADAM6 gene or ortholog or homolog or fragment thereof that is functional in a male mouse; forming a fertilized cell; allowing the fertilized cell to develop into an embryo; and, gestating the embryo in a surrogate to obtain a mouse.

In one embodiment, the fertilization is achieved by mating a male mouse and a female mouse. In one embodiment, the female mouse comprises the ADAM6 gene or ortholog or homolog or fragment thereof. In one embodiment, the male mouse comprises the ADAM6 gene or ortholog or homolog or fragment thereof.

In one aspect, use of a nucleic acid sequence encoding a mouse ADAM6 protein or an ortholog or homolog thereof or a functional fragment of the corresponding ADAM6 protein for restoring or enhancing the fertility of a mouse having a genome comprising a modification of an immunoglobulin heavy chain locus is provided, wherein the modification reduces or eliminates endogenous ADAM6 function.

In one embodiment, the nucleic acid sequence is integrated into the genome of the mouse at an ectopic position. In one embodiment, the nucleic acid sequence is integrated into the genome of the mouse at an endogenous immunoglobulin locus. In a specific embodiment, the endogenous immunoglobulin locus is a heavy chain locus. In one embodiment, the nucleic acid sequence is integrated into the genome of the mouse at a position other than an endogenous immunoglobulin locus.

In one aspect, use of the mouse as described herein for the manufacture of a medicament (e.g., an antigen-binding protein), or for the manufacture of a sequence encoding a variable sequence of a medicament (e.g., an antigen-binding protein), for the treatment of a human disease or disorder is provided.

In one aspect, a genetically modified mouse cell is provided, wherein the cell is incapable of expressing a heavy chain comprising rearranged endogenous immunoglobulin heavy chain gene segments, and the cell comprises a functional ADAM6 gene that encodes a mouse ADAM6 protein or functional fragment thereof. In one embodiment, the cell further comprises an insertion of human immunoglobulin gene segments. In a specific embodiment, the human immunoglobulin gene segments are heavy chain gene segments that are operably linked to mouse heavy chain constant regions such that upon rearrangement encode a functional heavy chain of an antibody that comprises a human variable region.

Genetically modified non-human animals, embryos, cells, tissues, as well as nucleic acid constructs for modifying the non-human animals, and methods and compositions for making and using them, are provided. Animals and cells that generate lambda (λ) variable regions (human or non-human) in the context of a kappa (κ) light chain are provided, wherein the animals and cells comprise a modification of a heavy chain immunoglobulin locus that eliminates or reduces activity of an ADAM6 protein or homolog or ortholog thereof, wherein the animals further comprise a genetic modification that restores in whole or in part ADAM6 activity (or the activity of the homolog or ortholog thereof). Mice are provided that are fertile and express a human variable domain cognate with a human heavy chain variable domain, wherein the human λ variable domain is expressed in the mouse contiguous with a λ or κ constant region, and in various embodiments the λ or κ variable region is an endogenous (e.g., mouse or rat) constant region. Mice and cells that generate human λ variable regions in the context of a κ or a λ light chain, e.g., from an endogenous mouse light chain locus, are also provided. Also provided are methods for making antibodies that comprise lambda variable regions. Methods for selecting heavy chains that express with cognate lambda variable regions are also provided.

Chimeric and human antigen-binding proteins (e.g., antibodies), and nucleic acids encoding them, are provided that comprise somatically mutated variable regions, including antibodies that have light chains comprising a variable domain derived from a human Vλ and a human Jλ gene segment fused to a mouse light chain constant domain.

In one aspect, a mouse is provided that expresses a human variable region sequence on a light chain that comprises a mouse constant region. In one aspect, a mouse is provided that expresses a human λ variable region sequence on a light chain that comprises a κ constant region. In one aspect, a mouse is provided that expresses from an endogenous mouse light chain locus a light chain that comprises a human λ variable region sequence. In one aspect, a mouse is provided that comprises a rearranged light chain gene that comprises a human λ variable sequence linked to a mouse constant region sequence; in one embodiment, the mouse constant region sequence is a λ constant sequence; in one embodiment, the mouse constant region sequence is a κ constant sequence.

In one aspect, a genetically modified mouse is provided, wherein the mouse comprises an unrearranged human λ light chain variable gene segment (hVλ) and a human λ joining gene segment (hJλ). In one embodiment, the unrearranged hVλ and hJλ are at a mouse light chain locus. In one embodiment, the unrearranged hVλ and unrearranged ha, are on a transgene and operably linked to a human or mouse constant region sequence. In one embodiment, the unrearranged hVλ and unrearranged ha, are on an episome. In one embodiment, the mouse is capable of making an immunoglobulin that comprises a light chain that is derived from an unrearranged hVλ sequence and a hJλ sequence and a mouse light chain constant region ($C_L$) nucleic acid sequence. Methods and compositions for making and using genetically modified mice are also provided. Antibodies are provided that comprise (a) a human heavy chain variable domain ($hV_H$) fused to a mouse heavy chain constant region, and (b) a human V[ fused to a mouse $C_L$ domain; including wherein one or more of the variable domains are somatically mutated, e.g., during antibody or immune cell selection in a mouse of the invention. In one embodiment, the unrearranged hVλ and unrearranged hJλ are operably linked with a human or mouse κ constant region (Cκ). In one embodiment, the unrearranged hVλ and unrearranged hJλ are operably linked with a human or mouse λ constant region (Cλ).

In one aspect, a mouse is provided that comprises in its germline, at an endogenous mouse light chain locus, a human λ light chain variable region sequence, wherein the human lambda variable region sequence is expressed in a light chain that comprises a mouse immunoglobulin constant region gene sequence.

In one embodiment, the endogenous mouse light chain locus is a λ locus. In one embodiment, the endogenous mouse light chain locus is a κ locus.

In one embodiment, the mouse lacks an endogenous light chain variable sequence at the endogenous mouse light chain locus.

In one embodiment, all or substantially all endogenous mouse light chain variable region gene segments are replaced with one or more human λ variable region gene segments.

In one embodiment, the human λ light chain variable region sequence comprises a human Jλ sequence. In one embodiment, the human Jλ sequence is selected from the group consisting of Jλ1, Jλ2, Jλ3, Jλ7, and a combination thereof.

In one embodiment, the human λ light chain variable region sequence comprises a fragment of cluster A of the human light chain locus. In a specific embodiment, the fragment of cluster A of the human λ light chain locus extends from hVλ3-27 through hVλ3-1.

In one embodiment, the human λ light chain variable region sequence comprises a fragment of cluster B of the human light chain locus. In a specific embodiment, the fragment of cluster B of the human λ light chain locus extends from hVλ5-52 through hVλ1-40.

In one embodiment, the human λ light chain variable region sequence comprises a genomic fragment of cluster A and a genomic fragment of cluster B. In a one embodiment, the human λ light chain variable region sequence comprises at least one gene segment of cluster A and at least one gene segment of cluster B.

In one embodiment, more than 10% of the light chain naïve repertoire of the mouse is derived from at least two hVλ gene segments selected from 2-8, 2-23, 1-40, 5-45, and 9-49. In one embodiment, more than 20% of the light chain naïve repertoire of the mouse is derived from at least three hVλ gene segments selected from 2-8, 2-23, 1-40, 5-45, and 9-49. In one embodiment, more than 30% of the light chain naïve repertoire of the mouse is derived from at least four hVλ, gene segments selected from 2-8, 2-23, 1-40, 5-45, and 9-49.

In one aspect, a mouse is provided that expresses an immunoglobulin light chain that comprises a human λ variable sequence fused with a mouse constant region, wherein the mouse exhibits a κ usage to A usage ratio of about 1:1.

In one embodiment, the immunoglobulin light chain is expressed from an endogenous mouse light chain locus.

In one aspect, a mouse is provided that comprises a λ light chain variable region sequence (Vλ) and at least one J sequence (J), contiguous with a mouse κ light chain constant region sequence.

In one embodiment, the mouse lacks a functional mouse Vλ and/or mouse Jλ gene segment.

In one embodiment, the Vλ is a human Vλ (hVλ), and the J is a human Jλ (hJλ). In one embodiment, the hVλ and the hJλ are unrearranged gene segments.

In one embodiment, the mouse comprises a plurality of unrearranged hVλ gene segments and at least one hJλ gene segment. In a specific embodiment, the plurality of unrearranged hVλ gene segments are at least 12 gene segments, at least 28 gene segments, or at least 40 gene segments.

In one embodiment, the at least one hJλ gene segment is selected from the group consisting of Jλ1, Jλ2, Jλ3, Jλ7, and a combination thereof.

In one embodiment, an endogenous mouse λ light chain locus is deleted in whole or in part.

In one embodiment, the mouse κ light chain constant region sequence is at an endogenous mouse κ light chain locus.

In one embodiment, about 10% to about 45% of the B cells of the mouse express an antibody that comprises a light chain comprising a human λ light chain variable (Vλ) domain and a mouse κ light chain constant (Cκ) domain.

In one embodiment, the human κ variable domain is derived from a rearranged hVλ/hJλ sequence selected from the group consisting of 3-1/1, 3-1/7, 4-3/1, 4-3/7, 2-8/1, 3-9/1, 3-10/1, 3-10/3, 3-10/7, 2-14/1, 3-19/1, 2-23/1, 3-25/1, 1-40/1, 1-40/2, 1-40/3, 1-40/7, 7-43/1, 7-43/3, 1-44/1, 1-44/7, 5-45/1, 5-45/2, 5-45/7, 7-46/1, 7-46/2, 7-46/7, 9-49/1, 9-49/2, 9-49/7 and 1-51/1.

In one embodiment, the mouse further comprises a human Vκ-κ intergenic region from a human κ light chain locus, wherein the human Vκ-Jκ intergenic region is contiguous with the Vλ sequence and the J sequence. In a specific embodiment, the human Vκ-Jκ intergenic region is placed between the Vλ sequence and the J sequence.

In one aspect, a mouse is provided that comprises (a) at least 12 to at least 40 unrearranged human λ light chain variable region gene segments and at least one human Jλ gene segment at an endogenous mouse light chain locus; (b) a human Vκ-Jκ intergenic sequence located between the at least 12 to at least 40 human light chain variable region gene segments and the at least one human Jλ sequence; wherein the mouse express an antibody that comprises a light chain comprising a human Vλ domain and a mouse Cκ domain.

In one aspect, a mouse is provided that expresses an antibody comprising a light chain that comprises a λ variable sequence and a κ constant sequence.

In one embodiment, the mouse exhibits a κ usage to λ usage ratio of about 1:1.

In one embodiment, a population of immature B cells obtained from bone marrow of the mouse exhibits a κ usage to λ usage ratio of about 1:1.

In one aspect, a genetically modified mouse is provided, wherein the mouse comprises an unrearranged immunoglobulin Vλ and a Jλ gene segment operably linked to a mouse light chain locus that comprises a mouse $C_L$ gene.

In one embodiment, the Vλ and/or Jλ gene segments are human gene segments. In one embodiment, the Vλ and/or Jλ gene segments are mouse gene segments, and the $C_L$ is a mouse Cκ.

In one embodiment, the endogenous mouse light chain locus is a κ light chain locus. In one embodiment, the endogenous mouse light chain locus is a λ light chain locus.

In one embodiment, the unrearranged Vλ and Jλ gene segments are at an endogenous mouse light chain locus.

In one embodiment, the unrearranged immunoglobulin Vλ and Jλ gene segments are on a transgene.

In one embodiment, the mouse further comprises a replacement of one or more heavy chain V, D, and/or J gene segments with one or more human V, D, and/or J gene segments at an endogenous mouse heavy chain immunoglobulin locus.

In one embodiment, the mouse comprises an unrearranged immunoglobulin Vλ and a Jλ gene segment at an endogenous mouse κ light chain locus that comprises a mouse Cκ gene.

In one embodiment, the mouse comprises an unrearranged human immunoglobulin λ light chain variable gene segment (Vλ) and a λ joining gene segment (Jλ) at an endogenous mouse λ light chain locus that comprises a mouse Cλ gene.

In one embodiment, the light chain variable gene locus (the "$V_L$ locus") comprises at least one human Vλ (hVλ) gene segment. In one embodiment, the $V_L$ locus comprises at least one human Jλ (hJλ) gene segment. In another embodiment, $V_L$ locus comprises up to four hJλ gene segments. In one embodiment, the $V_L$ locus comprises a contiguous sequence comprising human λ and human κ genomic sequence.

In one embodiment, the κ light chain variable gene locus (the "κ locus") comprises at least one human Vλ (hVλ) gene segment. In one embodiment, the κ locus comprises at least one human Jλ (hJλ) gene segment. In one embodiment, the κ locus comprises up to four hJλ gene segments. In one embodiment, the κ locus comprises at least one hVλ and at least one hJλ, and lacks or substantially lacks a functional Vκ region gene segment and lacks or substantially lacks a functional Jκ region gene segment. In one embodiment, the mouse comprises no functional Vκ region gene segment. In one embodiment, the mouse comprises no functional Jκ region gene segment.

In one embodiment, the λ light chain variable gene locus (the "λ locus") comprises at least one hVλ gene segment. In one embodiment, the λ locus comprises at least one human Jλ (hJλ) gene segment. In another embodiment, the λ locus comprises up to four hJλ gene segments.

In one embodiment, the $V_L$ locus comprises a plurality of hVλs. In one embodiment, the plurality of hVλs are selected so as to result in expression of a λ light chain variable region repertoire that reflects about 10%, about 20%, about 30%, about 40%, about 50%, about 60%, about 70%, about 80%, or about 90% or more of the Vλ usage observed in a human. In one embodiment, the $V_L$ locus comprises gene segments hVλ 1-40, 1-44, 2-8, 2-14, 3-21, and a combination thereof.

In one embodiment, the hVλs include 3-1, 4-3, 2-8, 3-9, 3-10, 2-11, and 3-12. In a specific embodiment, the $V_L$ locus comprises a contiguous sequence of the human λ light chain locus that spans from Vλ3-12 to Vλ3-1. In one embodiment, the $V_L$ locus comprises at least 2, 3, 4, 5, 6, 7, 8, 9, 10, 11 or 12 hVλs. In a specific embodiment, the hVλs include 3-1, 4-3, 2-8, 3-9, 3-10, 2-11, and 3-12. In a specific embodiment, the $V_L$ locus comprises a contiguous sequence of the human λ locus that spans from Vλ3-12 to Vλ3-1. In one embodiment, the $V_L$ locus is at the endogenous κ locus. In a specific embodiment, the $V_L$ locus is at the endogenous κ locus and the endogenous λ light chain locus is deleted in part or completely. In one embodiment, the $V_L$ locus is at the endogenous λ locus. In a specific embodiment, the $V_L$ locus is at the endogenous locus and the endogenous κ locus is deleted in part or completely.

In one embodiment, the $V_L$ locus comprises 13 to 28 or more hVλs. In a specific embodiment, the hVλs include 2-14, 3-16, 2-18, 3-19, 3-21, 3-22, 2-23, 3-25, and 3-27. In a specific embodiment, the κ locus comprises a contiguous sequence of the human λ locus that spans from Vλ3-27 to Vλ3-1. In one embodiment, the $V_L$ locus is at the endogenous κ locus. In a specific embodiment, the $V_L$ locus is at the endogenous κ locus and the endogenous λ light chain locus is deleted in part or completely. In another embodiment, the $V_L$ locus is at the endogenous λ locus. In a specific embodiment, the $V_L$ locus is at the endogenous λ locus and the endogenous κ locus is deleted in part or completely.

In one embodiment, the $V_L$ locus comprises 29 to 40 hVλs. In a specific embodiment, the κ locus comprises a contiguous sequence of the human λ locus that spans from Vλ3-29 to Vλ3-1, and a contiguous sequence of the human λ locus that spans from Vλ5-52 to Vλ1-40. In a specific embodiment, all or substantially all sequence between hVλ1-40 and hVλ3-29 in the genetically modified mouse consists essentially of a human λ sequence of approximately 959 bp found in nature (e.g., in the human population) downstream of the hVλ1-40 gene segment (downstream of the 3' untranslated portion), a restriction enzyme site (e.g., PI-ScelI), followed by a human λ sequence of approximately 3,431 bp upstream of the hVλ3-29 gene segment found in nature. In one embodiment, the $V_L$ locus is at the endogenous mouse κ locus. In a specific embodiment, the $V_L$ locus is at the endogenous mouse κ locus and the endogenous mouse λ light chain locus is deleted in part or completely. In another embodiment, the $V_L$ locus is at the endogenous mouse λ locus. In a specific embodiment, the $V_L$ locus is at the endogenous mouse λ locus and the endogenous mouse κ locus is deleted in part or completely.

In one embodiment, the $V_L$ locus comprises at least one hJλ. In one embodiment, the $V_L$ locus comprises a plurality of hJλs. In one embodiment, the $V_L$ locus comprises at least 2, 3, 4, 5, 6, or 7 hJλ. In a specific embodiment, the $V_L$ locus comprises four hJλ. In a specific embodiment, the four hJλs are hJλ1, hJλ2, hJλ3, and hJλ7. In one embodiment, the V$_L$ locus is a κ locus. In a specific embodiment, the V$_L$ locus is at the endogenous κ locus and the endogenous λ light chain locus is deleted in part or completely. In one embodiment, the V$_L$ locus comprises one hJλ. In a specific embodiment, the one hJλ is hJλ1. In one embodiment, the V$_L$ locus is at the endogenous κ locus. In a specific embodiment, the V$_L$ locus is at the endogenous κ locus and the endogenous λ light chain locus is deleted in part or completely. In another embodiment, the V$_L$ locus is at the endogenous λ locus. In a specific embodiment, the V$_L$ locus is at the endogenous λ locus and the endogenous κ locus is deleted in part or completely.

In one embodiment, the V$_L$ locus comprises at least one hVλ, at least one hJλ, and a mouse Cκ gene. In one embodiment, the V$_L$ locus comprises at least one hVλ, at least one hJλ, and a mouse Cλ gene. In a specific embodiment, the mouse Cκ gene is Cκ2. In a specific embodiment, the mouse Cλ gene is at least 60%, at least 70%, at least 80%, at least 90%, at least 95%, 96%, 97%, 98%, or at least 99% identical to mouse Cλ2.

In one embodiment, the mouse comprises a replacement at the endogenous mouse κ locus of endogenous mouse Vκ gene segments with one or more hVλ gene segments, wherein the hVλ gene segments are operably linked to an endogenous mouse Cκ region gene, such that the mouse rearranges the human Vλ gene segments and expresses a reverse chimeric immunoglobulin light chain that comprises a human Vλ domain and a mouse Cκ. In one embodiment, 90-100% of unrearranged mouse Vκ gene segments are replaced with at least one unrearranged hVλ gene segment. In a specific embodiment, all or substantially all of the endogenous mouse Vκ gene segments are replaced with at least one unrearranged hVλ gene segment. In one embodiment, the replacement is with at least 12, at least 28, or at least 40 unrearranged hVλ gene segments. In one embodiment, the replacement is with at least 7 functional unrearranged hVλ gene segments, at least 16 functional unrearranged hVλ gene segments, or at least 27 functional unrearranged hVλ gene segments. In one embodiment, the mouse comprises a replacement of all mouse Jκ gene segments with at least one unrearranged hJλ gene segment. In one embodiment, the at least one unrearranged hJλ gene segment is selected from Jλ1, Jλ2, Jλ3, Jλ4, Jλ5, Jλ6, Jλ7, and a combination thereof. In a specific embodiment, the one or more hVλ gene segment is selected from a 3-1, 4-3, 2-8, 3-9, 3-10, 2-11, 3-12, 2-14, 3-16, 2-18, 3-19, 3-21, 3-22, 2-23, 3-25, 3-27, 1-40, 7-43, 1-44, 5-45, 7-46, 1-47, 5-48, 9-49, 1-50, 1-51, a 5-52 hVλ gene segment, and a combination thereof. In a specific embodiment, the at least one unrearranged hJλ gene segment is selected from Jλ1, Jλ2, Jλ3, Jλ7, and a combination thereof.

In one embodiment, the mouse comprises a replacement of endogenous mouse Vλ gene segments at the endogenous mouse λ locus with one or more human Vλ gene segments at the endogenous mouse λ locus, wherein the hVλ gene segments are operably linked to a mouse Cλ region gene, such that the mouse rearranges the hVλ gene segments and expresses a reverse chimeric immunoglobulin light chain that comprises a hVλ domain and a mouse Cλ. In a specific embodiment, the mouse Cλ gene is Cλ2. In a specific embodiment, the mouse Cλ gene is at least 60%, at least 70%, at least 80%, at least 90%, at least 95%, or at least 98% identical to mouse Cλ2. In one embodiment, 90-100% of unrearranged mouse Vλ gene segments are replaced with at least one unrearranged hVλ gene segment. In a specific embodiment, all or substantially all of the endogenous mouse Vλ gene segments are replaced with at least one unrearranged hVλ gene segment. In one embodiment, the replacement is with at least 12, at least 28, or at least 40 unrearranged hVλ gene segments. In one embodiment, the replacement is with at least 7 functional unrearranged hVλ gene segments, at least 16 functional unrearranged hVλ gene segments, or at least 27 functional unrearranged hVλ gene segments. In one embodiment, the mouse comprises a replacement of all mouse Jλ gene segments with at least one unrearranged hJλ gene segment. In one embodiment, the at least one unrearranged hJλ gene segment is selected from Jλ1, Jλ2, Jλ3, Jλ4, Jλ5, Jλ6, Jλ7, and a combination thereof. In a specific embodiment, the one or more hVλ gene segment is selected from a 3-1, 4-3, 2-8, 3-9, 3-10, 2-11, 3-12, 2-14, 3-16, 2-18, 3-19, 3-21, 3-22, 2-23, 3-25, 3-27, 1-40, 7-43, 1-44, 5-45, 7-46, 1-47, 5-48, 9-49, 1-50, 1-51, a 5-52 hVλ gene segment, and a combination thereof. In a specific embodiment, the at least one unrearranged hJλ gene segment is selected from Jλ1, Jλ2, Jλ3, Jλ7, and a combination thereof.

In one aspect, a genetically modified mouse is provided that comprises a human Vκ-Jκ intergenic region sequence located at an endogenous mouse κ light chain locus.

In one embodiment, the human Vκ-Jκ intergenic region sequence is at an endogenous κ light chain locus of a mouse that comprises a hVλ and hJλ gene segment, and the human Vκ-Jκ intergenic region sequence is disposed between the hVλ and hJλ gene segments. In a specific embodiment, the hVλ and hJλ gene segments are capable of recombining to form a functional human λ light chain variable domain in the mouse.

In one embodiment, a mouse is provided that comprises a plurality of hVλ's and one or more hJλ's, and the human Vκ-Jκ intergenic region sequence is disposed, with respect to transcription, downstream of the proximal or 3' most hVλ sequence and upstream or 5' of the first hJλ sequence.

In one embodiment, the human Vκ-Jκ intergenic region is a region located about 130 bp downstream or 3' of a human Vκ4-1 gene segment, about 130 bp downstream of the 3' untranslated region of the human Vκ4-1 gene segment, and spans to about 600 bp upstream or 5' of a human Jκ1 gene segment. In a specific embodiment, the human Vκ-Jκ intergenic region is about 22.8 kb in size. In one embodiment, the Vκ-Jκ intergenic region is about 90% or more, 91% or more, 92% or more, 93% or more, 94% or more, or about 95% or more identical with a human Vκ-Jκ intergenic region extending from the end of the 3' untranslated region of a human Vκ4-1 gene segment to about 600 bp upstream of a human Jκ1 gene segment. In one embodiment, the Vκ-Jκ intergenic region comprises SEQ ID NO:158. In a specific embodiment, the Vκ-Jκ intergenic region comprises a functional fragment of SEQ ID NO:158. In a specific embodiment, the Vκ-Jκ intergenic region is SEQ ID NO:158.

In one aspect, a non-human animal, a non-human cell (e.g., an ES cell or a pluripotent cell), a non-human embryo, or a non-human tissue are provided that comprise the recited human Vκ-Jκ intergenic region sequence, wherein the intergenic region sequence is ectopic. In a specific embodiment, the ectopic sequence is placed at a humanized endogenous non-human immunoglobulin locus. In one embodiment, the non-human animal is selected from a mouse, a rat, a hamster, a goat, a cow, a sheep, and a non-human primate.

In one aspect, an isolated nucleic acid construct is provided that comprises the recited human Vκ-Jκ intergenic region sequence. In one embodiment, the nucleic acid construct comprises targeting arms to target the human Vκ-Jκ intergenic region sequence to a mouse light chain locus. In a specific embodiment, the mouse light chain locus is a κ locus. In a specific embodiment, the targeting arms target the human Vκ-Jκ intergenic region to a modified endogenous mouse κ locus, wherein the targeting is to a position between a hVλ sequence and a hJλ sequence.

In one aspect, a genetically modified mouse is provided, wherein the mouse comprises no more than two light chain alleles, wherein the light chain alleles comprise (a) an unrearranged immunoglobulin human Vλ and a Jλ gene segment at an endogenous mouse light chain locus that comprises a mouse $C_L$ gene; and, (b) an unrearranged immunoglobulin $V_L$ and a $J_L$ gene segment at an endogenous mouse light chain locus that comprises a mouse $C_L$ gene.

In one embodiment, the endogenous mouse light chain locus is a κ locus. In another embodiment, the endogenous mouse light chain locus is a λ locus.

In one embodiment, the no more than two light chain alleles are selected from a κ allele and a λ allele, two κ alleles, and two λ alleles. In a specific embodiment, one of the two light chain alleles is a λ allele that comprises a Cκ gene.

In one embodiment, the mouse comprises one functional immunoglobulin light chain locus and one nonfunctional light chain locus, wherein the functional light chain locus comprises an unrearranged immunoglobulin human Vλ and a Jλ gene segment at an endogenous mouse κ light chain locus that comprises a mouse Cκ gene.

In one embodiment, the mouse comprises one functional immunoglobulin light chain locus and one nonfunctional light chain locus, wherein the functional light chain locus comprises an unrearranged immunoglobulin human Vλ and a Jλ gene segment at an endogenous mouse λ light chain locus that comprises a mouse Cλ gene. In one embodiment, the Cλ gene is Cλ2. In a specific embodiment, the mouse Cλ gene is at least 60%, at least 70%, at least 80%, at least 90%, at least 95%, or at least 98% identical to mouse Cλ2.

In one embodiment, the mouse further comprises at least one immunoglobulin heavy chain allele. In one embodiment, the at least one immunoglobulin heavy chain allele comprises a human $V_H$ gene segment, a human $D_H$ gene segment, and a human $J_H$ gene segment at an endogenous mouse heavy chain locus that comprises a human heavy chain gene that expresses a human/mouse heavy chain. In a specific embodiment, the mouse comprises two immunoglobulin heavy chain alleles, and the mouse expresses a human/mouse heavy chain.

In one embodiment, the mouse comprises a first light chain allele that comprises an unrearranged hVκ and an unrearranged hJκ, at an endogenous mouse κ locus that comprises an endogenous Cκ gene; and a second light chain allele that comprises an unrearranged hVλ and an unrearranged hJλ at an endogenous mouse κ locus that comprises an endogenous Cκ gene. In a specific embodiment, the first and the second light chain alleles are the only functional light chain alleles of the genetically modified mouse. In a specific embodiment, the mouse comprises a nonfunctional λ locus. In one embodiment, the genetically modified mouse does not express a light chain that comprises a λ constant region.

In one embodiment, the mouse comprises a first light chain allele that comprises an unrearranged hVκ and an unrearranged hJκ, at an endogenous mouse κ locus that comprises an endogenous Cκ gene; and a second light chain allele that comprises an unrearranged hVλ and an unrearranged hJλ, at an endogenous mouse λ locus that comprises an endogenous Cλ gene. In a specific embodiment, the first and the second light chain alleles are the only functional light chain alleles of the genetically modified mouse. In one embodiment, the endogenous Cλ gene is Cλ2. In a specific embodiment, the mouse Cλ gene is at least 60%, at least 70%, at least 80%, at least 90%, at least 95%, or at least 98% identical to mouse Cλ2.

In one embodiment, the mouse comprises six immunoglobulin alleles, wherein the first allele comprises an unrearranged immunoglobulin Vλ and Jλ gene segment at an endogenous mouse κ light chain locus that comprises a mouse Cκ gene, the second comprises an unrearranged immunoglobulin Vκ and Jκ gene segment at an endogenous mouse κ light chain locus that comprises a mouse Cκ gene, the third comprises an unrearranged immunoglobulin Vλ and Jλ gene segment at an endogenous mouse λ light chain locus that comprises a mouse Cλ gene, the fourth and fifth each independently comprise an unrearranged $V_H$ and $D_H$ and $J_H$ gene segment at an endogenous mouse heavy chain locus that comprises a mouse heavy chain gene, and the sixth comprises either (a) an unrearranged immunoglobulin Vλ and Jλ gene segment at an endogenous mouse λ light chain locus that comprises a mouse Cλ gene, (b) a λ locus that is nonfunctional, or (c) a deletion in whole or in part of the λ locus.

In one embodiment, the first allele comprises an unrearranged hVλ and hJλ. In one embodiment, the second allele comprises an unrearranged hVκ and hJκ. In one embodiment, the third allele comprises an unrearranged hVλ and hJλ. In one embodiment, the fourth and fifth each independently comprise an unrearranged $hV_H$ and $hD_H$ and $hJ_H$. In one embodiment, the sixth allele comprises an endogenous mouse λ locus that is deleted in whole or in part.

In one embodiment, the mouse comprises six immunoglobulin alleles, wherein the first allele comprises an unrearranged immunoglobulin Vλ and Jλ gene segment at an endogenous mouse λ light chain locus that comprises a mouse Cλ gene, the second comprises an unrearranged immunoglobulin Vλ and Jλ gene segment at an endogenous mouse λ light chain locus that comprises a mouse Cλ gene, the third comprises an unrearranged immunoglobulin Vκ and Jκ gene segment at an endogenous mouse κ light chain locus that comprises a mouse Cκ gene, the fourth and fifth each independently comprise an unrearranged $V_H$ and $D_H$ and $J_H$ gene segment at an endogenous mouse heavy chain locus that comprises a mouse heavy chain gene, and the sixth comprises either (a) an unrearranged immunoglobulin Vκ and Jκ gene segment at an endogenous mouse κ light chain locus that comprises a mouse Cκ gene, (b) a κ locus that is nonfunctional, or (c) a deletion of one or more elements of the κ locus.

In one embodiment, the first allele comprises an unrearranged hVλ and hJλ gene segment. In one embodiment, the second allele comprises an unrearranged hVλ and hJλ gene segment. In one embodiment, the third allele comprises an unrearranged hVκ and hJκ gene segment. In one embodiment, the fourth and fifth each independently comprise an unrearranged $hV_H$ and $hD_H$ and $hJ_H$ gene segment. In one embodiment, the sixth allele comprises an endogenous mouse κ locus that is functionally silenced.

In one embodiment, the genetically modified mouse comprises a B cell that comprises a rearranged antibody gene comprising a rearranged hVλ domain operably linked to a mouse $C_L$ domain. In one embodiment, the mouse $C_L$ domain is selected from a mouse Cκ and a mouse Cλ domain. In a specific embodiment, the mouse Cλ domain is derived from a Cλ2 gene. In a specific embodiment, the mouse Cλ domain is derived from a Cλ domain that is at least 60%, at least 70%, at least 80%, at least 90%, at least 95%, or at least 98% identical to mouse Cλ2.

In one aspect, a genetically modified mouse is provided that expresses a Vλ region on a $C_L$ that is a Cκ. In one aspect, a genetically modified mouse is provided that expresses a hVλ region on a $C_L$ selected from a human Cκ, a human Cλ, or a mouse Cκ. In one aspect, a genetically modified mouse is provided that expresses a hVλ region on a mouse Cκ.

In one embodiment, about 10-50% of the splenocytes of the mouse are B cells (i.e., CD19-positive), or which about 9-28% express an immunoglobulin light chain comprising a hVλ domain fused to a mouse Cκ domain.

In a specific embodiment, about 23-34% of the splenocytes of the mouse are B cells (i.e., CD19-positive), or which about 9-11% express an immunoglobulin light chain comprising a hVλ domain fused to a mouse Cκ domain.

In a specific embodiment, about 19-31% of the splenocytes of the mouse are B cells (i.e., CD19-positive), or which about 9-17% express an immunoglobulin light chain comprising a hVλ domain fused to a mouse Cκ domain.

In a specific embodiment, about 21-38% of the splenocytes of the mouse are B cells (i.e., CD19-positive), or which about 24-27% express an immunoglobulin light chain comprising a hVλ domain fused to a mouse Cκ domain.

In a specific embodiment, about 10-14% of the splenocytes of the mouse are B cells (i.e., CD19-positive), or which about 9-13% express an immunoglobulin light chain comprising a hVλ domain fused to a mouse Cκ domain.

In a specific embodiment, about 31-48% of the splenocytes of the mouse are B cells CD19-positive), or which about 15-21% express an immunoglobulin light chain comprising a hVλ domain fused to a mouse Cκ domain. In a specific embodiment, about 30-38% of the splenocytes of the mouse are B cells (i.e., CD19-positive), of which about 33-48% express an immunoglobulin light chain comprising a hVλ domain fused to a mouse Cκ domain.

In one embodiment, about 52-70% of the bone marrow of the mouse are B cells (i.e., CD19-positive), or which about 31-47% of the immature B cells (i.e., CD19-positive/B220-intermediate positive/IgM-positive) express an immunoglobulin light chain comprising a hVλ domain fused to a mouse Cκ domain.

In one embodiment, about 60% of the bone marrow of the mouse are B cells (i.e., CD19-positive), or which about 38.3% of the immature B cells (i.e., CD19-positive/B220-intermediate positive/IgM-positive) express an immunoglobulin light chain comprising a hVλ domain fused to a mouse Cκ domain.

In one embodiment, the mouse expresses an antibody comprising a light chain that comprises a variable domain derived from a human V and a human J gene segment, and a constant domain derived from a mouse constant region gene. In one embodiment, the mouse constant region gene is a Cκ gene. In another embodiment, the mouse constant region gene is a Cλ gene. In a specific embodiment, the Cλ region is Cλ2. In a specific embodiment, the mouse Cλ gene is derived from a Cλ gene that is at least 60%, at least 70%, at least 80%, at least 90%, at least 95%, or at least 98% identical to mouse Cλ2. In a specific embodiment, the antibody further comprises a heavy chain comprising a variable domain derived from a human V, a human D and a human J gene segment, and a heavy chain constant domain derived from a mouse heavy chain constant region gene. In one embodiment, the mouse heavy chain constant region gene comprises a hinge-CH2-CH3 sequence of a heavy chain constant domain. In another embodiment, the mouse heavy chain constant region gene comprises a CH1-hinge-CH2-CH3 sequence of a heavy chain constant domain. In another embodiment, the mouse heavy chain constant region gene comprises a CH1-CH2-CH3-CH4 sequence of a heavy chain constant domain. In another embodiment, the mouse heavy chain constant region gene comprises a CH2-CH3-CH4 sequence of a heavy chain constant domain.

In one embodiment, the mouse expresses an antibody comprising a light chain that comprises a rearranged human Vλ-Jλ sequence and a mouse Cκ sequence. In one embodiment, the rearranged human Vλ-Jλ sequence is derived from a rearrangement of hVλ gene segments selected from a 3-1, 4-3, 2-8, 3-9, 3-10, 2-14, 3-19, 2-23, 3-25, 1-40, 7-43, 1-44, 5-45, 7-46, 1-47, 9-49, and a 1-51 gene segment. In one embodiment, the rearranged human Vλ-Jλ sequence is derived from a rearrangement of hJλ gene segments selected from Jλ1, Jλ2, Jλ3, and a Jλ7 gene segment.

In one embodiment, the mouse expresses an antibody comprising a light chain that comprises a rearranged immunoglobulin λ light chain variable region comprising a human Vλ/Jλ sequence selected from 3-1/1, 3-1/7, 4-3/1, 4-3/7, 2-8/1, 3-9/1, 3-10/1, 3-10/3, 3-10/7, 2-14/1, 3-19/1, 2-23/1, 3-25/1, 1-40/1, 1-40/2, 1-40/3, 1-40/7, 7-43/1, 7-43/3, 1-44/1, 1-44/7, 5-45/1, 5-45/2, 5-45/7, 7-46/1, 7-46/2, 7-46/7, 9-49/1, 9-49/2, 9-49/7 and 1-51/1. In a specific embodiment, the B cell expresses an antibody comprising a human immunoglobulin heavy chain variable domain fused with a mouse heavy chain constant domain, and a human immunoglobulin λ light chain variable domain fused with a mouse κ light chain constant domain.

In one aspect, a mouse is provided that expresses an antibody comprising (a) a heavy chain comprising a heavy chain variable domain derived from an unrearranged human heavy chain variable region gene segment, wherein the heavy chain variable domain is fused to a mouse heavy chain constant ($C_H$) region; and, (b) a light chain comprising a light chain variable domain derived from an unrearranged hVλ and a hJλ, wherein the light chain variable domain is fused to a mouse $C_L$ region.

In one embodiment, the mouse comprises (i) a heavy chain locus that comprises a replacement of all or substantially all functional endogenous mouse V, D and J gene segments with all or substantially all functional human V, D, and J gene segments, a mouse $C_H$ gene, (ii) a first κ light chain locus comprising a replacement of all or substantially all functional endogenous mouse Vκ and Jκ gene segments with all, substantially all, or a plurality of, functional hVλ and hJλ gene segments, and a mouse Cl gene, (iii) a second κ light chain locus comprising a replacement of all or substantially all functional endogenous mouse Vκ and Jκ gene segments with all, substantially all, or a plurality of, functional hVκ and hJκ gene segments, and a mouse Cκ gene. In one embodiment, the mouse does not express an antibody that comprises a Cλ region. In one embodiment, the mouse comprises a deletion of a Cλ gene and/or a Vλ and/or a Jλ gene segment. In one embodiment, the mouse comprises a nonfunctional λ light chain locus. In a specific embodiment, the λ light chain locus is deleted in whole or in part.

In one embodiment, the mouse comprises (i) a heavy chain locus that comprises a replacement of all or substantially all functional endogenous mouse V, D and J gene segments with all or substantially all functional human V, D, and J gene segments, a mouse $C_H$ gene, (ii) a first λ light chain locus comprising a replacement of all or substantially all functional endogenous mouse Vλ and Jλ gene segments with all, substantially all, or a plurality of, functional hVλ and hJλ gene segments, and a mouse Cλ gene, (iii) a second λ light chain locus comprising a replacement of all or substantially all functional endogenous mouse Vλ and Jλ gene segments with all, substantially all, or a plurality of, functional hVλ and hJλ gene segments, and a mouse Cλ gene. In a specific embodiment, the mouse Cλ gene is Cλ2. In a specific embodiment, the mouse Cλ gene is derived from a Cλ gene that is at least 60%, at least 70%, at least 80%, at least 90%, at least 95%, or at least 98% identical to mouse Cλ2.

In one embodiment, the mouse comprises a deletion of a Cκ gene and/or a Vλ and/or a Jλ gene segment. In one embodiment, the mouse comprises a nonfunctional κ light chain locus.

In one aspect, a genetically modified mouse that expresses an antibody is provided, wherein greater than 10%, greater than 15%, greater than 20%, greater than 25%, greater than 30%, greater than 35%, greater than 40%, greater than 60%, greater than 70%, greater than 80%, or greater than 90% of total IgG antibody produced by the mouse comprises a λ-derived variable domain, and wherein the mouse expresses antibodies comprising a κ-derived variable domain fused with a mouse Cκ region. In specific embodiments, about 15-40%, 20-40%, 25-40%, 30-40%, or 35-40% of total antibody produced by the mouse comprises a λ-derived variable domain.

In one embodiment, the λ-derived variable domain is derived from a hVλ and a hJλ. In one embodiment, the λ-derived variable domain is in a light chain that comprises a mouse Cκ region. In a specific embodiment, the λ-derived variable region is in a light chain that comprises a mouse Cλ region. In another specific embodiment, the Cλ region is a Cλ2 region. In one embodiment, the κ-derived variable domain is derived from a hVλ and a hJκ, and in a specific embodiment is in a light chain that comprises a mouse Cκ region.

In one aspect, an isolated DNA construct is provided that comprises an upstream homology arm and a downstream homology arm, wherein the upstream and the downstream homology arms target the construct to a mouse κ locus, and the construct comprises a functional unrearranged hVλ segment and a functional unrearranged hJλ segment, and a selection or marker sequence.

In one aspect, an isolated DNA construct is provided, comprising, from 5' to 3' with respect to the direction of transcription, a targeting arm for targeting a mouse λ sequence upstream of mouse Vλ2, a selection cassette flanked 5' and 3' with recombinase recognition sites, and a targeting arm for targeting a mouse λ sequence 3' of mouse Jλ2. In one embodiment, the selection cassette is a Frt'ed Hyg-TK cassette. In one embodiment, the 3' targeting arm comprises mouse Cλ2, Jλ4, Cλ4, and mouse enhancer 2.4.

In one aspect, an isolated DNA construct is provided, comprising, from 5' to 3' with respect to the direction of transcription, a targeting arm for targeting the mouse λ locus 5' with respect to Vλ1, a selection cassette flanked 5' and 3' with recombinase recognition sites, and a 3' targeting arm for targeting a mouse λ sequence 3' with respect to mouse Cλ1. In one embodiment, the selection cassette is a loxed neomycin cassette. In one embodiment, the 3' targeting arm comprises the mouse λ 3' enhancer and mouse λ 3' enhancer 3.1.

In one aspect, an isolated DNA construct is provided, comprising from 5' to 3' with respect to the direction of transcription, a targeting arm for targeting the mouse λ locus 5' with respect to Vλ2, a selection cassette flanked 5' and 3' with recombinase recognition sites, and a 3' targeting arm for targeting a mouse λ sequence 3' with respect to mouse Jλ2 and 5' with respect to mouse Cλ2. In one embodiment, the selection cassette is a Frt'ed hygromycin-TK cassette. In one embodiment, the 3' targeting arm comprises the mouse Cλ2-Jλ4-Cλ4 gene segments and mouse λ enhancer 2.4.

In one aspect, an isolated DNA construct is provided, comprising, from 5' to 3' with respect to the direction of transcription, a targeting arm for targeting the mouse λ locus 5' with respect to Vλ2, a selection cassette flanked 5' and 3' with recombinase recognition sites, a human genomic fragment comprising a contiguous region of the human λ light chain locus from hVλ3-12 downstream to the end of hJλ1, and a 3' targeting arm for targeting a mouse λ sequence 3' with respect to mouse Jλ2. In one embodiment, the selection cassette is a Frt'ed neomycin cassette. In one embodiment, the 3' targeting arm comprises the mouse Cλ2-Jλ4-Cλ4 gene segments and mouse λ enhancer 2.4.

In one aspect, an isolated DNA construct is provided, comprising a contiguous region of the human λ light chain locus from hVλ3-12 downstream to the end of hJλ1.

In one aspect, an isolated DNA construct is provided, comprising, from 5' to 3' with respect to the direction of transcription, a targeting arm for targeting the mouse λ locus 5' with respect to Vλ2, a selection cassette flanked 5' and 3' with recombinase recognition sites and a human genomic fragment comprising a contiguous region of the human λ light chain locus from hVλ3-27 downstream to the end of hVλ2-8. In one embodiment, the selection cassette is a Frt'ed hygromycin cassette. In one embodiment, the human genomic fragment comprises a 3' targeting arm. In a specific embodiment, the 3' targeting arm comprises about 53 kb of the human λ light chain locus from hVλ3-12 downstream to the end of hVλ2-8.

In one aspect, an isolated DNA construct is provided, comprising a contiguous region of the human λ light chain locus from hVλ3-27 downstream to the end of hVλ3-12.

In one aspect, an isolated DNA construct is provided, comprising, from 5' to 3' with respect to the direction of transcription, a targeting arm for targeting the mouse λ locus 5' with respect to Vλ2, a selection cassette flanked 5' and 3' with recombinase recognition sites, a first human genomic fragment comprising a contiguous region of the human λ light chain locus from hVλ5-52 downstream to the end of hVλ1-40, a restriction enzyme site, and a second human genomic fragment comprising a contiguous region of the human λ light chain locus from hVλ3-29 downstream to the end of hVλ82K. In one embodiment, the selection cassette is a Frt'ed neomycin cassette. In one embodiment, the restriction enzyme site is a site for a homing endonuclease. In a specific embodiment, the homing endonuclease is PI-Scel. In on embodiment, the second human genomic fragment is a 3' targeting arm. In a specific embodiment, the 3' targeting arm comprises about 27 kb of the human λ light chain locus from hVλ3-29 downstream to the end of hVλ82K.

In one aspect, an isolated DNA construct is provided, comprising a contiguous region of the human λ light chain locus from hVλ5-52 downstream to the end of hVλ1-40.

In one aspect, an isolated DNA construct is provided, comprising, from 5' to 3' with respect to the direction of transcription, a targeting arm for targeting the mouse κ locus 5' with respect to the endogenous Vκ gene segments, two juxtaposed recombinase recognition sites, a selection cassette 3' to the juxtaposed recombinase recognition sites, and a 3' targeting arm for targeting a mouse κ sequence 5' with respect to the κ light chain variable gene segments. In one embodiment, the juxtaposed recombinase recognition sites are in opposite orientation with respect to one another. In a specific embodiment, the recombinase recognition sites are different. In another specific embodiment, the recombinase recognition sites are a loxP site and a lox511 site. In one embodiment, the selection cassette is a neomycin cassette.

In one aspect, an isolated DNA construct is provided, comprising, from 5' to 3' with respect to the direction of transcription, a targeting arm for targeting the mouse κ locus 5' with respect to the mouse Jκ gene segments, a selection cassette, a recombinase recognition site 3' to the selection cassette, and a 3' targeting arm for targeting a mouse κ sequence 3' with respect to the mouse Jκ gene segments and 5' to the mouse κ intronic enhancer. In one embodiment, the selection cassette is a hygromycin-TK cassette. In one embodiment, the recombinase recognition site is in the same direction with respect to transcription as the selection cassette. In a specific embodiment, the recombinase recognition site is a loxP site.

In one aspect, an isolated DNA construct is provided, comprising, from 5' to 3' with respect to the direction of transcription, a first mouse genomic fragment comprising sequence 5' of the endogenous mouse Vκ gene segments, a first recombinase recognition site, a second recombinase recognition site, and a second mouse genomic fragment comprising sequence 3' of the endogenous mouse Jκ gene segments and 5' of the mouse κ intronic enhancer.

In one aspect, a genetically modified mouse is provided, wherein the genetic modification comprises a modification with one or more of the DNA constructs described above or herein.

In one aspect, use of an isolated DNA construct to make a mouse as described herein is provided. In one aspect, use of an isolated DNA construct as described herein in a method for making an antigen-binding protein is provided.

In one aspect, a non-human stem cell is provided that comprises a targeting vector that comprises a DNA construct as described above and herein. In one aspect, a non-human stem cell is provided, wherein the non-human stem cell is derived from a mouse described herein.

In one embodiment, the non-human stem cell is an embryonic stem (ES) cell. In a specific embodiment, the ES cell is a mouse ES cell.

In one aspect, use of a non-human stem cell as described herein to make a mouse as described herein is provided. In one aspect, use of a non-human stem cell as described herein to make an antigen-binding protein is provided.

In one aspect, a mouse embryo is provided, wherein the mouse embryo comprises a genetic modification as provided herein. In one embodiment, a host mouse embryo that comprises a donor ES cell is provided, wherein the donor ES cell comprises a genetic modification as described herein. In one embodiment, the mouse embryo is a pre-morula stage embryo. In a specific embodiment, the pre-morula stage embryo is a 4-cell stage embryo or an 8-cell stage embryo. In another specific embodiment, the mouse embryo is a blastocyst.

In one aspect, use of a mouse embryo as described herein to make a mouse as described herein is provided. In one aspect, use of a mouse embryo as described herein to make an antigen-binding protein is provided.

In one aspect, a non-human cell is provided, wherein the non-human cell comprises a rearranged immunoglobulin light chain gene sequence derived from a genetically modified mouse as described herein. In one embodiment, the cell is a B cell. In one embodiment, the cell is a hybridoma. In one embodiment, the cell encodes an immunoglobulin light chain variable domain and/or an immunoglobulin heavy chain variable domain that is somatically mutated.

In one aspect, a non-human cell is provided, wherein the non-human cell comprises a rearranged immunoglobulin light chain gene sequence derived from a genetically modified mouse as described herein. In one embodiment, the cell is a B cell. In one embodiment, the cell is a hybridoma. In one embodiment, the cell encodes an immunoglobulin light chain variable domain and/or an immunoglobulin heavy chain variable domain that is somatically mutated.

In one aspect, use of a non-human cell as described herein to make a non-human animal as described herein is provided. In one aspect, use of a non-human cell as described herein to make an antigen-binding protein is provided. In one embodiment, the non-human animal is selected from a mouse, a rat, a hamster, a sheep, a goat, a cow, and a non-human primate.

In one aspect, a mouse B cell is provided that expresses an immunoglobulin light chain that comprises (a) a variable region derived from a hVλ gene segment and a hJλ gene segment; and, (b) a mouse $C_L$ gene. In one embodiment, the mouse $C_L$ gene is selected from a Cκ and a Cλ gene. In a specific embodiment, the Cλ gene is Cλ2. In a specific embodiment, the mouse Cλ gene is derived from a Cλ gene that is at least 60%, at least 70%, at least 80%, at least 90%, at least 95%, or at least 98% identical to mouse Cλ2. In one embodiment, the mouse B cell further expresses a cognate heavy chain that comprises (c) a variable region derived from a hV$_H$, a hD$_H$, and (d) a hJ$_H$ segment. In one embodiment, the B cell does not comprise a rearranged λ gene. In another embodiment, the B cell does not comprise a rearranged κ gene.

In one aspect, a method for making an antibody in a genetically modified non-human animal is provided, comprising: (a) exposing a genetically modified non-human animal to an antigen, wherein the animal has a genome comprising at least one hVλ and at least one hJλ at an endogenous light chain locus, wherein the endogenous light chain locus comprises a non-human $C_L$ gene; (b) allowing the genetically modified animal to develop an immune response to the antigen; and, (c) isolating from the animal of (b) an antibody that specifically recognizes the antigen, or isolating from the animal of (b) a cell comprising an immunoglobulin domain that specifically recognizes the antigen, wherein the antibody comprises a light chain derived from a hVλ, a hJλ and an animal $C_L$ gene. In a specific embodiment, the non-human $C_L$ gene is a mouse Cκ gene. In one embodiment, the non-human animal is selected from a mouse, a rat, a hamster, a rabbit, a sheep, a goat, a cow, and a non-human primate.

In one embodiment, a method for making an antibody in a genetically modified non-human animal is provided, comprising: (a) exposing a genetically modified animal to an antigen, wherein the animal has a genome comprising at least one hVλ at an endogenous κ locus and at least one hJλ at the κ locus, wherein the κ locus comprises a non-human Cκ gene; (b) allowing the genetically modified animal to develop an immune response to the antigen; and, (c) isolating from the animal of (b) an antibody that specifically recognizes the antigen, or isolating from the mouse of (b) a cell comprising an immunoglobulin domain that specifically recognizes the antigen, wherein the antibody comprises a light chain derived from a hVλ, a hJλ and a non-human Cκ gene.

In one embodiment, the κ light chain constant gene is selected from a human Cκ gene and a mouse Cκ gene.

In one aspect, a method for making an antibody in a genetically modified non-human animal is provided, comprising: (a) exposing a genetically modified non-human animal to an antigen, wherein the animal has a genome comprising at least one hVλ at a λ light chain locus and at least one Jλ at the λ light chain locus, wherein the λ light chain locus comprises a non-human Cλ gene; (b) allowing the genetically modified animal to develop an immune response to the antigen; and, (c) isolating from the animal of (b) an antibody that specifically recognizes the antigen, or isolating from the animal of (b) a cell comprising an immunoglobulin domain that specifically recognizes the antigen, or identifying in the animal of B a nucleic acid sequence encoding a heavy and/or light chain variable domain that binds the antigen, wherein the antibody comprises a light chain derived from a hVλ, a hJλ and a non-human Cλ gene. In one embodiment, the non-human animal is selected from a mouse, a rat, a hamster, a sheep, a goat, a cow, and a non-human primate.

In one embodiment, the λ light chain constant gene is selected from a human Cλ gene and a non-human Cλ gene. In one embodiment, the λ light chain constant gene is a human CX gene. In a specific embodiment, the human Cλ gene is selected from Cλ1, Cλ2, Cλ3 and Cλ7. In one embodiment, the λ light chain constant gene is a mouse or rat Cλ gene. In a specific embodiment, the mouse Cλ gene is selected from Cλ1, Cλ2 and Cλ3. In a more specific embodiment, the mouse Cλ gene is Cλ2. In another specific embodiment, the mouse Cλ gene is derived from a Cλ gene that is at least 60%, at least 70%, at least 80%, at least 90%, at least 95%, or at least 98% identical to mouse Cλ2.

In one aspect, a method for making a rearranged antibody gene in a genetically modified non-human animal is provided, comprising: (a) exposing a genetically modified non-human animal to an antigen, wherein the genetic modification comprises a hVλ and a hJλ at an endogenous light chain locus, wherein the endogenous light chain locus comprises a non-human $C_L$ gene or functional fragment thereof; and, (b) identifying a rearranged immunoglobulin gene in said non-human animal, wherein the rearranged immunoglobulin gene comprises a λ light chain variable region gene segment and a $C_L$ gene or functional fragment thereof.

In one embodiment, the method further comprises cloning a nucleic acid sequence encoding a heavy and/or light chain variable region from the animal, wherein the heavy and/or light chain variable region is from an antibody that comprises a human Vλ and a mouse $C_L$.

In one embodiment, the mouse $C_L$ gene or functional fragment thereof is selected from a human $C_L$ gene and a mouse $C_L$ gene, or functional fragment thereof.

In one embodiment, a method for making a rearranged antibody gene in a genetically modified non-human animal is provided, comprising: (a) exposing a genetically modified non-human animal to an antigen, wherein the genetic modification comprises a hVλ and a hJλ at a κ light chain locus, wherein the κ light chain locus comprises a non-human Cκ gene or functional fragment thereof; and, (b) identifying a rearranged immunoglobulin gene in said animal, wherein the rearranged immunoglobulin gene comprises a λ light chain variable region gene segment and a Cκ gene or functional fragment thereof.

In one embodiment, the κ light chain constant gene or functional fragment thereof is selected from a human Cκ gene and a non-human (e.g., mouse or rat) Cκ gene, or a functional fragment thereof.

In one embodiment, the method further comprises cloning a nucleic acid sequence encoding a heavy and/or light chain variable region from the animal, wherein the heavy and/or light chain variable region is from an antibody that comprises a human Vλ and a non-human (e.g., mouse or rat) Cκ.

In one embodiment, a method for making a rearranged antibody gene in a genetically modified non-human animal is provided, comprising: (a) exposing a genetically modified non-human animal to an antigen, wherein the genetic modification comprises a hVλ and a hJκ at a non-human κ light chain locus, wherein the λ light chain locus comprises a non-human Cλ gene or functional fragment thereof; and, (b) identifying a rearranged immunoglobulin gene in said animal, wherein the rearranged immunoglobulin gene comprises a λ light chain variable region gene segment and a Cλ gene or functional fragment thereof.

In one embodiment, the λ light chain constant gene or functional fragment thereof is selected from a human Cλ gene and a mouse or rat Cλ gene, or a functional fragment thereof. In a specific embodiment, the λ light chain constant gene is a mouse or rat Cλ gene, or a functional fragment thereof.

In one embodiment, the method further comprises cloning a nucleic acid sequence encoding a heavy and/or light chain variable region from the animal, wherein the heavy and/or light chain variable region is from an antibody that comprises a human Vλ and a non-human (e.g., mouse or rat) Cλ.

In one aspect, a method for making an antibody is provided, comprising exposing a non-human animal as described herein to an antigen, allowing the animal to mount an immune response that comprises making an antibody that specifically binds the antigen, identifying a rearranged nucleic acid sequence in the animal that encodes heavy chain and a rearranged nucleic acid sequence in the animal that encodes a cognate light chain variable domain sequence of an antibody, wherein the antibody specifically binds the antigen, and employing the nucleic acid sequences of the heavy and light chain variable domains fused to human constant domains to make a desired antibody, wherein the desired antibody comprises a light chain that comprises a Vλ domain fused to a $C_L$ domain. In one embodiment, the Vλ domain is human and the $C_L$ domain is a human or mouse or rat Cλ domain. In one embodiment, the Vλ domain is mouse or rat and the $C_L$ domain is a human or mouse Cκ domain.

In one embodiment, a method for making an antibody is provided, comprising exposing a non-human animal as described herein to an antigen, allowing the animal to mount an immune response that comprises making an antibody that specifically binds the antigen, identifying a rearranged nucleic acid sequence in the mouse that encodes a heavy chain and a rearranged nucleic acid sequence in the animal that encodes a cognate light chain variable domain sequence of an antibody, wherein the antibody specifically binds the antigen, and employing the nucleic acid sequences of the heavy and light chain variable domains fused to nucleic acid sequences of human constant domains to make a desired antibody, wherein the desired antibody comprises a light chain that comprises a Vλ domain fused to a Cκ domain.

In one embodiment, a method for making an antibody is provided, comprising exposing a non-human animal as described herein to an antigen, allowing the animal to mount an immune response that comprises making an antibody that specifically binds the antigen, identifying a rearranged nucleic acid sequence in the animal that encodes a heavy chain variable domain and a rearranged nucleic acid sequence that encodes a cognate light chain variable domain sequence of an antibody, wherein the antibody specifically binds the antigen, and employing the nucleic acid sequences fused to nucleic acid sequences that encode a human heavy chain constant domain and a human light chain constant domain to make an antibody derived from human sequences, wherein the antibody that specifically binds the antigen comprises a light chain that comprises a human Vλ domain fused to a non-human (e.g., mouse or rat) Cλ region.

In one embodiment, the Cλ region is mouse, and in one embodiment is selected from Cλ1, Cλ2 and Cλ3. In a specific embodiment, the mouse Cλ region is Cλ2.

In one aspect, a method for making a rearranged antibody light chain variable region gene sequence is provided, comprising (a) exposing a non-human animal as described herein to an antigen; (b) allowing the animal to mount an immune response; (c) identifying a cell in the animal that comprises a nucleic acid sequence that encodes a rearranged human Vλ domain sequence fused with a non-human $C_L$ domain, wherein the cell also encodes a cognate heavy chain comprising a human $V_H$ domain and a non-human $C_H$ domain, and wherein the cell expresses an antibody that binds the antigen; (d) cloning from the cell a nucleic acid sequence encoding the human Vλ domain and a nucleic acid sequence encoding the cognate human $V_H$ domain; and, (e) using the cloned nucleic acid sequence encoding the human Vλ domain and the cloned nucleic acid sequence encoding the cognate human $V_H$ domain to make a fully human antibody. In one embodiment, the non-human animal and non-human domains are selected from mouse and rat.

In one embodiment, a method for making a rearranged antibody light chain variable region gene sequence is provided, comprising (a) exposing a non-human animal as described in this disclosure to an antigen; (b) allowing the animal to mount an immune response; (c) identifying a cell in the animal that comprises a nucleic acid sequence that encodes a rearranged human Vλ domain sequence contiguous on the same nucleic acid molecule with a nucleic acid sequence encoding a Cκ domain of the non-human animal, wherein the cell also encodes a cognate heavy chain comprising a human $V_H$ domain and a $C_H$ domain of the non-human animal, and wherein the cell expresses an antibody that binds the antigen; (d) cloning from the cell a nucleic acids sequence encoding the human Vλ domain and a nucleic acid sequence encoding the cognate human $V_H$ domain; and, (e) using the cloned nucleic acid sequence encoding the human Vλ domain and the cloned nucleic acid sequence encoding the cognate human $V_H$ domain to make a fully human antibody.

In one embodiment, a method for making a rearranged antibody light chain variable region gene sequence is provided, comprising (a) exposing a non-human animal as described herein to an antigen; (b) allowing the animal to mount an immune response to the antigen; (c) identifying a cell in the animal that comprises DNA that encodes a rearranged human Vλ domain sequence fused with a non-human Cλ domain of the animal, wherein the cell also encodes a cognate heavy chain comprising a human $V_H$ domain and a non-human $C_H$ domain of the animal, and wherein the cell expresses an antibody that binds the antigen; (d) cloning from the cell a nucleic acid sequence encoding the rearranged human Vλ domain and a nucleic acid sequence encoding the cognate human $V_H$ domain; and, (e) using the cloned nucleic acid sequence encoding the human Vλ domain and the cloned nucleic acid sequence encoding the cognate human $V_H$ domain to make a fully human antibody. In one embodiment, the non-human animal is mouse and the Cλ domain is mouse Cλ2. In a specific embodiment, the mouse Cλ domain is derived from a Cλ gene that is at least 60%, at least 70%, at least 80%, at least 90%, at least 95%, or at least 98% identical to mouse Cλ2.

In one aspect, a genetically modified non-human animal is provided that expresses a human λ-derived light chain fused to an endogenous light chain constant region ($C_L$), wherein the animal, upon immunization with antigen, makes an antibody comprising a human Vλ domain fused to a non-human $C_L$ domain of the animal. In one embodiment, the non-human $C_L$ domain is selected from a Cκ domain and a Cλ domain. In one embodiment, the $C_L$ domain is a Cκ domain. In one embodiment, the animal is a mouse. In one embodiment, the mouse $C_L$ domain is a Cλ domain. In a specific embodiment, the Cλ domain is Cλ2. In a specific embodiment, the mouse Cλ domain is derived from a Cλ gene that is at least 60%, at least 70%, at least 80%, at least 90%, at least 95%, or at least 98% identical to mouse Cλ2.

In one aspect, a genetically modified non-human animal comprising a modified endogenous κ or λ light chain locus as described herein is provided that expresses a plurality of immunoglobulin λ light chains associated with a plurality of immunoglobulin heavy chains. In one embodiment, the heavy chain comprises a human sequence. In various embodiments, the human sequence is selected from a variable sequence, a $C_H1$, a hinge, a $C_H2$, a $C_H3$, and a combination thereof. In one embodiment, the plurality of immunoglobulin λ light chains comprises a human sequence. In various embodiments, the human sequence is selected from a variable sequence, a constant sequence, and a combination thereof. In one embodiment, the animal comprises a disabled endogenous immunoglobulin locus and expresses the heavy chain and/or the λ light chain from a transgene or extrachromosomal episome. In one embodiment, the animal comprises a replacement at an endogenous (non-human) locus of some or all endogenous non-human heavy chain gene segments (i.e., V, D, J), and/or some or all endogenous non-human heavy chain constant sequences (e.g., $C_H1$, hinge, $C_H2$, $C_H3$, or a combination thereof), and/or some or all endogenous non-human light chain sequences (e.g., V, J, constant, or a combination thereof), with one or more human immunoglobulin sequences. In one embodiment, the non-human animal is a mouse.

In one aspect, a non-human animal suitable for making antibodies that have a human λ-derived light chain is provided, wherein all or substantially all antibodies made in the non-human animal are expressed with a human λ-derived light chain. In one embodiment, the human λ-derived light chain is expressed from an endogenous light chain locus. In one embodiment, the endogenous light chain locus is a κ light chain locus. In a specific embodiment, the animal is a mouse and the κ light chain locus is a mouse κ light chain locus.

In one aspect, a method for making a λ-derived light chain for a human antibody is provided, comprising obtaining from a non-human animal as described herein a light chain sequence and a heavy chain sequence, and employing the light chain sequence and the heavy chain sequence in making a human antibody.

In one aspect, a method for making an antigen-binding protein is provided, comprising exposing a non-human animal as described herein to an antigen; allowing the non-human animal to mount an immune response; and obtaining from the non-human animal an antigen-binding protein that binds the antigen, or obtaining from the non-human animal a sequence to be employed in making an antigen-binding protein that binds the antigen.

In one aspect, a cell derived from a non-human animal (e.g., a mouse or rat) as described herein is provided. In one embodiment, the cell is selected from an embryonic stem cell, a pluripotent cell, an induced pluripotent cell, a B cell, and a hybridoma.

In one aspect, a cell is provided that comprises a genetic modification as described herein. In one embodiment, the cell is a mouse cell. In one embodiment, the cell is selected from a hybridoma and a quadroma. In one embodiment, the cell expresses an immunoglobulin light chain that comprises a human λ variable sequence fused with a mouse constant sequence. In a specific embodiment, the mouse constant sequence is a mouse κ constant sequence.

In one aspect, a tissue derived from a non-human animal as described herein is provided.

In one aspect, use of a non-human animal or a cell as described herein to make an antigen-binding protein is provided. In one embodiment, the antigen-binding protein is a human protein. In one embodiment, the human protein is a human antibody.

In one aspect, an antigen-binding protein made by a non-human animal, cell, tissue, or method as described herein is provided. In one embodiment, the antigen-binding protein is a human protein. In one embodiment, the human protein is a human antibody.

Any of the embodiments and aspects described herein can be used in conjunction with one another, unless otherwise indicated or apparent from the context. Other embodiments will become apparent to those skilled in the art from a review of the ensuing description.

BRIEF DESCRIPTION OF THE FIGURES

FIG. 3B shows a representative calculation of observed probe copy number in parental and modified ES cells for a first insertion of human immunoglobulin heavy chain gene segments. Observed probe copy number for probes A through F were calculated as $2/2^{\Delta\Delta Ct}$. $\Delta\Delta Ct$ is calculated as ave[$\Delta Ct$(sample)−med$\Delta Ct$(control)] where $\Delta Ct$ is the difference in Ct between test and reference probes (between 4 and 6 reference probes depending on the assay). The term med$\Delta Ct$(control) is the median $\Delta Ct$ of multiple (>60) non-targeted DNA samples from parental ES cells. Each modified ES cell clone was assayed in sextuplicate. To calculate copy numbers of IgH probes G and H in parental ES cells, these probes were assumed to have copy number of 1 in modified ES cells and a maximum Ct of 35 was used even though no amplification was observed.

FIG. 3C shows a representative calculation of copy numbers for four mice of each genotype calculated using only probes D and H. Wild-type mice: WT Mice; Mice heterozygous for a first insertion of human immunoglobulin gene segments: HET Mice; Mice homozygous for a first insertion of human immunoglobulin gene segments: Homo Mice.

Markers M1, M2 and M3 are low range, mid range and lambda ladder PFG markers, respectively (New England BioLabs, Ipswich, Mass.).

Figure 5A:
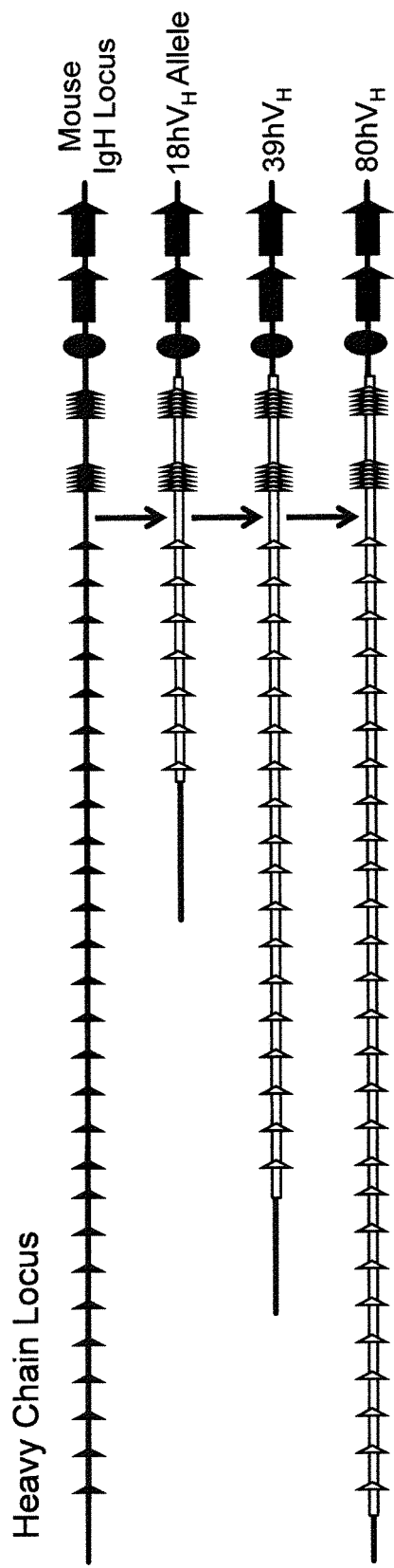

FIG. 5A shows a schematic illustration, not to scale, of sequential modifications of the mouse immunoglobulin heavy chain locus with increasing amounts of human immunoglobulin heavy chain gene segments. Homozygous mice were made from each of the three different stages of heavy chain humanization. Open symbols indicate human sequence; closed symbols indicate mouse sequence.

Figure 5B:
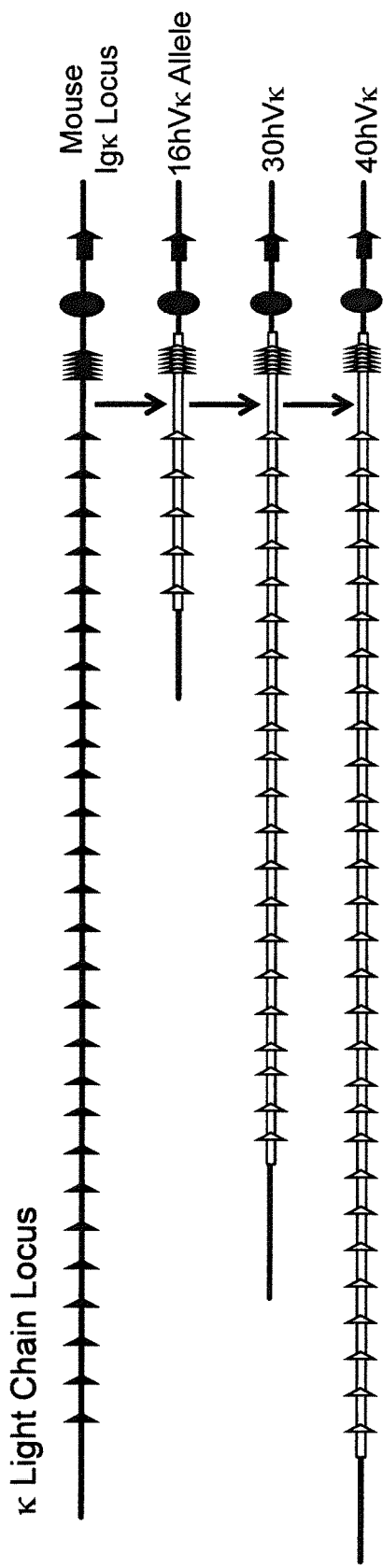

FIG. 5B shows a schematic illustration, not to scale, of sequential modifications of the mouse immunoglobulin κ light chain locus with increasing amounts of human immunoglobulin κ light chain gene segments. Homozygous mice were made from each of the three different stages of κ light chain humanization. Open symbols indicate human sequence; closed symbols indicate mouse sequence.

Figure 6:
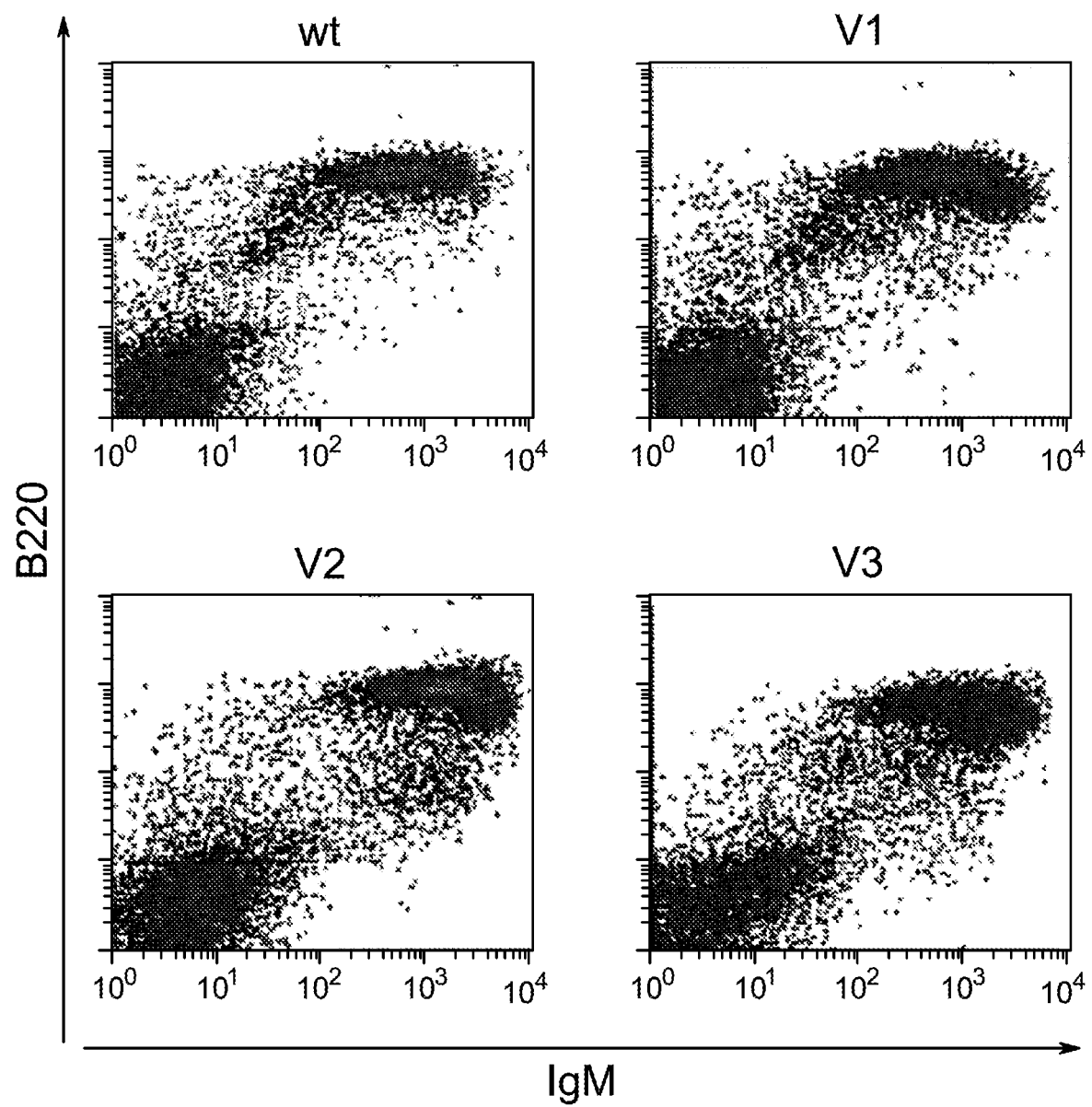
Figure 6:
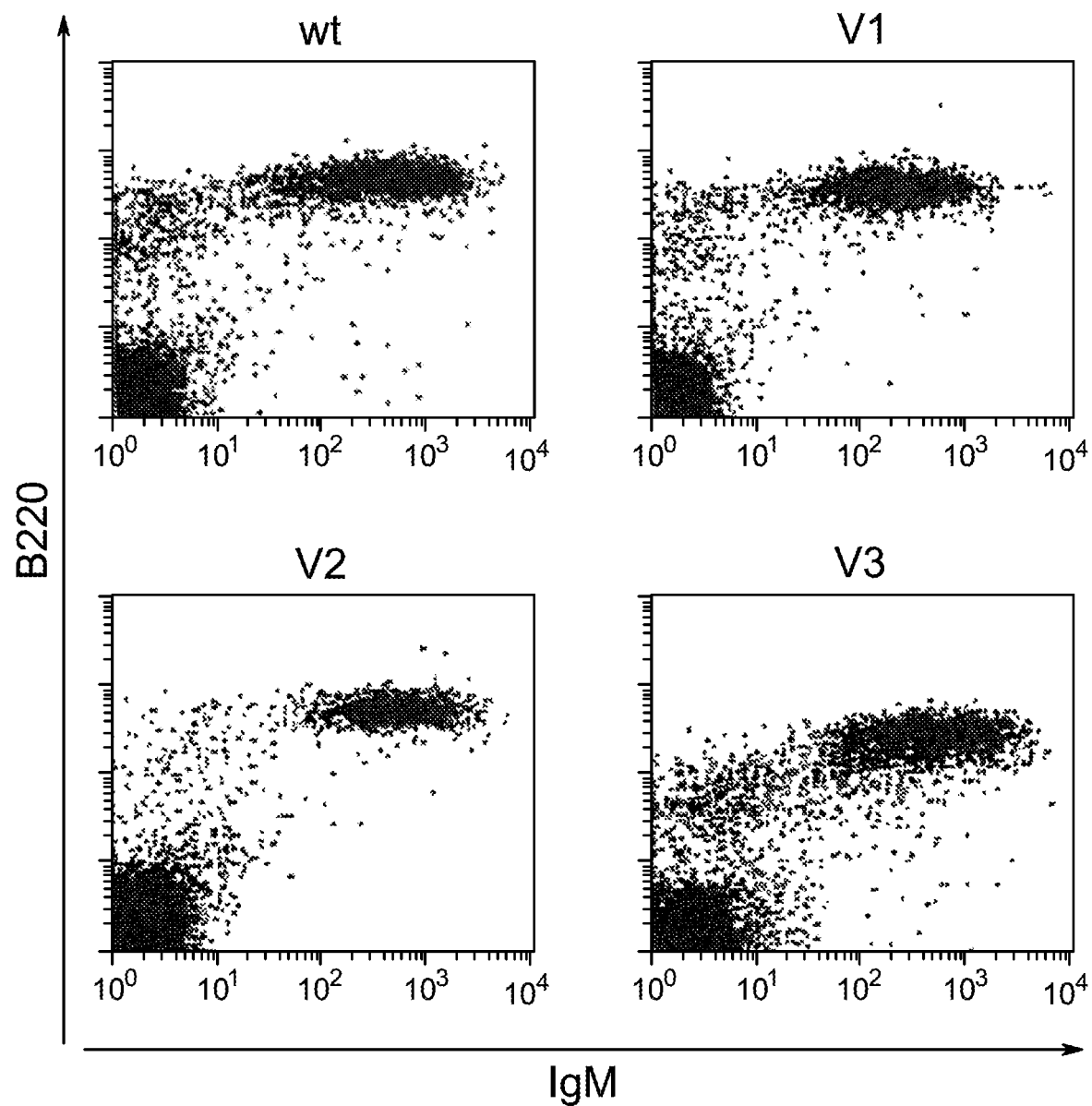
Figure 6:
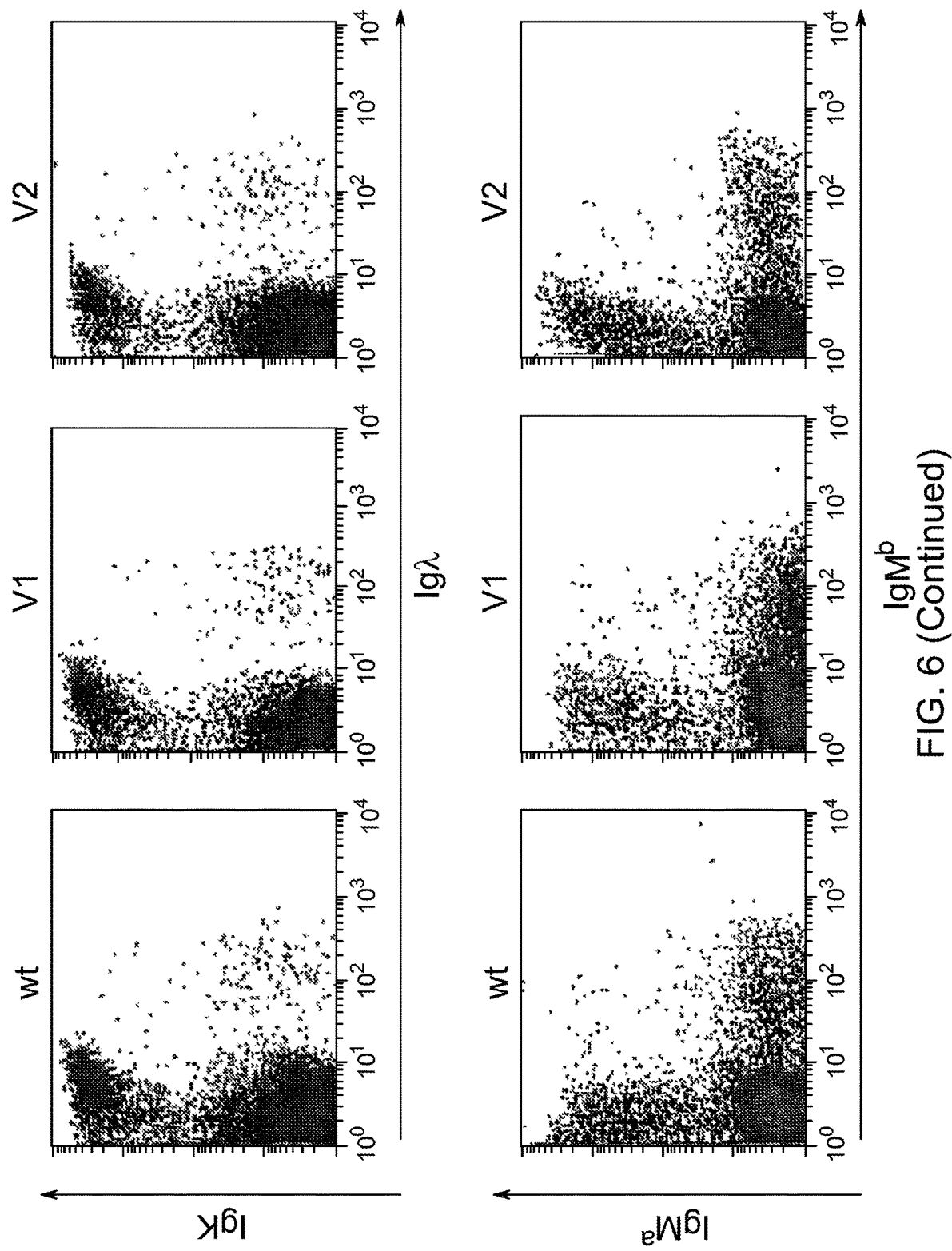

FIG. 6 shows FACS dot plots of B cell populations in wild type and VELOCIMMUNE® humanized mice. Cells from spleen (top row, third row from top and bottom row) or inguinal lymph node (second row from top) of wild type (wt), VELOCIMMUNE® 1 (V1), VELOCIMMUNE® 2 (V2) or VELOCIMMUNE® 3 (V3) mice were stained for surface IgM expressing B cells (top row, and second row from top), surface immunoglobulin containing either κ or λ light chains (third row from top) or surface IgM of specific haplotypes (bottom row), and populations separated by FACS.

FIG. 7A shows representative heavy chain CDR3 sequences of randomly selected VELOCIMMUNE® antibodies around the $V_H$-$D_H$-$J_H$ (CDR3) junction, demonstrating junctional diversity and nucleotide additions. Heavy chain CDR3 sequences are grouped according to $D_H$ gene segment usage, the germline of which is provided above each group in bold. $V_H$ gene segments for each heavy chain CDR3 sequence are noted within parenthesis at the 5' end of each sequence (e.g., 3-72 is human $V_H$3-72). $J_H$ gene segments for each heavy chain CDR3 are noted within parenthesis at the 3' end of each sequence (e.g., 3 is human $J_H$3). SEQ ID NOs for each sequence shown are as follows proceeding from top to bottom: SEQ ID NO:21; SEQ ID NO:22; SEQ ID NO:23; SEQ ID NO:24; SEQ ID NO:25; SEQ ID NO:26; SEQ ID NO:27; SEQ ID NO:28; SEQ ID NO:29; SEQ ID NO:30; SEQ ID NO:31; SEQ ID NO:32; SEQ ID NO:33; SEQ ID NO:34; SEQ ID NO:35; SEQ ID NO:36; SEQ ID NO:37; SEQ ID NO:38; SEQ ID NO:39.

FIG. 7B shows representative light chain CDR3 sequences of randomly selected VELOCIMMUNE® antibodies around the Vκ-Jκ (CDR3) junction, demonstrating junctional diversity and nucleotide additions. Vλ gene segments for each light chain CDR3 sequence are noted within parenthesis at the 5' end of each sequence (e.g., 1-6 is human Vκ1-6). Jκ gene segments for each light chain CDR3 are noted within parenthesis at the 3' end of each sequence (e.g., 1 is human Jκ1). SEQ ID NOs for each sequence shown are as follows proceeding from top to bottom: SEQ ID NO:40; SEQ ID NO:41; SEQ ID NO:42; SEQ ID NO:43; SEQ ID NO:44; SEQ ID NO:45; SEQ ID NO:46; SEQ ID NO:47; SEQ ID NO:48; SEQ ID NO:49; SEQ ID NO:50; SEQ ID NO:51; SEQ ID NO:52; SEQ ID NO:53; SEQ ID NO:54; SEQ ID NO:55; SEQ ID NO:56; SEQ ID NO:57; SEQ ID NO:58.

Figure 8:
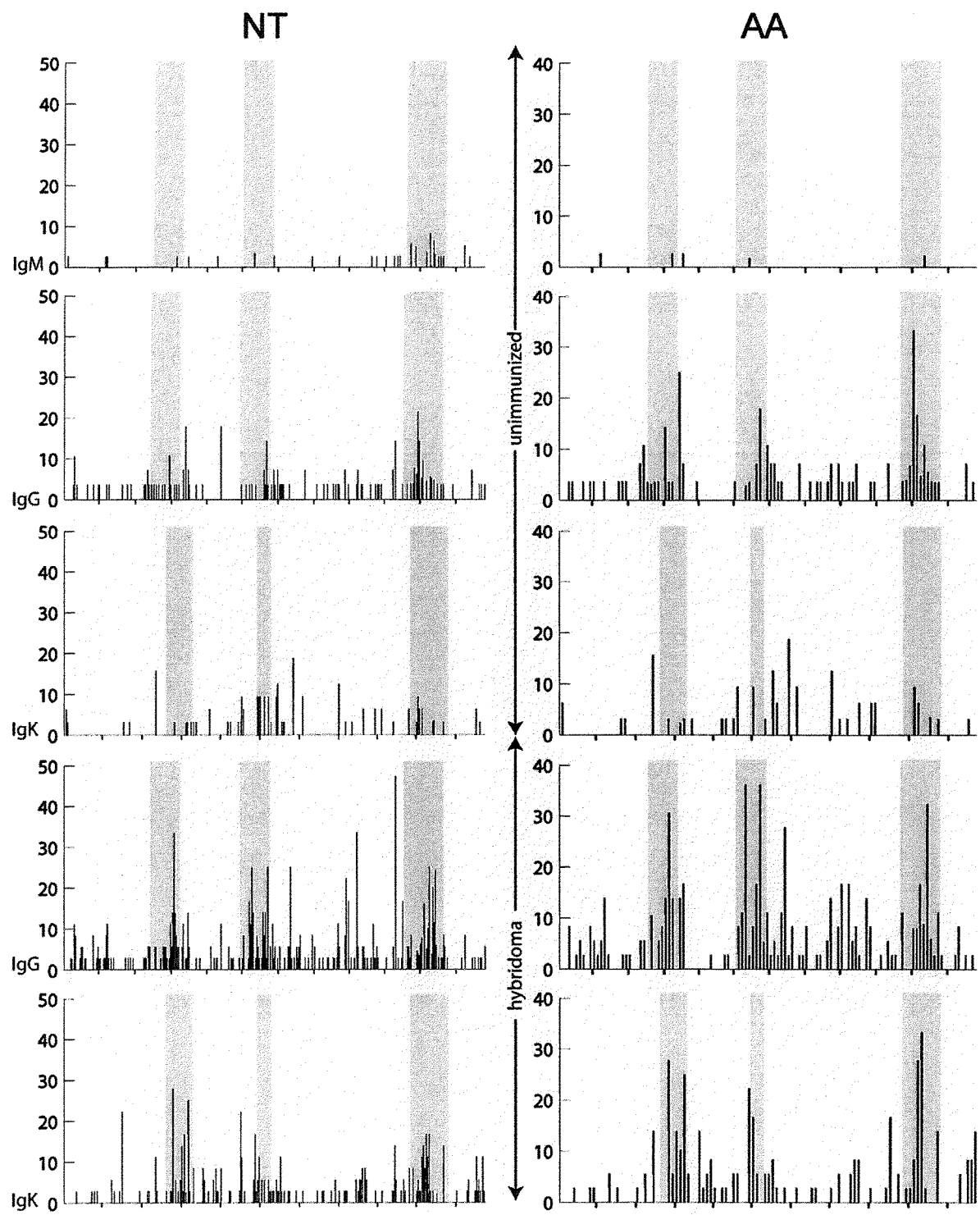

FIG. 8 shows somatic hypermutation frequencies of heavy and light chains of VELOCIMMUNE® antibodies scored (after alignment to matching germline sequences) as percent of sequences changed at each nucleotide (NT; left column) or amino acid (AA; right column) position among sets of 38 (unimmunized IgM), 28 (unimmunized IgG), 32 (unimmunized Igκ from IgG), 36 (immunized IgG) or 36 (immunized Igκ from IgG) sequences. Shaded bars indicate the locations of CDRs.

Figure 9A:
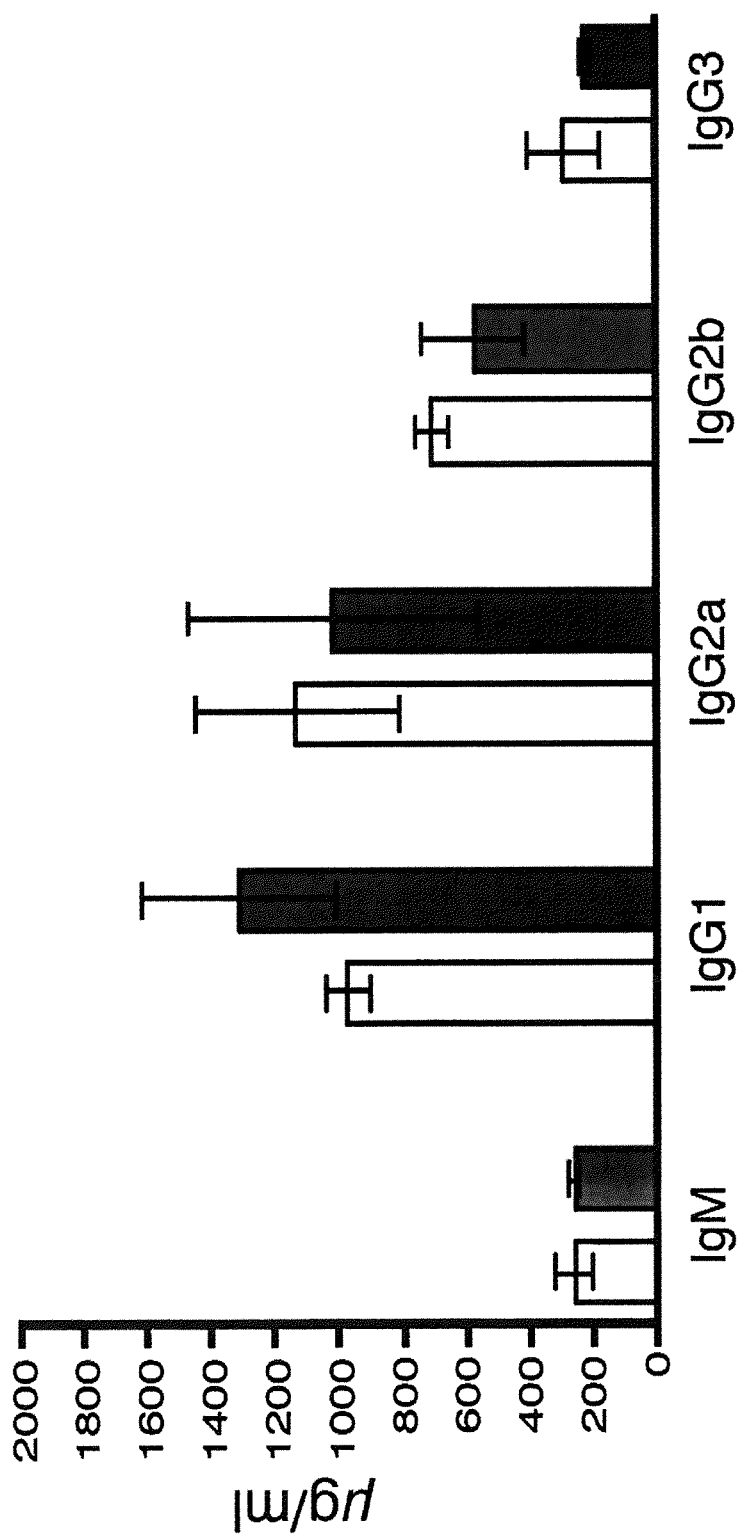

FIG. 9A shows levels of serum immunoglobulin for IgM and IgG isotypes in wild type (open bars) or VELOCIMMUNE® mice (closed bars).

Figure 9B:
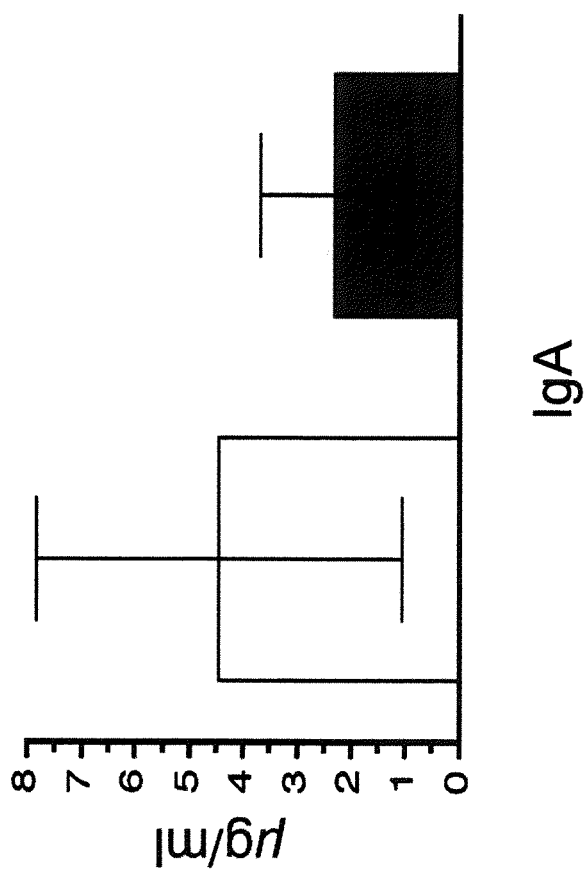

FIG. 9B shows levels of serum immunoglobulin for IgA isotype in wild type (open bars) or VELOCIMMUNE® mice (closed bars).

Figure 9C:
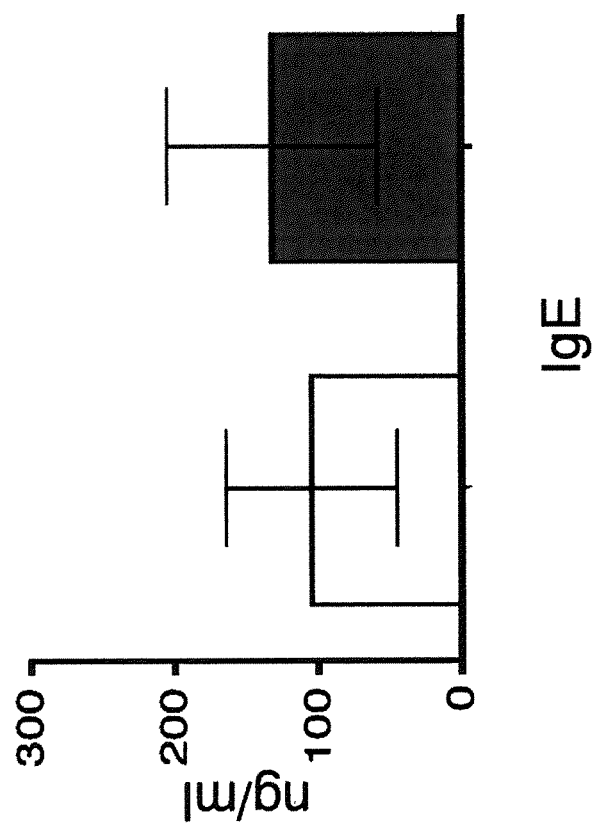

FIG. 9C shows levels of serum immunoglobulin for IgE isotype in wild type (open bars) or VELOCIMMUNE® mice (closed bars).

Figure 10A:
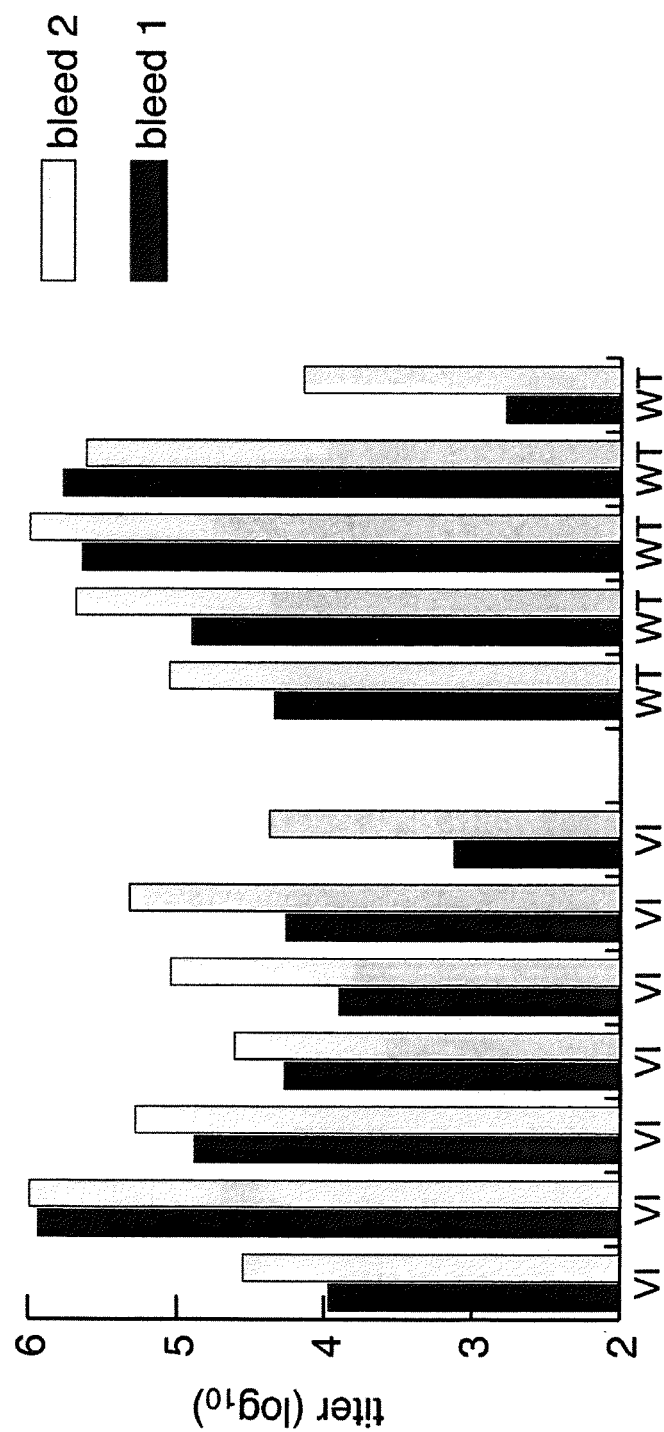

FIG. 10A shows antigen-specific IgG titers against interleukin-6 receptor (IL-6R) of serum from seven VELOCIMMUNE® (VI) and five wild type (WT) mice after two (bleed 1) or three (bleed 2) rounds of immunization with ectodomain of IL-6R.

Figure 10B:
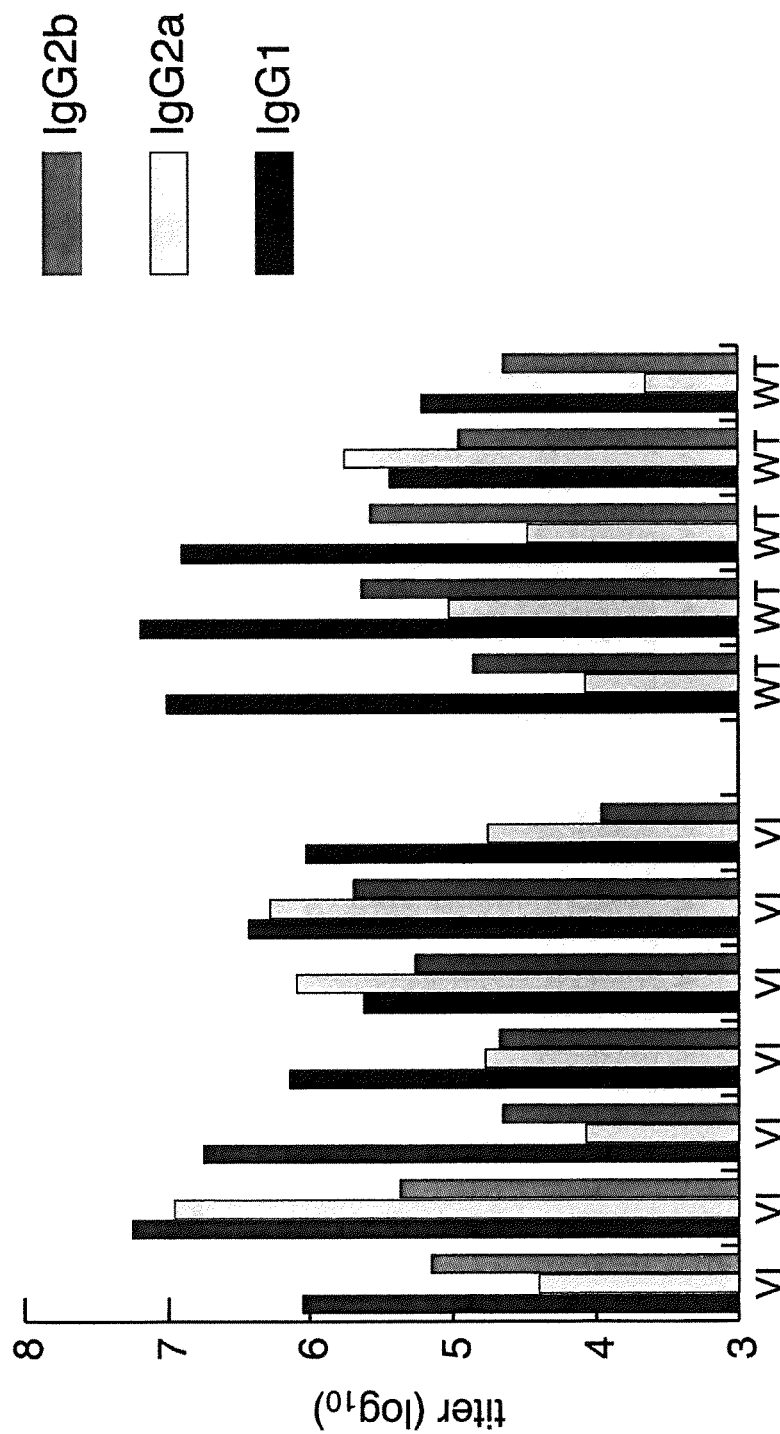

FIG. 10B shows IL-6R-specific IgG isotype-specific titers from seven VELOCIMMUNE® (VI) and five wild type (WT) mice.

Figure 11A:
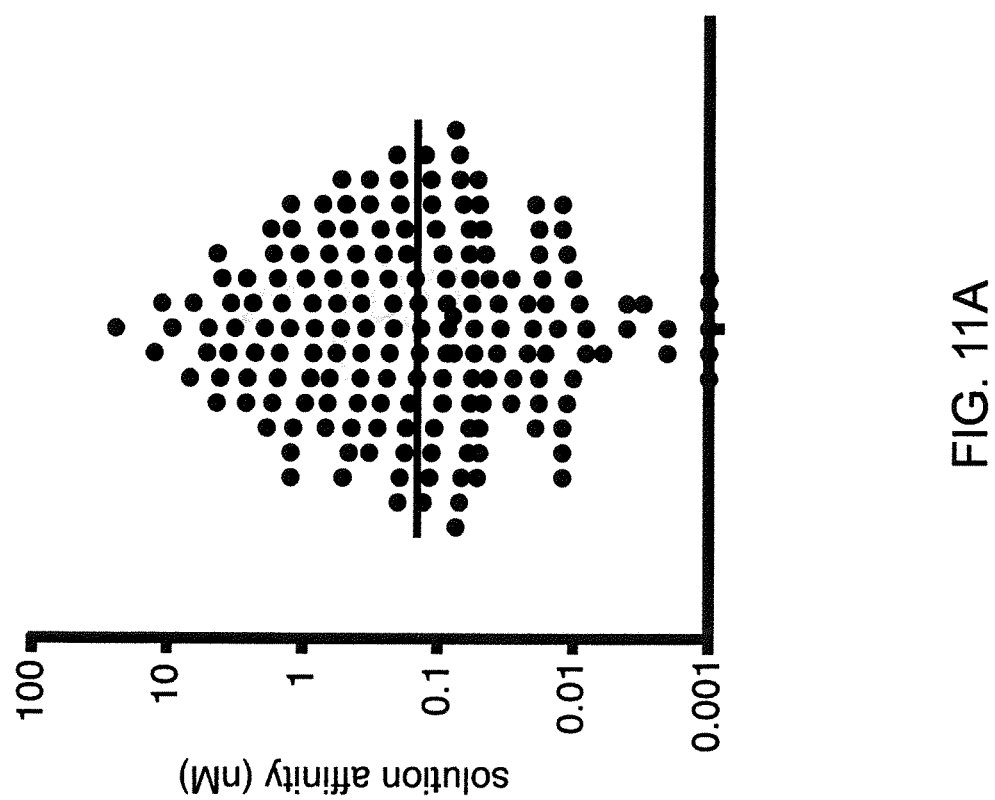

FIG. 11A shows the affinity distribution of anti-interleukin-6 receptor monoclonal antibodies generated in VELOCIMMUNE® mice.

Figure 11B:
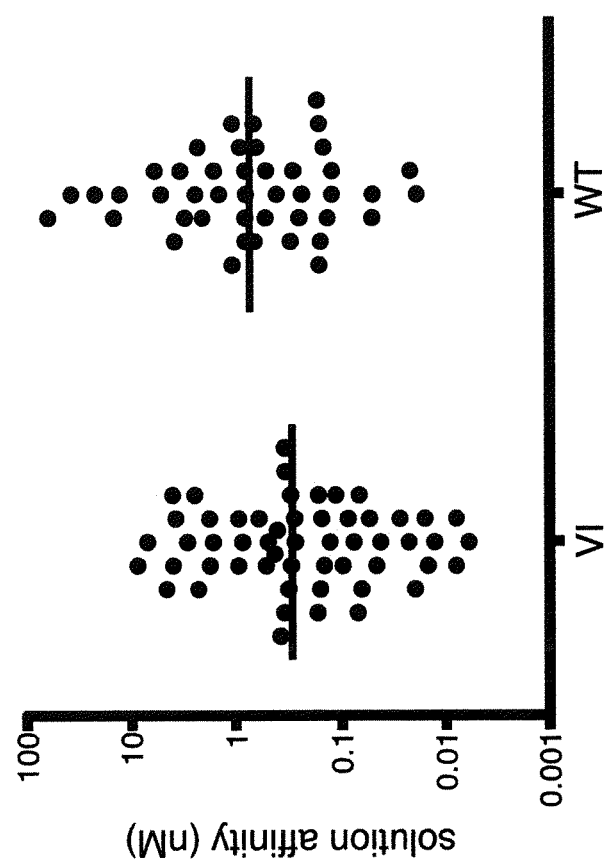

FIG. 11B shows the antigen-specific blocking of anti-interleukin-6 receptor monoclonal antibodies generated in VELOCIMMUNE® (VI) and wild type (WT) mice.

Figure 12:
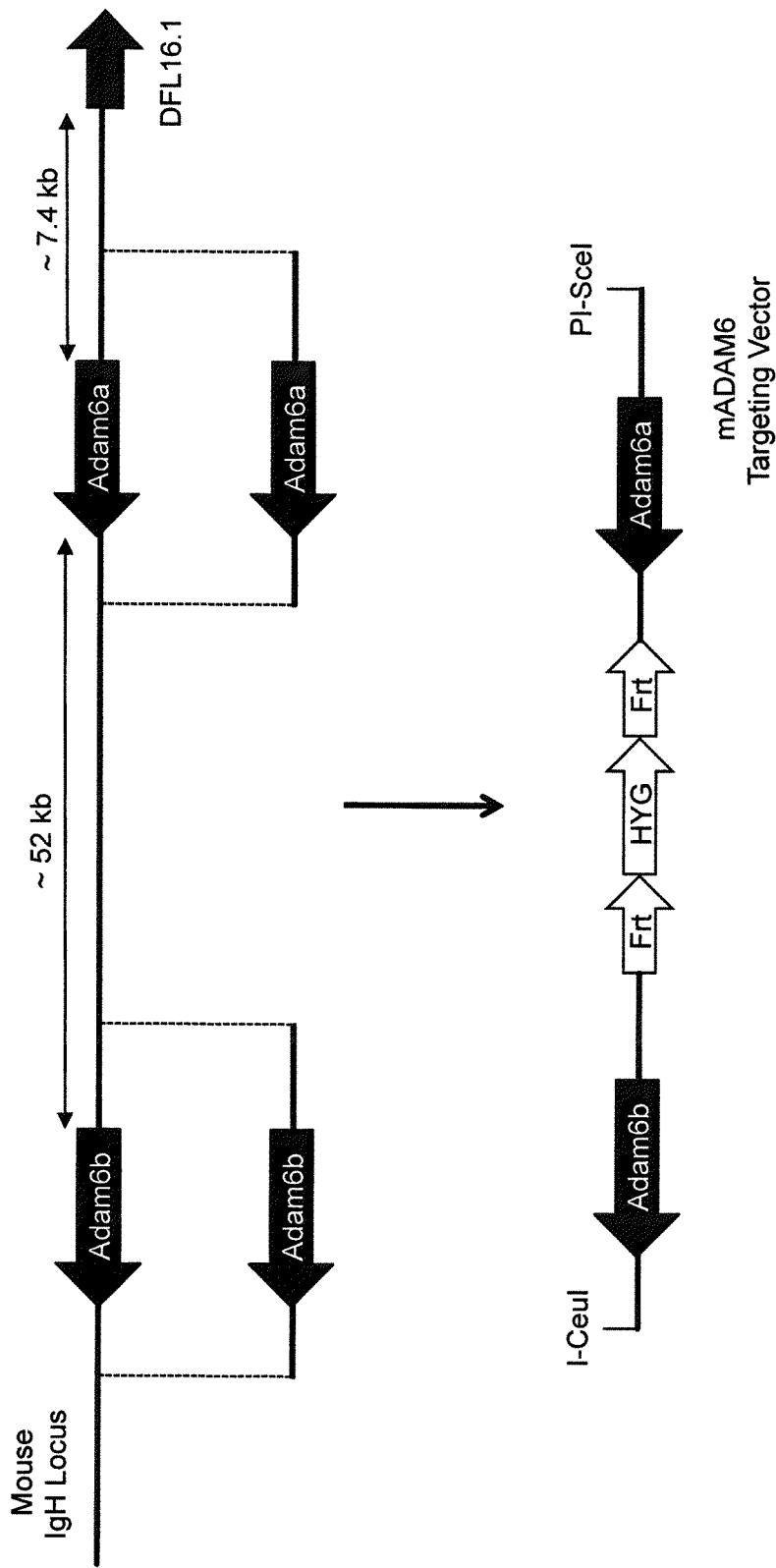

FIG. 12 shows a schematic illustration, not to scale, of mouse ADAM6a and ADAM6b genes in a mouse immunoglobulin heavy chain locus. A targeting vector (mADAM6 Targeting Vector) used for insertion of mouse ADAM6a and ADAM6b into a humanized endogenous heavy chain locus is shown with a selection cassette (HYG: hygromycin) flanked by site-specific recombination sites (Frt) including engineered restriction sites on the 5' and 3' ends.

Figure 13:
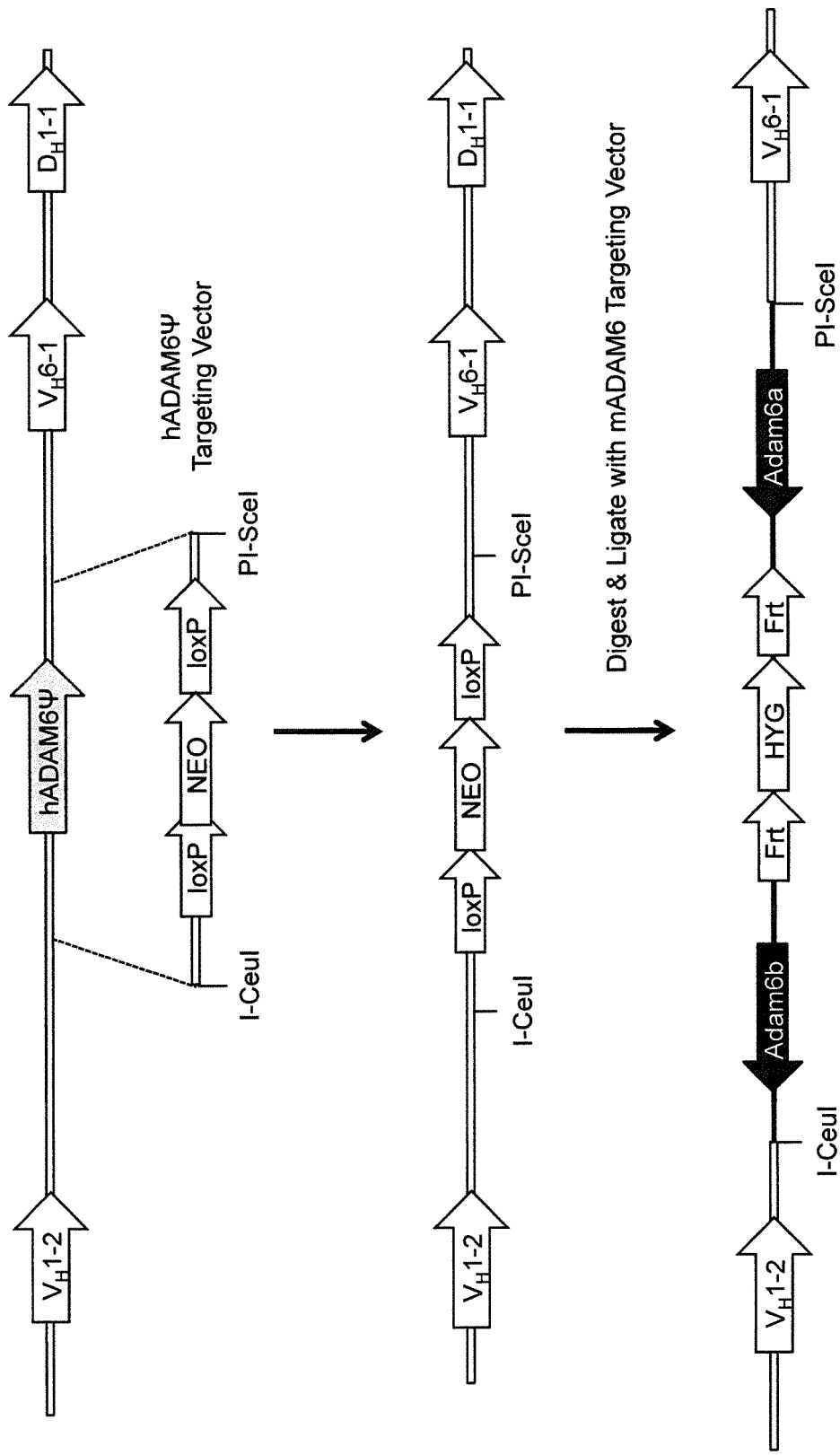

FIG. 13 shows a schematic illustration, not to scale, of a human ADAM6 pseudogene (hADAM6Ψ) located between human heavy chain variable gene segments 1-2 ($V_H$1-2) and 6-1 ($V_H$6-1). A targeting vector for bacterial homologous recombination (hADAM6Ψ Targeting Vector) to delete a human ADAM6 pseudogene and insert unique restriction sites into a human heavy chain locus is shown with a selection cassette (NEO: neomycin) flanked by site-specific recombination sites (loxP) including engineered restriction sites on the 5' and 3' ends. An illustration, not to scale, of the resulting targeted humanized heavy chain locus containing a genomic fragment that encodes for the mouse ADAM6a and ADAM6b genes including a selection cassette flanked by site-specific recombination sites is shown.

Figure 14A:
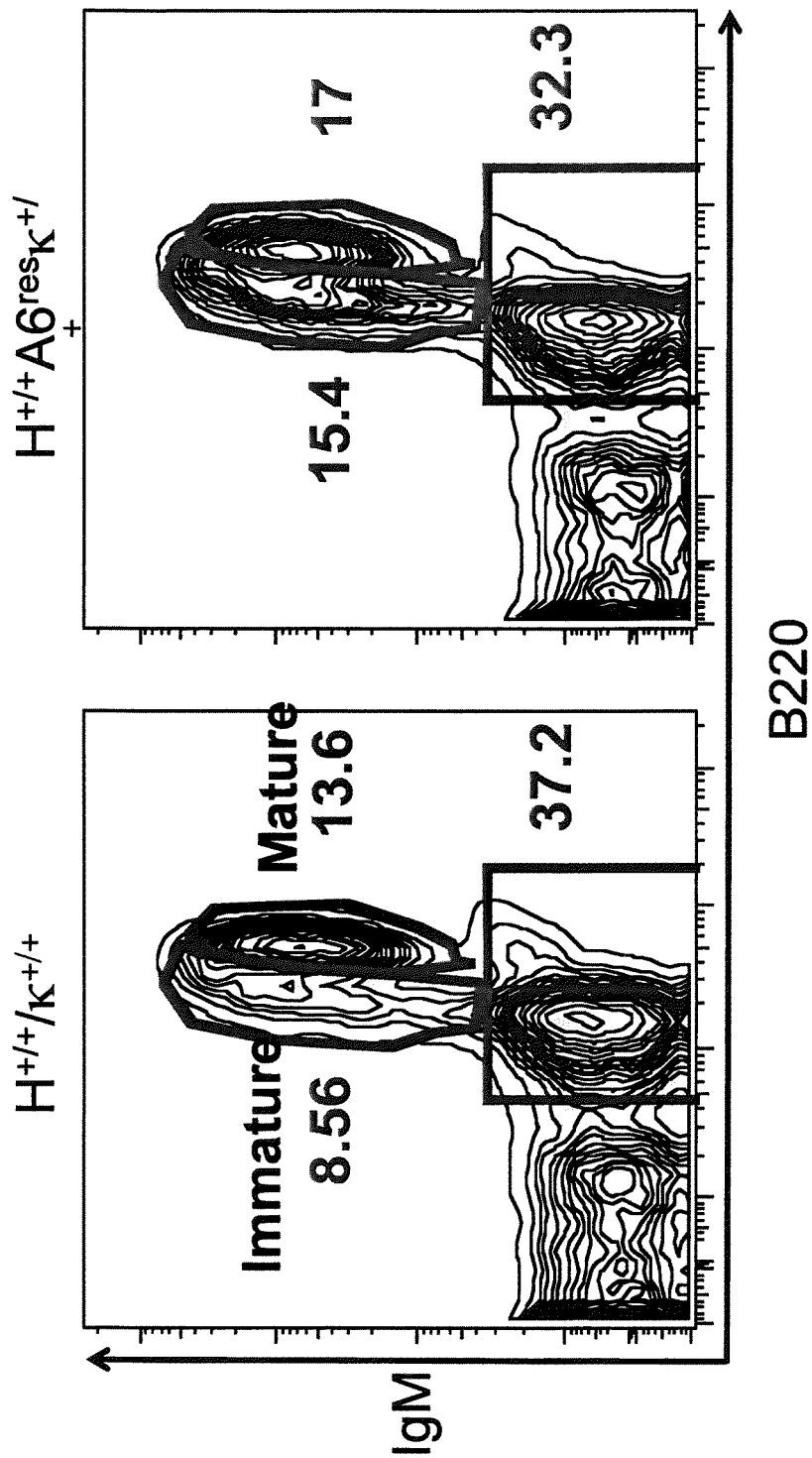

FIG. 14A shows FACS contour plots of lymphocytes gated on singlets for surface expression of IgM and B220 in the bone marrow for mice homozygous for human heavy and human κ light chain variable gene loci ($H^{+/+}κ^{+/+}$) and mice homozygous for human heavy and human κ light chain variable gene loci having an inserted mouse genomic fragment comprising mouse ADAM6 genes ($H^{+/+}A6^{res}κ^{+/+}$). Percentage of immature ($B220^{int}IgM^+$) and mature ($B220^{high}IgM^+$) B cells is noted in each contour plot.

Figure 14B:
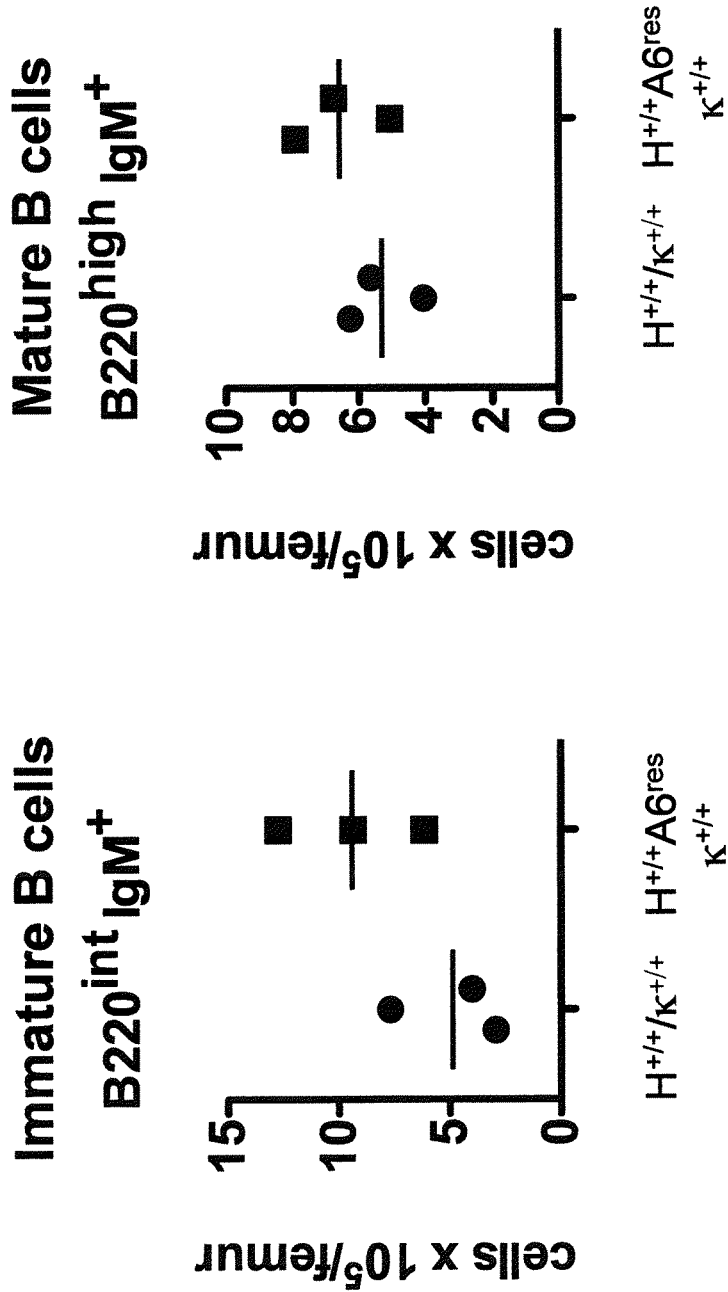

FIG. 14B shows the total number of immature ($B220^{int}IgM^+$) and mature ($B220^{high}M^+$) B cells in the bone marrow isolated from femurs of mice homozygous for human heavy and human κ light chain variable gene loci ($H^{+/+}K^{+/+}$) and mice homozygous for human heavy and human κ light chain variable gene loci having an ectopic mouse genomic fragment encoding mouse ADAM6 genes ($H^{+/+}A6^{res}κ^{+/+}$).

Figure 15A:
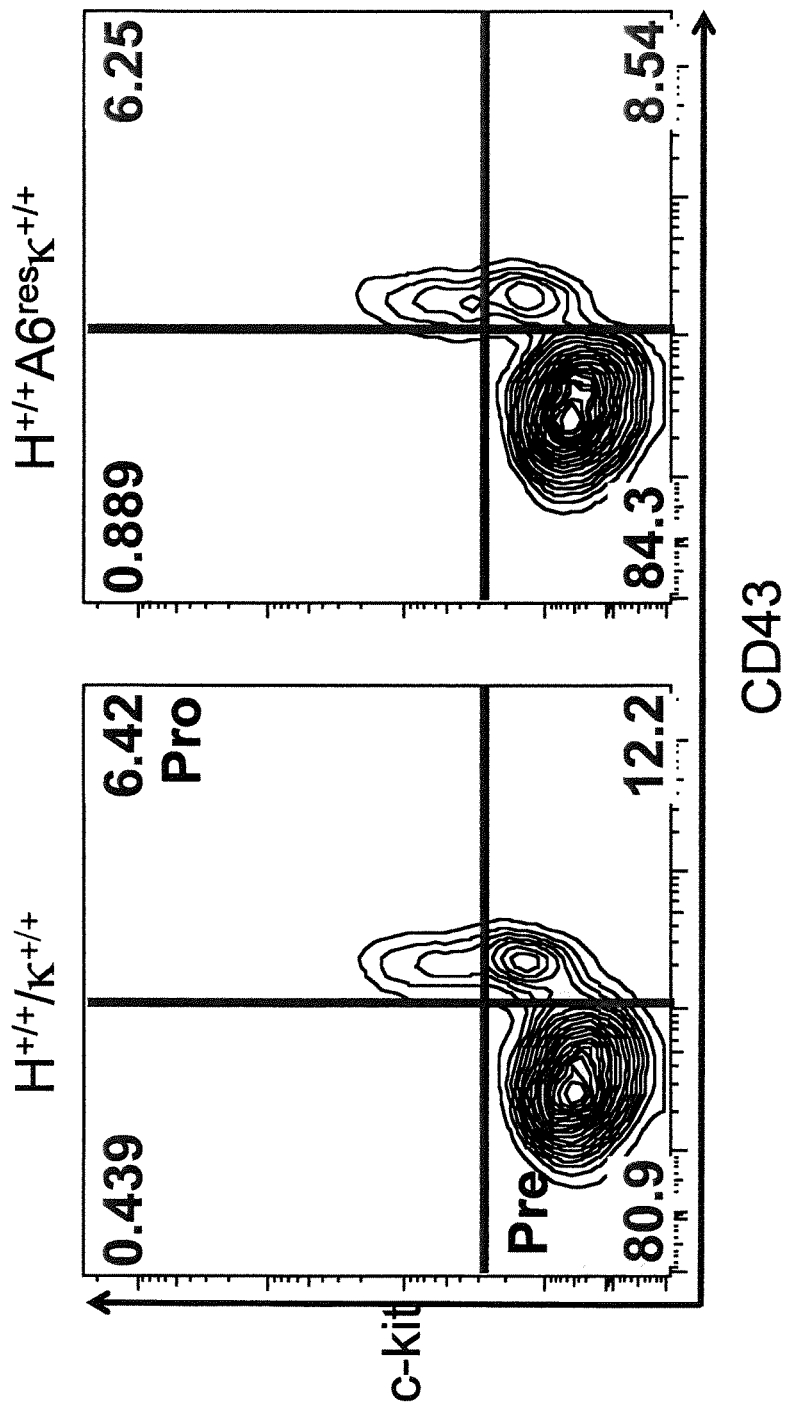

FIG. 15A shows FACS contour plots of CD19$^+$-gated B cells for surface expression of ckit and CD43 in the bone marrow for mice homozygous for human heavy and human κ light chain variable gene loci (H$^{+/+}$κ$^{+/+}$) and mice homozygous for human heavy and human κ light chain variable gene loci having an ectopic mouse genomic fragment encoding mouse ADAM6 genes (H$^{+/+}$A6$^{res}$κ$^{+/+}$). Percentage of pro-B (CD19$^+$CD43$^+$ckit$^+$) and pre-B (CD19$^+$CD43$^-$ckit$^-$) cells is noted in the upper right and lower left quadrants, respectively, of each contour plot.

Figure 15B:
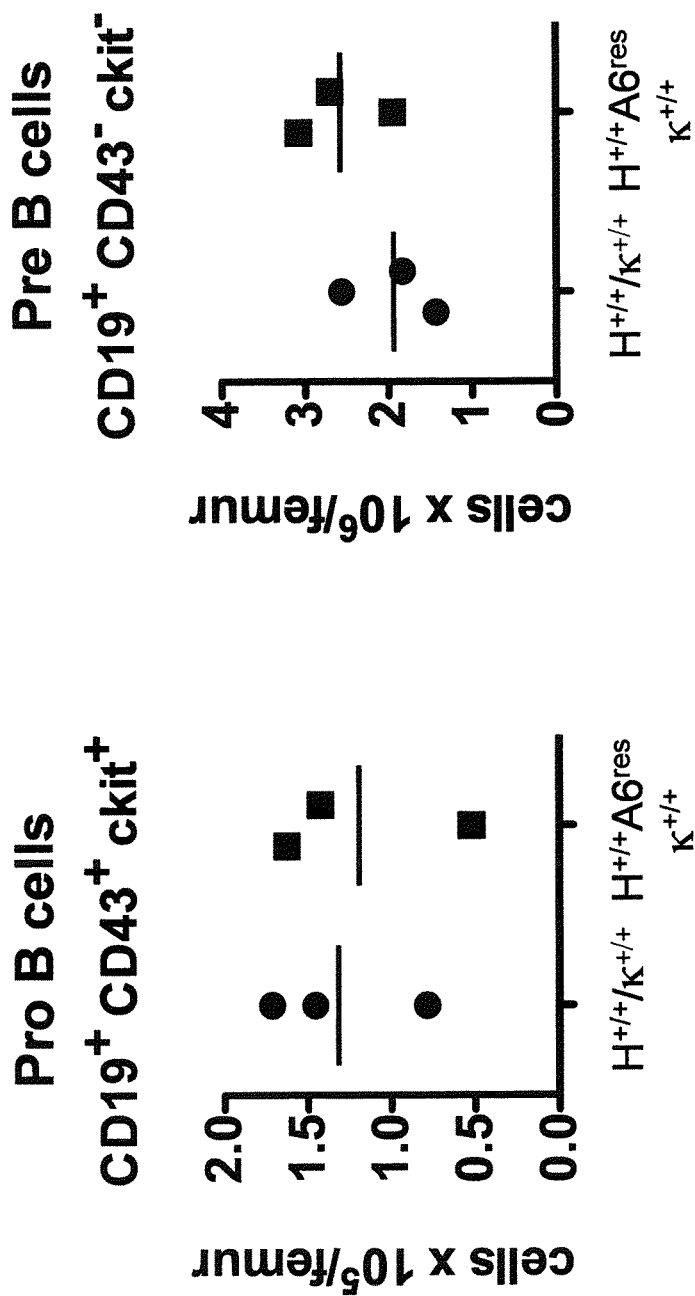

FIG. 15B shows the total number of pro-B cells (CD19$^+$CD43$^+$ckit$^+$) and pre-B cells (CD19$^+$CD43$^-$ckit$^-$) in the bone marrow isolated from femurs of mice homozygous for human heavy and human κ light chain variable gene loci (H$^{+/+}$κ$^{+/+}$) and mice homozygous for human heavy and human κ light chain variable gene loci having an ectopic mouse genomic fragment comprising mouse ADAM6 genes (H$^{+/+}$A6$^{res}$κ$^{+/+}$).

Figure 16A:
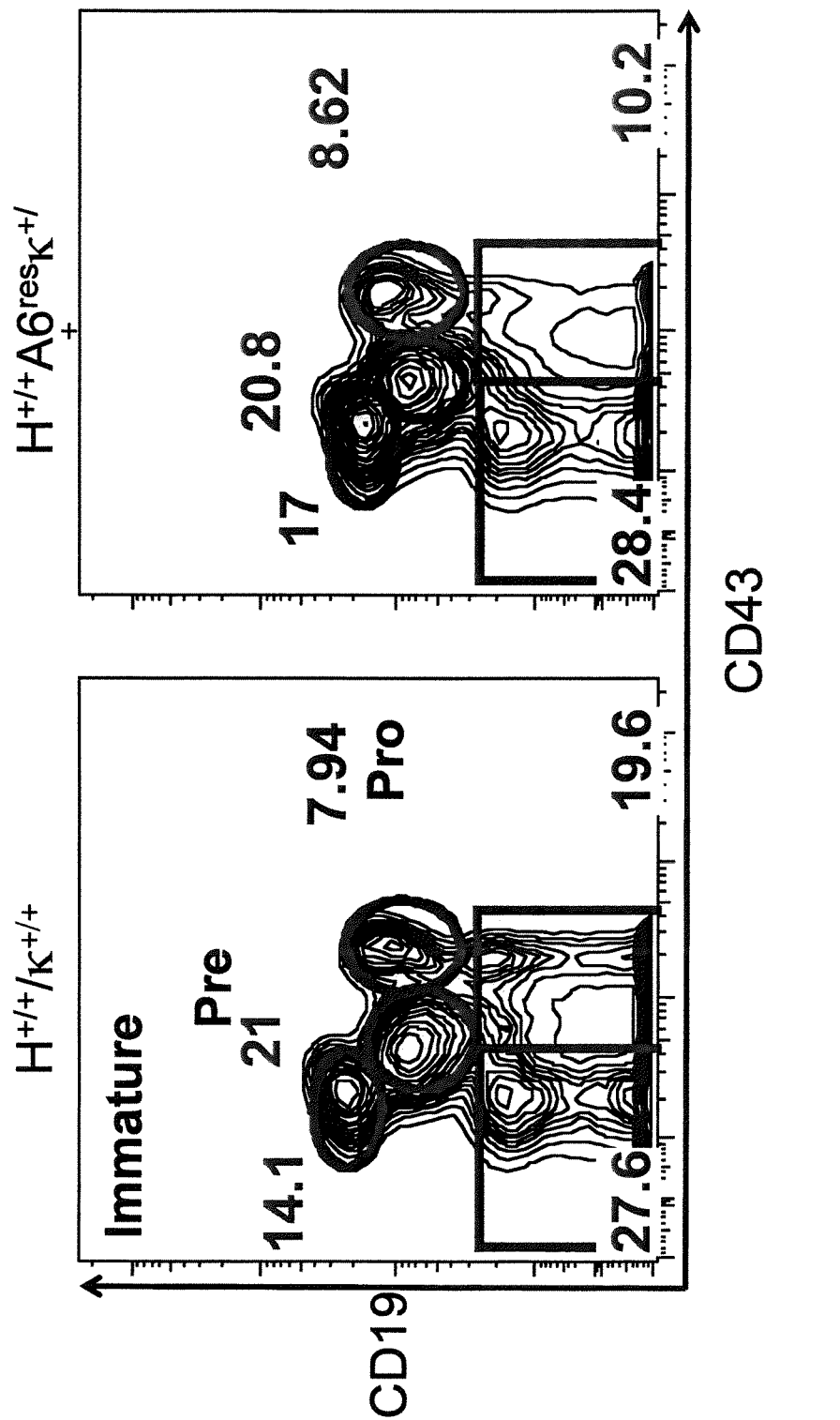

FIG. 16A shows FACS contour plots of lymphocytes gated on singlets for surface expression of CD19 and CD43 in the bone marrow for mice homozygous for human heavy and human κ light chain variable gene loci (H$^{+/+}$κ$^{+/+}$) and mice homozygous for human heavy and human κ light chain variable gene loci having an ectopic mouse genomic fragment encoding mouse ADAM6 genes (H$^{+/+}$A6$^{res}$κ$^{++}$). Percentage of immature B (CD19$^+$CD43$^-$), pre-B (CD19$^+$CD43$^{int}$) and pro-B (CD19$^+$CD43$^+$) cells is noted in each contour plot.

Figure 16B:
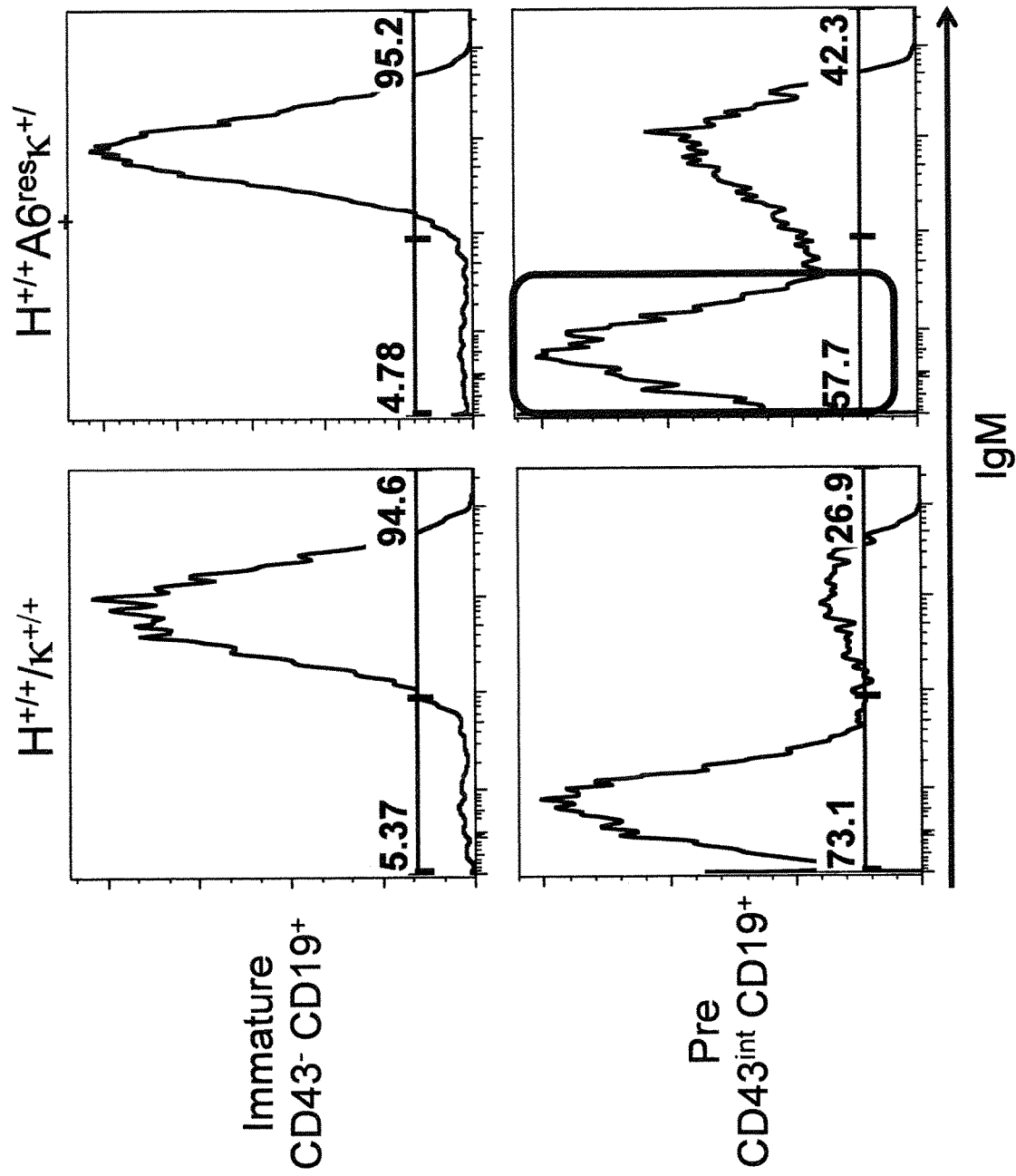

FIG. 16B shows histograms of immature B (CD19$^+$CD43$^-$) and pre-B (CD19$^+$CD43$^{int}$) cells in the bone marrow of mice homozygous for human heavy and human κ light chain variable gene loci (H$^{+/+}$κ$^{+/+}$) and mice homozygous for human heavy and human κ light chain variable gene loci having an ectopic mouse genomic fragment encoding mouse ADAM6 genes (H$^{+/+}$A6$^{res}$κ$^{+/+}$).

Figure 17A:
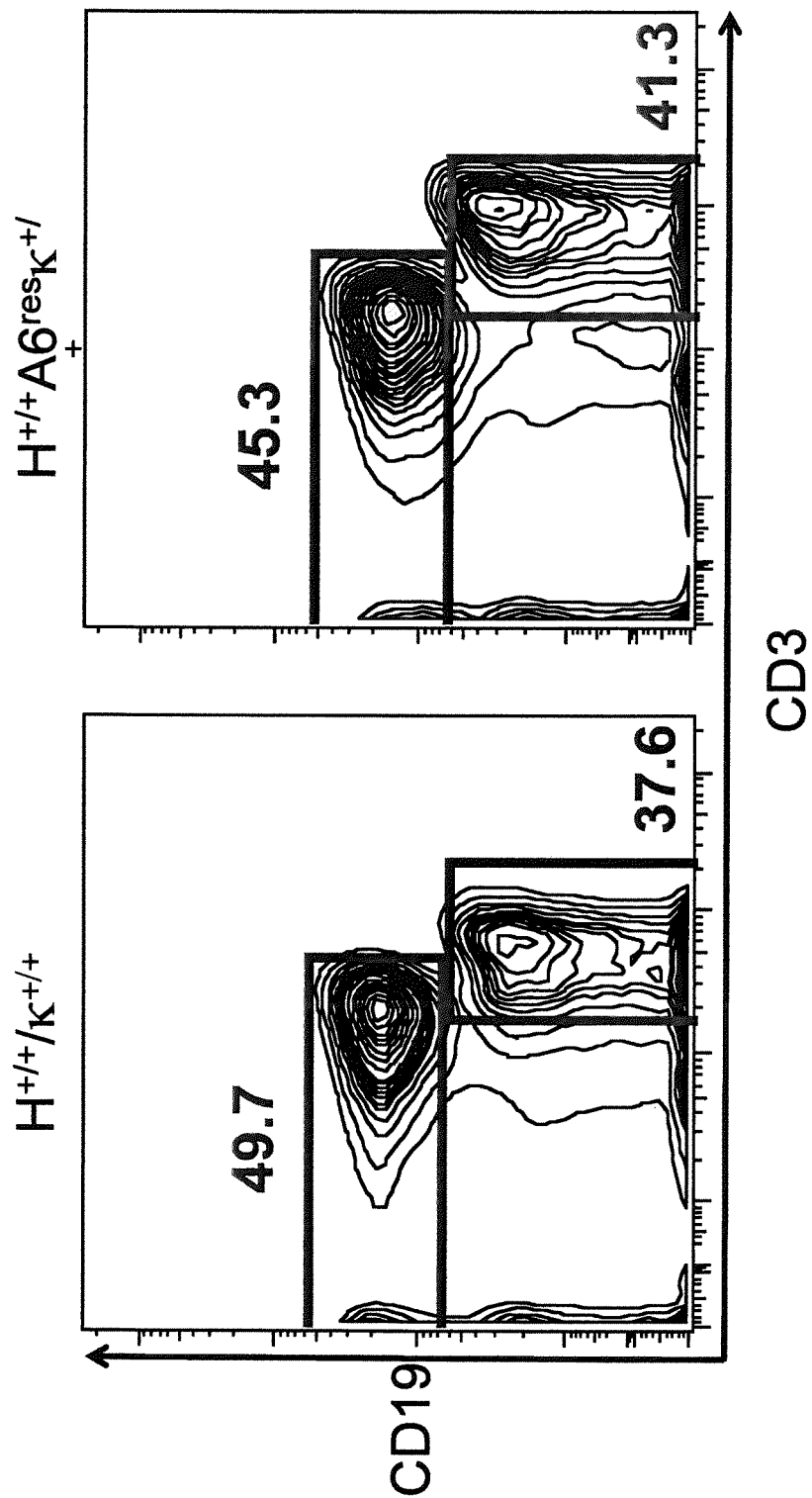

FIG. 17A shows FACS contour plots of lymphocytes gated on singlets for surface expression of CD19 and CD3 in splenocytes for mice homozygous for human heavy and human κ light chain variable gene loci (H$^{+/+}$κ$^{+/+}$) and mice homozygous for human heavy and human κ light chain variable gene loci having an ectopic mouse genomic fragment encoding mouse ADAM6 genes (H$^{+/+}$A6κ$^{+/+}$). Percentage of B (CD19$^+$CD3$^-$) and T (CD19$^-$CD3$^+$) cells is noted in each contour plot.

Figure 17B:
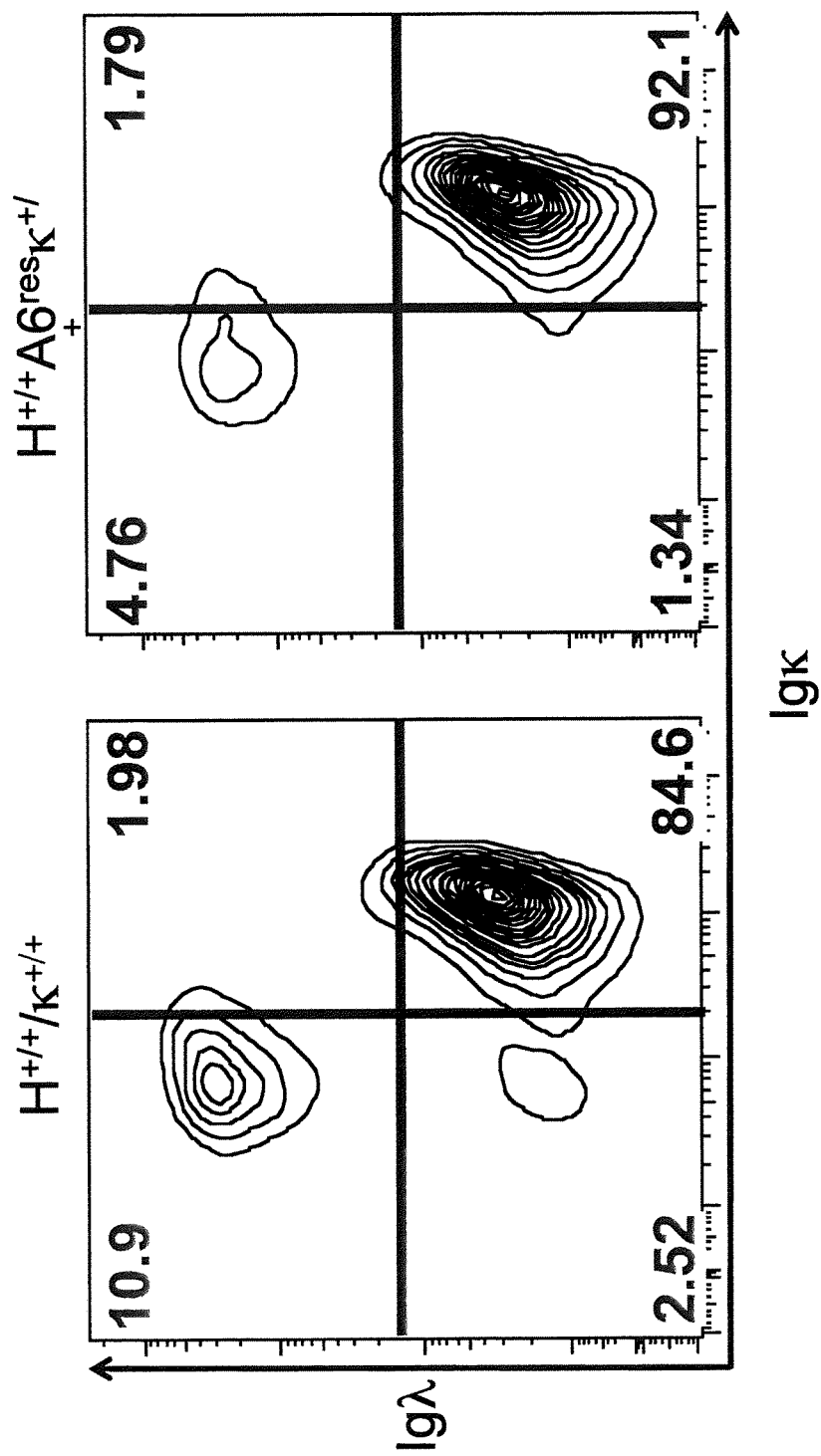

FIG. 17B shows FACs contour plots for CD19$^+$-gated B cells for surface expression of Igλ and Igκ light chain in the spleen of mice homozygous for human heavy and human κ light chain variable gene loci (H$^{+/+}$κ$^{+/+}$) and mice homozygous for human heavy and human κ light chain variable gene loci having an ectopic mouse genomic fragment encoding mouse ADAM6 genes (H$^{+/+}$A6$^{res}$κ$^{+/+}$). Percentage of Igκ$^+$ (upper left quadrant) and Igκ$^+$ (lower right quadrant) B cells is noted in each contour plot.

Figure 17C:
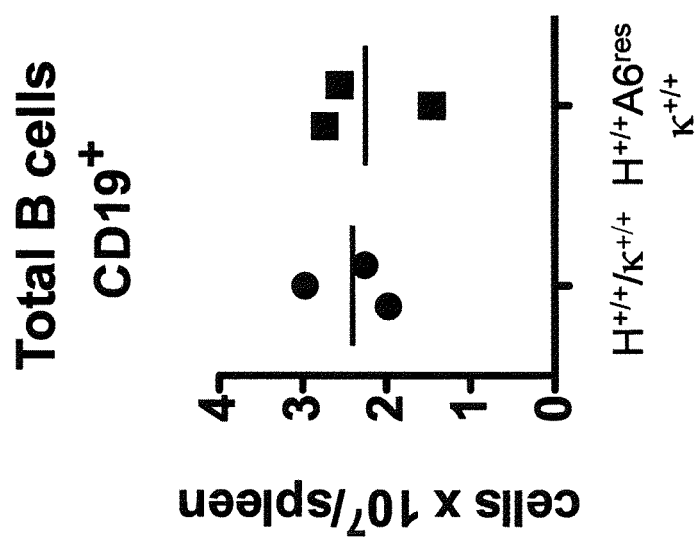

FIG. 17C shows the total number of CD19$^+$ B cells in the spleen of mice homozygous for human heavy and human κ light chain variable gene loci (H$^{+/+}$κ$^{+/+}$) and mice homozygous for human heavy and human κ light chain variable gene loci having an ectopic mouse genomic fragment encoding mouse ADAM6 genes (H$^{+/+}$A6$^{res}$κ$^{+/+}$).

Figure 18A:
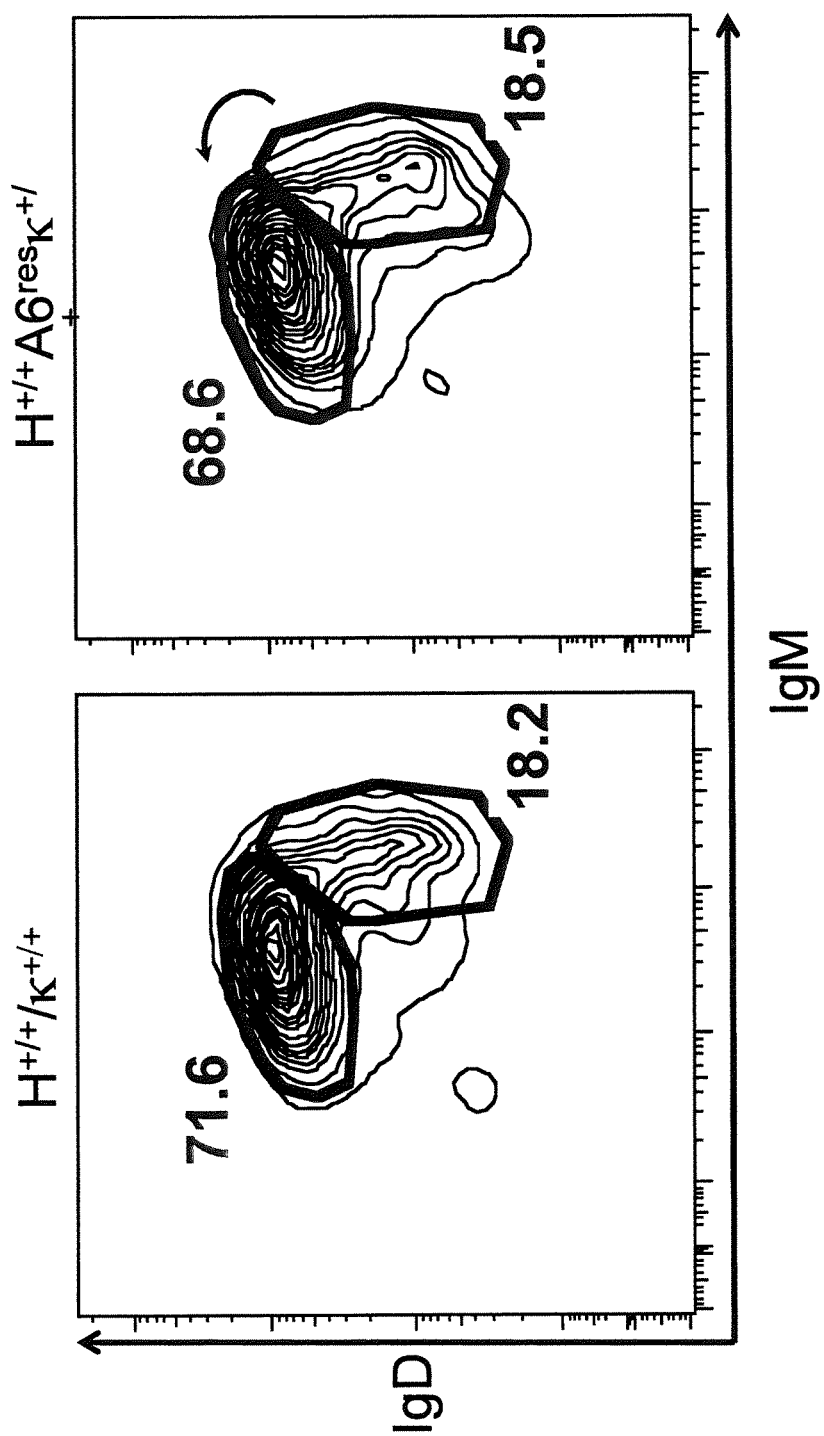

FIG. 18A shows FACs contour plots of CD19$^+$-gated B cells for surface expression of IgD and IgM in the spleen of mice homozygous for human heavy and human κ light chain variable gene loci (H$^{+/+}$κ$^{+/+}$) and mice homozygous for human heavy and human κ light chain variable gene loci having an ectopic mouse genomic fragment encoding mouse ADAM6 genes (H$^{+/+}$A6$^{res}$κ$^{+/+}$). Percentage of mature B cells (CD19$^+$IgD$^{high}$IgM$^{int}$) is noted for each contour plot. The arrow on the right contour plot illustrates the process of maturation for B cells in relation to IgM and IgD surface expression.

Figure 18B:
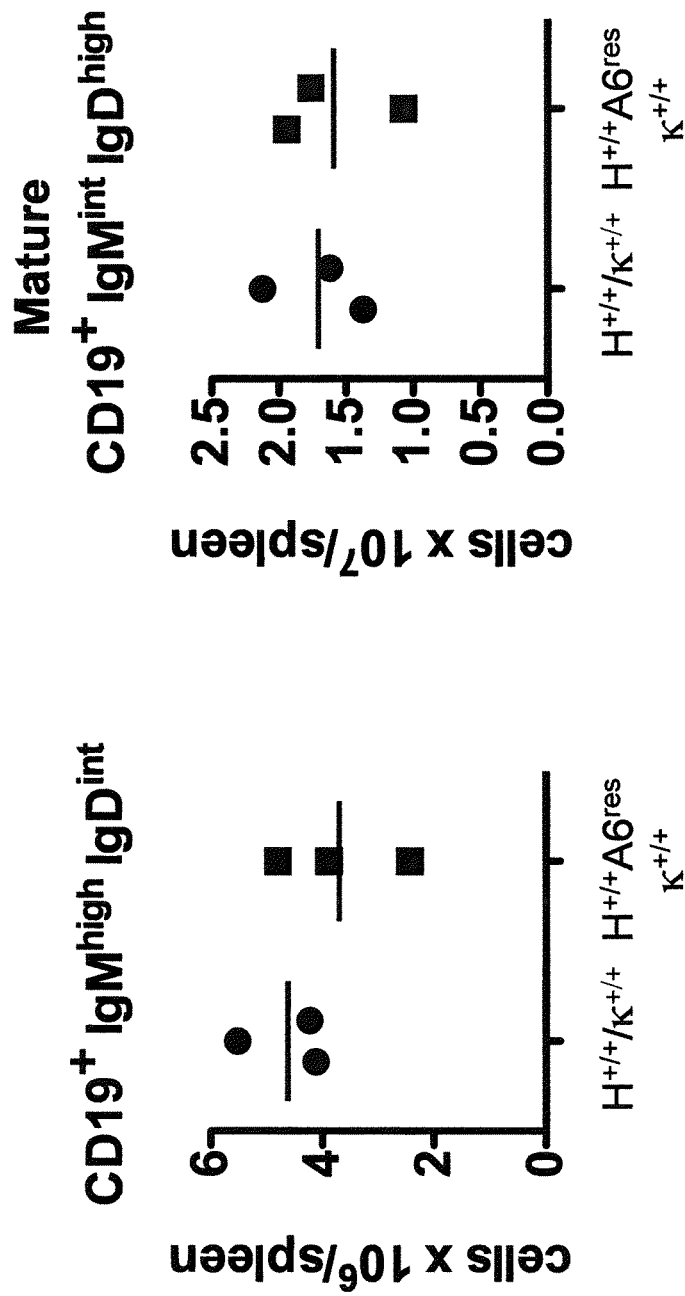

FIG. 18B shows the total number of B cells in the spleen of mice homozygous for human heavy and human κ light chain variable gene loci (H$^{+/+}$κ$^{+/+}$) and mice homozygous for human heavy and human κ light chain variable gene loci having an ectopic mouse genomic fragment encoding mouse ADAM6 genes (H$^{+/+}$A6$^{res}$κ$^{+/+}$) during maturation from CD19$^+$IgM$^{high}$IgD$^{int}$ to CD19$^+$IgM$^{int}$IgD$^{high}$.

Figure 19:
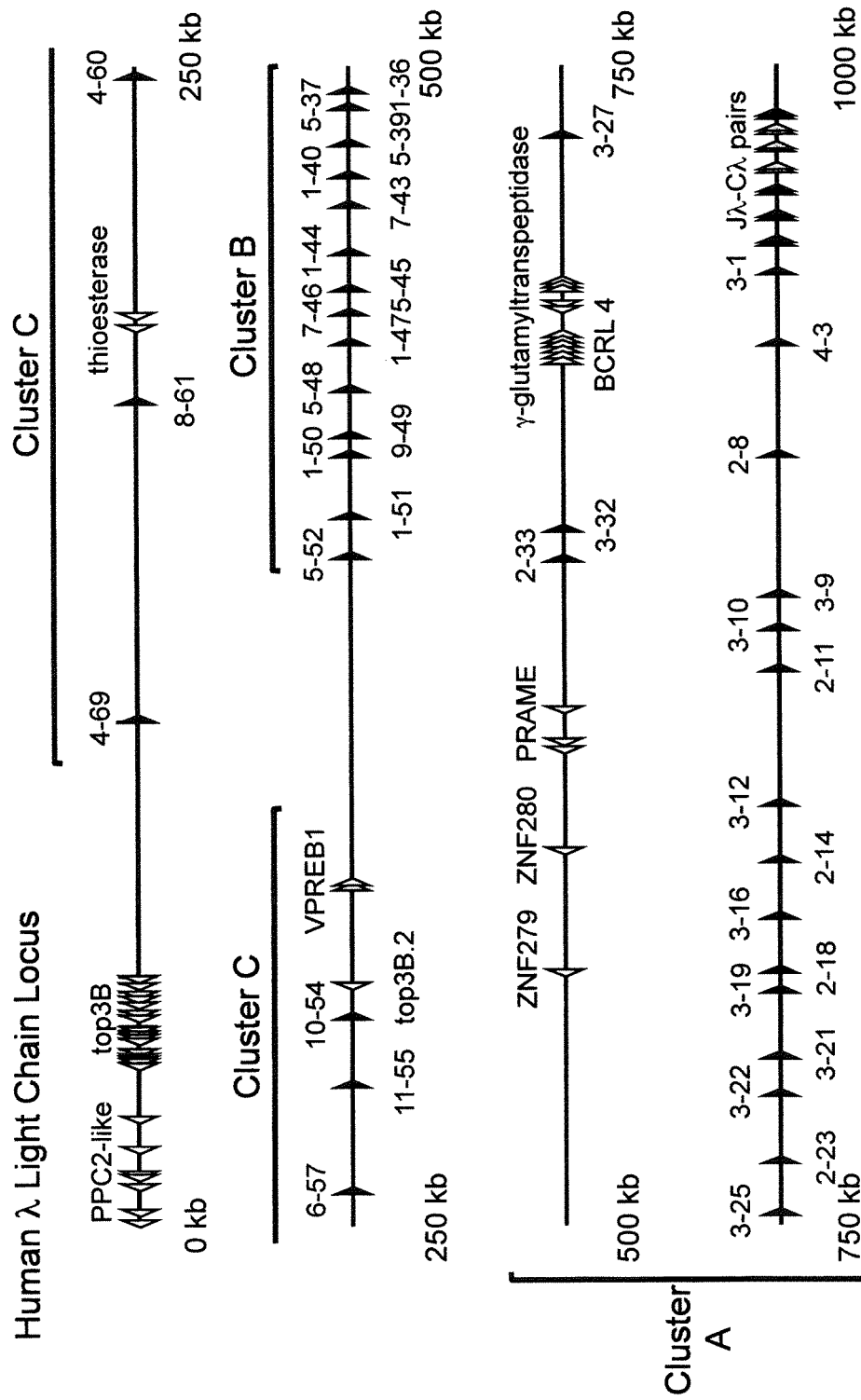

FIG. 19 shows a detailed illustration, not to scale, of the human light chain locus including the clusters of Vλ gene segments (A, B and C) and the Jλ and Cλ region pairs (J-C pairs)

Figure 20:
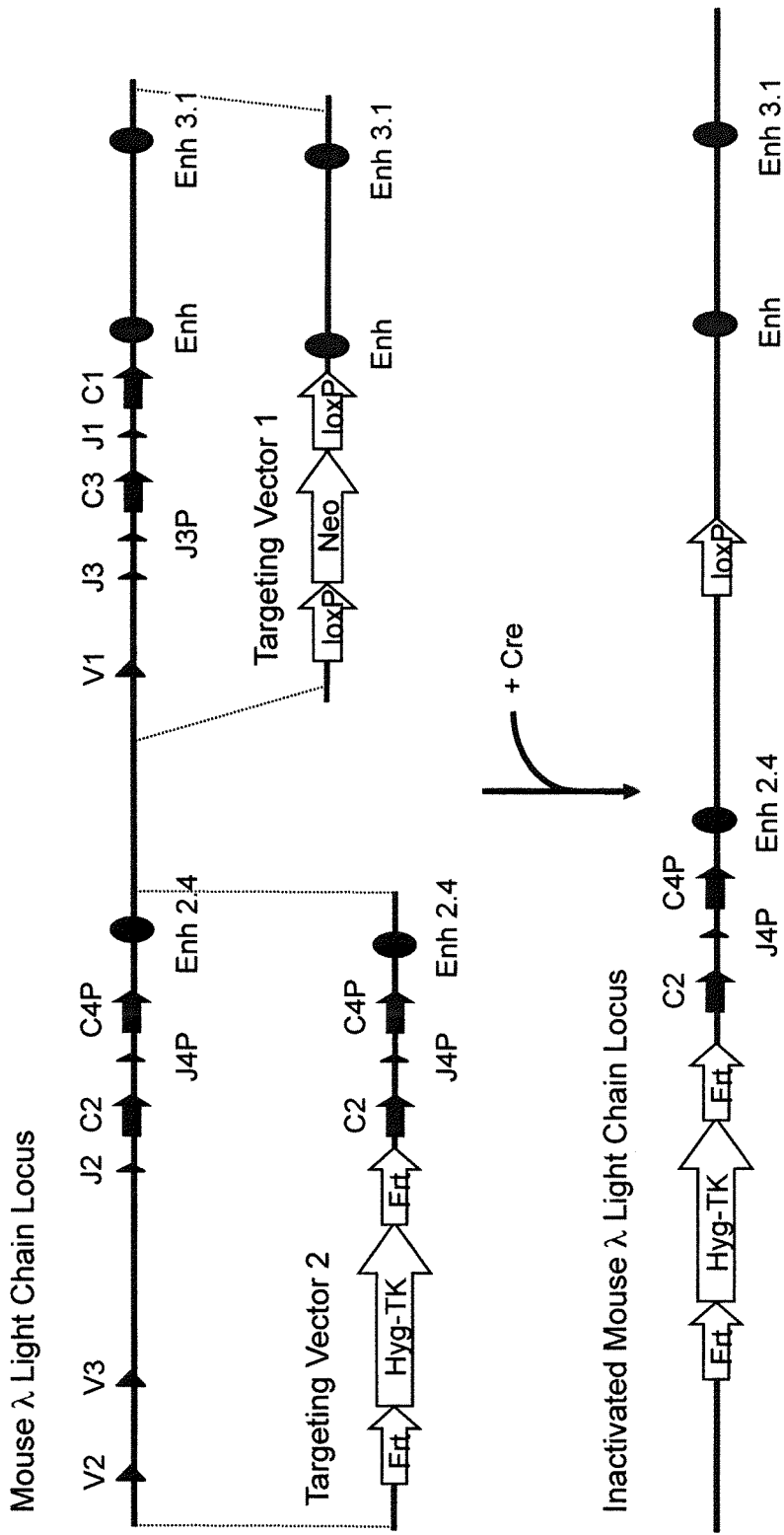

FIG. 20 shows a general illustration, not to scale, of a targeting strategy used to inactivate the endogenous mouse λ light chain locus.

Figure 21:
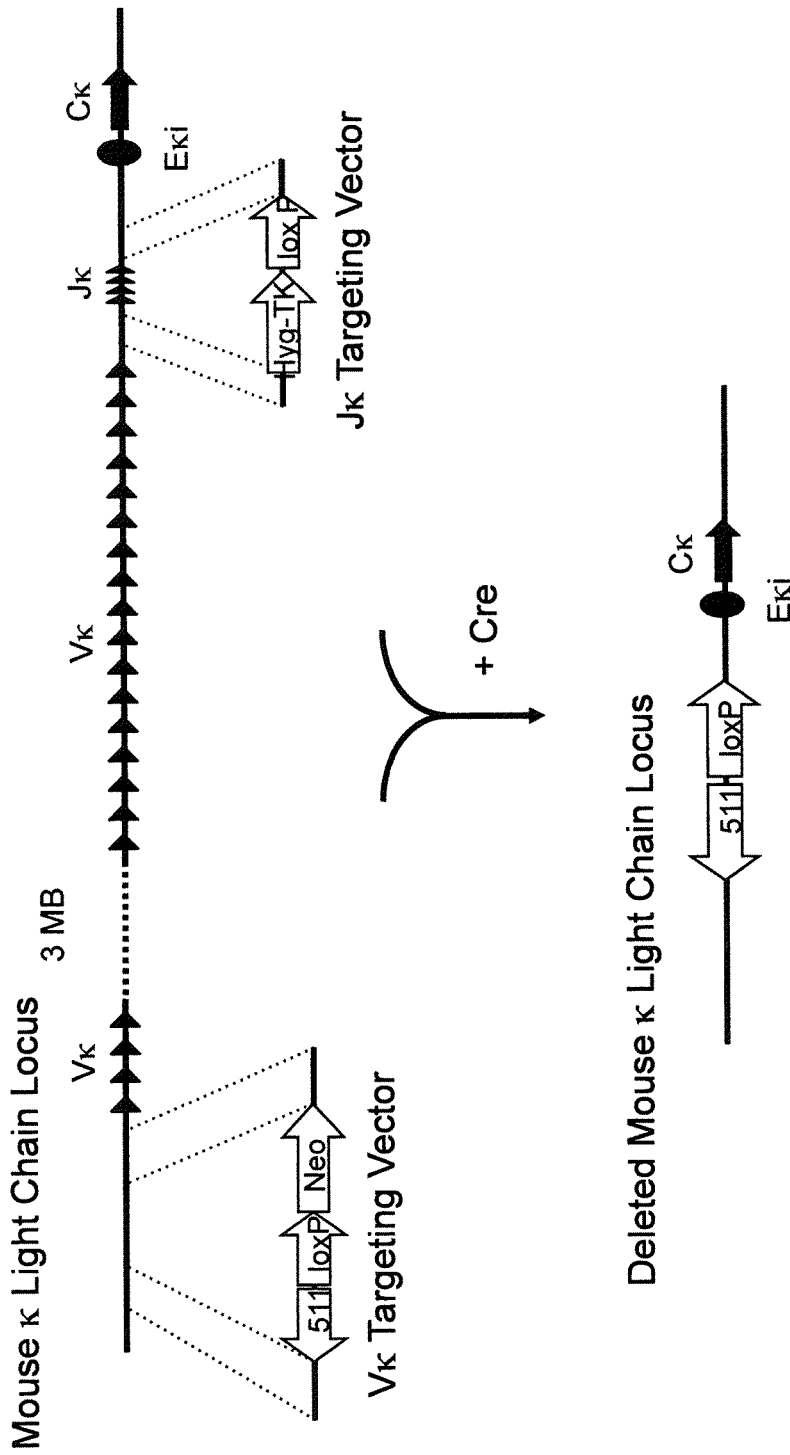

FIG. 21 shows a general illustration, not to scale, of a targeting strategy used to inactivate the endogenous mouse κ light chain locus.

Figure 22A:
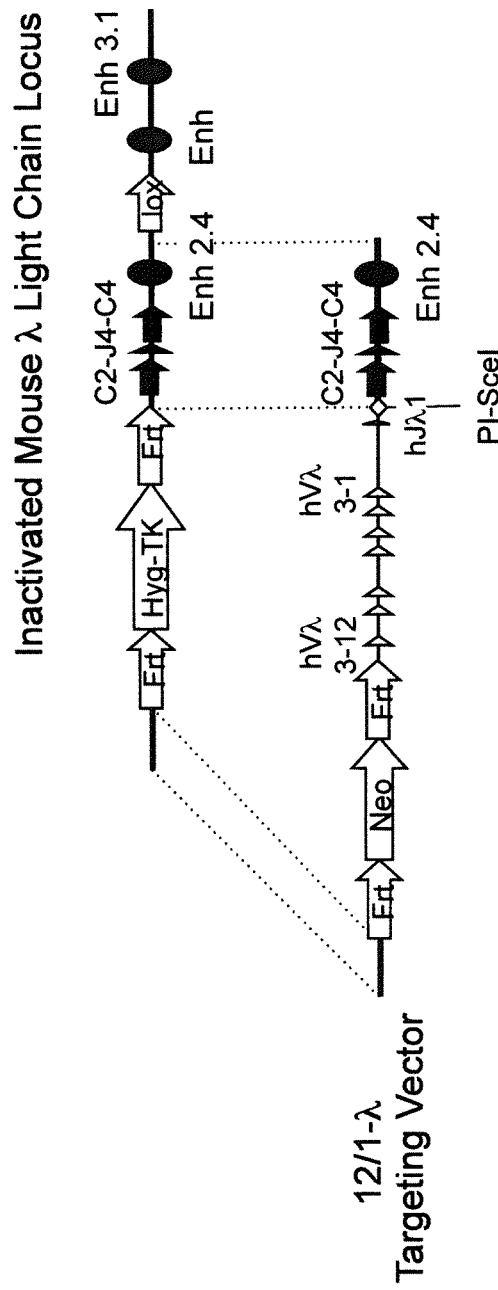

FIG. 22A shows a general illustration, not to scale of an initial targeting vector for targeting the endogenous mouse λ light chain locus with human λ light chain sequences including 12 hVλ gene segments and hJλ1 gene segment (12/1-λ Targeting Vector).

Figure 22B:
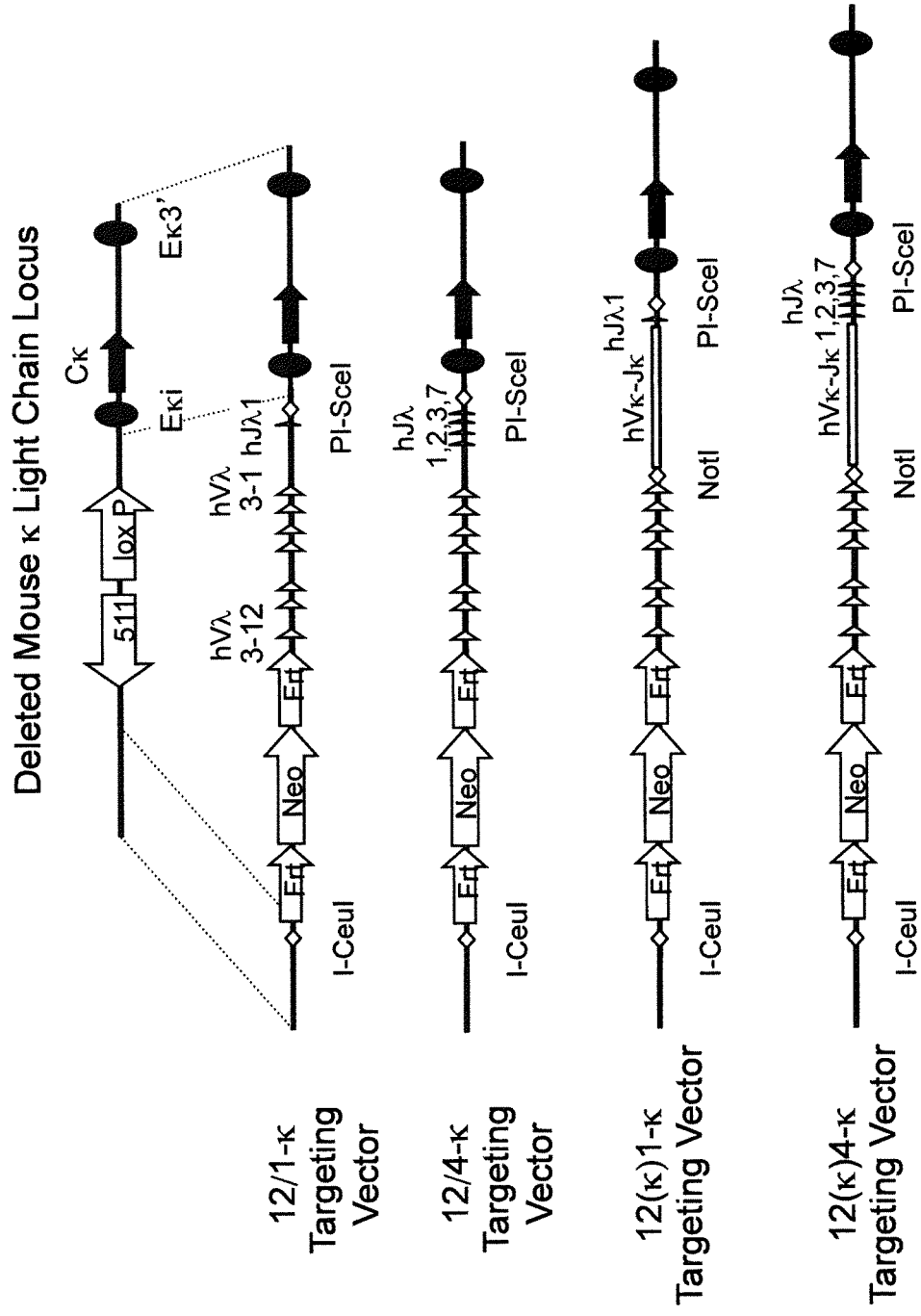

FIG. 22B shows a general illustration, not to scale, of four initial targeting vectors for targeting the endogenous mouse κ light chain locus with human λ light chain sequences including 12 hVλ gene segments and hJλ1 gene segment (12/1-κ Targeting Vector), 12 hVλ gene segments and hJλ1, 2, 3 and 7 gene segments (12/4-κ Targeting Vector), 12 hVλ gene segments, a human Vκ-Jκ genomic sequence and hJλ1 gene segment (12(κ)1-κ Targeting Vector) and 12 hVλ gene segments, a human Vκ-Jκ genomic sequence and hJλ1, 2, 3 and 7 gene segments (12(κ)4-κ Targeting Vector).

Figure 23A:
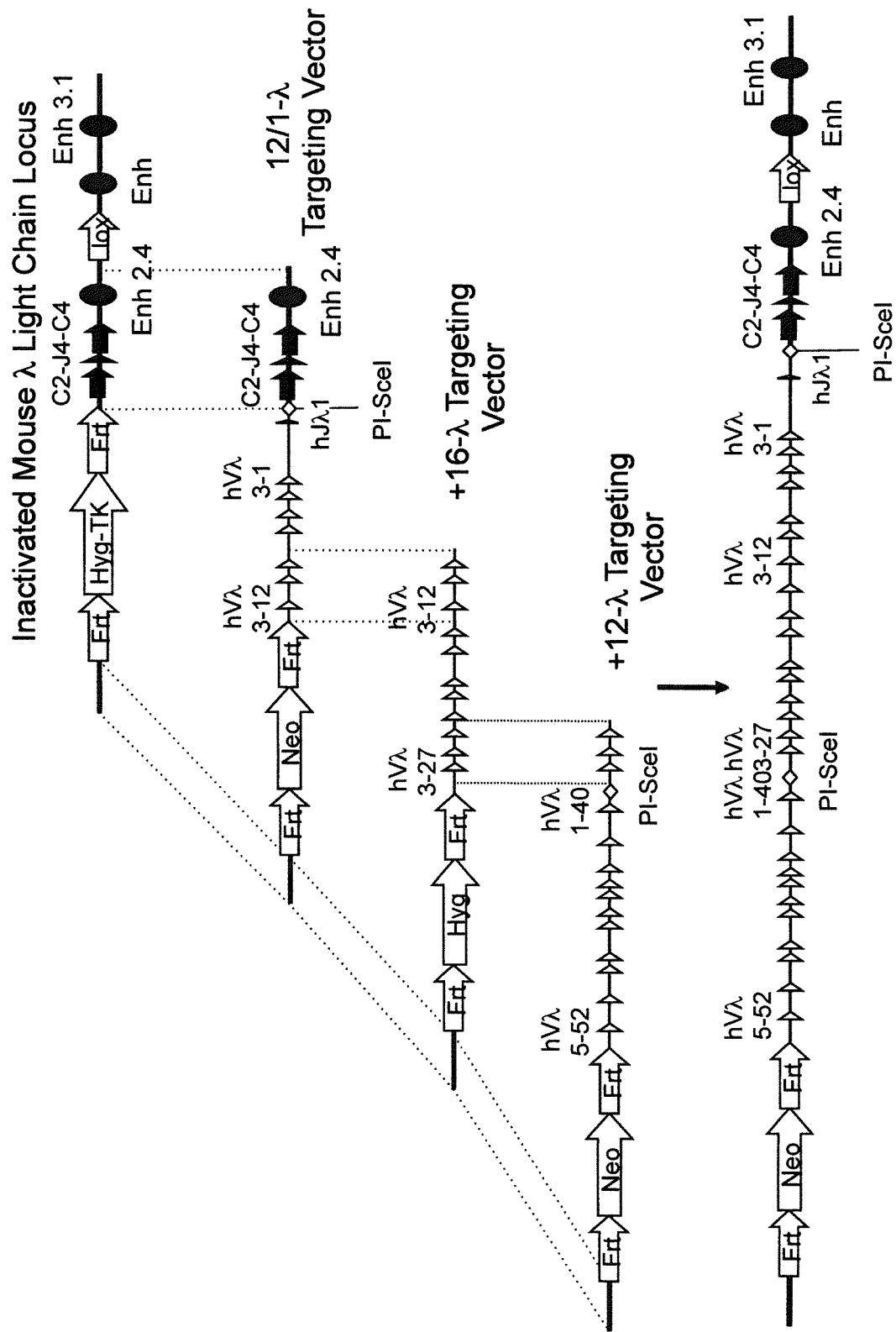

FIG. 23A shows a general illustration, not to scale, of a targeting strategy for progressive insertion of 40 hVλ gene segments and a single hJλ gene segment into the mouse λ light chain locus.

Figure 23B:
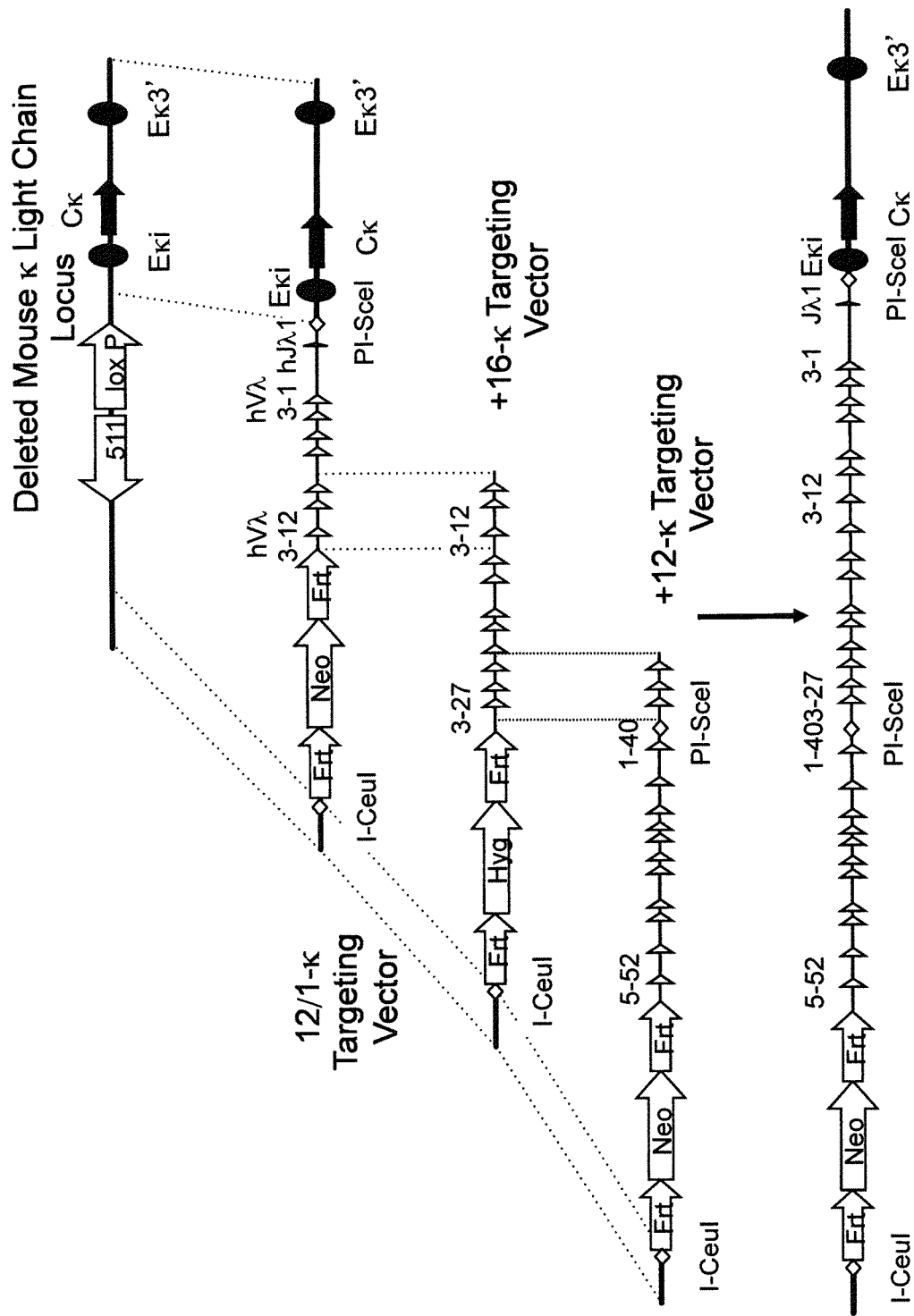

FIG. 23B shows a general illustration, not to scale, of a targeting strategy for progressive insertion of 40 hVλ gene segments and a single hJλ gene segment into the mouse κ locus.

Figure 24:
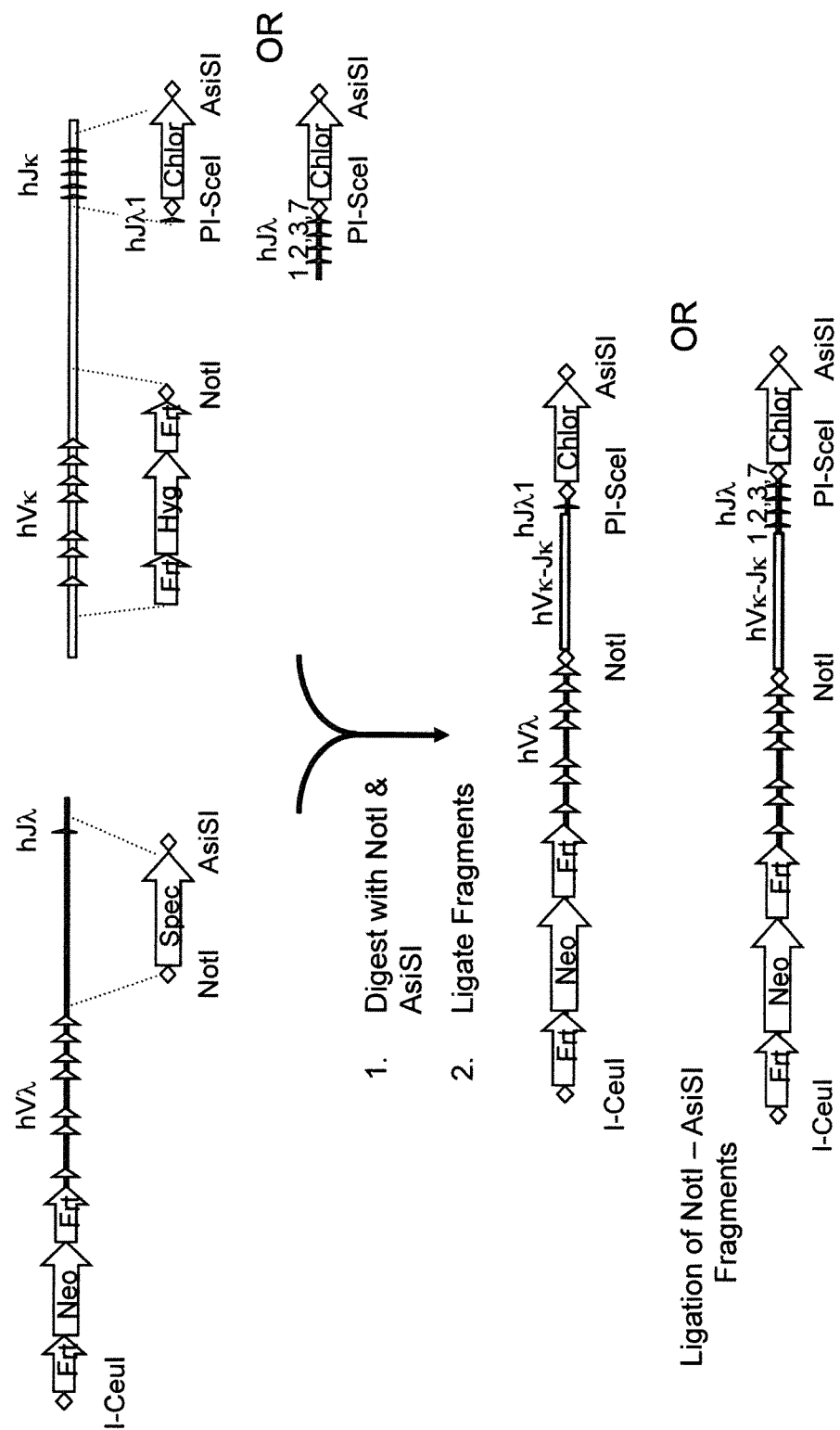

FIG. 24 show a general illustration, not to scale, of the targeting and molecular engineering steps employed to make unique human λ-κ hybrid targeting vectors for construction of a hybrid light chain locus containing a human κ intergenic sequence, multiple hJλ gene segments or both.

Figure 25A:
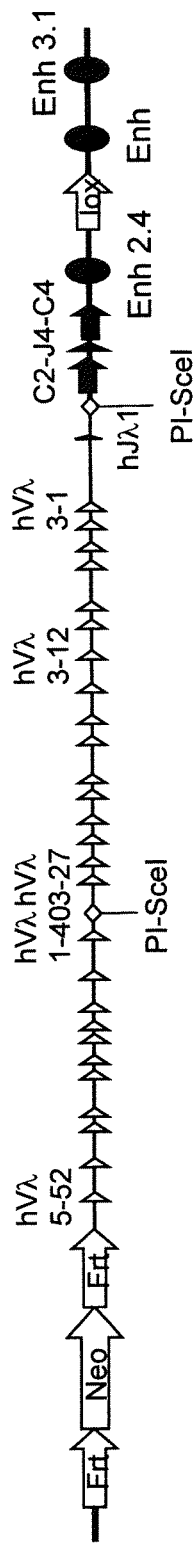

FIG. 25A shows a general illustration, not to scale, of the locus structure for a modified mouse λ light chain locus containing 40 hVλ gene segments and a single hJλ gene segment operably linked to the endogenous Cλ2 gene.

Figure 25B:
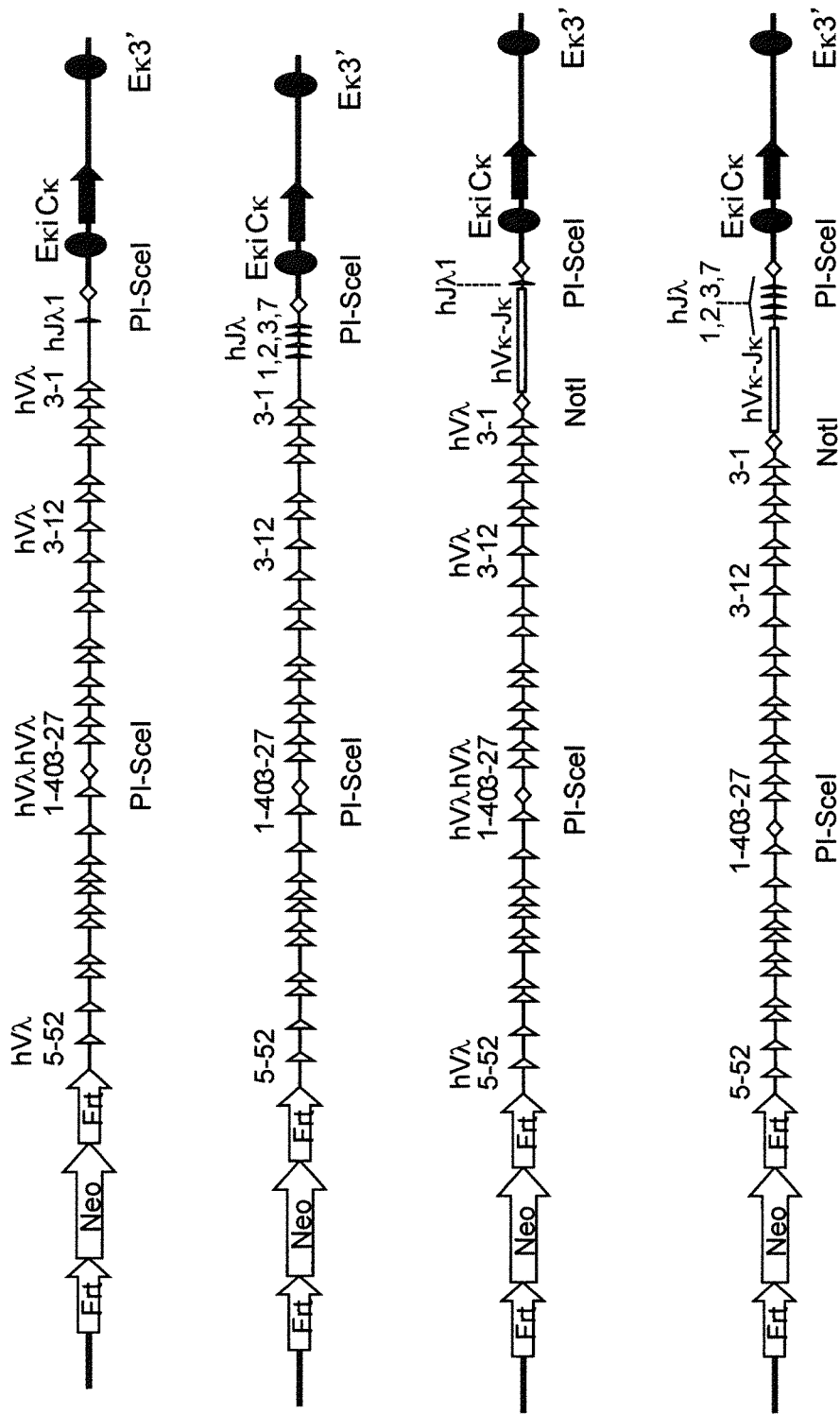

FIG. 25B shows a general illustration, not to scale, of the locus structure for four independent, modified mouse κ light chain loci containing 40 hVλ gene segments and either one or four hJλ gene segments with or without a contiguous human Vκ-Jκ genomic sequence operably linked to the endogenous Cκ gene.

Figure 26A:
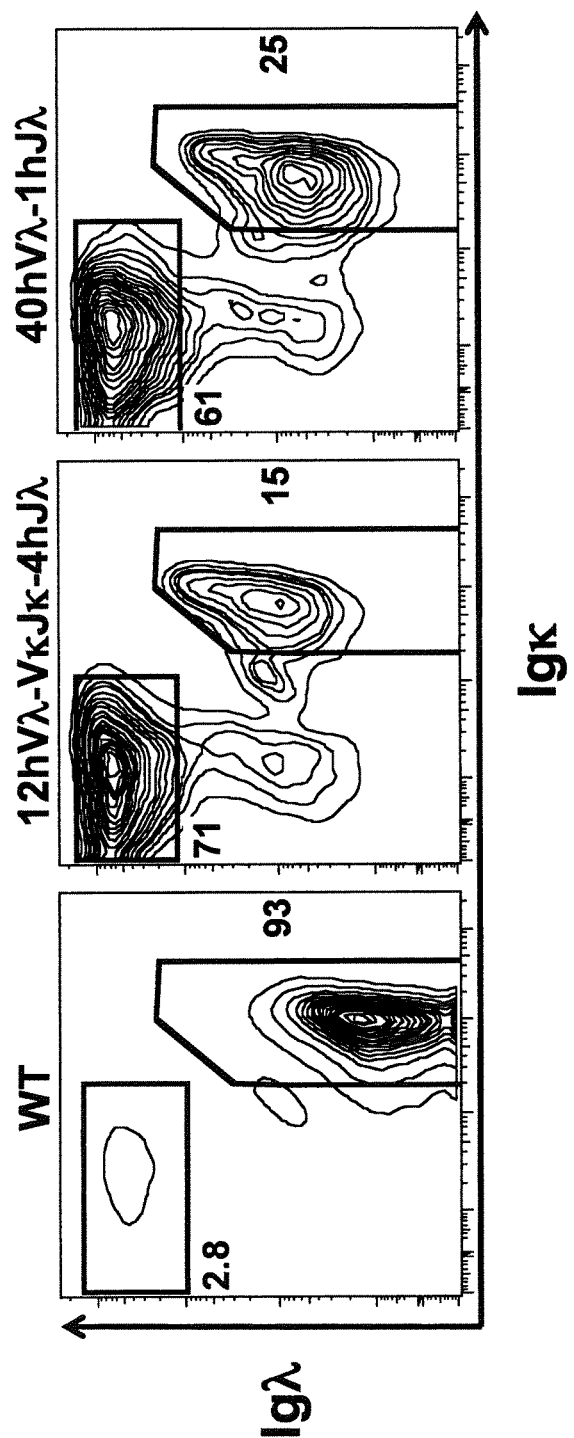

FIG. 26A shows contour plots of Igλ$^+$ and Igκ$^+$ splenocytes gated on CD19$^+$ from a wild type mouse (WT), a mouse homozygous for 12 hVλ and four hJλ gene segments including a human Vκ-Jκ genomic sequence (12hVλ-VκJκ-4hJλ) and a mouse homozygous for 40 hVλ and one hJλ gene segment (40hVλ-1hJλ).

Figure 26B:
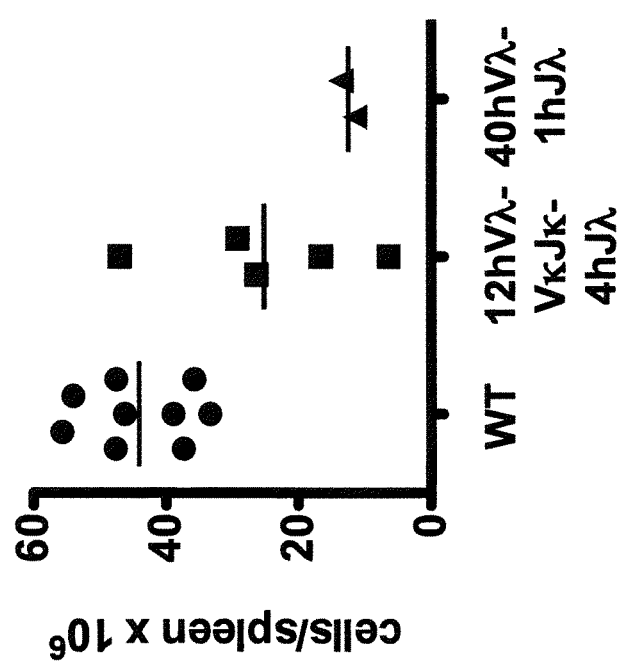

FIG. 26B shows the total number of CD19$^+$ B cells in harvested spleens from wild type (WT), mice homozygous for 12 hVλ and four hJλ gene segments including a human Vκ-Jκ genomic sequence (12hVλ-VκJκ-4hJλ) and mice homozygous for 40 hVλ and one hJλ gene segment (40hVλ-1hJλ).

Figure 27A:
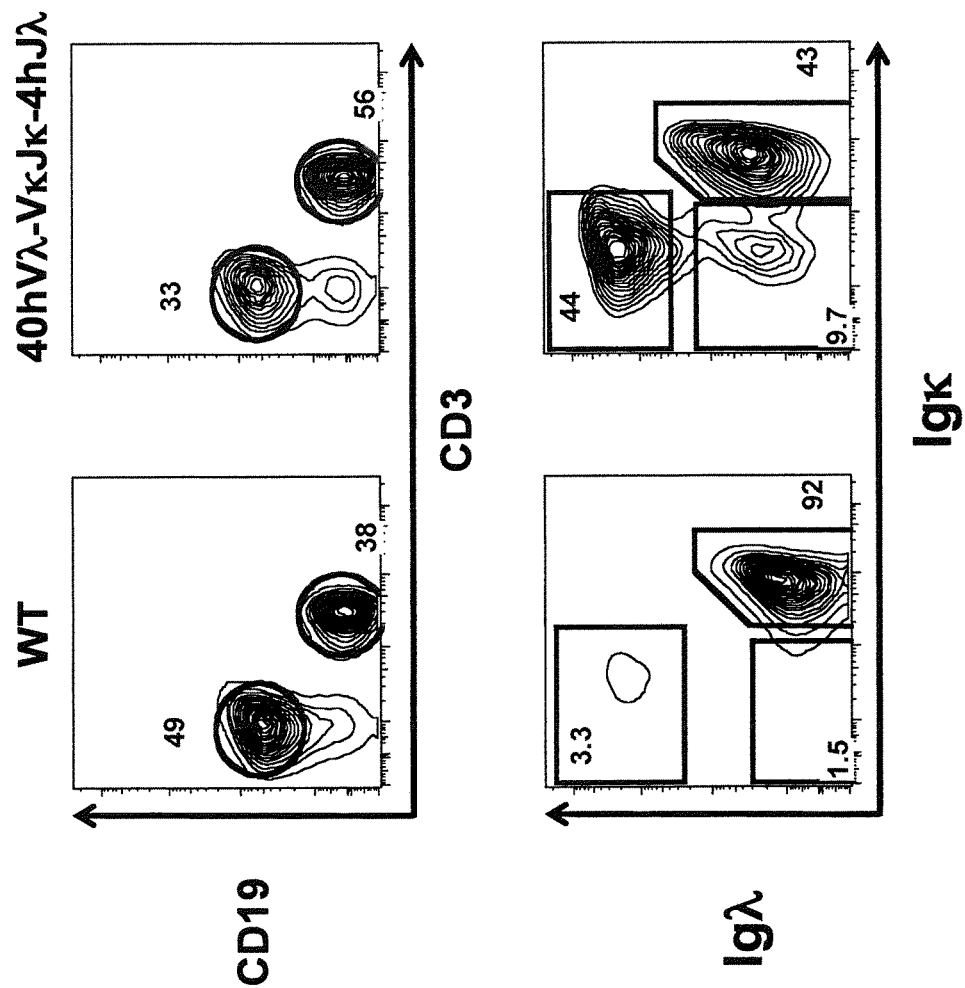

FIG. 27A, in the top panel, shows contour plots of splenocytes gated on singlets and stained for B and T cells (CD19+ and CD3+, respectively) from a wild type mouse (WT) and a mouse homozygous for 40 hVλ and four Jλ gene segments including a human Vκ-Jκ genomic sequence (40hVλ-VκJκ-4hJλ). The bottom panel shows contour plots of splenocytes gated on CD19+ and stained for Igλ+ and Igκ+ expression from a wild type mouse (WT) and a mouse homozygous for 40 hVλ and four Jλ gene segments including a human Vκ-Jκ genomic sequence (40hVλ-VκJκ-4hJλ).

Figure 27B:
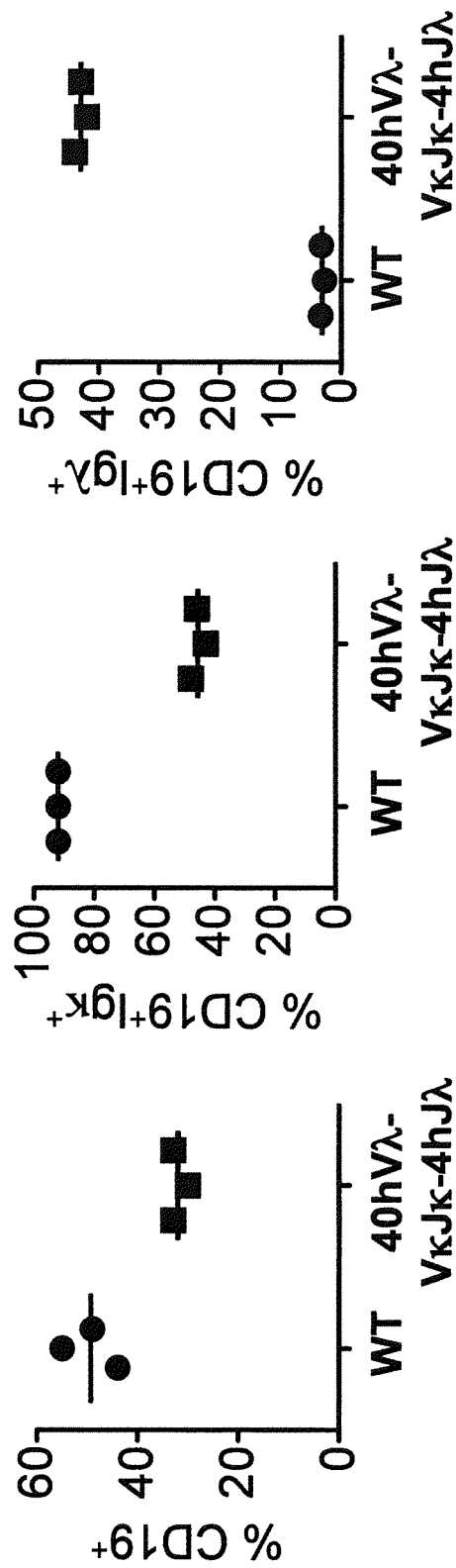

FIG. 27B shows the total number of CD19+, CD19+Igκ+ and CD19+Igλ+ B cells in harvested spleens from wild type mice (WT) and mice homozygous for 40 hVλ and four Jλ gene segments including a human Vκ-Jκ genomic sequence (40hVλ-VκJκ-4hJλ).

Figure 27C:
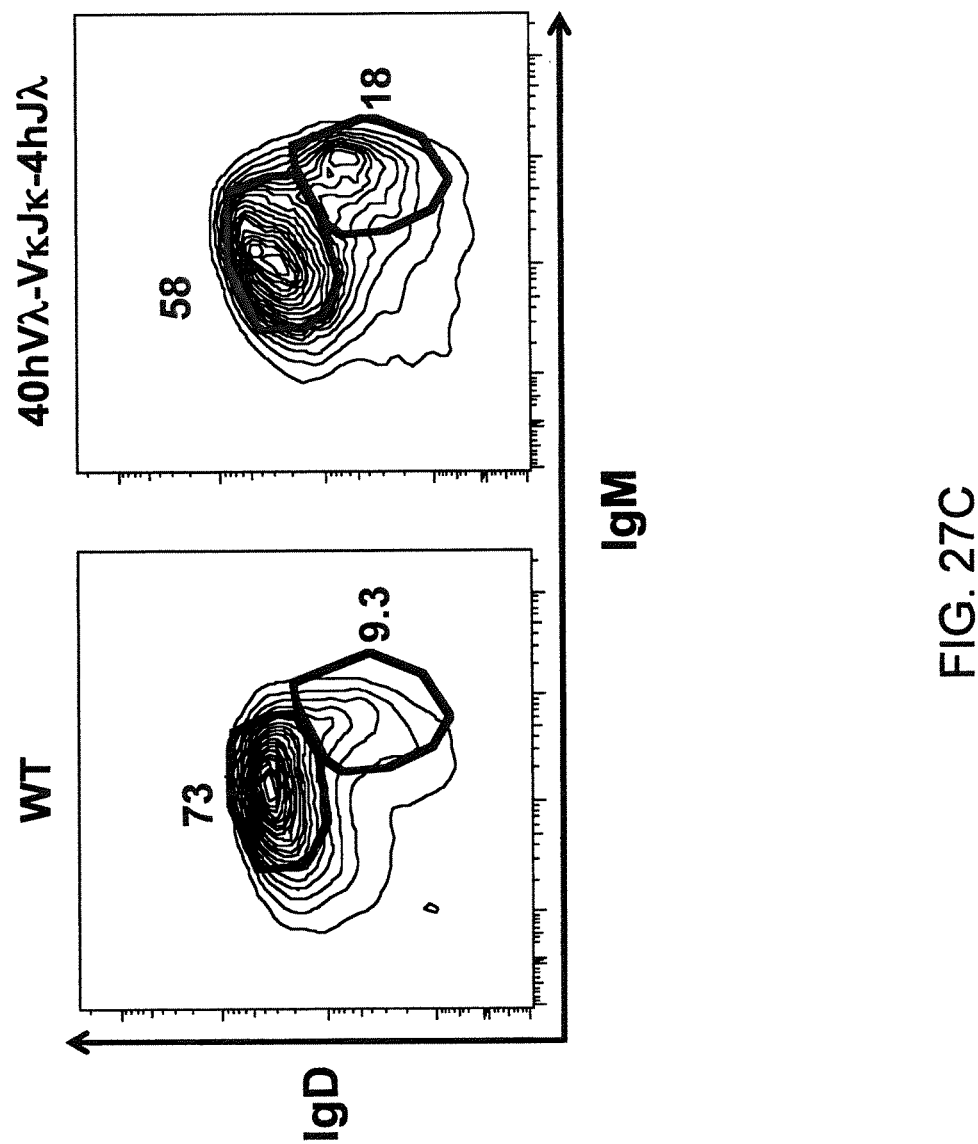

FIG. 27C shows contour plots of splenocytes gated on CD19+ and stained for immunoglobulin D (IgD) and immunoglobulin M (IgM) from a wild type mouse (WT) and a mouse homozygous for 40 hVλ and four Jλ gene segments including a human Vκ-Jκ genomic sequence (40hVλ-VκJκ-4hJλ). Mature (72 for WT, 51 for 40hVλ-VκJκ-4hJλ) and transitional (13 for WT, 22 for 40hVλ-VκJκ-4hJλ) B cells are noted on each of the contour plots.

Figure 27D:
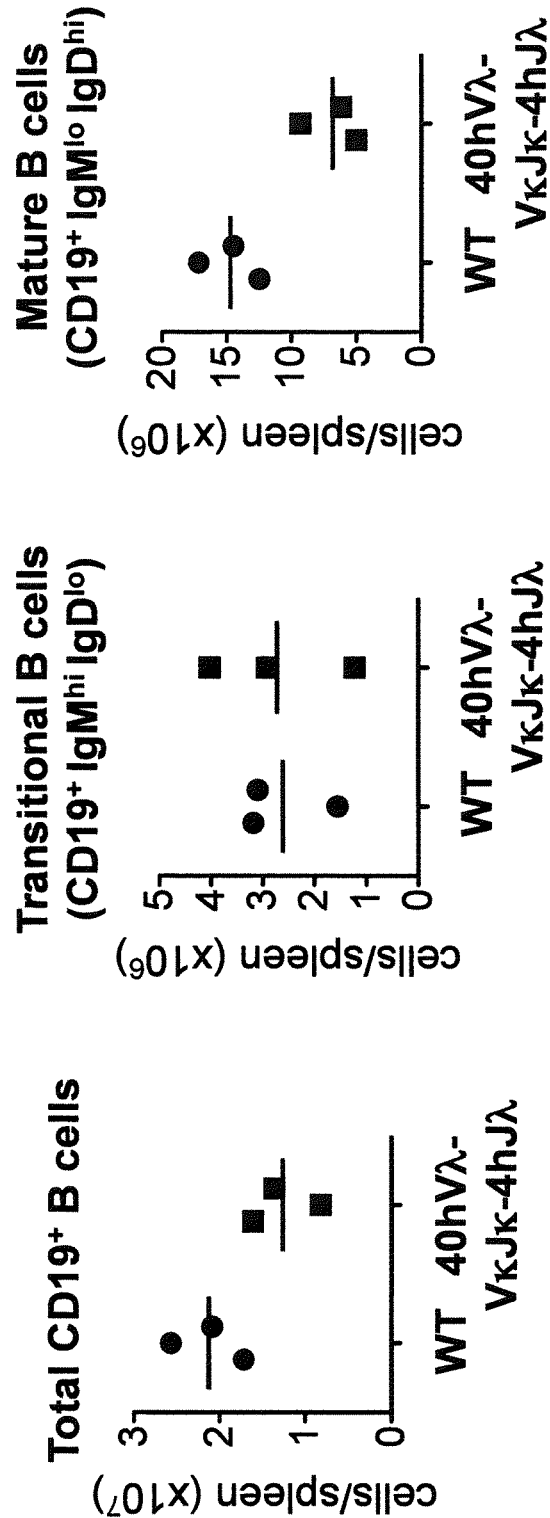

FIG. 27D shows the total number of CD19+ B cells, transitional B cells (CD19+IgM$^{hi}$IgD$^{lo}$) and mature B cells (CD19+IgM$^{lo}$IgD$^{hi}$) in harvested spleens from wild type mice (WT) and mice homozygous for 40 hVλ and four Jλ gene segments including a human Vκ-Jκ genomic sequence (40hVλ-VκJκ-4hJλ).

Figure 28A:
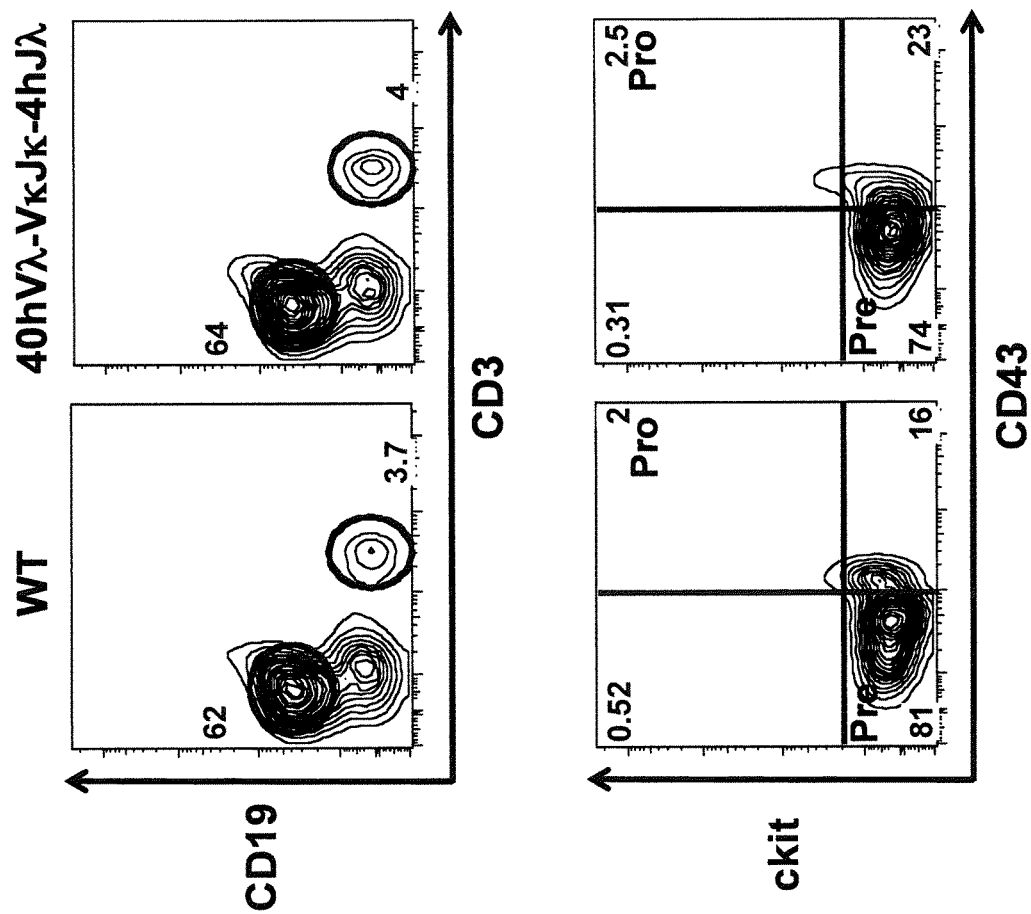

FIG. 28A, in the top panel, shows contour plots of bone marrow stained for B and T cells (CD19+ and CD3+, respectively) from a wild type mouse (WT) and a mouse homozygous for 40 hVλ and four Jλ gene segments including a human Vκ-Jκ genomic sequence (40hVλ-VκJκ-4hJλ). The bottom panel shows contour plots of bone marrow gated on CD19+ and stained for ckit+ and CD43+ from a wild type mouse (WT) and a mouse homozygous for 40 hVλ and four Jλ gene segments including a human Vκ-Jκ genomic sequence (40hVλ-VκJκ-4hJλ). Pro and Pre B cells are noted on the contour plots of the bottom panel.

Figure 28B:
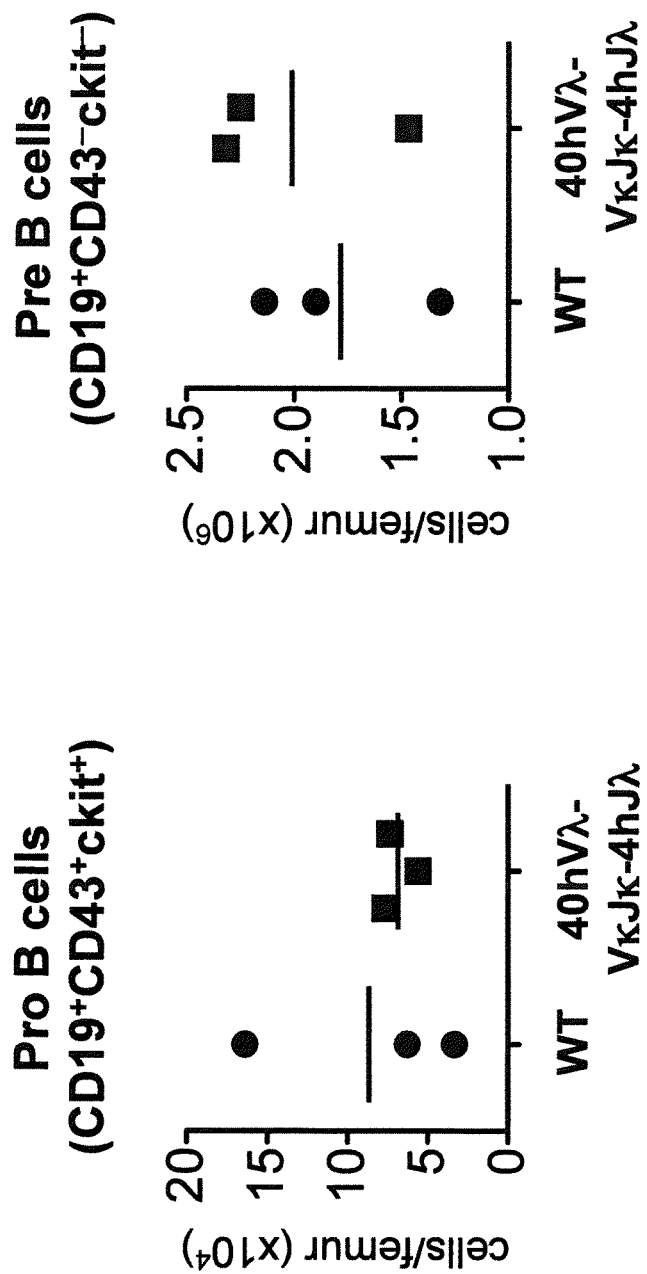

FIG. 28B shows the number of Pro (CD19+CD43+ckit+) and Pre (CD19+CD43−ckit−) B cells in bone marrow harvested from the femurs of wild type mice (WT) and mice homozygous for 40 hVλ and four Jλ gene segments including a human Vκ-Jκ genomic sequence (40hVλ-VκJκ-4hJλ).

Figure 28C:
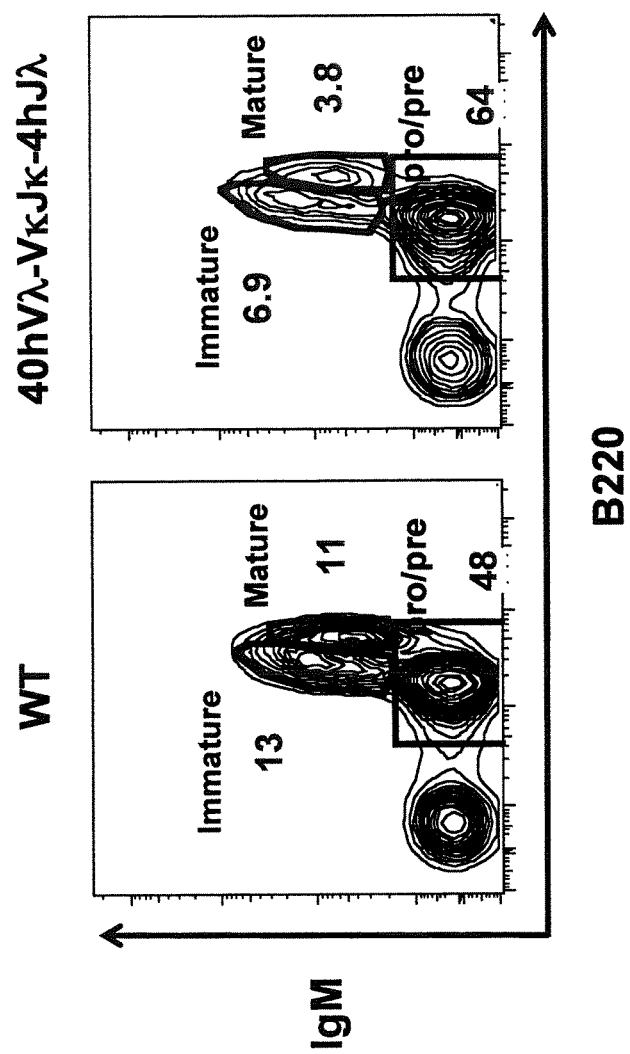

FIG. 28C shows contour plots of bone marrow gated on singlets stained for immunoglobulin M (IgM) and B220 from a wild type mouse (WT) and a mouse homozygous for 40 hVλ and four Jλ gene segments including a human Vκ-Jκ genomic sequence (40hVλ-VκJκ-4hJλ). Immature, mature and pro/pre B cells are noted on each of the contour plots.

Figure 28D:
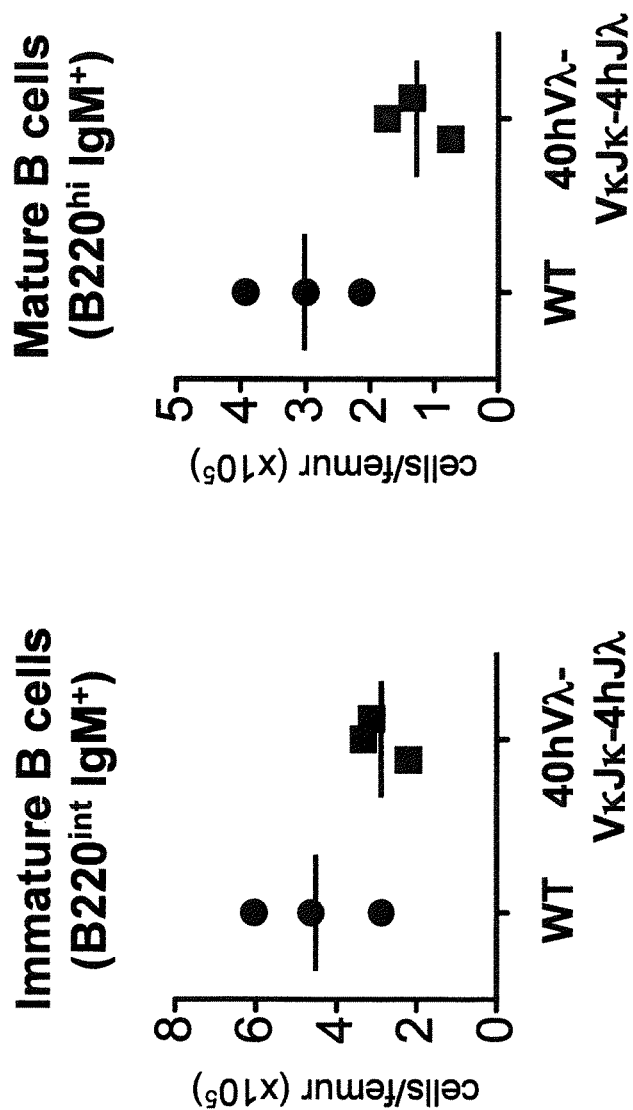

FIG. 28D shows the total number of immature (B220$^{int}$IgM+) and mature (B220$^{hi}$IgM+) B cells in bone marrow isolated from the femurs of wild type mice (WT) and mice homozygous for 40 hVλ and four Jλ gene segments including a human Vκ-Jκ genomic sequence (40hVλ-VκJκ-4hJλ).

Figure 28E:
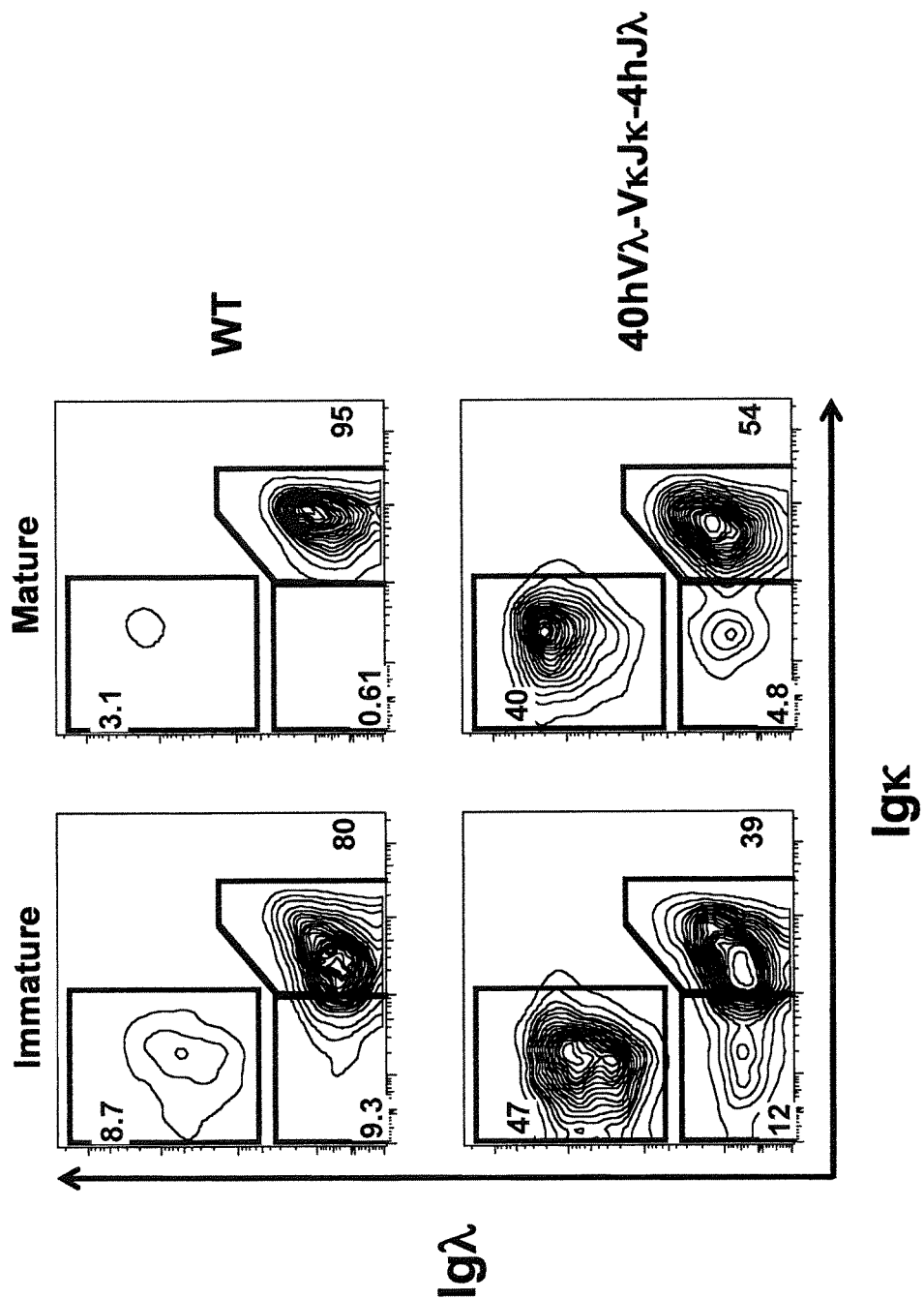

FIG. 28E shows contour plots of bone marrow gated on immature (B220$^{int}$IgM+) and mature (B220$^{hi}$IgM+) B cells stained for Igλ and Igκ expression isolated from the femurs of a wild type mouse (WT) and a mouse homozygous for 40 hVλ and four Jλ gene segments including a human Vκ-Jκ genomic sequence (40hVλ-VκJκ-4hJλ).

FIG. 29 shows a nucleotide sequence alignment of the Vλ-Jλ-Cκ junction of eighteen independent RT-PCR clones amplified from splenocyte RNA of mice bearing human λ light chain gene sequences at an endogenous mouse κ light chain locus. A6=SEQ ID NO:115; B6=SEQ ID NO:116; F6=SEQ ID NO:117; B7=SEQ ID NO:118; E7=SEQ ID NO:119; F7=SEQ ID NO:120; C8=SEQ ID NO:121; E12=SEQ ID NO:122; 1-4=SEQ ID NO:123; 1-20=SEQ ID NO:124; 3B43=SEQ ID NO:125; 5-8=SEQ ID NO:126; 5-19=SEQ ID NO:127; 1010=SEQ ID NO:128; 11A1=SEQ ID NO:129; 7A8=SEQ ID NO:130; 3A3=SEQ ID NO:131; 2-7=SEQ ID NO:132. Lower case bases indicate non-germline bases resulting from either mutation and/or N addition during recombination. Consensus amino acids within the Framework 4 region (FWR4) encoded by the nucleotide sequence of hJλ1 and mouse Cκ are noted at the bottom of the sequence alignment.

FIG. 30 shows a nucleotide sequence alignment of the Vλ-Jλ-Cκ junction of twelve independent RT-PCR clones amplified from splenocyte RNA of mice bearing human λ light chain gene sequences including a contiguous human Vκ-Jκ genomic sequence at an endogenous mouse κ light chain locus. 5-2=SEQ ID NO:145; 2-5=SEQ ID NO:146; 1-3=SEQ ID NO:147; 4B-1=SEQ ID NO:148; 3B-5=SEQ ID NO:149; 7A-1=SEQ ID NO:150; 5-1=SEQ ID NO:151; 4A-1=SEQ ID NO:152; 11A-1=SEQ ID NO:153; 5-7=SEQ ID NO:154; 5-4=SEQ ID NO:155; 2-3=SEQ ID NO:156. Lower case bases indicate non-germline bases resulting from either mutation and/or N addition during recombination. Consensus amino acids within the Framework 4 region (FWR4) encoded by the nucleotide sequence of each human Jλ and mouse Cκ are noted at the bottom of the sequence alignment.

FIG. 31 shows a nucleotide sequence alignment of the Vλ-Jλ-Cλ junction of three independent RT-PCR clones amplified from splenocyte RNA of mice bearing human λ light chain gene sequences at an endogenous mouse λ light chain locus. 2D1=SEQ ID NO:159; 2D9=SEQ ID NO:160; 3E15=SEQ ID NO:161. Lower case bases indicate non-germline bases resulting from either mutation and/or N addition during recombination. Consensus amino acids within the Framework 4 region (FWR4) encoded by the nucleotide sequence of hJλ1 and mouse Cλ2 are noted at the bottom of the sequence alignment.

DETAILED DESCRIPTION

This invention is not limited to particular methods, and experimental conditions described, as such methods and conditions may vary. It is also to be understood that the terminology used herein is for the purpose of describing particular embodiments only, and is not intended to be limiting, since the scope of the present invention is defined by the claims.

Unless defined otherwise, all terms and phrases used herein include the meanings that the terms and phrases have attained in the art, unless the contrary is clearly indicated or clearly apparent from the context in which the term or phrase is used. Although any methods and materials similar or equivalent to those described herein can be used in the practice or testing of the present invention, particular methods and materials are now described. All publications mentioned are hereby incorporated by reference.

The phrase "substantial" or "substantially" when used to refer to an amount of gene segments (e.g., "substantially all" V gene segments) includes both functional and non functional gene segments and include, in various embodiments, e.g., 80% or more, 85% or more, 90% or more, 95% or more 96% or more, 97% or more, 98% or more, or 99% or more of all gene segments; in various embodiments, "substantially all" gene segments includes, e.g., at least 95%, 96%, 97%, 98%, or 99% of functional (i.e., non-pseudogene) gene segments.

The term "replacement" includes wherein a DNA sequence is placed into a genome of a cell in such a way as to replace a sequence within the genome with a heterologous sequence (e.g., a human sequence in a mouse), at the locus of the genomic sequence. The DNA sequence so placed may include one or more regulatory sequences that are part of source DNA used to obtain the sequence so placed (e.g., promoters, enhancers, 5'- or 3'-untranslated regions, appropriate recombination signal sequences, etc.). For example, in various embodiments, the replacement is a substitution of an endogenous sequence for a heterologous sequence that results in the production of a gene product from the DNA sequence so placed (comprising the heterologous sequence), but not expression of the endogenous sequence; the replacement is of an endogenous genomic sequence with a DNA sequence that encodes a protein that has a similar function as a protein encoded by the endogenous genomic sequence (e.g., the endogenous genomic sequence encodes an immunoglobulin gene or domain, and the DNA fragment encodes one or more human immunoglobulin genes or domains). In various embodiments, an endogenous gene or fragment thereof is replaced with a corresponding human gene or fragment thereof. A corresponding human gene or fragment thereof is a human gene or fragment that is an ortholog of, a homolog of, or is substantially identical or the same in structure and/or function, as the endogenous gene or fragment thereof that is replaced.

The term "contiguous" includes reference to occurrence on the same nucleic acid molecule, e.g., two nucleic acid sequences are "contiguous" if they occur on the same nucleic molecule but are interrupted by another nucleic acid sequence. For example, a rearranged V(D)J sequence is "contiguous" with a constant region gene sequence, although the final codon of the V(D)J sequence is not followed immediately by the first codon of the constant region sequence. In another example, two V gene segment sequences are "contiguous" if they occur on the same genomic fragment, although they may be separated by sequence that does not encode a codon of the V region, e.g., they may be separated by a regulatory sequence, e.g., a promoter or other noncoding sequence. In one embodiment, a contiguous sequence includes a genomic fragment that contains genomic sequences arranged as found in a wild-type genome.

The phrase "derived from" when used concerning a variable region "derived from" a cited gene or gene segment includes the ability to trace the sequence back to a particular unrearranged gene segment or gene segments that were rearranged to form a gene that expresses the variable domain (accounting for, where applicable, splice differences and somatic mutations).

The phrase "functional" when used concerning a variable region gene segment or joining gene segment refers to usage in an expressed antibody repertoire; e.g., in humans Vλ gene segments 3-1, 4-3, 2-8, etc. are functional, whereas Vλ gene segments 3-2, 3-4, 2-5, etc. are nonfunctional.

A "heavy chain locus" includes a location on a chromosome, e.g., a mouse chromosome, wherein in a wild-type mouse heavy chain variable ($V_H$), heavy chain diversity ($D_H$), heavy chain joining ($J_H$), and heavy chain constant ($C_H$) region DNA sequences are found.

A "κ locus" includes a location on a chromosome, e.g., a mouse chromosome, wherein in a wild-type mouse κ variable (Vκ), κ joining (Jκ), and κ constant (Cκ) region DNA sequences are found.

A "λ locus" includes a location on a chromosome, e.g., a mouse chromosome, wherein in a wild-type mouse λ variable (Vλ), λ joining (Jλ), and λ constant (Cλ) region DNA sequences are found.

The term "cell," when used in connection with expressing a sequence includes any cell that is suitable for expressing a recombinant nucleic acid sequence. Cells include those of prokaryotes and eukaryotes (single-cell or multiple-cell), bacterial cells (e.g., strains of E. coli Bacillus spp., Streptomyces spp., etc.), mycobacteria cells, fungal cells, yeast cells (e.g., S. cerevisiae, S. pombe, P. pastoris, P. methanolica, etc.), plant cells, insect cells (e.g., SF-9, SF-21, baculovirus-infected insect cells, Trichoplusia ni, etc.), non-human animal cells, human cells, B cells, or cell fusions such as, for example, hybridomas or quadromas. In some embodiments, the cell is a human, monkey, ape, hamster, rat, or mouse cell. In some embodiments, the cell is eukaryotic and is selected from the following cells: CHO (e.g., CHO K1, DXB-11 CHO, Veggie-CHO), COS (e.g., COS-7), retinal cell, Vero, CV1, kidney (e.g., HEK293, 293 EBNA, MSR 293, MDCK, HaK, BHK), HeLa, HepG2, WI38, MRC 5, Colo205, HB 8065, HL-60, (e.g., BHK21), Jurkat, Daudi, A431 (epidermal), CV-1, U937, 3T3, L cell, C127 cell, SP2/0, NS-0, MMT 060562, Sertoli cell, BRL 3A cell, HT1080 cell, myeloma cell, tumor cell, and a cell line derived from an aforementioned cell. In some embodiments, the cell comprises one or more viral genes, e.g. a retinal cell that expresses a viral gene (e.g., a PER.C6™ cell).

The phrase "complementarity determining region," or the term "CDR," includes an amino acid sequence encoded by a nucleic acid sequence of an organism's immunoglobulin genes that normally (i.e., in a wild-type animal) appears between two framework regions in a variable region of a light or a heavy chain of an immunoglobulin molecule (e.g., an antibody or a T cell receptor). A CDR can be encoded by, for example, a germline sequence or a rearranged or unrearranged sequence, and, for example, by a naïve or a mature B cell or a T cell. In some circumstances (e.g., for a CDR3), CDRs can be encoded by two or more sequences (e.g., germline sequences) that are not contiguous (e.g., in an unrearranged nucleic acid sequence) but are contiguous in a B cell nucleic acid sequence, e.g., as the result of splicing or connecting the sequences (e.g., V-D-J recombination to form a heavy chain CDR3).

The phrase "gene segment," or "segment" includes reference to a V (light or heavy) or D or J (light or heavy) immunoglobulin gene segment, which includes unrearranged sequences at immunoglobulin loci (in e.g., humans and mice) that can participate in a rearrangement (mediated by, e.g., endogenous recombinases) to form a rearranged V/J or V/D/J sequence. Unless indicated otherwise, the V, D, and J segments comprise recombination signal sequences (RSS) that allow for V/J recombination or V/D/J recombination according to the 12/23 rule. Unless indicated otherwise, the segments further comprise sequences with which they are associated in nature or functional equivalents thereof (e.g., for V segments promoter(s) and leader(s)).

The term "unrearranged" includes the state of an immunoglobulin locus wherein V gene segments and J gene segments (for heavy chains, D gene segments as well) are maintained separately but are capable of being joined to form a rearranged V(D)J gene that comprises a single V,(D),J of the V(D)J repertoire.

The phrase "micromolar range" is intended to mean 1-999 micromolar; the phrase "nanomolar range" is intended to mean 1-999 nanomolar; the phrase "picomolar range" is intended to mean 1-999 picomolar.

The term "non-human animals" is intended to include any non-human animals such as cyclostomes, bony fish, cartilaginous fish such as sharks and rays, amphibians, reptiles, mammals, and birds. Suitable non-human animals include mammals. Suitable mammals include non-human primates, goats, sheep, pigs, dogs, cows, and rodents. Suitable non-human animals are selected from the rodent family including rat and mouse. In one embodiment, the non-human animals are mice.

The mouse as a genetic model has been greatly enhanced by transgenic and knockout technologies, which have allowed for the study of the effects of the directed overexpression or deletion of specific genes. Despite all of its advantages, the mouse still presents genetic obstacles that render it an imperfect model for human diseases and an imperfect platform to test human therapeutics or make them. First, although about 99% of human genes have a mouse homolog (Waterston, R. H. et al. (2002) Initial sequencing and comparative analysis of the mouse genome. Nature 420, 520-562.), potential therapeutics often fail to cross-react, or cross-react inadequately, with mouse orthologs of the intended human targets. To obviate this problem, selected target genes can be "humanized," that is, the mouse gene can be eliminated and replaced by the corresponding human orthologous gene sequence (e.g., U.S. Pat. No. 6,586,251, 6,596,541 and 7,105,348, incorporated herein by reference). Initially, efforts to humanize mouse genes by a "knockout-plus-transgenic humanization" strategy entailed crossing a mouse carrying a deletion (i.e., knockout) of the endogenous gene with a mouse carrying a randomly integrated human transgene (see, e.g., Bril, W. S. et al. (2006) Tolerance to factor VIII in a transgenic mouse expressing human factor VIII cDNA carrying an Arg(593) to Cys substitution. Thromb Haemost 95, 341-347; Homanics, G. E. et al. (2006) Production and characterization of murine models of classic and intermediate maple syrup urine disease. BMC Med Genet 7, 33; Jamsai, D. et al. (2006) A humanized BAC transgenic/knockout mouse model for HbE/beta-thalassemia. Genomics 88(3):309-15; Pan, Q. et al. (2006) Different role for mouse and human CD3delta/epsilon heterodimer in preT cell receptor (preTCR) function: human CD3delta/epsilon heterodimer restores the defective preTCR function in CD3gamma- and CD3gammadelta-deficient mice. Mol Immunol 43, 1741-1750). But those efforts were hampered by size limitations; conventional knockout technologies were not sufficient to directly replace large mouse genes with their large human genomic counterparts. A straightforward approach of direct homologous replacement, in which an endogenous mouse gene is directly replaced by the human counterpart gene at the same precise genetic location of the mouse gene (i.e., at the endogenous mouse locus), is rarely attempted because of technical difficulties. Until now, efforts at direct replacement involved elaborate and burdensome procedures, thus limiting the length of genetic material that could be handled and the precision with which it could be manipulated.

Exogenously introduced human immunoglobulin transgenes rearrange in precursor B-cells in mice (Alt, F. W., Blackwell, T. K., and Yancopoulos, G. D. (1985). Immunoglobulin genes in transgenic mice. Trends Genet 1, 231-236). This finding was exploited by engineering mice using the knockout-plus-transgenic approach to express human antibodies (Green, L. L. et al. (1994) Antigen-specific human monoclonal antibodies from mice engineered with human Ig heavy and light chain YACs. Nat Genet 7, 13-21; Lonberg, N. (2005). Human antibodies from transgenic animals. Nat Biotechnol 23, 1117-1125; Lonberg, N. et al. (1994) Antigen-specific human antibodies from mice comprising four distinct genetic modifications. Nature 368, 856-859; Jakobovits, A. et al. (2007) From XenoMouse technology to panitumumab, the first fully human antibody product from transgenic mice. Nat Biotechnol 25, 1134-1143). The endogenous mouse immunoglobulin heavy chain and κ light chain loci were inactivated in these mice by targeted deletion of small but critical portions of each endogenous locus, followed by introducing human immunoglobulin gene loci as randomly integrated large transgenes, as described above, or minichromosomes (Tomizuka, K. et al. (2000) Double trans-chromosomic mice: maintenance of two individual human chromosome fragments containing Ig heavy and kappa loci and expression of fully human antibodies. Proc Natl Acad Sci USA 97, 722-727). Such mice represented an important advance in genetic engineering; fully human monoclonal antibodies isolated from them yielded promising therapeutic potential for treating a variety of human diseases (Gibson, T. B. et al. (2006) Randomized phase III trial results of panitumumab, a fully human anti-epidermal growth factor receptor monoclonal antibody, in metastatic colorectal cancer. Clin Colorectal Cancer 6, 29-31; Jakobovits et al., 2007; Kim, Y. H. et al. (2007) Clinical efficacy of zanolimumab (HuMax-CD4): two Phase II studies in refractory cutaneous T-cell lymphoma. Blood 109(11):4655-62; Lonberg, 2005; Maker, A. V. et al. (2005) Tumor regression and autoimmunity in patients treated with cytotoxic T lymphocyte-associated antigen 4 blockade and interleukin 2: a phase I/II study. Ann Surg Oncol 12, 1005-1016; McClung, M. R., Lewiecki, E. M. et al. (2006) Denosumab in postmenopausal women with low bone mineral density. N Engl J Med 354, 821-831). But, as discussed above, these mice exhibit compromised B cell development and immune deficiencies when compared to wild type mice. Such problems potentially limit the ability of the mice to support a vigorous humoral response and, consequently, generate fully human antibodies against some antigens. The deficiencies may be due to: (1) inefficient functionality due to the random introduction of the human immunoglobulin transgenes and resulting incorrect expression due to a lack of upstream and downstream control elements (Garrett, F. E. et al. (2005) Chromatin architecture near a potential 3' end of the igh locus involves modular regulation of histone modifications during B-Cell development and in vivo occupancy at CTCF sites. Mol Cell Biol 25, 1511-1525; Manis, J. P. et al. (2003) Elucidation of a downstream boundary of the 3' IgH regulatory region. Mal Immunol 39, 753-760; Pawlitzky, I. et al. (2006) Identification of a candidate regulatory element within the 5' flanking region of the mouse Igh locus defined by pro-B cell-specific hypersensitivity associated with binding of PU.1, Pax5, and E2A. J Immunol 176, 6839-6851); (2) inefficient interspecies interactions between human constant domains and mouse components of the B-cell receptor signaling complex on the cell surface, which may impair signaling processes required for normal maturation, proliferation, and survival of B cells (Hombach, J. et al. (1990) Molecular components of the B-cell antigen receptor complex of the IgM class. Nature 343, 760-762); and (3) inefficient interspecies interactions between soluble human immunoglobulins and mouse Fc receptors that might reduce affinity selection (Rao, S. P. et al. (2002) Differential expression of the inhibitory IgG Fc receptor FcgammaRllB on germinal center cells: implications for selection of high-affinity B cells. J Immunol 169, 1859-1868) and immunoglobulin serum concentrations (Brambell, F. W. et al. (1964). A Theoretical Model of Gamma-Globulin Catabolism. Nature 203, 1352-1354; Junghans, R. P., and Anderson, C. L. (1996). The protection receptor for IgG catabolism is the beta2-microglobulin-containing neonatal intestinal transport receptor. Proc Natl Acad Sci USA 93, 5512-5516; Rao et al., 2002; Hjelm, F. et al. (2006) Antibody-mediated regulation of the immune response. Scand J Immunol 64, 177-184; Nimmerjahn, F., and Ravetch, J. V. (2007). Fc-receptors as regulators of immunity. Adv Immunol 96, 179-204). These deficiencies can be corrected by in situ humanization of only the variable regions of the mouse immunoglobulin loci within their natural locations at the endogenous heavy and light chain loci. This would effectively result in mice that make "reverse chimeric" (i.e., human V: mouse C) antibodies which would be capable of normal interactions and selection with the mouse environment based on retaining mouse constant regions. Further such reverse chimeric antibodies may be readily reformatted into fully human antibodies for therapeutic purposes.

Genetically modified animals that comprise a replacement at the endogenous immunoglobulin heavy chain locus with heterologous (e.g., from another species) immunoglobulin sequences can be made in conjunction with replacements at endogenous immunoglobulin light chain loci or in conjunction with immunoglobulin light chain transgenes (e.g., chimeric immunoglobulin light chain transgenes or fully human fully mouse, etc.). The species from which the heterologous immunoglobulin heavy chain sequences are derived can vary widely; as with immunoglobulin light chain sequences employed in immunoglobulin light chain sequence replacements or immunoglobulin light chain transgenes.

Immunoglobulin variable region nucleic acid sequences, e.g., V, D, and/or J segments, are in various embodiments obtained from a human or a non-human animal. Non-human animals suitable for providing V, D, and/or J segments include, for example bony fish, cartilaginous fish such as sharks and rays, amphibians, reptiles, mammals, birds (e.g., chickens). Non-human animals include, for example, mammals. Mammals include, for example, non-human primates, goats, sheep, pigs, dogs, bovine (e.g., cow, bull, buffalo), deer, camels, ferrets and rodents and non-human primates (e.g., chimpanzees, orangutans, gorillas, marmosets, rhesus monkeys baboons). Suitable non-human animals are selected from the rodent family including rats, mice, and hamsters. In one embodiment, the non-human animals are mice. As clear from the context, various non-human animals can be used as sources of variable domains or variable region gene segments (e.g., sharks, rays, mammals (e.g., camels, rodents such as mice and rats).

According to the context, non-human animals are also used as sources of constant region sequences to be used in connection with variable sequences or segments, for example, rodent constant sequences can be used in transgenes operably linked to human or non-human variable sequences (e.g., human or non-human primate variable sequences operably linked to, e.g., rodent, e.g., mouse or rat or hamster, constant sequences). Thus, in various embodiments, human V, D, and/or J segments are operably linked to rodent (e.g., mouse or rat or hamster) constant region gene sequences. In some embodiments, the human V, D, and/or J segments (or one or more rearranged VDJ or VJ genes) are operably linked or fused to a mouse, rat, or hamster constant region gene sequence in, e.g., a transgene integrated at a locus that is not an endogenous immunoglobulin locus.

In a specific embodiment, a mouse is provided that comprises a replacement of $V_H$, $D_H$, and $J_R$ gene segments at an endogenous immunoglobulin heavy chain locus with one or more human $V_H$, $D_H$, and $J_R$ segments, wherein the one or more human $V_H$, $D_H$, and $J_H$ segments are operably linked to an endogenous immunoglobulin heavy chain constant gene; wherein the mouse comprises a transgene at a locus other than an endogenous immunoglobulin locus, wherein the transgene comprises an unrearranged or rearranged human $V_L$ and human $J_L$ segment operably linked to a mouse or rat or human constant region.

In a specific embodiment, a mouse is provided that comprises an insertion of on or more human $V_H$, $D_H$ and $J_H$ gene segments at an endogenous immunoglobulin heavy chain locus. In one embodiment, the insertion is upstream of an endogenous immunoglobulin heavy chain constant gene; in one embodiment, the insertion is downstream of an endogenous variable (V) gene segment; in one embodiment, the insertion is downstream of an endogenous diversity (D) gene segment; in one embodiment, the insertion is downstream of an endogenous joining (J) gene segment. In various embodiments, the insertion is such that the one or more human $V_H$, $D_H$ and $J_H$ gene segments are positioned in operable linkage with one or more endogenous heavy chain constant genes.

A method for a large in situ genetic replacement of the mouse germline immunoglobulin variable gene loci with human germline immunoglobulin variable gene loci while maintaining the ability of the mice to generate offspring is described. Specifically, the precise replacement of six megabases of both the mouse heavy chain and κ light chain immunoglobulin variable gene loci with their human counterparts while leaving the mouse constant regions intact is described. As a result, mice have been created that have a precise replacement of their entire germline immunoglobulin variable repertoire with equivalent human germline immunoglobulin variable sequences, while maintaining mouse constant regions. The human variable regions are linked to mouse constant regions to form chimeric human-mouse immunoglobulin loci that rearrange and express at physiologically appropriate levels. The antibodies expressed are "reverse chimeras," i.e., they comprise human variable region sequences and mouse constant region sequences. These mice having humanized immunoglobulin variable regions that express antibodies having human variable regions and mouse constant regions are called VELCOIMMUNE® mice.

VELOCIMMUNE® humanized mice exhibit a fully functional humoral immune system that is essentially indistinguishable from that of wild-type mice. They display normal cell populations at all stages of B cell development. They exhibit normal lymphoid organ morphology. Antibody sequences of VELOCIMMUNE® mice exhibit normal V(D)J rearrangement and normal somatic hypermutation frequencies. Antibody populations in these mice reflect isotype distributions that result from normal class switching (e.g., normal isotype cis-switching). Immunizing VELOCIMMUNE® mice results in robust humoral immune responses that generate a large, diverse antibody repertoires having human immunoglobulin variable domains suitable as therapeutic candidates. This platform provides a plentiful source of naturally affinity-matured human immunoglobulin variable region sequences for making pharmaceutically acceptable antibodies and other antigen-binding proteins.

It is the precise replacement of mouse immunoglobulin variable sequences with human immunoglobulin variable sequences that allows for making VELOCIMMUNE® mice.

Yet even a precise replacement of endogenous mouse immunoglobulin sequences at heavy and light chain loci with equivalent human immunoglobulin sequences, by sequential recombineering of very large spans of human immunoglobulin sequences, may present certain challenges due to divergent evolution of the immunoglobulin loci between mouse and man. For example, intergenic sequences interspersed within the immunoglobulin loci are not identical between mice and humans and, in some circumstances, may not be functionally equivalent. Differences between mice and humans in their immunoglobulin loci can still result in abnormalities in humanized mice, particularly when humanizing or manipulating certain portions of endogenous mouse immunoglobulin heavy chain loci. Some modifications at mouse immunoglobulin heavy chain loci are deleterious. Deleterious modifications can include, for example, loss of the ability of the modified mice to mate and produce offspring. In various embodiments, engineering human immunoglobulin sequences in the genome of a mouse includes methods that maintain endogenous sequences that when absent in modified mouse strains are deleterious. Exemplary deleterious effects may include inability to propagate modified strains, loss of function of essential genes, inability to express polypeptides, etc. Such deleterious effects may be directly or indirectly related to the modification engineered into the genome of the mouse.

Figure 1A:
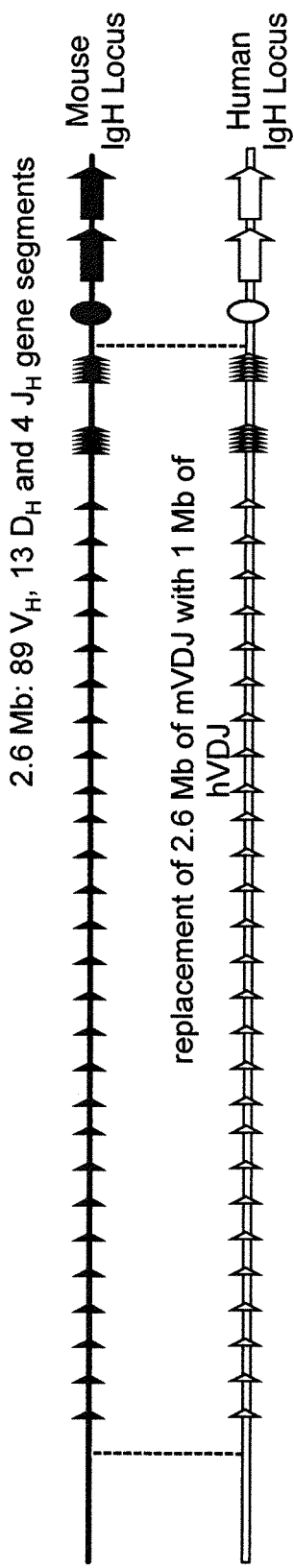
FIG. 1A shows a general illustration, not to scale, of direct genomic replacement of about three megabases (Mb) of a mouse immunoglobulin heavy chain variable gene locus (closed symbols) with about one megabase (Mb) of the human immunoglobulin heavy chain variable gene locus (open symbols).
Figure 1B:
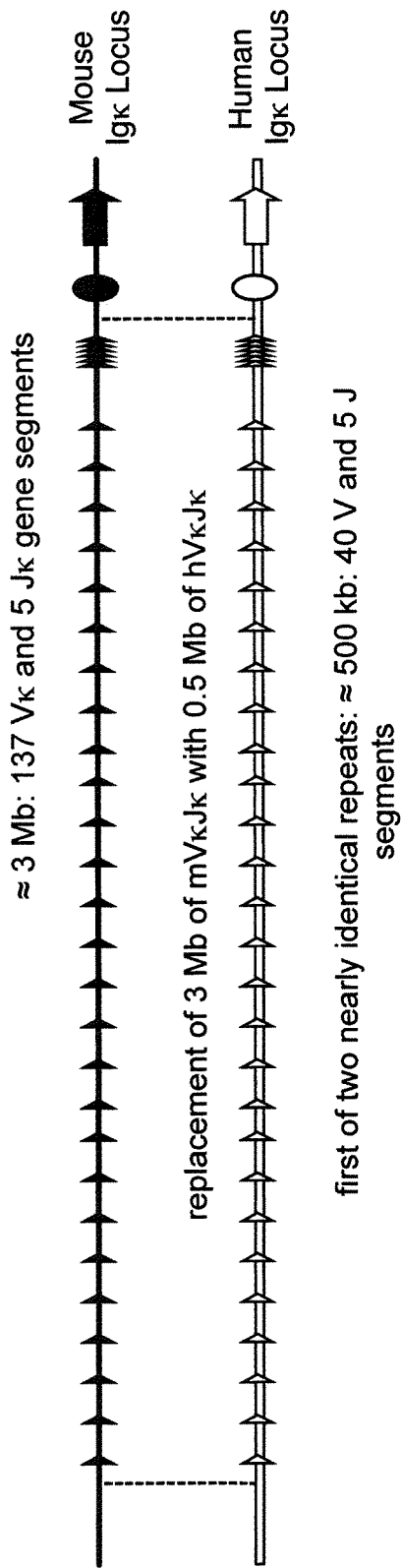
FIG. 1B shows a general illustration, not to scale, of direct genomic replacement of about three megabases (Mb) of a mouse immunoglobulin κ light chain variable gene locus (closed symbols) with about 0.5 megabases (Mb) of the first, or proximal, of two nearly identical repeats of the human immunoglobulin κ light chain variable gene locus (open symbols).

A precise, large-scale, in situ replacement of six megabases of the variable regions of the mouse heavy and light chain immunoglobulin loci ($V_H$-$D_H$-$J_H$ and Vκ-Jκ) with the corresponding 1.4 megabases human genomic sequences was performed, while leaving the flanking mouse sequences intact and functional within the hybrid loci, including all mouse constant chain genes and locus transcriptional control regions (FIG. 1A and FIG. 1B). Specifically, the human $V_H$, $D_H$, $J_H$, Vκ and Jκ gene sequences were introduced through stepwise insertion of 13 chimeric BAC targeting vectors bearing overlapping fragments of the human germline variable loci into mouse ES cells using VELOCIGENE® genetic engineering technology (see, e.g., U.S. Pat. No. 6,586,251 and Valenzuela, D. M. et al. (2003). High-throughput engineering of the mouse genome coupled with high-resolution expression analysis. Nat Biotechnol 21, 652-659).

Humanization of the mouse immunoglobulin genes represents the largest genetic modification to the mouse genome to date. While previous efforts with randomly integrated human immunoglobulin transgenes have met with some success (discussed above), direct replacement of the mouse immunoglobulin genes with their human counterparts dramatically increases the efficiency with which fully-human antibodies can be efficiently generated in otherwise normal mice. Further, such mice exhibit a dramatically increased diversity of fully-human antibodies that can be obtained after immunization with virtually any antigen, as compared with mice bearing disabled endogenous loci and fully human antibody transgenes. Multiple versions of replaced, humanized loci exhibit completely normal levels of mature and immature B cells, in contrast to mice with randomly integrated human transgenes, which exhibit significantly reduced B cell populations at various stages of differentiation. While efforts to increase the number of human gene segments in human transgenic mice have reduced such defects, the expanded immunoglobulin repertoires have not altogether corrected reductions in B cell populations as compared to wild-type mice.

Notwithstanding the near wild-type humoral immune function observed in mice with replaced immunoglobulin loci (i.e., VELOCIMMUNE® mice), there are other challenges encountered when employing a direct replacement of the immunoglobulin that is not encountered in some approaches that employ randomly integrated transgenes. Differences in the genetic composition of the immunoglobulin loci between mice and humans has lead to the discovery of sequences beneficial for the propagation of mice with replaced immunoglobulin gene segments. Specifically, mouse ADAM genes located within the endogenous immunoglobulin locus are optimally present in mice with replaced immunoglobulin loci, due to their role in fertility.

Genomic Location and Function of Mouse ADAM6

Male mice that lack the ability to express any functional ADAM6 protein surprisingly exhibit a defect in the ability of the mice to mate and to generate offspring. The mice lack the ability to express a functional ADAM6 protein by virtue of a replacement of all or substantially all mouse immunoglobulin variable region gene segments with human variable region gene segments. The loss of ADAM6 function results because the ADAM6 locus is located within a region of the endogenous mouse immunoglobulin heavy chain variable region gene locus, proximal to the 3' end of the $V_H$ gene segment locus that is upstream of the $D_H$ gene segments. In order to breed mice that are homozygous for a replacement of all or substantially all endogenous mouse heavy chain variable gene segments with human heavy chain variable gene segments, it is generally a cumbersome approach to set up males and females that are each homozygous for the replacement and await a productive mating. Successful litters are low in frequency and size. Instead, males heterozygous for the replacement have been employed to mate with females homozygous for the replacement to generate progeny that are heterozygous for the replacement, then breed a homozygous mouse therefrom. The inventors have determined that the likely cause of the loss in fertility in the male mice is the absence in homozygous male mice of a functional ADAM6 protein.

In various aspects, male mice that comprise a damaged (i.e., nonfunctional or marginally functional) ADAM6 gene exhibit a reduction or elimination of fertility. Because in mice (and other rodents) the ADAM6 gene is located in the immunoglobulin heavy chain locus, the inventors have determined that in order to propagate mice, or create and maintain a strain of mice, that comprise a replaced immunoglobulin heavy chain locus, various modified breeding or propagation schemes are employed. The low fertility, or infertility, of male mice homozygous for a replacement of the endogenous immunoglobulin heavy chain variable gene locus renders maintaining such a modification in a mouse strain difficult. In various embodiments, maintaining the strain comprises avoiding infertility problems exhibited by male mice homozygous for the replacement.

In one aspect, a method for maintaining a strain of mouse as described herein is provided. The strain of mouse need not comprise an ectopic ADAM6 sequence, and in various embodiments the strain of mouse is homozygous or heterozygous for a knockout (e.g., a functional knockout) of ADAM6.

The mouse strain comprises a modification of an endogenous immunoglobulin heavy chain locus that results in a reduction or loss in fertility in a male mouse. In one embodiment, the modification comprises a deletion of a regulatory region and/or a coding region of an ADAM6 gene. In a specific embodiment, the modification comprises a modification of an endogenous ADAM6 gene (regulatory and/or coding region) that reduces or eliminates fertility of a male mouse that comprises the modification; in a specific embodiment, the modification reduces or eliminates fertility of a male mouse that is homozygous for the modification.

In one embodiment, the mouse strain is homozygous or heterozygous for a knockout (e.g., a functional knockout) or a deletion of an ADAM6 gene.

In one embodiment, the mouse strain is maintained by isolating from a mouse that is homozygous or heterozygous for the modification a cell, and employing the donor cell in host embryo, and gestating the host embryo and donor cell in a surrogate mother, and obtaining from the surrogate mother a progeny that comprises the genetic modification. In one embodiment, the donor cell is an ES cell. In one embodiment, the donor cell is a pluripotent cell, e.g., an induced pluripotent cell.

In one embodiment, the mouse strain is maintained by isolating from a mouse that is homozygous or heterozygous for the modification a nucleic acid sequence comprising the modification, and introducing the nucleic acid sequence into a host nucleus, and gestating a cell comprising the nucleic acid sequence and the host nucleus in a suitable animal. In one embodiment, the nucleic acid sequence is introduced into a host oocyte embryo.

In one embodiment, the mouse strain is maintained by isolating from a mouse that is homozygous or heterozygous for the modification a nucleus, and introducing the nucleus into a host cell, and gestating the nucleus and host cell in a suitable animal to obtain a progeny that is homozygous or heterozygous for the modification.

In one embodiment, the mouse strain is maintained by employing in vitro fertilization (IVF) of a female mouse (wild-type, homozygous for the modification, or heterozygous for the modification) employing a sperm from a male mouse comprising the genetic modification. In one embodiment, the male mouse is heterozygous for the genetic modification. In one embodiment, the male mouse is homozygous for the genetic modification.

In one embodiment, the mouse strain is maintained by breeding a male mouse that is heterozygous for the genetic modification with a female mouse to obtain progeny that comprises the genetic modification, identifying a male and a female progeny comprising the genetic modification, and employing a male that is heterozygous for the genetic modification in a breeding with a female that is wild-type, homozygous, or heterozygous for the genetic modification to obtain progeny comprising the genetic modification. In one embodiment, the step of breeding a male heterozygous for the genetic modification with a wild-type female, a female heterozygous for the genetic modification, or a female homozygous for the genetic modification is repeated in order to maintain the genetic modification in the mouse strain.

In one aspect, a method is provided for maintaining a mouse strain that comprises a replacement of an endogenous immunoglobulin heavy chain variable gene locus with one or more human immunoglobulin heavy chain sequences, comprising breeding the mouse strain so as to generate heterozygous male mice, wherein the heterozygous male mice are bred to maintain the genetic modification in the strain. In a specific embodiment, the strain is not maintained by any breeding of a homozygous male with a wild-type female, or a female homozygous or heterozygous for the genetic modification.

The ADAM6 protein is a member of the ADAM family of proteins, where ADAM is an acronym for A Disintegrin And Metalloprotease. The ADAM family of proteins is large and diverse, with diverse functions including cell adhesion. Some members of the ADAM family are implicated in spermatogenesis and fertilization. For example, ADAM2 encodes a subunit of the protein fertilin, which is implicated in sperm-egg interactions. ADAM3, or cyritestin, appears necessary for sperm binding to the zona pellucida. The absence of either ADAM2 or ADAM3 results in infertility. It has been postulated that ADAM2, ADAM3, and ADAM6 form a complex on the surface of mouse sperm cells.

The human ADAM6 gene, normally found between human $V_H$ gene segments $V_H1$-2 and $V_H6$-1, appears to be a pseudogene (FIG. 12). In mice, there are two ADAM6 genes—ADAM6a and ADAM6b—that are found in an intergenic region between mouse $V_H$ and $D_H$ gene segments, and in the mouse the ADAM6a and ADAM6b genes are oriented in opposite transcriptional orientation to that of the surrounding immunoglobulin gene segments (FIG. 12). In mice, a functional ADAM6 locus is apparently required for normal fertilization. A functional ADAM6 locus or sequence, then, refers to an ADAM6 locus or sequence that can complement, or rescue, the drastically reduced fertilization exhibited in male mice with missing or nonfunctional endogenous ADAM6 loci.

The position of the intergenic sequence in mice that encodes ADAM6a and ADAM6b renders the intergenic sequence susceptible to modification when modifying an endogenous mouse heavy chain. When $V_H$ gene segments are deleted or replaced, or when $D_H$ gene segments are deleted or replaced, there is a high probability that a resulting mouse will exhibit a severe deficit in fertility. In order to compensate for the deficit, the mouse is modified to include a nucleotide sequence that encodes a protein that will complement the loss in ADAM6 activity due to a modification of the endogenous mouse ADAM6 locus. In various embodiments, the complementing nucleotide sequence is one that encodes a mouse ADAM6a, a mouse ADAM6b, or a homolog or ortholog or functional fragment thereof that rescues the fertility deficit. Alternatively, suitable methods to preserve the endogenous ADAM6 locus can be employed, while rendering the endogenous immunoglobulin heavy chain sequences flanking the mouse ADAM6 locus incapable of rearranging to encode a functional endogenous heavy chain variable region. Exemplary alternative methods include manipulation of large portions of mouse chromosomes that position the endogenous immunoglobulin heavy chain variable region loci in such a way that they are incapable of rearranging to encode a functional heavy chain variable region that is operably linked to an endogenous heavy chain constant gene. In various embodiments, the methods include inversions and/or translocations of mouse chromosomal fragments containing endogenous immunoglobulin heavy chain gene segments.

The nucleotide sequence that rescues fertility can be placed at any suitable position. It can be placed in the intergenic region, or in any suitable position in the genome (i.e., ectopically). In one embodiment, the nucleotide sequence can be introduced into a transgene that randomly integrates into the mouse genome. In one embodiment, the sequence can be maintained episomally, that is, on a separate nucleic acid rather than on a mouse chromosome. Suitable positions include positions that are transcriptionally permissive or active, e.g., a ROSA26 locus (Zambrowicz et al., 1997, *PNAS USA* 94:3789-3794), a BT-5 locus (Michael et al., 1999, *Mech. Dev.* 85:35-47), or an Oct4 locus (Wallace et al., 2000, *Nucleic Acids Res.* 28:1455-1464). Targeting nucleotide sequences to transcriptionally active loci are described, e.g., in U.S. Pat. No. 7,473,557, herein incorporated by reference.

Alternatively, the nucleotide sequence that rescues fertility can be coupled with an inducible promoter so as to facilitate optimal expression in the appropriate cells and/or tissues, e.g., reproductive tissues. Exemplary inducible promoters include promoters activated by physical (e.g., heat shock promoter) and/or chemical means (e.g., IPTG or Tetracycline).

Further, expression of the nucleotide sequence can be linked to other genes so as to achieve expression at specific stages of development or within specific tissues. Such expression can be achieved by placing the nucleotide sequence in operable linkage with the promoter of a gene expressed at a specific stage of development. For example, immunoglobulin sequences from one species engineered into the genome of a host species are place in operable linkage with a promoter sequence of a CD19 gene (a B cell specific gene) from the host species. B cell-specific expression at precise developmental stages when immunoglobulins are expressed is achieved.

Yet another method to achieve robust expression of an inserted nucleotide sequence is to employ a constitutive promoter. Exemplary constitutive promoters include SV40, CMV, UBC, EF1A, PGK and CAGG. In a similar fashion, the desired nucleotide sequence is placed in operable linkage with a selected constitutive promoter, which provides high level of expression of the protein(s) encoded by the nucleotide sequence.

The term "ectopic" is intended to include a displacement, or a placement at a position that is not normally encountered in nature (e.g., placement of a nucleic acid sequence at a position that is not the same position as the nucleic acid sequence is found in a wild-type mouse). The term in various embodiments is used in the sense of its object being out of its normal, or proper, position. For example, the phrase "an ectopic nucleotide sequence encoding . . . " refers to a nucleotide sequence that appears at a position at which it is not normally encountered in the mouse. For example, in the case of an ectopic nucleotide sequence encoding a mouse ADAM6 protein (or an ortholog or homolog or fragment thereof that provides the same or similar fertility benefit on male mice), the sequence can be placed at a different position in the mouse's genome than is normally found in a wild-type mouse. In such cases, novel sequence junctions of mouse sequence will be created by placing the sequence at a different position in the mouse's genome than in a wild-type mouse. A functional homolog or ortholog of mouse ADAM6 is a sequence that confers a rescue of fertility loss (e.g., loss of the ability of a male mouse to generate offspring by mating) that is observed in an ADAM6$^{-/-}$ mouse. Functional homologs or orthologs include proteins that have at least about 89% identity or more, e.g., up to 99% identity, to the amino acid sequence of ADAM6a and/or to the amino acid sequence of ADAM6b, and that can complement, or rescue ability to successfully mate, of a mouse that has a genotype that includes a deletion or knockout of ADAM6a and/or ADAM6b.

The ectopic position can be anywhere (e.g., as with random insertion of a transgene containing a mouse ADAM6 sequence), or can be, e.g., at a position that approximates (but is not precisely the same as) its location in a wild-type mouse (e.g., in a modified endogenous mouse immunoglobulin locus, but either upstream or downstream of its natural position, e.g., within a modified immunoglobulin locus but between different gene segments, or at a different position in a mouse V-D intergenic sequence). One example of an ectopic placement is maintaining the position normally found in wild-type mice within the endogenous immunoglobulin heavy chain locus while rendering the surrounding endogenous heavy chain gene segments incapable of rearranging to encode a functional heavy chain containing an endogenous heavy chain constant region. In this example, this may be accomplished by inversion of the chromosomal fragment containing the endogenous immunoglobulin heavy chain variable loci, e.g. using engineered site-specific recombination sites placed at positions flanking the variable region locus. Thus, upon recombination the endogenous heavy chain variable region loci are placed at a great distance away from the endogenous heavy chain constant region genes thereby preventing rearrangement to encode a functional heavy chain containing an endogenous heavy chain constant region. Other exemplary methods to achieve functional silencing of the endogenous immunoglobulin heavy chain variable gene locus while maintaining a functional ADAM6 locus will apparent to persons of skill upon reading this disclosure and/or in combination with methods known in the art. With such a placement of the endogenous heavy chain locus, the endogenous ADAM6 genes are maintained and the endogenous immunoglobulin heavy chain locus is functionally silenced.

Another example of an ectopic placement is placement within a humanized immunoglobulin heavy chain locus. For example, a mouse comprising a replacement of one or more endogenous $V_H$ gene segments with human $V_H$ gene segments, wherein the replacement removes an endogenous ADAM6 sequence, can be engineered to have a mouse ADAM6 sequence located within sequence that contains the human $V_H$ gene segments. The resulting modification would generate an (ectopic) mouse ADAM6 sequence within a human gene sequence, and the (ectopic) placement of the mouse ADAM6 sequence within the human gene sequence can approximate the position of the human ADAM6 pseudogene (i.e., between two V segments) or can approximate the position of the mouse ADAM6 sequence (i.e., within the V-D intergenic region). The resulting sequence junctions created by the joining of a (ectopic) mouse ADAM6 sequence within or adjacent to a human gene sequence (e.g., an immunoglobulin gene sequence) within the germline of the mouse would be novel as compared to the same or similar position in the genome of a wild-type mouse.

In various embodiments, non-human animals are provided that lack an ADAM6 or ortholog or homolog thereof, wherein the lack renders the non-human animal infertile, or substantially reduces fertility of the non-human animal. In various embodiments, the lack of ADAM6 or ortholog or homolog thereof is due to a modification of an endogenous immunoglobulin heavy chain locus. A substantial reduction in fertility is, e.g., a reduction in fertility (e.g., breeding frequency, pups per litter, litters per year, etc.) of about 50%, 60%, 70%, 80%, 90%, or 95% or more. In various embodiments, the non-human animals are supplemented with a mouse ADAM6 gene or ortholog or homolog or functional fragment thereof that is functional in a male of the non-human animal, wherein the supplemented ADAM6 gene or ortholog or homolog or functional fragment thereof rescues the reduction in fertility in whole or in substantial part. A rescue of fertility in substantial part is, e.g., a restoration of fertility such that the non-human animal exhibits a fertility that is at least 70%, 80%, or 90% or more as compared with an unmodified (i.e., an animal without a modification to the ADAM6 gene or ortholog or homolog thereof) heavy chain locus.

The sequence that confers upon the genetically modified animal (i.e., the animal that lacks a functional ADAM6 or ortholog or homolog thereof, due to, e.g., a modification of a immunoglobulin heavy chain locus) is, in various embodiments, selected from an ADAM6 gene or ortholog or homolog thereof. For example, in a mouse, the loss of ADAM6 function is rescued by adding, in one embodiment, a mouse ADAM6 gene. In one embodiment, the loss of ADAM6 function in the mouse is rescued by adding an ortholog or homolog of a closely related specie with respect to the mouse, e.g., a rodent, e.g., a mouse of a different strain or species, a rat of any species, a rodent; wherein the addition of the ortholog or homolog to the mouse rescues the loss of fertility due to loss of ADAM6 function or loss of an ADAM6 gene. Orthologs and homologs from other species, in various embodiments, are selected from a phylogenetically related species and, in various embodiments, exhibit a percent identity with the endogenous ADAM6 (or ortholog) that is about 80% or more, 85% or more, 90% or more, 95% or more, 96% or more, or 97% or more; and that rescue ADAM6-related or (in a non-mouse) ADAM6 ortholog-related loss of fertility. For example, in a genetically modified male rat that lacks ADAM6 function (e.g., a rat with an endogenous immunoglobulin heavy chain variable region replaced with a human immunoglobulin heavy chain variable region, or a knockout in the rat immunoglobulin heavy chain region), loss of fertility in the rat is rescued by addition of a rat ADAM6 or, in some embodiments, an ortholog of a rat ADAM6 (e.g., an ADAM6 ortholog from another rat strain or species, or, in one embodiment, from a mouse).

Thus, in various embodiments, genetically modified animals that exhibit no fertility or a reduction in fertility due to modification of a nucleic acid sequence encoding an ADAM6 protein (or ortholog or homolog thereof) or a regulatory region operably linked with the nucleic acid sequence, comprise a nucleic acid sequence that complements, or restores, the loss in fertility where the nucleic acid sequence that complements or restores the loss in fertility is from a different strain of the same species or from a phylogenetically related species. In various embodiments, the complementing nucleic acid sequence is an ADAM6 ortholog or homolog or functional fragment thereof. In various embodiments, the complementing ADAM6 ortholog or homolog or functional fragment thereof is from a non-human animal that is closely related to the genetically modified animal having the fertility defect. For example, where the genetically modified animal is a mouse of a particular strain, an ADAM6 ortholog or homolog or functional fragment thereof can be obtained from a mouse of another strain, or a mouse of a related species. In one embodiment, where the genetically modified animal comprising the fertility defect is of the order Rodentia, the ADAM6 ortholog or homolog or functional fragment thereof is from another animal of the order Rodentia. In one embodiment, the genetically modified animal comprising the fertility defect is of a suborder Myomoropha (e.g., jerboas, jumping mice, mouse-like hamsters, hamsters, New World rats and mice, voles, true mice and rats, gerbils, spiny mice, crested rats, climbing mice, rock mice, white-tailed rats, malagasy rats and mice, spiny dormice, mole rats, bamboo rats, zokors), and the ADAM6 ortholog or homolog or functional fragment thereof is selected from an animal of order Rodentia, or of the suborder Myomorpha.

In one embodiment, the genetically modified animal is from the superfamily Dipodoidea, and the ADAM6 ortholog or homolog or functional fragment thereof is from the superfamily Muroidea. In one embodiment, the genetically modified animal is from the superfamily Muroidea, and the ADAM6 ortholog or homolog or functional fragment thereof is from the superfamily Dipodoidea.

In one embodiment, the genetically modified animal is a rodent. In one embodiment, the rodent is selected from the superfamily Muroidea, and the ADAM6 ortholog or homolog is from a different species within the superfamily Muroidea. In one embodiment, the genetically modified animal is from a family selected from Calomyscidae (e.g., mouse-like hamsters), Cricetidae (e.g., hamster, New World rats and mice, voles), Muridae (true mice and rats, gerbils, spiny mice, crested rats), Nesomyidae (climbing mice, rock mice, with-tailed rats, Malagasy rats and mice), Platacanthomyidae (e.g., spiny dormice), and Spalacidae (e.g., mole rates, bamboo rats, and zokors); and the ADAM6 ortholog or homolog is selected from a different species of the same family. In a specific embodiment, the genetically modified rodent is selected from a true mouse or rat (family Muridae), and the ADAM6 ortholog or homolog is from a species selected from a gerbil, spiny mouse, or crested rat. In one embodiment, the genetically modified mouse is from a member of the family Muridae, and the ADAM6 ortholog or homolog is from a different species of the family Muridae. In a specific embodiment, the genetically modified rodent is a mouse of the family Muridae, and the ADAM6 ortholog or homolog is from a rat, gerbil, spiny mouse, or crested rat of the family Muridae.

In various embodiments, one or more rodent ADAM6 orthologs or homologs or functional fragments thereof of a rodent in a family restores fertility to a genetically modified rodent of the same family that lacks an ADAM6 ortholog or homolog (e.g., Cricetidae (e.g., hamsters, New World rats and mice, voles); Muridae (e.g., true mice and rats, gerbils, spiny mice, crested rats)).

In various embodiments, ADAM6 orthologs, homologs, and fragments thereof are assessed for functionality by ascertaining whether the ortholog, homolog, or fragment restores fertility to a genetically modified male non-human animal that lacks ADAM6 activity (e.g., a rodent, e.g., a mouse or rat, that comprises a knockout of ADAM6 or its ortholog). In various embodiments, functionality is defined as the ability of a sperm of a genetically modified animal lacking an endogenous ADAM6 or ortholog or homolog thereof to migrate an oviduct and fertilize an ovum of the same specie of genetically modified animal.

In various aspects, mice that comprise deletions or replacements of the endogenous heavy chain variable region locus or portions thereof can be made that contain an ectopic nucleotide sequence that encodes a protein that confers similar fertility benefits to mouse ADAM6 (e.g., an ortholog or a homolog or a fragment thereof that is functional in a male mouse). The ectopic nucleotide sequence can include a nucleotide sequence that encodes a protein that is an ADAM6 homolog or ortholog (or fragment thereof) of a different mouse strain or a different species, e.g., a different rodent species, and that confers a benefit in fertility, e.g., increased number of litters over a specified time period, and/or increased number of pups per litter, and/or the ability of a sperm cell of a male mouse to traverse through a mouse oviduct to fertilize a mouse egg.

In one embodiment, the ADAM6 is a homolog or ortholog that is at least 89% to 99% identical to a mouse ADAM6 protein (e.g., at least 89% to 99% identical to mouse ADAM6a or mouse ADAM6b). In one embodiment, the ectopic nucleotide sequence encodes one or more proteins independently selected from a protein at least 89% identical to mouse ADAM6a, a protein at least 89% identical to mouse ADAM6b, and a combination thereof. In one embodiment, the homolog or ortholog is a rat, hamster, mouse, or guinea pig protein that is or is modified to be about 89% or more identical to mouse ADAM6a and/or mouse ADAM6b. In one embodiment, the homolog or ortholog is or is at least 90%, 91%, 92%, 93%, 94%, 95%, 96%, 97%, 98%, or 99% identical to a mouse ADAM6a and/or mouse ADAM6b.

In one aspect, non-human animals are provided, wherein the non-human animals comprise (a) an insertion of one or more human Vλ and Jλ gene segments upstream of an non-human immunoglobulin light chain constant region, (b) an insertion of one or more human $V_H$, one or more human $D_H$ and one or more human $J_H$ gene segments upstream of an non-human immunoglobulin heavy chain constant region, and (c) a nucleotide sequence that encodes an ADAM6 protein or a functional fragment thereof. In one embodiment, the non-human heavy and/or light chain constant regions are rodent constant regions (e.g., selected from mouse, rat or hamster constant regions). In one embodiment, the non-human light chain constant region is a rodent constant region. In a specific embodiment, the light chain constant region is a mouse Cκ or a rat Cκ region. In a specific embodiment, the light chain constant region is a mouse Cλ or a rat Cκ region. Suitable non-human animals include rodents, e.g, mice, rats and hamsters. In one embodiment, the rodent is a mouse or a rat.

In one embodiment, the non-human animal comprises at least 12 to at least 40 human Vλ gene segments and at least one human Jλ gene segment. In a specific embodiment, the non-human animal comprises 12 human Vλ gene segments and at least one human Jλ gene segment. In a specific embodiment, the non-human animal comprises 28 human Vλ gene segments and at least one human Jλ gene segment. In one embodiment, the non-human animal comprises 40 human Vλ gene segments and at least one human Jλ gene segment. In various embodiments, the at least one human Jλ gene segment is selected from Jλ1, Jλ2, Jλ3 and Jλ7. In a specific embodiment, the non-human animal comprises at least four human Jλ gene segments. In one embodiment, the at least four human Jλ gene segments comprise at least Jλ1, Jλ2, Jλ3 and Jλ7.

In one embodiment, the nucleotide sequence that encodes an ADAM6 protein or functional fragment thereof is ectopic in the non-human animal. In one embodiment, the nucleotide sequence that encodes an ADAM6 protein or functional fragment thereof (that is functional in the non-human animal) is present the same location as compared to a wild-type non-human ADAM6 locus. In one embodiment, the non-human animal is a mouse and the nucleotide sequence encodes a mouse ADAM6 protein or functional fragment thereof and is present at an ectopic location in the genome of the non-human animal. In one embodiment the non-human animal is a mouse and the nucleotide sequence encodes a mouse ADAM6 protein or functional fragment thereof and is present within immunoglobulin gene segments. In a specific embodiment, the immunoglobulin gene segments are heavy chain gene segments. In one embodiment, the heavy chain gene segments are human. In one embodiment, the heavy chain gene segments are endogenous heavy chain gene segments of the non-human animal. In one embodiment, the mouse comprises an ectopic contiguous sequence comprising one or more endogenous unrearranged heavy chain gene segments, and the ADAM6 sequence is within the ectopic contiguous sequence.

In one embodiment, the non-human animal lacks an endogenous immunoglobulin $V_L$ and/or a $J_L$ gene segment at an endogenous immunoglobulin light chain locus. In one embodiment, the non-human animal comprises endogenous immunoglobulin $V_L$ and/or $J_L$ gene segments that are incapable of rearranging to form an immunoglobulin $V_L$ domain in the non-human animal. In one embodiment, all or substantially all endogenous immunoglobulin Vκ and Jκ gene segments are replaced with one or more human Vλ and Jλ gene segments. In one embodiment, all or substantially all endogenous immunoglobulin Vλ and Jλ gene segments are replaced with one or more human Vλ and Jλ gene segments. In one embodiment, all or substantially all endogenous immunoglobulin $V_L$ and $J_L$ gene segments are intact in the non-human animal and the non-human animal comprises one or more human Vλ gene segments and one or more human Jλ gene segments inserted between endogenous immunoglobulin $V_L$ and/or $J_L$ gene segments and an endogenous immunoglobulin light chain constant region. In a specific embodiment, the intact endogenous immunoglobulin $V_L$ and $J_L$ gene segments are rendered incapable of rearranging to form a $V_L$ domain of an antibody in the non-human animal. In various embodiments, the endogenous immunoglobulin light chain locus of the non-human animal is an immunoglobulin κ light chain locus. In various embodiments, the endogenous immunoglobulin light chain locus of the non-human animal is an immunoglobulin λ light chain locus. In various embodiments, the endogenous immunoglobulin $V_L$ and $J_L$ gene segments are Vκ and Jκ gene segments. In various embodiments, the endogenous immunoglobulin $V_L$ and $J_L$ gene segments are Vλ and Jλ gene segments.

In one embodiment, the non-human animal further comprises a human Vκ-Jκ intergenic region from a human κ light chain locus, wherein the human Vκ-Kκ intergenic region is contiguous with the one or more human Vλ and Jλ gene segments. In a specific embodiment, the human Vκ-Jκ intergenic region is placed between a human Vλ gene segment and a human Jλ gene segment.

In one aspect, cells and/or tissues derived from non-human animals as described herein are provided, wherein the cells and/or tissues comprise (a) an insertion of one or more human Vλ and λ gene segments upstream of an non-human immunoglobulin light chain constant region, (b) an insertion of one or more human $V_H$, one or more human $D_H$ and one or more human $J_H$ gene segments upstream of an non-human immunoglobulin heavy chain constant region, and (c) a nucleotide sequence that encodes an ADAM6 protein or a functional fragment thereof. In one embodiment, the non-human heavy and/or light chain constant regions are mouse constant regions. In one embodiment, the non-human heavy and/or light chain constant regions are rat constant regions. In one embodiment, the non-human heavy and/or light chain constant regions are hamster constant regions.

In one embodiment, the nucleotide sequence that encodes an ADAM6 protein or functional fragment thereof is ectopic in the cell and/or tissue. In one embodiment, the nucleotide sequence that encodes an ADAM6 protein or functional fragment thereof is present the same location as compared to a wild-type type non-human ADAM6 locus. In one embodiment the non-human cell and/or tissue is derived from a mouse and the nucleotide sequence encodes a mouse ADAM6 protein or functional fragment thereof and is present at an ectopic location. In one embodiment, the non-human cell and/or tissue is derived from a mouse and the nucleotide sequence encodes a mouse ADAM6 protein or functional fragment thereof and is present within immunoglobulin gene segments. In a specific embodiment, the immunoglobulin gene segments are heavy chain gene segments. In one embodiment, a contiguous sequence of endogenous heavy chain gene segments are placed ectopically in the non-human animal, wherein the contiguous sequence of ectopically placed endogenous heavy chain gene segments comprises an ADAM6 gene that is functional in the mouse (e.g., in a male mouse).

In one aspect, use of a non-human animal as described herein to make an antigen-binding protein is provided, wherein the non-human animal expresses (a) an antibody that comprises (i) an immunoglobulin light chain that comprises a human Vλ domain and a non-human light chain constant region and (ii) an immunoglobulin heavy chain that comprises a human $V_H$ domain and a non-human constant region; and (b) an ADAM6 protein or functional fragment thereof. In one embodiment, the antigen binding protein is human. In one embodiment, the non-human animal is a rodent and the non-human constant regions are rodent constant regions. In a specific embodiment, the rodent is a mouse.

In one aspect, a non-human cell or tissue derived from a non-human animal as described herein is provided. In one embodiment, the non-human cell or tissue comprises one or more human immunoglobulin Vλ gene segments and at least one human immunoglobulin Jλ gene segments contiguous with a non-human immunoglobulin light chain constant region gene and one or more human $V_H$, one or more human $D_H$ and one or more human $J_H$ gene segments contiguous with a non-human immunoglobulin heavy chain constant region gene, wherein the cell or tissue expresses an ADAM6 protein or functional fragment thereof. In one embodiment, the non-human light chain constant region gene is a mouse Cκ or mouse Cλ.

In one embodiment, the nucleotide sequence that encodes the ADAM6 protein or functional fragment thereof is ectopic. In one embodiment, the nucleotide sequence that encodes the ADAM6 protein or functional fragment thereof is located at a position that is the same as a wild-type non-human cell. In various embodiments, the non-human cell is a mouse B cell. In various embodiments, the non-human cell is an embryonic stem cell.

In one embodiment, the tissue is derived from spleen, bone marrow or lymph node of the non-human animal.

In one aspect, use of a cell or tissue derived from a non-human animal as described herein to make a hybridoma or quadroma is provided.

In one aspect, a non-human cell comprising a modified genome as described herein is provided, wherein the non-human cell is an oocyte, a host embryo, or a fusion of a cell from a non-human animal as described herein and a cell from a different non-human animal.

In one aspect, use of a cell or tissue derived from a non-human animal as described herein to make a fully human antibody is provided. In one embodiment, the fully human antibody comprises a human $V_H$ domain and a human Vλ domain isolated from a non-human animal as described herein.

In one aspect, a method for making an antibody that binds to an antigen of interest is provided, wherein the method comprises (a) exposing a non-human animal as described herein to an antigen of interest, (b) isolating one or more B lymphocytes of the non-human animal, wherein the one or more B lymphocytes express an antibody that binds the antigen of interest, and (c) identifying a nucleic acid sequence that encodes an immunoglobulin light chain of the antibody that binds that antigen of interest, wherein the immunoglobulin light chain comprises a human Vλ domain and a non-human light chain constant domain, and (d) employing the nucleic acid sequence of (c) with a human immunoglobulin light chain constant region nucleic acid sequence to make a human antibody that binds the antigen of interest.

In one embodiment, the non-human light chain constant domain is a mouse Cκ. In one embodiment, the non-human light chain constant domain is a mouse Cλ. In one embodiment, the non-human animal is a mouse.

In one aspect, a fertile male mouse comprising a modification at an immunoglobulin heavy chain locus is provided, wherein the fertile male mouse comprises an ectopic ADAM6 sequence that is functional in the male mouse.

Ectopic ADAM6 in Humanized Heavy Chain Mice

Developments in gene targeting, e.g., the development of bacterial artificial chromosomes (BACs), now enable the recombination of relatively large genomic fragments. BAC engineering has allowed for the ability to make large deletions, and large insertions, into mouse ES cells.

Mice that make human antibodies have been available for some time now. Although they represent an important advance in the development of human therapeutic antibodies, these mice display a number of significant abnormalities that limit their usefulness. For example, they display compromised B cell development. The compromised development may be due to a variety of differences between the transgenic mice and wild-type mice.

Human antibodies might not optimally interact with mouse pre B cell or B cell receptors on the surface of mouse cells that signal for maturation, proliferation, or survival during clonal selection. Fully human antibodies might not optimally interact with a mouse Fc receptor system; mice express Fc receptors that do not display a one-to-one correspondence with human Fc receptors. Finally, various mice that make fully human antibodies do not include all genuine mouse sequences, e.g., downstream enhancer elements and other locus control elements, which may be required for wild-type B cell development.

Mice that make fully human antibodies generally comprise endogenous immunoglobulin loci that are disabled in some way, and human transgenes that comprise variable and constant immunoglobulin gene segments are introduced into a random location in the mouse genome. As long as the endogenous locus is sufficiently disabled so as not to rearrange gene segments to form a functional immunoglobulin gene, the goal of making fully human antibodies in such a mouse can be achieved—albeit with compromised B cell development.

Although compelled to make fully human antibodies from the human transgene locus, generating human antibodies in a mouse is apparently an unfavored process. In some mice, the process is so unfavored as to result in formation of chimeric human variable/mouse constant heavy chains (but not light chains) through the mechanism of trans-switching. By this mechanism, transcripts that encode fully human antibodies undergo isotype switching in trans from the human isotype to a mouse isotype. The process is in trans, because the fully human transgene is located apart from the endogenous locus that retains an undamaged copy of a mouse heavy chain constant region gene. Although in such mice trans-switching is readily apparent the phenomenon is still insufficient to rescue B cell development, which remains frankly impaired. In any event, trans-switched antibodies made in such mice retain fully human light chains, since the phenomenon of trans-switching apparently does not occur with respect to light chains; trans-switching presumably relies on switch sequences in endogenous loci used (albeit differently) in normal isotype switching in cis. Thus, even when mice engineered to make fully human antibodies select a trans-switching mechanism to make antibodies with mouse constant regions, the strategy is still insufficient to rescue normal B cell development.

A primary concern in making antibody-based human therapeutics is making a sufficiently large diversity of human immunoglobulin variable region sequences to identify useful variable domains that specifically recognize particular epitopes and bind them with a desirable affinity, usually—but not always—with high affinity. Prior to the development of VELOCIMMUNE® mice (described herein), there was no indication that mice expressing human variable regions with mouse constant regions would exhibit any significant differences from mice that made human antibodies from a transgene. That supposition, however, was incorrect.

VELOCIMMUNE® mice, which contain a precise replacement of mouse immunoglobulin variable regions with human immunoglobulin variable regions at the endogenous mouse loci, display a surprising and remarkable similarity to wild-type mice with respect to B cell development. In a surprising and stunning development, VELOCIMMUNE® mice displayed an essentially normal, wild-type response to immunization that differed only in one significant respect from wild-type mice—the variable regions generated in response to immunization are fully human.

VELOCIMMUNE® mice contain a precise, large-scale replacement of germline variable regions of mouse immunoglobulin heavy chain (IgH) and immunoglobulin light chain (e.g., κ light chain, Igκ) with corresponding human immunoglobulin variable regions, at the endogenous loci. In total, about six megabases of mouse loci are replaced with about 1.5 megabases of human genomic sequence. This precise replacement results in a mouse with hybrid immunoglobulin loci that make heavy and light chains that have a human variable regions and a mouse constant region. The precise replacement of mouse $V_H$-$D_H$-$J_H$ and Vκ-Jκ segments leave flanking mouse sequences intact and functional at the hybrid immunoglobulin loci. The humoral immune system of the mouse functions like that of a wild-type mouse. B cell development is unhindered in any significant respect and a rich diversity of human variable regions is generated in the mouse upon antigen challenge.

VELOCIMMUNE® mice are possible because immunoglobulin gene segments for heavy and κ light chains rearrange similarly in humans and mice, which is not to say that their loci are the same or even nearly so—clearly they are not. However, the loci are similar enough that humanization of the heavy chain variable gene locus can be accomplished by replacing about three million base pairs of contiguous mouse sequence that contains all the $V_H$, $D_H$, and $J_H$ gene segments with about one million bases of contiguous human genomic sequence covering basically the equivalent sequence from a human immunoglobulin locus.

In some embodiments, further replacement of certain mouse constant region gene sequences with human gene sequences (e.g., replacement of mouse $C_H1$ sequence with human $C_H1$ sequence, and replacement of mouse $C_L$ sequence with human $C_L$ sequence) results in mice with hybrid immunoglobulin loci that make antibodies that have human variable regions and partly human constant regions, suitable for, e.g., making fully human antibody fragments, e.g., fully human Fab's. Mice with hybrid immunoglobulin loci exhibit normal variable gene segment rearrangement, normal somatic hypermutation, and normal class switching. These mice exhibit a humoral immune system that is indistinguishable from wild type mice, and display normal cell populations at all stages of B cell development and normal lymphoid organ structures—even where the mice lack a full repertoire of human variable region gene segments. Immunizing these mice results in robust humoral responses that display a wide diversity of variable gene segment usage.

The precise replacement of mouse germline variable region gene segments allows for making mice that have partly human immunoglobulin loci. Because the partly human immunoglobulin loci rearrange, hypermutate, and class switch normally, the partly human immunoglobulin loci generate antibodies in a mouse that comprise human variable regions. Nucleotide sequences that encode the variable regions can be identified and cloned, then fused (e.g., in an in vitro system) with any sequences of choice, e.g., any immunoglobulin isotype suitable for a particular use, resulting in an antibody or antigen-binding protein derived wholly from human sequences.

Large-scale humanization by recombineering methods were used to modify mouse embryonic stem (ES) cells to precisely replace up to three megabases of the mouse heavy chain immunoglobulin locus that included essentially all of the mouse $V_H$, $D_H$, and $J_H$ gene segments with equivalent human gene segments with up to a one megabase human genomic sequence containing some or essentially all human $V_H$, $D_H$, and $J_H$ gene segments. Up to a one-half megabase segment of the human genome comprising one of two repeats encoding essentially all human Vκ and Jκ gene segments was used to replace a three megabase segment of the mouse immunoglobulin κ light chain locus containing essentially all of the mouse Vκ and Jκ gene segments.

Mice with such replaced immunoglobulin loci can comprise a disruption or deletion of the endogenous mouse ADAM6 locus, which is normally found between the 3'-most $V_H$ gene segment and the 5'-most $D_H$ gene segment at the mouse immunoglobulin heavy chain locus. Disruption in this region can lead to reduction or elimination of functionality of the endogenous mouse ADAM6 locus. If the 3'-most $V_H$ gene segments of the human heavy chain repertoire are used in a replacement, an intergenic region containing a pseudogene that appears to be a human ADAM6 pseudogene is present between these $V_H$ gene segments, i.e., between human $V_H1$-2 and $V_H1$-6. However, male mice that comprise this human intergenic sequence exhibit a reduction in fertility.

Mice are described that comprise the replaced loci as described above, and that also comprise an ectopic nucleic acid sequence encoding a mouse ADAM6, where the mice exhibit essentially normal fertility. In one embodiment, the ectopic nucleic acid sequence comprises a mouse ADAM6a and/or a mouse ADAM6b sequence or functional fragments thereof placed between a human $V_H1$-2 gene segment and a human $V_H6$-1 gene segment at a modified endogenous heavy chain locus. In one embodiment, the ectopic nucleic acid sequence is SEQ ID NO:3, placed between human $V_H1$-2 and $V_H1$-6 at the modified endogenous heavy chain locus. The direction of transcription of the ADAM6 genes of SEQ ID NO:3 are opposite with respect to the direction of transcription of the surrounding human $V_H$ gene segments. Although examples herein show rescue of fertility by placing the ectopic sequence between the indicated human $V_H$ gene segments, skilled persons will recognize that placement of the ectopic sequence at any suitable transcriptionally-permissive locus in the mouse genome (or even extrachromosomally) will be expected to similarly rescue fertility in a male mouse.

The phenomenon of complementing a mouse that lacks a functional ADAM6 locus with an ectopic sequence that comprises a mouse ADAM6 gene or ortholog or homolog or functional fragment thereof is a general method that is applicable to rescuing any mice with nonfunctional or minimally functional endogenous ADAM6 loci. Thus, a great many mice that comprise an ADAM6-disrupting modification of the immunoglobulin heavy chain locus can be rescued with the compositions and methods of the invention. Accordingly, the invention comprises mice with a wide variety of modifications of immunoglobulin heavy chain loci that compromise endogenous ADAM6 function. Some (non-limiting) examples are provided in this description. In addition to the VELOCIMMUNE® mice described, the compositions and methods related to ADAM6 can be used in a great many applications, e.g., when modifying a heavy chain locus in a wide variety of ways.

In one aspect, a mouse is provided that comprises an ectopic ADAM6 sequence that encodes a functional ADAM6 protein (or ortholog or homolog or functional fragment thereof), a replacement of all or substantially all mouse $V_H$ gene segments with one or more human $V_H$ gene segments, a replacement of all or substantially all mouse $D_H$ gene segments and $J_H$ gene segments with human $D_H$ and human $J_H$ gene segments; wherein the mouse lacks a $C_H1$ and/or hinge region. In one embodiment, the mouse makes a single variable domain binding protein that is a dimer of immunoglobulin chains selected from: (a) human $V_H$—mouse $C_H1$—mouse $C_H2$—mouse $C_H3$; (b) human $V_H$—mouse hinge—mouse $C_H2$—mouse $C_H3$; and, (c) human $V_H$—mouse $C_H2$—mouse $C_H3$.

In one aspect, the nucleotide sequence that rescues fertility is placed within a human immunoglobulin heavy chain variable region sequence (e.g., between human $V_H1$-2 and $V_H1$-6 gene segments) in a mouse that has a replacement of one or more mouse immunoglobulin heavy chain variable gene segments ($mV_H$'s, $mD_H$'s, and/or $mJ_H$'s) with one or more human immunoglobulin heavy chain variable gene segments ($hV_H$'s, $hD_H$'s, and/or $hJ_H$'s), and the mouse further comprises a replacement of one or more mouse immunoglobulin κ light chain variable gene segments (mVκ's and/or mJκ's) with one or more human immunoglobulin κ light chain variable gene segments (hVκ's and/or hJκ's). In one embodiment, the nucleotide sequence is placed between a human $V_H1$-2 gene segment and a human $V_H1$-6 gene segment in a VELOCIMMUNE® mouse (U.S. Pat. Nos. 6,596,541 and 7,105,348, incorporated herein by reference). In one embodiment, the VELOCIMMUNE® mouse so modified comprises a replacement with all or substantially all human immunoglobulin heavy chain variable gene segments (all $hV_H$'s, $hD_H$'s, and $hJ_H$'s) and all or substantially all human immunoglobulin κ light chain variable gene segments (hVκ's and hJκ's).

In one embodiment, the one or more mouse immunoglobulin heavy chain variable gene segments comprises about three megabases of the mouse immunoglobulin heavy chain locus. In one embodiment, the one or more mouse immunoglobulin heavy chain variable gene segments comprises at least 89 $V_H$ gene segments, at least 13 $D_H$ gene segments, at least four $J_H$ gene segments or a combination thereof of the mouse immunoglobulin heavy chain locus. In one embodiment, the one or more human immunoglobulin heavy chain variable gene segments comprises about one megabase of a human immunoglobulin heavy chain locus. In one embodiment, the one or more human immunoglobulin heavy chain variable gene segments comprises at least 80 $V_H$ gene segments, at least 27 $D_H$ gene segments, at least six $J_H$ gene segments or a combination thereof of a human immunoglobulin heavy chain locus.

In one embodiment, the one or more mouse immunoglobulin κ light chain variable gene segments comprises about three megabases of the mouse immunoglobulin κ light chain locus. In one embodiment, the one or more mouse immunoglobulin κ light chain variable gene segments comprises at least 137 Vκ gene segments, at least five Jλ gene segments or a combination thereof of the mouse immunoglobulin κ light chain locus. In one embodiment, the one or more human immunoglobulin κ light chain variable gene segments comprises about one-half megabase of a human immunoglobulin κ light chain locus. In a specific embodiment, the one or more human immunoglobulin κ light chain variable gene segments comprises the proximal repeat (with respect to the immunoglobulin κ constant region) of a human immunoglobulin κ light chain locus. In one embodiment, the one or more human immunoglobulin κ light chain variable gene segments comprises at least 40Vκ gene segments, at least five Jκ gene segments or a combination thereof of a human immunoglobulin κ light chain locus.

In one embodiment, the nucleotide sequence is placed between two human immunoglobulin gene segments. In a specific embodiment, the two human immunoglobulin gene segments are heavy chain gene segments.

In one aspect, a functional mouse ADAM6 locus (or ortholog or homolog or functional fragment thereof) is present in the midst of mouse gene segments that are present at the endogenous mouse heavy chain variable region locus, said locus incapable of rearranging to encode a functional heavy chain containing an endogenous heavy chain constant region. In one embodiment, the endogenous mouse heavy chain locus comprises at least one and up to 89 $V_H$ gene segments, at least one and up to 13 $D_H$ gene segments, at least one and up to four $J_H$ gene segments and a combination thereof. In various embodiments, a functional mouse ADAM6 locus (or ortholog or homolog or functional fragment thereof) encodes one or more ADAM6 proteins that are functional in the mouse, wherein the one or more ADAM6 proteins comprise SEQ ID NO: 1, SEQ ID NO: 2 and/or a combination thereof.

In one aspect, a functional mouse ADAM6 locus (or ortholog or homolog or functional fragment thereof) is present in the midst of human $V_H$ gene segments that replace endogenous mouse $V_H$ gene segments. In one embodiment, at least 89 mouse $V_H$ gene segments are removed and replaced with one or more human $V_H$ gene segments, and the mouse ADAM6 locus is present immediately adjacent to the 3' end of the human $V_H$ gene segments, or between two human $V_H$ gene segments. In a specific embodiment, the mouse ADAM6 locus is present between two $V_H$ gene segments within about 20 kilo bases (kb) to about 40 kilo bases (kb) of the 3' terminus of the inserted human $V_H$ gene segments. In a specific embodiment, the mouse ADAM6 locus is present between two $V_H$ gene segments within about 29 kb to about 31 kb of the 3' terminus of the inserted human $V_H$ gene segments. In a specific embodiment, the mouse ADAM6 locus is present within about 30 kb of the 3' terminus of the inserted human $V_H$ gene segments. In a specific embodiment, the mouse ADAM6 locus is present within about 30,184 bp of the 3' terminus of the inserted human $V_H$ gene segments. In a specific embodiment, the replacement includes human $V_H$ gene segments $V_H1$-2 and $V_H6$-1, and the mouse ADAM6 locus is present downstream of the $V_H1$-2 gene segment and upstream of the $V_H6$-1 gene segment. In a specific embodiment, the mouse ADAM6 locus is present between a human $V_H1$-2 gene segment and a human $V_H6$-1 gene segment, wherein the 5' end of the mouse ADAM6 locus is about 13,848 bp from the 3' terminus of the human $V_H$1-2 gene segment and the 3' end of the ADAM6 locus is about 29,737 bp 5' of the human $V_H$6-1 gene segment. In a specific embodiment, the mouse ADAM6 locus comprises SEQ ID NO:3 or a fragment thereof that confers ADAM6 function within cells of the mouse. In a specific embodiment, the arrangement of human $V_H$ gene segments is then the following (from upstream to downstream with respect to direction of transcription of the human $V_H$ gene segments): human $V_H$1-2—mouse ADAM6 locus—human $V_H$6-1. In a specific embodiment, the ADAM6 pseudogene between human $V_H$1-2 and human $V_H$6-1 is replaced with the mouse ADAM6 locus. In one embodiment, the orientation of one or more of mouse ADAM6a and mouse ADAM6b of the mouse ADAM6 locus is opposite with respect to direction of transcription as compared with the orientation of the human $V_H$ gene segments. Alternatively, the mouse ADAM6 locus is present in the intergenic region between the 3'-most human $V_H$ gene segment and the 5'-most $D_H$ gene segment. This can be the case whether the 5'-most $D_H$ segment is mouse or human.

Similarly, a mouse modified with one or more human $V_L$ gene segments (e.g., Vκ or Vλ segments) replacing all or substantially all endogenous mouse $V_H$ gene segments can be modified so as to either maintain the endogenous mouse ADAM6 locus, as described above, e.g., by employing a targeting vector having a downstream homology arm that includes a mouse ADAM6 locus or functional fragment thereof, or to replace a damaged mouse ADAM6 locus with an ectopic sequence positioned between two human $V_L$ gene segments or between the human $V_L$ gene segments and a $D_H$ gene segment (whether human or mouse, e.g., Vλ+m/h$D_H$), or a J gene segment (whether human or mouse, e.g., Vκ+$J_H$). In one embodiment, the replacement includes two or more human $V_L$ gene segments, and the mouse ADAM6 locus or functional fragment thereof is present between the two 3'-most $V_L$ gene segments. In a specific embodiment, the arrangement of human $V_L$ gene segments is then the following (from upstream to downstream with respect to direction of transcription of the human gene segments): human $V_L$3'-1—mouse ADAM6 locus—human $V_L$3'. In one embodiment, the orientation of one or more of mouse ADAM6a and mouse ADAM6b of the mouse ADAM6 locus is opposite with respect to direction of transcription as compared with the orientation of the human $V_L$ gene segments. Alternatively, the mouse ADAM6 locus is present in the intergenic region between the 3'-most human $V_L$ gene segment and the 5'-most $D_H$ gene segment. This can be the case whether the 5'-most $D_H$ segment is mouse or human.

In one aspect, a mouse is provided with a replacement of one or more endogenous mouse $V_H$ gene segments, and that comprises at least one endogenous mouse $D_H$ gene segment. In such a mouse, the modification of the endogenous mouse $V_H$ gene segments can comprise a modification of one or more of the 3'-most $V_H$ gene segments, but not the 5'-most $D_H$ gene segment, where care is taken so that the modification of the one or more 3'-most $V_H$ gene segments does not disrupt or render the endogenous mouse ADAM6 locus nonfunctional. For example, in one embodiment the mouse comprises a replacement of all or substantially all endogenous mouse $V_H$ gene segments with one or more human $V_H$ gene segments, and the mouse comprises one or more endogenous $D_H$ gene segments and a functional endogenous mouse ADAM6 locus.

In another embodiment, the mouse comprises the modification of endogenous mouse 3'-most $V_H$ gene segments, and a modification of one or more endogenous mouse $D_H$ gene segments, and the modification is carried out so as to maintain the integrity of the endogenous mouse ADAM6 locus to the extent that the endogenous ADAM6 locus remains functional. In one example, such a modification is done in two steps: (1) replacing the 3'-most endogenous mouse $V_H$ gene segments with one or more human $V_H$ gene segments employing a targeting vector with an upstream homology arm and a downstream homology arm wherein the downstream homology arm includes all or a portion of a functional mouse ADAM6 locus; (2) then replacing and endogenous mouse $D_H$ gene segment with a targeting vector having an upstream homology arm that includes a all or a functional portion of a mouse ADAM6 locus.

In various aspects, employing mice that contain an ectopic sequence that encodes a mouse ADAM6 protein or an ortholog or homolog or functional homolog thereof are useful where modifications disrupt the function of endogenous mouse ADAM6. The probability of disrupting endogenous mouse ADAM6 function is high when making modifications to mouse immunoglobulin loci, in particular when modifying mouse immunoglobulin heavy chain variable regions and surrounding sequences. Therefore, such mice provide particular benefit when making mice with immunoglobulin heavy chain loci that are deleted in whole or in part, are humanized in whole or in part, or are replaced (e.g., with Vκ or Vλ sequences) in whole or in part. Methods for making the genetic modifications described for the mice described below are known to those skilled in the art.

Mice containing an ectopic sequence encoding a mouse ADAM6 protein, or a substantially identical or similar protein that confers the fertility benefits of a mouse ADAM6 protein, are particularly useful in conjunction with modifications to a mouse immunoglobulin heavy chain variable gene locus that disrupt or delete the endogenous mouse ADAM6 sequence. Although primarily described in connection with mice that express antibodies with human variable regions and mouse constant regions, such mice are useful in connection with any genetic modifications that disrupt endogenous mouse ADAM6 genes. Persons of skill will recognize that this encompasses a wide variety of genetically modified mice that contain modifications of mouse immunoglobulin heavy chain variable gene loci. These include, for example, mice with a deletion or a replacement of all or a portion of mouse immunoglobulin heavy chain gene segments, regardless of other modifications. Non-limiting examples are described below.

In some aspects, genetically modified mice are provided that comprise an ectopic mouse, rodent, or other ADAM6 gene (or ortholog or homolog or fragment) functional in a mouse, and one or more human immunoglobulin variable and/or constant region gene segments. In various embodiments, other ADAM6 gene orthologs or homologs or fragments functional in a mouse may include sequences from bovine, canine, primate, rabbit or other non-human sequences.

In one aspect, a mouse is provided that comprises an ectopic ADAM6 sequence that encodes a functional ADAM6 protein, a replacement of all or substantially all mouse $V_H$ gene segments with one or more human $V_H$ gene segments; a replacement of all or substantially all mouse $D_H$ gene segments with one or more human $D_H$ gene segments; and a replacement of all or substantially all mouse $J_H$ gene segments with one or more human $J_H$ gene segments.

In one embodiment, the mouse further comprises a replacement of a mouse $C_H$1 nucleotide sequence with a human $C_H$1 nucleotide sequence. In one embodiment, the mouse further comprises a replacement of a mouse hinge nucleotide sequence with a human hinge nucleotide sequence. In one embodiment, the mouse further comprises a replacement of an immunoglobulin light chain variable locus ($V_L$ and $J_L$) with a human immunoglobulin light chain variable locus. In one embodiment, the mouse further comprises a replacement of a mouse immunoglobulin light chain constant region nucleotide sequence with a human immunoglobulin light chain constant region nucleotide sequence. In a specific embodiment, the $V_L$, $J_L$, and $C_L$ are immunoglobulin κ light chain sequences. In a specific embodiment, the mouse comprises a mouse $C_H2$ and a mouse $C_H3$ immunoglobulin constant region sequence fused with a human hinge and a human $C_H1$ sequence, such that the mouse immunoglobulin loci rearrange to form a gene that encodes a binding protein comprising (a) a heavy chain that has a human variable region, a human $C_H1$ region, a human hinge region, and a mouse $C_H2$ and a mouse $C_H3$ region; and (b) a gene that encodes an immunoglobulin light chain that comprises a human variable domain and a human constant region.

In one aspect, a mouse is provided that comprises an ectopic ADAM6 sequence that encodes a functional ADAM6 protein, a replacement of all or substantially all mouse $V_H$ gene segments with one or more human $V_L$ gene segments, and optionally a replacement of all or substantially all $D_H$ gene segments and/or $J_H$ gene segments with one or more human $D_H$ gene segments and/or human $J_H$ gene segments, or optionally a replacement of all or substantially all $D_H$ gene segments and $J_H$ gene segments with one or more human $J_L$ gene segments.

In one embodiment, the mouse comprises a replacement of all or substantially all mouse $V_H$, $D_H$, and $J_H$ gene segments with one or more $V_L$, one or more $D_H$, and one or more J gene segments (e.g., Jλ or Jλ), wherein the gene segments are operably linked to an endogenous mouse hinge region, wherein the mouse forms a rearranged immunoglobulin chain gene that contains, from 5' to 3' in the direction of transcription, human $V_L$—human or mouse $D_H$—human or mouse J—mouse hinge—mouse $C_H2$—mouse $C_H3$. In one embodiment, the J region is a human Jκ region. In one embodiment, the J region is a human $J_H$ region. In one embodiment, the J region is a human Jλ region. In one embodiment, the human $V_L$ region is selected from a human Vλ region and a human Vκ region.

In specific embodiments, the mouse expresses a single variable domain antibody having a mouse or human constant region and a variable region derived from a human Vκ, a human $D_H$ and a human Jκ; a human Vκ, a human $D_H$, and a human $J_H$; a human Vλ, a human $D_H$, and a human Jλ; a human Vλ, a human $D_H$, and a human $J_H$; a human Vκ, a human $D_H$, and a human Jλ; a human Vλ, a human $D_H$, and a human Jκ. In specific embodiment, recombination recognition sequences are modified so as to allow for productive rearrangements to occur between recited V, D, and J gene segments or between recited V and J gene segments.

In one aspect, a mouse is provided that comprises an ectopic ADAM6 sequence that encodes a functional ADAM6 protein (or ortholog or homolog or functional fragment thereof), a replacement of all or substantially all mouse $V_H$ gene segments with one or more human $V_L$ gene segments, a replacement of all or substantially all mouse $D_H$ gene segment and $J_H$ gene segments with human $J_L$ gene segments; wherein the mouse lacks a $C_H1$ and/or hinge region.

In one embodiment, the mouse lacks a sequence encoding a $C_H1$ domain. In one embodiment, the mouse lacks a sequence encoding a hinge region. In one embodiment, the mouse lacks a sequence encoding a $C_H1$ domain and a hinge region.

In a specific embodiment, the mouse expresses a binding protein that comprises a human immunoglobulin light chain variable domain (λ or κ) fused to a mouse $C_H2$ domain that is attached to a mouse $C_H3$ domain.

In one aspect, a mouse is provided that comprises an ectopic ADAM6 sequence that encodes a functional ADAM6 protein (or ortholog or homolog or functional fragment thereof), a replacement of all or substantially all mouse $V_H$ gene segments with one or more human $V_L$ gene segments, a replacement of all or substantially all mouse $D_H$ and $J_H$ gene segments with human $J_L$ gene segments.

In one embodiment, the mouse comprises a deletion of an immunoglobulin heavy chain constant region gene sequence encoding a $C_H1$ region, a hinge region, a $C_H1$ and a hinge region, or a $C_H1$ region and a hinge region and a $C_H2$ region.

In one embodiment, the mouse makes a single variable domain binding protein comprising a homodimer selected from the following: (a) human $V_L$—mouse $C_H1$—mouse $C_H2$—mouse $C_H3$; (b) human $V_L$—mouse hinge—mouse $C_H2$—mouse $C_H3$; (c) human $V_L$—mouse $C_H2$—mouse $C_H3$.

In one aspect, a mouse is provided with a disabled endogenous heavy chain immunoglobulin locus, comprising a disabled or deleted endogenous mouse ADAM6 locus, wherein the mouse comprises a nucleic acid sequence that expresses a human or mouse or human/mouse or other chimeric antibody. In one embodiment, the nucleic acid sequence is present on a transgene integrated that is randomly integrated into the mouse genome. In one embodiment, the nucleic acid sequence is on an episome (e.g., a chromosome) not found in a wild-type mouse.

In one embodiment, the mouse further comprises a disabled endogenous immunoglobulin light chain locus. In a specific embodiment, the endogenous immunoglobulin light chain locus is selected from a kappa (κ) and a lambda (λ) light chain locus. In a specific embodiment, the mouse comprises a disabled endogenous κ light chain locus and a disabled light chain locus, wherein the mouse expresses an antibody that comprises a human immunoglobulin heavy chain variable domain and a human immunoglobulin light chain domain. In one embodiment, the human immunoglobulin light chain domain is selected from a human κ light chain domain and a human λ light chain domain. In a specific embodiment, the mouse comprises a disabled endogenous κ light chain locus, wherein the mouse expresses an antibody that comprises a human/mouse (i.e., human variable/mouse constant) immunoglobulin heavy chain and a human/mouse immunoglobulin light chain comprising a human Vλ domain. In one embodiment, the human/mouse immunoglobulin light chain comprises a mouse Cκ. In one embodiment, the human/mouse immunoglobulin light chain comprises a mouse Cλ. In a specific embodiment, the mouse Cλ is a Cλ2.

In one aspect, a genetically modified animal is provided that expresses a chimeric antibody and expresses an ADAM6 protein or ortholog or homolog thereof that is functional in the genetically modified animal.

In one embodiment, the genetically modified animal is selected from a mouse and a rat. In one embodiment, the genetically modified animal is a mouse, and the ADAM6 protein or ortholog or homolog thereof is from a mouse strain that is a different strain than the genetically modified animal. In one embodiment, the genetically modified animal is a rodent of family Cricetidae (e.g., a hamster, a New World rat or mouse, a vole), and the ADAM6 protein ortholog or homolog is from a rodent of family Muridae (e.g., true mouse or rat, gerbil, spiny mouse, crested rat). In one embodiment, the genetically modified animal is a rodent of the family Muridae, and the ADAM6 protein ortholog or homolog is from a rodent of family Cricetidae.

In one embodiment, the chimeric antibody comprises a human variable domain and a constant region sequence of a rodent. In one embodiment, the rodent is selected from a rodent of the family Cricetidae and a rodent of family Muridae, In a specific embodiment, the rodent of the family Cricetidae and of the family Muridae is a mouse. In a specific embodiment, the rodent of the family Cricetidae and of the family Muridae is a rat. In one embodiment, the chimeric antibody comprises a human variable domain and a constant domain from an animal selected from a mouse or rat; in a specific embodiment, the mouse or rat is selected from the family Cricetidae and the family Muridae. In one embodiment, the chimeric antibody comprises a human heavy chain variable domain, a human light chain variable domain and a constant region sequence derived from a rodent selected from mouse and rat, wherein the human heavy chain variable domain and the human light chain are cognate. In a specific embodiment, cognate includes that the human heavy chain and the human light chain variable domains are from a single B cell that expresses the human light chain variable domain and the human heavy chain variable domain together and present the variable domains together on the surface of an individual B cell.

In one embodiment, the chimeric antibody is expressed from an immunoglobulin locus. In one embodiment, the heavy chain variable domain of the chimeric antibody is expressed from a rearranged endogenous immunoglobulin heavy chain locus. In one embodiment, the light chain variable domain of the chimeric antibody is expressed from a rearranged endogenous immunoglobulin light chain locus. In one embodiment, the heavy chain variable domain of the chimeric antibody and/or the light chain variable domain of the chimeric antibody is expressed from a rearranged transgene (e.g., a rearranged nucleic acid sequence derived from an unrearranged nucleic acid sequence integrated into the animal's genome at a locus other than an endogenous immunoglobulin locus). In one embodiment, the light chain variable domain of the chimeric antibody is expressed from a rearranged transgene (e.g., a rearranged nucleic acid sequence derived from an unrearranged nucleic acid sequence integrated into the animal's genome at a locus other than an endogenous immunoglobulin locus).

In a specific embodiment, the transgene is expressed from a transcriptionally active locus, e.g., a ROSA26 locus, e.g., a murine (e.g., mouse) ROSA26 locus.

In one aspect, a non-human animal is provided, comprising a humanized immunoglobulin heavy chain locus, wherein the humanized immunoglobulin heavy chain locus comprises a non-human ADAM6 sequence or ortholog or homolog thereof.

In one embodiment, the non-human animal is a rodent selected from a mouse, a rat, and a hamster.

In one embodiment, the non-human ADAM6 ortholog or homolog is a sequence that is orthologous and/or homologous to a mouse ADAM6 sequence, wherein the ortholog or homolog is functional in the non-human animal.

In one embodiment, the non-human animal is selected from a mouse, a rat, and a hamster and the ADAM6 ortholog or homolog is from a non-human animal selected from a mouse, a rat, and a hamster. In a specific embodiment, the non-human animal is a mouse and the ADAM6 ortholog or homolog is from an animal that is selected from a different mouse species, a rat, and a hamster. In specific embodiment, the non-human animal is a rat, and the ADAM6 ortholog or homolog is from a rodent that is selected from a different rat species, a mouse, and a hamster. In a specific embodiment, the non-human animal is a hamster, and the ADAM6 ortholog or homolog is form a rodent that is selected from a different hamster species, a mouse, and a rat.

In a specific embodiment, the non-human animal is from the suborder Myomorpha, and the ADAM6 sequence is from an animal selected from a rodent of superfamily Dipodoidea and a rodent of the superfamily Muroidea. In a specific embodiment, the rodent is a mouse of superfamily Muroidea, and the ADAM6 ortholog or homolog is from a mouse or a rat or a hamster of superfamily Muroidea.

In one embodiment, the humanized heavy chain locus comprises one or more human $V_H$ gene segments, one or more human $D_H$ gene segments and one or more human $J_H$ gene segments. In a specific embodiment, the one or more human $V_H$ gene segments, one or more human $D_H$ gene segments and one or more human $J_H$ gene segments are operably linked to one or more human, chimeric and/or rodent (e.g., mouse or rat) constant region genes. In one embodiment, the constant region genes are mouse. In one embodiment, the constant region genes are rat. In one embodiment, the constant region genes are hamster. In one embodiment, the constant region genes comprise a sequence selected from a hinge, a $C_H2$, a $C_H3$, and a combination thereof. In specific embodiment, the constant region genes comprise a hinge, a $C_H2$, and a $C_H3$ sequence.

In one embodiment, the non-human ADAM6 sequence is contiguous with a human immunoglobulin heavy chain sequence. In one embodiment, the non-human ADAM6 sequence is positioned within a human immunoglobulin heavy chain sequence. In a specific embodiment, the human immunoglobulin heavy chain sequence comprises a V, D and/or J gene segment.

In one embodiment, the non-human ADAM6 sequence is juxtaposed with a V gene segment. In one embodiment, the non-human ADAM6 sequence is positioned between two V gene segments. In one embodiment, the non-human ADAM6 sequence is juxtaposed between a V and a D gene segment. In one embodiment, the mouse ADAM6 sequence is positioned between a V and a J gene segment. In one embodiment, the mouse ADAM6 sequence is juxtaposed between a D and a J gene segment.

In one aspect, a genetically modified non-human animal is provided, comprising a B cell that expresses a human $V_H$ domain cognate with a human $V_L$ domain from an immunoglobulin locus, wherein the non-human animal expresses a non-immunoglobulin non-human protein from the immunoglobulin locus. In one embodiment, the non-immunoglobulin non-human protein is an ADAM protein. In a specific embodiment, the ADAM protein is an ADAM6 protein or homolog or ortholog or functional fragment thereof.

In one embodiment the non-human animal is a rodent (e.g., mouse or rat). In one embodiment, the rodent is of family Muridae. In one embodiment, the rodent is of subfamily Murinae. In a specific embodiment, the rodent of subfamily Murinae is selected from a mouse and a rat.

In one embodiment, the non-immunoglobulin non-human protein is a rodent protein. In one embodiment, the rodent is of family Muridae. In one embodiment, the rodent is of subfamily Murinae. In a specific embodiment, the rodent is selected from a mouse, a rat, and a hamster.

In one embodiment, the human $V_H$ and $V_L$ domains are attached directly or through a linker to an immunoglobulin constant domain sequence. In a specific embodiment, the constant domain sequence comprises a sequence selected from a hinge, a $C_H2$ a $C_H3$, and a combination thereof. In a specific embodiment, the human $V_L$ domain is selected from a Vκ or a Vλ domain.

In one aspect, a genetically modified non-human animal is provided, comprising in its germline a human immunoglobulin sequence, wherein the sperm of a male non-human animal is characterized by an in vivo migration defect. In one embodiment, the in vivo migration defect comprises an inability of the sperm of the male non-human animal to migrate from a uterus through an oviduct of a female non-human animal of the same species. In one embodiment, the non-human animal lacks a nucleotide sequence that encodes and ADAM6 protein or functional fragment thereof. In a specific embodiment, the ADAM6 protein or functional fragment thereof includes an ADAM6a and/or an ADAM6b protein or functional fragments thereof. In one embodiment, the non-human animal is a rodent. In a specific embodiment, the rodent is selected from a mouse, a rat, and a hamster.

In one aspect, a non-human animal is provided, comprising a human immunoglobulin sequence contiguous with a non-human sequence that encodes an ADAM6 protein or ortholog or homolog or functional fragment thereof. In one embodiment, the non-human animal is a rodent. In a specific embodiment, the rodent is selected from a mouse, a rat, and a hamster.

In one embodiment, the human immunoglobulin sequence is an immunoglobulin heavy chain sequence. In one embodiment, the immunoglobulin sequence comprises one or more $V_H$ gene segments. In one embodiment, the human immunoglobulin sequence comprises one or more $D_H$ gene segments. In one embodiment, the human immunoglobulin sequence comprises one or more $J_H$ gene segments. In one embodiment, the human immunoglobulin sequence comprises one or more $V_H$ gene segments, one or more $D_H$ gene segments and one or more $J_H$ gene segments.

In one embodiment, the immunoglobulin sequence comprises one or more $V_H$ gene segments have a high frequency in natural human repertoires. In a specific embodiment, the one or more $V_H$ gene segments comprise no more than two $V_H$ gene segments, no more than three $V_H$ gene segments, no more than four $V_H$ gene segments, no more than five $V_H$ gene segments, no more than six $V_H$ gene segments, no more than seven $V_H$ gene segments, no more than eight $V_H$ gene segments, no more than nine $V_H$ gene segments, no more than 10 $V_H$ gene segments, no more than 11 $V_H$ gene segments, no more than 12 $V_H$ gene segments, no more than 13 $V_H$ gene segments, no more than 14 $V_H$ gene segments, no more than 15 $V_H$ gene segments, no more than 16, $V_H$ gene segments, no more than 17 $V_H$ gene segments, no more than 18 $V_H$ gene segments, no more than 19 $V_H$ gene segments, no more than 20 $V_H$ gene segments, no more than 21 $V_H$ gene segments, no more than 22 $V_H$ gene segments or no more than 23 $V_H$ gene segments.

In a specific embodiment, the one or more $V_H$ gene segments comprise five $V_H$ gene segments. In a specific embodiment, the one or more $V_H$ gene segments comprise 10 $V_H$ gene segments. In a specific embodiment, the one or more $V_H$ gene segments comprise 15 $V_H$ gene segments. In a specific embodiment, the one or more $V_H$ gene segments comprise 20 $V_H$ gene segments.

In various embodiments, the $V_H$ gene segments are selected from $V_H6$-1, $V_H1$-2, $V_H1$-3, $V_H2$-5, $V_H3$-7, $V_H1$-8, $V_H3$-9, $V_H3$-11, $V_H3$-13, $V_H3$-15, $V_H3$-16, $V_H1$-18, $V_H3$-20, $V_H3$-21, $V_H3$-23, $V_H1$-24, $V_H2$-26, $V_H4$-28, $V_H3$-30, $V_H4$-31, $V_H3$-33, $V_H4$-34, $V_H3$-35, $V_H3$-38, $V_H4$-39, $V_H3$-43, $V_H1$-45, $V_H1$-46, $V_H3$-48, $V_H3$-49, $V_H5$-51, $V_H3$-53, $V_H1$-58, $V_H4$-59, $V_H4$-61, $V_H3$-64, $V_H3$-66, $V_H1$-69, $v_H2$-70, $V_H3$-72, $V_H3$-73 and $V_H3$-74. In various embodiments, the $V_H$ gene segments are selected from $V_H1$-2, $V_H1$-8, $V_H1$-18, $V_H1$-46, $V_H1$-69, $V_H3$-7, $V_H3$-9, $V_H3$-11, $V_H3$-13, $V_H3$-15, $V_H3$-21, $V_H3$-23, $V_H3$-30, $V_H3$-33, $V_H3$-43, $V_H3$-48, $V_H4$-31, $V_H4$-34, $V_H4$-39, $V_H4$-59, $V_H5$-51 and $V_H6$-1. In various embodiments, the $V_H$ gene segments are selected from $V_H1$-18, $V_H1$-46, $V_H1$-69, $V_H3$-7, $V_H3$-11, $V_H3$-15, $V_H3$-21, $V_H3$-23, $V_H3$-30, $V_H3$-33, $V_H3$-48, $V_H4$-34, $V_H4$-39, $V_H4$-59 and $V_H5$-51. In various embodiments, the $V_H$ gene segments are selected from $V_H1$-18, $V_H1$-69, $V_H3$-7, $V_H3$-11, $V_H3$-15, $V_H3$-21, $V_H3$-23, $V_H3$-30, $V_H3$-43, $V_H3$-48, $V_H4$-39, $V_H4$-59 and $V_H5$-51. In various embodiments, the $V_H$ gene segments are selected from $V_H1$-18, $V_H3$-11, $V_H3$-21, $V_H3$-23, $V_H3$-30, $V_H4$-39 and $V_H4$-59. In various embodiments, the $V_H$ gene segments are selected from $V_H1$-18, $V_H3$-21, $V_H3$-23, $V_H3$-30 and $V_H4$-39. In various embodiments, the $V_H$ gene segments are selected from $V_H1$-18, $V_H3$-23 and $V_H4$-39. In various embodiments, the $V_H$ gene segments are selected from $V_H3$-21, $V_H3$-23 and $V_H3$-30. In various embodiments, the $V_H$ gene segments are selected from $V_H3$-23, $V_H3$-30 and $V_H4$-39.

In a specific embodiment, human immunoglobulin sequence comprises at least 18 $V_H$ gene segments, 27 $D_H$ gene segments and six $J_H$ gene segments. In a specific embodiment, the human immunoglobulin sequence comprises at least 39 $V_H$ gene segments, 27 $D_H$ gene segments and six $J_H$ gene segments. In a specific embodiment, the human immunoglobulin sequence comprises at least 80 $V_H$ gene segments, 27 $D_H$ gene segments and six $J_H$ gene segments.

In one embodiment, the non-human animal is a mouse, and the mouse comprises a replacement of endogenous mouse $V_H$ gene segments with one or more human $V_H$ gene segments, wherein the human $V_H$ gene segments are operably linked to a mouse $C_H$ region gene, such that the mouse rearranges the human $V_H$ gene segments and expresses a reverse chimeric immunoglobulin heavy chain that comprises a human $V_H$ domain and a mouse $C_H$. In one embodiment, 90-100% of unrearranged mouse $V_H$ gene segments are replaced with at least one unrearranged human $V_H$ gene segment. In a specific embodiment, all or substantially all of the endogenous mouse $V_H$ gene segments are replaced with at least one unrearranged human $V_H$ gene segment. In one embodiment, the replacement is with at least 19, at least 39, or at least 80 or 81 unrearranged human $V_H$ gene segments. In one embodiment, the replacement is with at least 12 functional unrearranged human $V_H$ gene segments, at least 25 functional unrearranged human $V_H$ gene segments, or at least 43 functional unrearranged human $V_H$ gene segments. In one embodiment, the mouse comprises a replacement of all mouse $D_H$ and $J_H$ segments with at least one unrearranged human $D_H$ segment and at least one unrearranged human $J_H$ segment. In one embodiment, the at least one unrearranged human $D_H$ segment is selected from 1-1, 1-7, 1-26, 2-8, 2-15, 3-3, 3-10, 3-16, 3-22, 5-5, 5-12, 6-6, 6-13, 7-27, and a combination thereof. In one embodiment, the at least one unrearranged human $J_H$ segment is selected from 1, 2, 3, 4, 5, 6, and a combination thereof. In a specific embodiment, the one or more human $V_H$ gene segment is selected from a 1-2, 1-8, 1-24, 1-69, 2-5, 3-7, 3-9, 3-11, 3-13, 3-15, 3-20, 3-23, 3-30, 3-33, 3-48, 3-53, 4-31, 4-39, 4-59, 5-51, a 6-1 human $V_H$ gene segment, and a combination thereof.

In various embodiments, the human immunoglobulin sequence is in operable linkage with a constant region in the germline of the non-human animal (e.g., the rodent, e.g., the mouse, rat, or hamster). In one embodiment, the constant region is a human, chimeric human/mouse or chimeric human/rat or chimeric human/hamster, a mouse, a rat, or a hamster constant region. In one embodiment, the constant region is a rodent (e.g., mouse or rat or hamster) constant region. In a specific embodiment, the rodent is a mouse or rat. In various embodiments, the constant region comprises at least a $C_H2$ domain and a $C_H3$ domain.

In one embodiment, the human immunoglobulin heavy chain sequence is located at an immunoglobulin heavy chain locus in the germline of the non-human animal (e.g., the rodent, e.g., the mouse or rat or hamster). In one embodiment, the human immunoglobulin heavy chain sequence is located at a non-immunoglobulin heavy chain locus in the germline of the non-human animal, wherein the non-heavy chain locus is a transcriptionally active locus. In a specific embodiment, the non-heavy chain locus is a ROSA26 locus.

In various aspects, the non-human animal further comprises a human immunoglobulin light chain sequence (e.g., one or more unrearranged light chain V and J sequences, or one or more rearranged VJ sequences) in the germline of the non-human animal. In a specific embodiment, the immunoglobulin light chain sequence is an immunoglobulin λ light chain sequence. In one embodiment, the human immunoglobulin light chain sequence comprises one or more Vλ gene segments. In one embodiment, the human immunoglobulin light chain sequence comprises one or more Jλ gene segments. In one embodiment, the human immunoglobulin light chain sequence comprises one or more Vλ gene segments and one or more Jλ gene segments.

In a specific embodiment, the human immunoglobulin light chain sequence comprises at least 12 Vλ gene segments and one Jλ gene segments. In a specific embodiment, the human immunoglobulin light chain sequence comprises at least 12 Vλ gene segments and four Jλ gene segments.

In a specific embodiment, the human immunoglobulin light chain sequence comprises at least 28 Vλ gene segments and one Jλ gene segments. In a specific embodiment, the human immunoglobulin light chain sequence comprises at least 28 Vλ gene segments and four Jλ gene segments.

In a specific embodiment, the human immunoglobulin light chain sequence comprises at least 40 Vλ gene segments and one Jλ gene segments. In a specific embodiment, the human immunoglobulin light chain sequence comprises at least 40 Vλ gene segments and four Jλ gene segments.

In various embodiments, the human immunoglobulin light chain sequence is in operable linkage with a constant region in the germline of the non-human animal (e.g., rodent, e.g., mouse or rat or hamster). In one embodiment, the constant region is a human, chimeric human/rodent, mouse, rat, or hamster constant region. In a specific embodiment, the constant region is a mouse or rat constant region. In a specific embodiment, the constant region is a mouse κ constant (mCκ) region or a rat κ constant (rCκ) region. In a specific embodiment, the constant region is a mouse λ constant (mCl) region or a rat λ constant (rCλ) region. In one embodiment, the mouse Cλ region is a mouse Cλ2 region.

In one embodiment, the human immunoglobulin light chain sequence is located at an immunoglobulin light chain locus in the germline of the non-human animal. In a specific embodiment, the immunoglobulin light chain locus in the germline of the non-human animal is an immunoglobulin κ light chain locus. In a specific embodiment, the immunoglobulin light chain locus in the germline of the non-human animal is an immunoglobulin λ light chain locus. In one embodiment, the human immunoglobulin light chain sequence is located at a non-immunoglobulin light chain locus in the germline of the non-human animal that is transcriptionally active. In a specific embodiment, the non-immunoglobulin locus is a ROSA26 locus.

In one aspect, a method of making a human antibody is provided, wherein the human antibody comprises variable domains derived from one or more variable region nucleic acid sequences encoded in a cell of a non-human animal as described herein.

In one aspect, a pharmaceutical composition is provided, comprising a polypeptide that comprises antibody or antibody fragment that is derived from one or more variable region nucleic acid sequences isolated from a non-human animal as described herein. In one embodiment, the polypeptide is an antibody. In one embodiment, the polypeptide is a heavy chain only antibody. In one embodiment, the polypeptide is a single chain variable fragment (e.g., an scFv).

In one aspect, use of a non-human animal as described herein to make an antibody is provided. In various embodiments, the antibody comprises one or more variable domains that are derived from one or more variable region nucleic acid sequences isolated from the non-human animal. In a specific embodiment, the variable region nucleic acid sequences comprise immunoglobulin heavy chain gene segments. In a specific embodiment, the variable region nucleic acid sequences comprise immunoglobulin light chain gene segments.

Mice Expressing Human λ Variable Domains

Genetically modified non-human animals (e.g., mice, rats, etc) comprising a modification that reduces fertility due to loss of an ADAM protein activity (e.g., ADAM6-dependent) can be bred with non-human animals as described herein that comprise human λ variable sequences at endogenous non-human, or (e.g., transgenic) human, constant light genes. For example, non-human animals such as mice or rats that comprise a damaged ADAM6 gene (or a deleted ADAM6 gene), e.g., animals with humanized immunoglobulin heavy chain loci, are combined with mice that comprise a light chain locus (endogenous or transgenic) that comprises human λ segments and JL segments linked to human or non-human (e.g., endogenous mouse or rat) light chain constant region genes, wherein the non-human animals comprise an activity that restores the ADAM-dependent fertility. The genetic modification that restores the ADAM-dependent fertility can be in either non-human animal, e.g., in a mouse with a humanized heavy chain, or in a mouse with humanized λ variable segments. Progeny comprise genes that form a humanized heavy chain (i.e., result in expressing a human heavy chain variable domain) and a humanized light chain locus (i.e., result in expressing a human light chain variable domain, fused to a human or non-human λ or κ region), wherein animals exhibit a fertility that is increased as compared with a mouse that lacks the ADAM6 activity or activity of an ortholog or homolog of ADAM6.

VELOCIMMUNE® genetically engineered mice comprise a replacement of unrearranged V(D)J gene segments at endogenous mouse loci with human V(D)J gene segments. VELOCIMMUNE® mice express chimeric antibodies having human variable domains and mouse constant domains (see, e.g., U.S. Pat. No. 7,605,237). Most other reports concern mice that express fully human antibodies from fully human transgenes in mice that have disabled endogenous immunoglobulin loci.

Antibody light chains are encoded by one of two separate loci: kappa (κ) and lambda (λ). Mouse antibody light chains are primarily of the κ type. Mice that make mouse antibodies, and modified mice that make fully human or chimeric human-mouse antibodies, display a bias in light chain usage. Humans also exhibit light chain bias, but not so pronounced as in mice; the ratio of κ light chains to λ light chains in mice is about 95:5, whereas in humans the ratio is about 60:40. The more pronounced bias in mice is not thought to severely affect antibody diversity, because in mice the λ variable locus is not so diverse in the first instance. This is not so in humans. The human λ light chain locus is richly diverse.

The human λ light chain locus extends over 1,000 kb and contains over 80 genes that encode variable (V) or joining (J) segments (FIG. 19). Within the human λ light chain locus, over half of all observed Vλ domains are encoded by the gene segments 1-40, 1-44, 2-8, 2-14, and 3-21. Overall, about 30 or so of the human Vλ gene segments are believed to be functional. There are seven Jλ gene segments, only four of which are regarded as generally functional Jλ gene segments—Jλ1, Jλ2, Jλ3, and Jλ7.

The λ light chain locus in humans is similar in structure to the λ locus of both mice and humans in that the human λ light chain locus has several variable region gene segments that are capable of recombining to form a functional light chain protein. The human λ light chain locus contains approximately 70 V gene segments and 7 Jλ-Cλ gene segment pairs. Only four of these Jλ-Cλ gene segment pairs appear to be functional. In some alleles, a fifth Jλ-Cλ gene segment pair is reportedly a pseudo gene (Cλ6). The 70 Vλ gene segments appear to contain 38 functional gene segments. The 70 Vλ sequences are arranged in three clusters, all of which contain different members of distinct V gene family groups (clusters A, B and C; FIG. 19). This is a potentially rich source of relatively untapped diversity for generating antibodies with human V regions in non-human animals.

In stark contrast, the mouse light chain locus contains only two or three (depending on the strain) mouse Vλ region gene segments (FIG. 20). At least for this reason, the severe κ bias in mice is not thought to be particularly detrimental to total antibody diversity.

According published maps of the mouse λ light chain locus, the locus consists essentially of two clusters of gene segments within a span of approximately 200 kb (FIG. 20). The two clusters contain two sets of V, J, and C genes that are capable of independent rearrangement: Vλ2-Jλ2-Cλ2-Jλ4-Cλ4 and Vλ1-Jλ3-Cλ3-Jλ1-Cλ1. Although Vλ2 has been found to recombine with all Jλ gene segments, Vλ1 appears to exclusively recombine with Cλ1. Cλ4 is believed to be a pseudo gene with defective splice sites.

The mouse κ light chain locus is strikingly different. The structure and number of gene segments that participate in the recombination events leading to a functional light chain protein from the mouse κ locus is much more complex (FIG. 21). Thus, mouse λ light chains do not greatly contribute to the diversity of an antibody population in a typical mouse.

Exploiting the rich diversity of the human λ light chain locus in mice would likely result in, among other things, a source for a more complete human repertoire of light chain V domains. Previous attempts to tap this diversity used human transgenes containing chunks of the human λ light chain locus randomly incorporated into the mouse genome (see, e.g., U.S. Pat. Nos. 6,998,514 and 7,435,871). Mice containing these randomly integrated transgenes reportedly express fully human λ light chains, however, in some cases, one or both endogenous light chain loci remain intact. This situation is not desirable as the human λ light chain sequences contend with the mouse light chain (κ or λ) in the expressed antibody repertoire of the mouse.

In contrast, the inventors describe genetically modified mice that are capable of expressing one or more λ light chain nucleic acid sequences directly from a mouse light chain locus, including by replacement at an endogenous mouse light chain locus. Genetically modified mice capable of expressing human λ light chain sequences from an endogenous locus may be further bred to mice that comprise a human heavy chain locus and thus be used to express antibodies comprising V regions (heavy and light) that are fully human. In various embodiments. The V regions express with mouse constant regions. In various embodiments, no endogenous mouse immunoglobulin gene segments are present and the V regions express with human constant regions. These antibodies would prove useful in numerous applications, both diagnostic as well as therapeutic.

Many advantages can be realized for various embodiments of expressing binding proteins derived from human Vλ and Jλ gene segments in mice. Advantages can be realized by placing human λ sequences at an endogenous light chain locus, for example, the mouse κ or λ locus. Antibodies made from such mice can have light chains that comprise human Vλ domains fused to a mouse $C_L$ region, specifically a mouse Cκ or Cλ region. The mice will also express human Vλ domains that are suitable for identification and cloning for use with human $C_L$ regions, specifically Cκ and/or Cλ regions. Because B cell development in such mice is otherwise normal, it is possible to generate compatible Vλ domains (including somatically mutated Vλ domains) in the context of either Cλ or Cκ regions.

Genetically modified mice are described that comprise an unrearranged Vλ gene segment at an immunoglobulin κ or λ light chain locus. Mice that express antibodies that comprise a light chain having a human Vλ domain fused to a Cκ and/or Cλ region are described.

In one aspect, a genetically modified non-human animal is described that comprises (1) one or more unrearranged human Vλ gene segments and one or more unrearranged human Jλ gene segments at an endogenous immunoglobulin light chain locus of the non-human animal, (2) one or more human $V_H$ gene segments, one more human $D_H$ gene segments, and one or more human $J_H$ gene segments at an endogenous immunoglobulin heavy chain locus of the non-human animal, wherein the non-human animal is capable of expressing an ADAM6 protein or functional fragment thereof, wherein the ADAM6 protein is functional in a male of the non-human animal. In one aspect, a genetically modified non-human animal is described that express antibodies containing heavy chains that comprise human $V_H$ domains and non-human heavy chain constant regions and light chains that comprise human Vλ domains and non-human light chain constant regions, wherein the non-human animals are capable of expressing an ADAM6 protein or functional fragment thereof. In various embodiments, the non-human animal is a rodent. In one embodiment, the rodent is a mouse or a rat.

In one embodiment, the non-human light chain constant domain is a Cκ or a Cλ domain. In one embodiment, the ADAM6 protein or functional fragment thereof is encoded by an ectopic sequence in the germline of the mouse. In one embodiment, the ADAM6 protein or functional fragment thereof is encoded by an endogenous sequence of the non-human animal.

In one embodiment, the endogenous light chain locus of the non-human animal is an immunoglobulin λ light chain locus. In one embodiment, the endogenous light chain locus of the non-human animal is an immunoglobulin κ light chain locus.

In one embodiment, the non-human animal lacks an endogenous $V_L$ and/or $J_L$ gene segment at the endogenous light chain locus. In a specific embodiment, the $V_L$ and/or $J_L$ gene segment are a Vκ and/or Jκ gene segment. In a specific embodiment, the VL and/or JL gene segment are a Vλ and/or Jλ gene segment.

In one embodiment, the $V_L$ and $J_L$ gene segments of the non-human animal are replaced by one or more human Vλ and one or more human Jλ gene segments. In a specific embodiment, the $V_L$ and $J_L$ gene segments of the non-human animal are κ gene segments. In a specific embodiment, the $V_L$ and $J_L$ gene segments of the non-human animal are λ gene segments.

In one embodiment, the one or more human Vλ gene segments are from a fragment of cluster A of the human immunoglobulin λ light chain locus. In a specific embodiment, the fragment of cluster A extends from human Vλ3-27 through human Vλ3-1. In a specific embodiment, the fragment of cluster A extends from human Vλ3-12 through human Jλ1. In one embodiment, the one or more human Vλ gene segments are from a fragment of cluster B of the human immunoglobulin λ light chain locus. In a specific embodiment, the fragment of cluster B extends from human Vλ5-52 through human Vλ1-40. In a specific embodiment, the one or more human Vλ gene segments are from a fragment of cluster A and from a fragment of cluster B of the human immunoglobulin λ light chain locus as described herein.

In one embodiment, the non-human animal comprises at least 12 human Vλ gene segments. In one embodiment, the non-human animal comprises at least 28 human Vλ gene segments. In one embodiment, the non-human animal comprises at least 40 human Vλ gene segments.

In one embodiment, the at least one human Jλ gene segment is selected from the group consisting of Jλ1, Jλ2, Jλ3, Jλ7, and a combination thereof.

In one aspect, a fertile non-human male animal is provided, wherein the fertile non-human animal expresses (1) an immunoglobulin light chain comprising a human Vλ domain or a human Vκ domain, and (2) an immunoglobulin heavy chain comprising a human $V_H$ domain, wherein the male non-human animal comprises a modified heavy chain variable region locus and an ectopic ADAM8 gene that is functional in the male non-human animal. In one embodiment, the male non-human animal is a mouse.

In one aspect, use of a non-human animal as described herein to make an antigen-binding protein is provided. In one embodiment, the antigen-binding protein is human. In one embodiment, the antigen-binding protein is an antibody. In one embodiment, the antigen-binding protein comprises a human $V_H$ domain and/or a human Vλ domain derived from a non-human animal as described herein.

In one aspect, a cell or tissue derived from a non-human animal as described herein is provided. In one embodiment, the tissue is derived from a spleen, bone marrow or a lymph node. In one embodiment, the cell is a B cell. In one embodiment, the cell is an embryonic stem (ES) cell. In one embodiment, the cell is a germ cell.

In one aspect, an oocyte comprising a diploid genome of a genetically modified non-human animal as described herein is provided.

Sterile Transcripts of the Immunoglobulin κ Light Chain Locus

Variations on the theme of expressing human immunoglobulin λ sequences in mice are reflected in various embodiments of genetically modified mice capable of such expression. Thus, in some embodiments, the genetically modified mice comprise certain non-coding sequence(s) from a human locus. In one embodiment, the genetically modified mouse comprises human Vλ and Jλ gene segments at an endogenous κ light chain locus, and further comprises a human κ light chain genomic fragment. In a specific embodiment, the human κ light chain genomic fragment is a non-coding sequence naturally found between a human Vκ gene segment and a human Jκ gene segment.

The human and mouse κ light chain loci contain sequences that encode sterile transcripts that lack either a start codon or an open reading frame, and that are regarded as elements that regulate transcription of the κ light chain loci. These sterile transcripts arise from an intergenic sequence located downstream or 3' of the most proximal Vκ gene segment and upstream or 5' of the κ light chain intronic enhancer (Eκi) that is upstream of the κ light chain constant region gene (Cκ). The sterile transcripts arise from rearrangement of the intergenic sequence to form a VκJκ1 segment fused to a Cκ.

A replacement of the κ light chain locus upstream of the Cκ gene would remove the intergenic region encoding the sterile transcripts. Therefore, in various embodiments, a replacement of mouse κ light chain sequence upstream of the mouse Cκ gene with human λ light chain gene segments would result in a humanized mouse κ light chain locus that contains human Vλ and Jλ gene segments but not the κ light chain intergenic region that encodes the sterile transcripts.

As described herein, humanization of the endogenous mouse κ light chain locus with human λ light chain gene segments, wherein the humanization removes the intergenic region, results in a striking drop in usage of the κ light chain locus, coupled with a marked increase in λ light chain usage. Therefore, although a humanized mouse that lacks the intergenic region is useful in that it can make antibodies with human light chain variable domains (e.g., human λ or κ domains), usage from the locus decreases.

Also described is humanization of the endogenous mouse κ light chain locus with human Vλ and Jλ gene segments coupled with an insertion of a human κ intergenic region to create a Vλ locus that contains, with respect to transcription, between the final human Vλ gene segment and the first human Jλ gene segment, a κ intergenic region; which exhibits a B cell population with a higher expression than a locus that lacks the κ intergenic region. This observation is consistent with a hypothesis that the intergenic region directly through a sterile transcript, or indirectly—suppresses usage from the endogenous λ light chain locus. Under such a hypothesis, including the intergenic region would result in a decrease in usage of the endogenous λ light chain locus, leaving the mouse a restricted choice but to employ the modified (λ into κ) locus to generate antibodies.

In various embodiments, a replacement of mouse κ light chain sequence upstream of the mouse Cκ gene with human λ light chain sequence further comprises a human κ light chain intergenic region disposed, with respect to transcription, between the 3' untranslated region of the 3' most Vλ gene segment and 5' to the first human Jλ gene segment. Alternatively, such an intergenic region may be omitted from a replaced endogenous κ light chain locus (upstream of the mouse Cκ gene) by making a deletion in the endogenous λ light chain locus. Likewise, under this embodiment, the mouse generates antibodies from an endogenous κ light chain locus containing human λ light chain sequences.

Approaches to Engineering Mice to Express Human Vλ Domains

Various approaches to making genetically modified mice that make antibodies that contain a light chain that has a human Vλ domain fused to an endogenous $C_L$ (e.g. Cκ or Cλ) region are described. Genetic modifications are described that, in various embodiments, comprise a deletion of one or both endogenous light chain loci. For example, to eliminate mouse light chains from the endogenous antibody repertoire a deletion of a first Vλ-Jλ-Cλ gene cluster and replacement, in whole or in part, of the Vλ-Jλ gene segments of a second gene cluster with human Vλ-Jλ gene segments can be made. Genetically modified mouse embryos, cells, and targeting constructs for making the mice, mouse embryos, and cells are also provided.

The deletion of one endogenous Vλ-Jλ-Cλ gene cluster and replacement of the Vλ-Jλ gene segments of another endogenous Vλ-Jλ-Cλ gene cluster employs a relatively minimal disruption in natural antibody constant region association and function in the animal, in various embodiments, because endogenous Cλ genes are left intact and therefore retain normal functionality and capability to associate with the constant region of an endogenous heavy chain. Thus, in such embodiments the modification does not affect other endogenous heavy chain constant regions dependent upon functional light chain constant regions for assembly of a functional antibody molecule containing two heavy chains and two light chains. Further, in various embodiments the modification does not affect the assembly of a functional membrane-bound antibody molecule involving an endogenous heavy chain and a light chain, e.g., a hVλ domain linked to a mouse Cλ region. Because at least one functional Cλ gene is retained at the endogenous locus, animals containing a replacement of the Vλ-Jλ gene segments of an endogenous Vλ-Jλ-Cλ gene cluster with human Vλ-Jλ gene segments should be able to make normal λ light chains that are capable of binding antigen during an immune response through the human Vλ-Jλ gene segments present in the expressed antibody repertoire of the animal.

A schematic illustration (not to scale) of a deleted endogenous mouse Vλ-Jλ-Cλ gene cluster is provided in FIG. 20. As illustrated, the mouse λ light chain locus is organized into two gene clusters, both of which contain function gene segments capable of recombining to form a function mouse λ light chain. The endogenous mouse Vλ1-Jλ3-Cλ3-Jλ1-Cλ1 gene cluster is deleted by a targeting construct (Targeting Vector 1) with a neomycin cassette flanked by recombination sites. The other endogenous gene cluster (Vλ2-Vλ3-Jλ2-Cλ2-Jλ2-Cλ4) is deleted in part by a targeting construct (Targeting Vector 2) with a hygromycin-thymidine kinase cassette flanked by recombination sites. In this second targeting event, the Cλ2-Jλ4-Cλ4 endogenous gene segments are retained. The second targeting construct (Targeting Vector 2) is constructed using recombination sites that are different than those in the first targeting construct (Targeting Vector 1) thereby allowing for the selective deletion of the selection cassette after a successful targeting has been achieved. The resulting double-targeted locus is functionally silenced in that no endogenous λ light chain can be produced. This modified locus can be used for the insertion of human Vλ and Jλ gene segments to create an endogenous mouse λ locus comprising human Vλ and Jλ gene segments, whereby, upon recombination at the modified locus, the animal produces λ light chains comprising rearranged human Vλ and Jλ gene segments linked to an endogenous mouse Cλ gene segment.

Genetically modifying a mouse to render endogenous λ gene segments nonfunctional, in various embodiments, results in a mouse that exhibits exclusively κ light chains in its antibody repertoire, making the mouse useful for evaluating the role of λ light chains in the immune response, and useful for making an antibody repertoire comprising Vκ domains but not Vλ domains.

A genetically modified mouse that expresses a hVλ linked to a mouse Cλ gene having been recombined at the endogenous mouse λ light chain locus can be made by any method known in the art. A schematic illustration (not to scale) of the replacement of the endogenous mouse Vλ2-Vλ3-Jλ2 gene segments with human Vλ and Jλ gene segments is provided in FIG. 22A. As illustrated, an endogenous mouse λ light chain locus that had been rendered nonfunctional is replaced by a targeting construct (12/1-λ Targeting Vector) that includes a neomycin cassette flanked by recombination sites. The Vλ2-Vλ3-Jλ2 gene segments are replaced with a genomic fragment containing human λ sequence that includes 12 hVλ gene segments and a single hJλ gene segment.

Thus, this first approach positions one or more hVλ gene segments at the endogenous λ light chain locus contiguous with a single hJλ gene segment (FIG. 22A).

Further modifications to the modified endogenous λ light chain locus can be achieved with using similar techniques to insert more hVλ gene segments. For example, schematic illustrations of two additional targeting constructs (+16-λ and +12-λ Targeting Vectors) used for progressive insertion of addition human hVλ gene segments are provided in FIG. 23A. As illustrated, additional genomic fragments containing specific human hVλ gene segments are inserted into the modified endogenous λ light chain locus in successive steps using homology provided by the previous insertion of human λ light chain sequences. Upon recombination with each targeting construct illustrated, in sequential fashion, 28 additional hVλ gene segments are inserted into the modified endogenous λ light chain locus. This creates a chimeric locus that produces a λ light chain protein that comprises human Vλ-Jλ gene segments linked to a mouse Cλ gene.

The above approaches to insert human λ light chain gene segments at the mouse λ locus, maintains the enhancers positioned downstream of the Cλ2-Jλ4-Cλ4 gene segments (designated Enh 2.4, Enh and Enh 3.1 FIG. 22A and FIG. 23A). This approach results in a single modified allele at the endogenous mouse λ light chain locus (FIG. 25A).

Compositions and methods for making a mouse that expresses a light chain comprising hVλ and Jλ gene segments operably linked to a mouse Cλ gene segment, are provided, including compositions and method for making a mouse that expresses such genes from an endogenous mouse λ light chain locus. The methods include selectively rendering one endogenous mouse Vλ-Jλ-Cλ gene cluster nonfunctional (e.g., by a targeted deletion), and employing a hVλ and Jλ gene segments at the endogenous mouse λ light chain locus to express a hVλ domain in a mouse.

Alternatively, in a second approach, human λ light chain gene segments may be positioned at the endogenous κ light chain locus. The genetic modification, in various embodiments, comprises a deletion of the endogenous κ light chain locus. For example, to eliminate mouse κ light chains from the endogenous antibody repertoire a deletion of the mouse Vκ and Jκ gene segments can be made. Genetically modified mouse embryos, cells, and targeting constructs for making the mice, mouse embryos, and cells are also provided.

For the reasons stated above, the deletion of the mouse Vκ and Jκ gene segments employs a relatively minimal disruption. A schematic illustration (not to scale) of deleted mouse Vκ and Jκ gene segments is provided in FIG. 21. The endogenous mouse Vκ and Jκ gene segments are deleted via recombinase-mediated deletion of mouse sequences position between two precisely positioned targeting vectors each employing site-specific recombination sites. A first targeting vector (Jκ Targeting Vector) is employed in a first targeting event to delete the mouse Jκ gene segments. A second targeting vector (Vκ Targeting Vector) is employed in a second, sequential targeting event to delete a sequence located 5' of the most distal mouse Vκ gene segment. Both targeting vectors contain site-specific recombination sites thereby allowing for the selective deletion of both selection cassettes and all intervening mouse κ light chain sequences after a successful targeting has been achieved. The resulting deleted locus is functionally silenced in that no endogenous κ light chain can be produced. This modified locus can be used for the insertion of hVλ and Jλ gene segments to create an endogenous mouse κ locus comprising hVλ and Jλ gene segments, whereby, upon recombination at the modified locus, the animal produces λ light chains comprising rearranged hVλ and Jλ gene segments operably linked to an endogenous mouse Cκ gene segment. Various targeting vectors comprising human λ light chain sequences can be used in conjunction with this deleted mouse κ locus to create a hybrid light chain locus containing human λ gene segments operably linked with a mouse Cκ region.

Thus, a second approach positions one or more human Vλ gene segments are positioned at the mouse κ light chain locus contiguous with a single human Jλ gene segment (12/1-κ Targeting Vector, FIG. 22B).

In various embodiments, modifications to this approach can be made to add gene segments and/or regulatory sequences to optimize the usage of the human λ light chain sequences from the mouse κ locus within the mouse antibody repertoire.

In a third approach, one or more hVλ gene segments are positioned at the mouse κ light chain locus contiguous with four hJλ gene sequences (12/4-κ Targeting Vector FIG. 22B).

In a third approach, one or more hVλ gene segments are positioned at the mouse κ light chain locus contiguous with a human κ intergenic sequence and a single hJλ gene sequence (12(κ)1-κ Targeting Vector, FIG. 22B).

In a fourth approach, one or more hVλ gene segments are positioned at the mouse κ light chain locus contiguous with a human κ intergenic sequence four hJλ gene sequences (12(κ)4-κ Targeting Vector FIG. 22B).

All of the above approaches to insert human λ light chain gene segments at the mouse κ locus, maintain the κ intronic enhancer element upstream of the Cκ gene (designated Eκi, FIG. 22B and FIG. 23B) and the 3' κ enhancer downstream of the Cκ gene (designated Eκ3', FIG. 22B and FIG. 23B). The approaches result in four separate modified alleles at the endogenous mouse κ light chain locus (FIG. 25B).

In various embodiments, genetically modified mouse comprise a knockout of the endogenous mouse λ light chain locus. In one embodiment, the λ light chain locus is knocked out by a strategy that deletes the region spanning Vλ2 to Jλ2, and the region spanning Vλ1 to Cλ1 (FIG. 20). Any strategy that reduces or eliminates the ability of the endogenous λ light chain locus to express endogenous λ domains is suitable for use with embodiments in this disclosure.

Lambda Domain Antibodies from Genetically Modified Mice

Mice comprising human λ sequences at either the mouse κ or λ light chain locus will express a light chain that comprises a hVλ region fused to a mouse $C_L$ (Cκ or Cλ) region. These are advantageously bred to mice that (a) comprise a functionally silenced light chain locus (e.g., a knockout of the endogenous mouse κ or λ light chain locus); (b) comprise an endogenous mouse λ light chain locus that comprises hV and hJ gene segments operably linked to an endogenous mouse Cλ gene; (c) comprise an endogenous mouse κ light chain locus that comprises hVκ and hJκ gene segments operably linked to an endogenous mouse Cκ gene; and, (d) a mouse in which one κ allele comprises hVκs and hJκs; the other κ allele comprising hVλs and hJλs; one λ allele comprising hVλs and hJλs and one λ allele silenced or knocked out, or both λ alleles comprising hVλs and hJλs; and, two heavy chain alleles that each comprise $hV_Hs$, $hD_Hs$, and $hJ_Hs$.

The antibodies that comprise the hVλ domains expressed in the context of either Cκ or Cλ are used to make fully human antibodies by cloning the nucleic acids encoding the hVλ domains into expression constructs that bear genes encoding human Cλ. Resulting expression constructs are transfected into suitable host cells for expressing antibodies that display a fully hVλ domain fused to hCλ.

EXAMPLES

The following examples are provided so as to describe how to make and use methods and compositions of the invention, and are not intended to limit the scope of what the inventors regard as their invention. Unless indicated otherwise, temperature is indicated in Celsius, and pressure is at or near atmospheric.

Example 1

Humanization of Mouse Immunoglobulin Genes

Human and mouse bacterial artificial chromsomes (BACs) were used to engineer 13 different BAC targeting vectors (BACvecs) for humanization of the mouse immunoglobulin heavy chain and κ light chain loci. Tables 1 and 2 set forth detailed descriptions of the steps performed for the construction of all BACvecs employed for the humanization of the mouse immunoglobulin heavy chain and κ light chain loci, respectively.

Identification of human and mouse BACs. Mouse BACs that span the 5' and 3' ends of the immunoglobulin heavy chain and κ light chain loci were identified by hybridization of filters spotted with BAC library or by PCR screening mouse BAC library DNA pools. Filters were hybridized under standard conditions using probes that corresponded to the regions of interest. Library pools were screened by PCR using unique primer pairs that flank the targeted region of interest. Additional PCR using the same primers was performed to deconvolute a given well and isolate the corresponding BAC of interest. Both BAC filters and library pools were generated from 129 SvJ mouse ES cells (Incyte Genomics/Invitrogen). Human BACs that cover the entire immunoglobulin heavy chain and κ light chain loci were identified either by hybridization of filters spotted with BAC library (Caltech B, C, or D libraries & RPCI-11 library, Research Genetics/Invitrogen) through screening human BAC library pools (Caltech library, Invitrogen) by a PCR-based method or by using a BAC end sequence database (Caltech D library, TIGR).

Construction of BACvecs by bacterial homologous recombination and ligation. Bacterial homologous recombination (BHR) was performed as described (Valenzuela et al., 2003; Zhang, Y., Buchholz, F., Muyrers, J. P., and Stewart, A. F. (1998). A new logic for DNA engineering using recombination in *Escherichia coli*. Nat Genet 20, 123-128). In most cases, linear fragments were generated by ligating PCR-derived homology boxes to cloned cassettes followed by gel isolation of ligation products and electroporation into BHR-competent bacteria harboring the target BAC. After selection on appropriate antibiotic petri dishes, correctly recombined BACs were identified by PCR across both novel junctions followed by restriction analysis on pulsed-field gels (Schwartz, D. C., and Cantor, C. R. (1984). Separation of yeast chromosome-sized DNAs by pulsed field gradient gel electrophoresis. Cell 37, 67-75) and spot-checking by PCR using primers distributed across the human sequences.

Figure 4A:
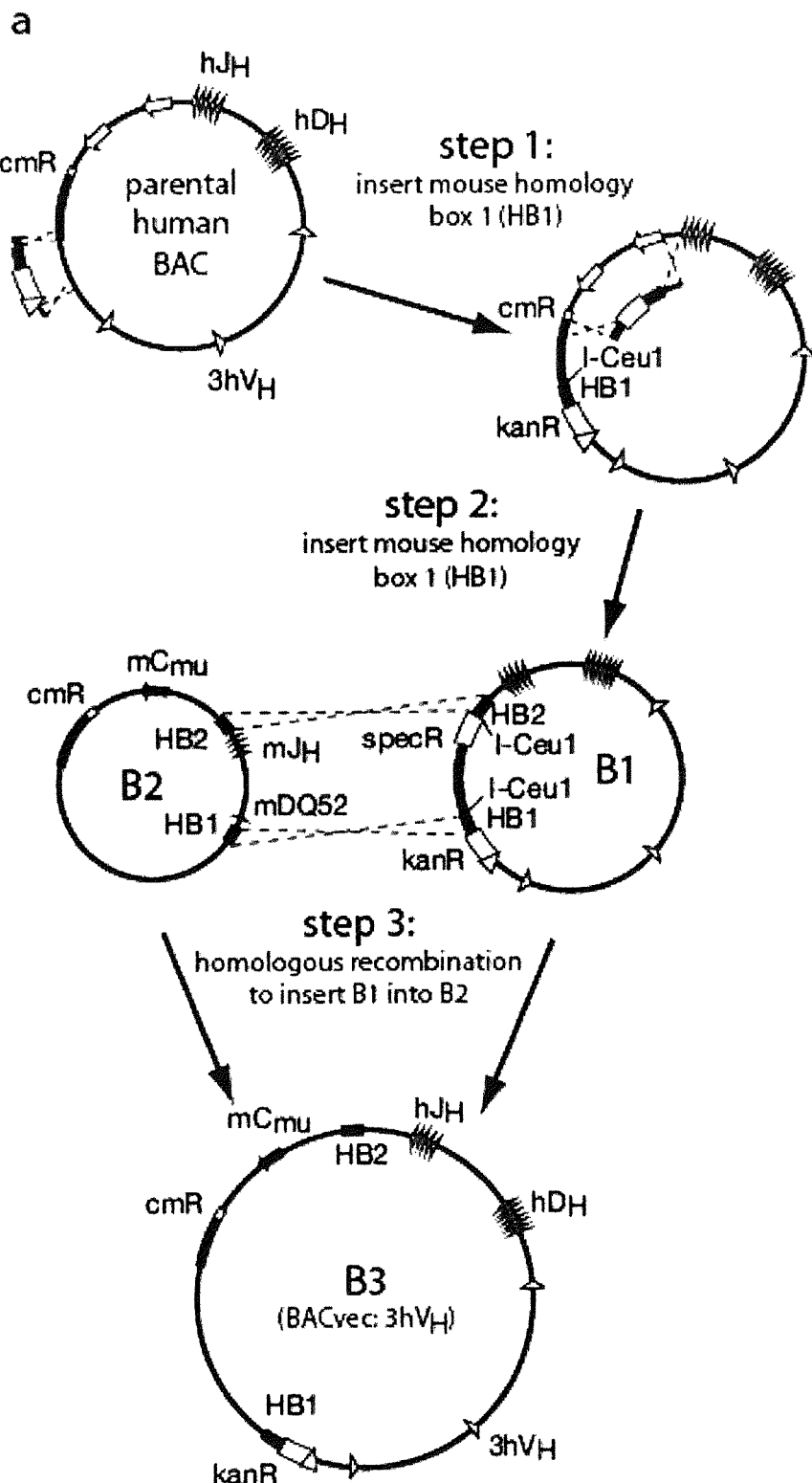
FIG. 4A shows a detailed illustration, not to scale, of the three steps employed for construction of a 3hV$_H$ BACvec by bacterial homologous recombination (BHR). Human (open symbols) and mouse (closed symbols) immunoglobulin gene segments, selection cassettes (open rectangles) and site-specific recombination sites (open triangles) inserted from targeting vectors are shown.
Figure 4B:
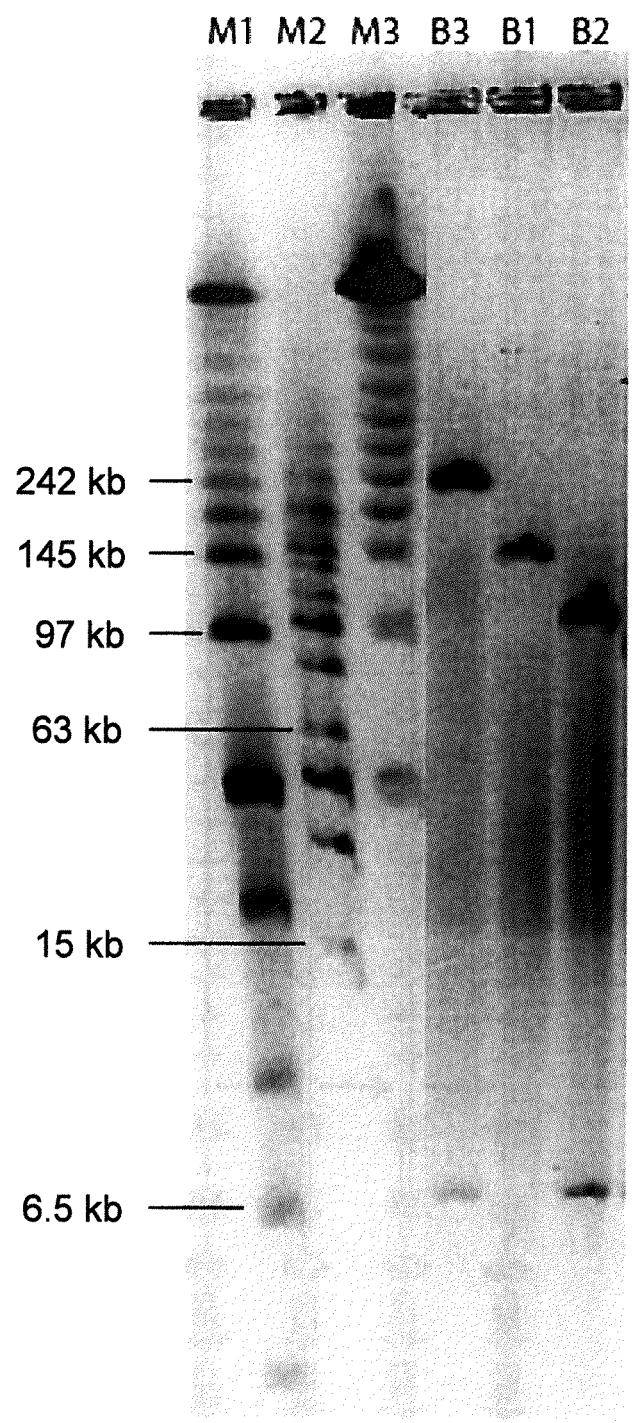
FIG. 4B shows pulse-field gel electrophoresis (PFGE) of three BAC clones (B1, B2 and B3) after NotI digestion.

A $3hV_H$ BACvec was constructed using three sequential BHR steps for the initial step of humanization of the immunoglobulin heavy chain locus (FIG. 4A and Table 1). In the first step (Step 1), a cassette was introduced into a human parental BAC upstream from the human $V_H1$-3 gene segment that contains a region of homology to the mouse immunoglobulin heavy chain locus (HB1), a gene that confers kanamycin resistance in bacteria and G418 resistance in animals cells (kanR) and a site-specific recombination site (e.g., loxP). In the second step (Step 2), a second cassette was introduced just downstream from the last $J_H$ segment that contains a second region of homology to the mouse immunoglobulin heavy chain locus (HB2) and a gene that confers resistance in bacteria to spectinomycin (specR). This second step included deleting human immunoglobulin heavy chain locus sequences downstream from $J_H6$ and the BAC vector chloramphenicol resistance gene (cmR). In the third step (Step 3), the doubly modified human BAC (B1) was then linearized using I-Ceul sites that had been added during the first two steps and integrated into a mouse BAC (B2) by BHR through the two regions of homology (HB1 and HB2). The drug selections for first (cmlkan), second (spec/kan) and third (cm/kan) steps were designed to be specific for the desired products. Modified BAC clones were analyzed by pulse-filed gel electrophoresis (PFGE) after digestion with restriction enzymes to determine appropriate construction (FIG. 4B).

In a similar fashion, 12 additional BACvecs were engineered for humanization of the heavy chain and κ light chain loci. In some instances, BAC ligation was performed in lieu of BHR to conjoin two large BACs through introduction of rare restriction sites into both parental BACvecs by BHR along with careful placement of selectable markers. This allowed for the survival of the desired ligation product upon selection with specific drug marker combinations. Recombinant BACs obtained by ligation after digestion with rare restriction enzymes were identified and screened in a similar fashion to those obtained by BHR (as described above).

TABLE 1

| BACvec | Step | Description | Process |
|---|---|---|---|
| $3hV_H$ | 1 | Insert upstream mouse homology box into human proximal BAC CTD-2572o2 | BHR |
| | 2 | Insert downstream mouse homology box into human proximal BAC CTD-2572o2 | BHR |
| | 3 | Insert 3hVH/27hDH/9hJH into mouse proximal BAC CT7-302a07 to create 3hVH BACvec | BHR |
| DC | 1 | Insert cassette at distal end of mouse IgH locus using mouse BAC CT7-253i20 | BHR |
| $18hV_H$ | 1 | Insert specR marker at downstream end of 3hVH insertion using human BAC CTD-2572o2 | BHR |
| | 2 | Insert I-Ceul and Not sites flanking puroR at upstream end of 3hVH insertion | BHR |
| | 3 | Insert Not site at downstream end of Rel2-408p02 BAC (≈10 kb downstream of VH2-5) | BHR |
| | 4 | Insert I-Ceu1 site at upstream end of Rel2-408p02 BAC (≈23 kb upstream of VH1-18) | BHR |
| | 5 | Ligate 184 kb fragment from step 4 into 153 kb vector from step 2 | Ligation |
| | 6 | Trim human homology from CTD-2572o2 BAC deleting ≈85 kb and leaving 65 kb homology to 3hVH | BHR |
| | 7 | Insert cassette and Not site at distal end of mouse IgH locus in CT7-253i20 BAC | BHR |
| | 8 | Subclone mouse distal homology arm for insertion upstream from human BACs | Ligation |
| | 9 | Insert 20 kb mouse arm upstream of Rel2-408p02 | BHR |
| | 10 | Swap selection cassette from hygR to neoR to create 18hVH BACvec | BHR |
| $39hV_H$ | 1 | Insert ICeul and PIScel sites flanking hygR into distal end of human BAC CTD-2534n10 | BHR |
| | 2 | Insert CmR at proximal end of CTD-2534n10 BAC to allow for selection for ligation to RP11-72n10 BAC | BHR |
| | 3 | Insert PIScel site into RP11-72n10 BAC for ligation to CTD-2534n10 BAC | BHR |
| | 4 | Insert ICeul and Ascl sites flanking puroR at distal end of RP11-72n10 BAC | BHR |
| | 5 | Ligate 161 kb fragment from construct of step 4 into construct of step 2 replacing hygR | Ligation |
| | 6 | Insert neoR and Ascl site at proximal end of mouse distal homology arm using CT7-253i20 BAC | BHR |
| | 7 | Insert specR and ICeul site at distal end of mouse distal homology arm | BHR |
| | 8 | Ligate mouse distal homology arm onto human insert from step 5 | Ligation |
| | 9 | Swap selection cassette from neo to hyg using UbCp and pA as homolgy boxes to create 39hVH BACvec | BHR |
| $53hV_H$ | 1 | Insert specR at proximal end of human CTD-3074b5 BAC | BHR |
| | 2 | Insert Ascl site at distal end of human CTD-3074b5 BAC | BHR |
| | 3 | Insert hygR and Ascl site at proximal end of mouse distal homology arm using CT7-253i20 BAC | BHR |
| | 4 | Ligate mouse distal homology arm onto construct from step 2 | Ligation |
| | 5 | Swap selection cassette from hyg to neo using UbCp and pA as homolgy boxes to create 53hVH BACvec | BHR |
| $70hV_H$ | 1 | Insert PIScel and ICeul sites flanking spec at distal end of human CTD-2195p5 | BHR |
| | 2 | Insert ICeul site at proximal end of RP11-926p12 BAC for ligation to CTD-2195p5 BAC | BHR |
| | 3 | Insert PIScel and Ascl sites at distal end of RP11-926p12 BAC for ligation of mouse arm | BHR |
| | 4 | Ligate mouse distal homology arm onto construct from step 3 | Ligation |
| | 5 | Ligate mouse distal homology arm and hIgH fragment from RP11-926p12 BAC onto CTD-2195p5 BAC to create 70 hVH BACvec | Ligation |

TABLE 1-continued

| BACvec | Step | Description | Process |
|---|---|---|---|
| 80hV$_H$ | 1 | Insert ICeuI and AscI sites flanking hygR at distal end of CTD-2313e3 BAC | BHR |
| | 2 | Ligate mouse dista homology arm onto human CTD-2313e3 BAC from step 1 to create 80hVH BACvec | Ligation |

TABLE 2

| BACvec | Step | Description | Process |
|---|---|---|---|
| Igκ-PC | 1 | Insert loxP site within mouse J-C intron using CT7-254m04 BAC | BHR |
| Igκ-DC | 1 | Insert loxP site at distal end of mouse IgK locus using CT7-302g12 | BHR BAC |
| 6hVκ | 1 | Insert PIScel site ≈400 bp downstream from hJκ5 in CTD-2366j12 BAC | BHR |
| | 2 | Insert ICeuI and AscI sites flanking hygR at distal end of CTD-2366j12 BAC | BHR |
| | 3 | Insert ICeuI and PI-ScelI sites flanking puroR ≈xxbp downstream from mJκx using CT7-254m04 BAC | BHR |
| | 4 | Insert hIgVκ/Jκ upstream from mouse Enhκ/Cκ using construct from step 3 | Ligation |
| | 5 | Replace cmR in construct of step 4 with specR | BHR |
| | 6 | Insert Neo selection cassette at distal end of mouse Igκ locus using CT7-302g12 BAC | BHR |
| | 7 | Ligate mouse distal homology arm upstream of human insert in construct of step 6 to create 6hVκ BACvec | Ligation |
| 16hVκ | 1 | Insert NeoR at distal end of RP11-1061b13 BAC | BHR |
| | 2 | Replace cmR in construct of step 1 with specR | BHR |
| | 3 | Insert Hyg selection cassette at distal end of mouse Igκ locus using CT7-302g12 | BHR BAC |
| | 4 | Ligate mouse distal homology arm upstream of human insert from construct of step 2 to create 16hVκ BACvec | Ligation |
| 30hVκ | 1 | Insert HygR at distal end of RP11-99g6 BAC | BHR |
| | 2 | Replace cmR in construct of step 1 with specR | BHR |
| | 3 | Insert Neo selection cassette at distal end of mouse Igκ locus using CT7-302g12 BAC | BHR |
| | 4 | Ligate mouse distal homology arm upstream of human insert from construct of step 2 to create 30hVκ BACvec | Ligation |
| 40hVκ | 1 | Insert NeoR at distal end of hIgH locus in CTD-2559d6 BAC | BHR |
| | 2 | Replace cmR in construct of step 1 with specR | BHR |
| | 3 | Ligate mouse distal homology arm upstream of hIgH locus in construct of step 2 to create 40hVκ BACvec | Ligation |

Modification of embryonic stem (ES) cells and generation of mice. ES cell (F1H4) targeting was performed using the VELOCIGENE® genetic engineering method as described (Valenzuela et al., 2003). Derivation of mice from modified ES cells by either blastocyst (Valenzuela et al., 2003) or 8-cell injection (Poueymirou et al., 2007) was as described. Targeted ES cells and mice were confirmed by screening DNA from ES cells or mice with unique sets of probes and primers in a PCR based assay (e.g., FIGS. 3A, 3B and 3C). All mouse studies were overseen and approved by Regeneron's Institutional Animal Care and Use Committee (IACUC).

Karyotype Analysis and Fluorescent in situ Hybridization (FISH). Karyotype Analysis was performed by Coriell Cell Repositories (Coriell Institute for Medical Research, Camden, N.J.). FISH was performed on targeted ES cells as described (Valenzuela et al., 2003). Probes corresponding to either mouse BAC DNA or human BAC DNA were labeled by nick translation (Invitrogen) with the fluorescently labeled dUTP nucleotides spectrum orange or spectrum green (Vysis).

Immunoglobulin Heavy Chain Variable Gene Locus. Humanization of the variable region of the heavy chain locus was achieved in nine sequential steps by the direct replacement of about three million base pairs (Mb) of contiguous mouse genomic sequence containing all V$_H$, D$_N$ and J$_H$ gene segments with about one Mb of contiguous human genomic sequence containing the equivalent human gene segments (FIG. 1A and Table 1) using VELOCIGENE® genetic engineering technology (see, e.g., U.S. Pat. No. 6,586,251 and Valenzuela et al., 2003).

The intron between J$_H$ gene segments and constant region genes (the J-C intron) contains a transcriptional enhancer (Neuberger, M. S. (1983). Expression and regulation of immunoglobulin heavy chain gene transfected into lymphoid cells. Embo J 2, 1373-1378) followed by a region of simple repeats required for recombination during isotype switching (Kataoka, T., Kawakami, T., Takahashi, N., and Honjo, T. (1980). Rearrangement of immunoglobulin gamma 1-chain gene and mechanism for heavy-chain class switch. Proc Natl Acad Sci USA 77, 919-923). The junction between human V$_H$-D$_H$-J$_H$ region and the mouse C$_H$ region (the proximal junction) was chosen to maintain the mouse heavy chain intronic enhancer and switch domain in order preserve both efficient expression and class switching of the humanized heavy chain locus within the mouse. The exact nucleotide position of this and subsequent junctions in all the replacements was possible by use of the VELOCIGENE® genetic engineering method (supra), which employed bacterial homologous recombination driven by synthesized oligonucleotides. Thus, the proximal junction was placed about 200 bp downstream from the last J$_H$ gene segment and the distal junction was placed several hundred upstream of the most 5' V$_H$ gene segment of the human locus and about 9 kb downstream from the mouse V$_H$1-86 gene segment, also known as J558.55. The mouse V$_H$1-86 (J558.55) gene segment is the most distal heavy chain variable gene segment, reported to be a pseudogene in C57BL/6 mice, but potentially active, albeit with a poor RSS sequence, in the targeted 129 allele. The distal end of the mouse heavy chain locus reportedly may contain control elements that regulate locus expression and/or rearrangement (Pawlitzky et al., 2006).

Figure 2A:
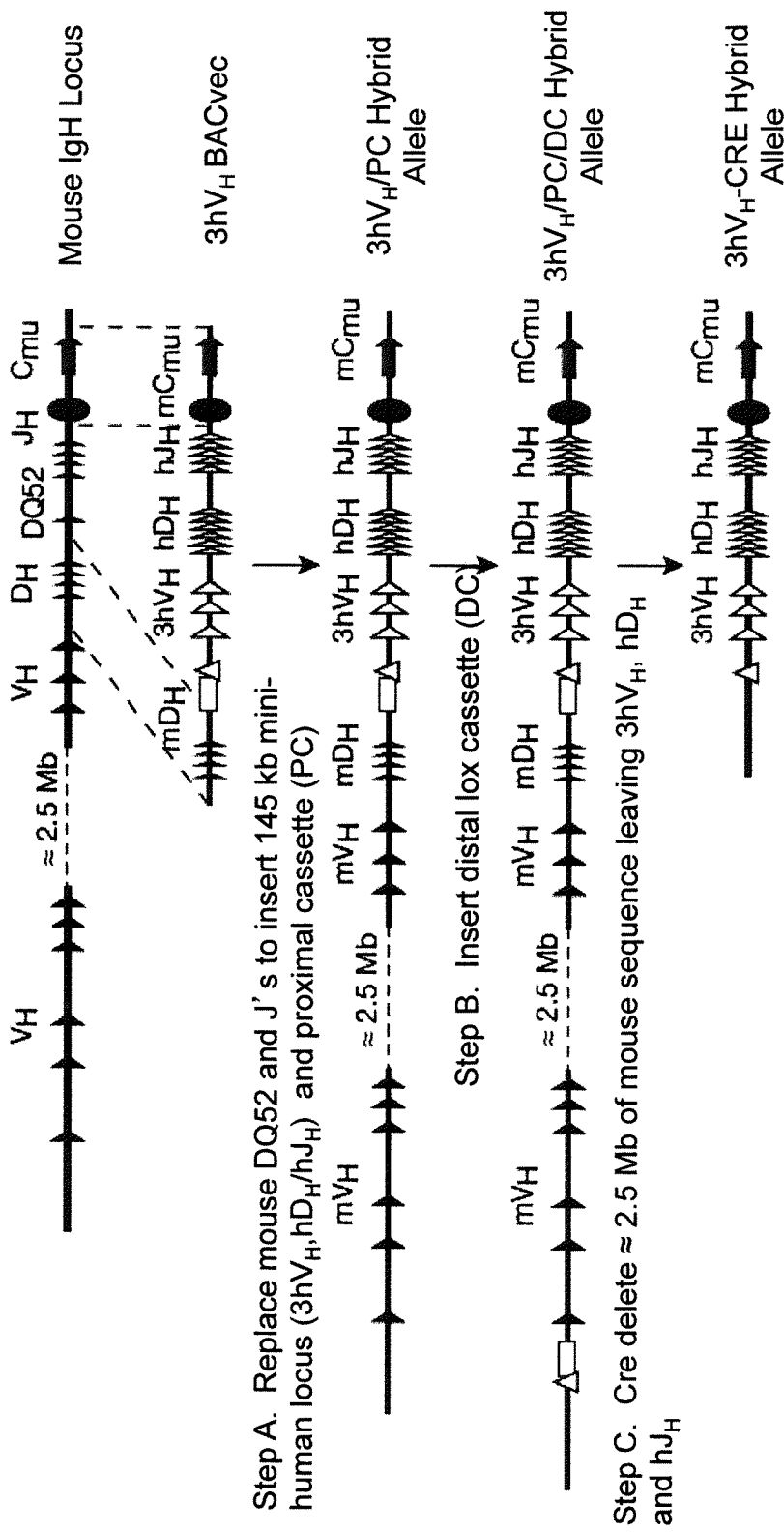
FIG. 2A shows a detailed illustration, not to scale, of three initial steps (A-C) for direct genomic replacement of a mouse immunoglobulin heavy chain variable gene locus that results in deletion of all mouse $V_H$, $D_H$ and $J_H$ gene segments and replacement with three human $V_H$, all human $D_H$ and $J_H$ gene segments. A targeting vector for a first insertion of human immunoglobulin heavy chain gene segments is shown (3hV$_H$ BACvec) with a 67 kb 5' mouse homology arm, a selection cassette (open rectangle), a site-specific recombination site (open triangle), a 145 kb human genomic fragment and an 8 kb 3' mouse homology arm. Human (open symbols) and mouse (closed symbols) immunoglobulin gene segments, additional selection cassettes (open rectangles) and site-specific recombination sites (open triangles) inserted from subsequent targeting vectors are shown.
Figure 3A:
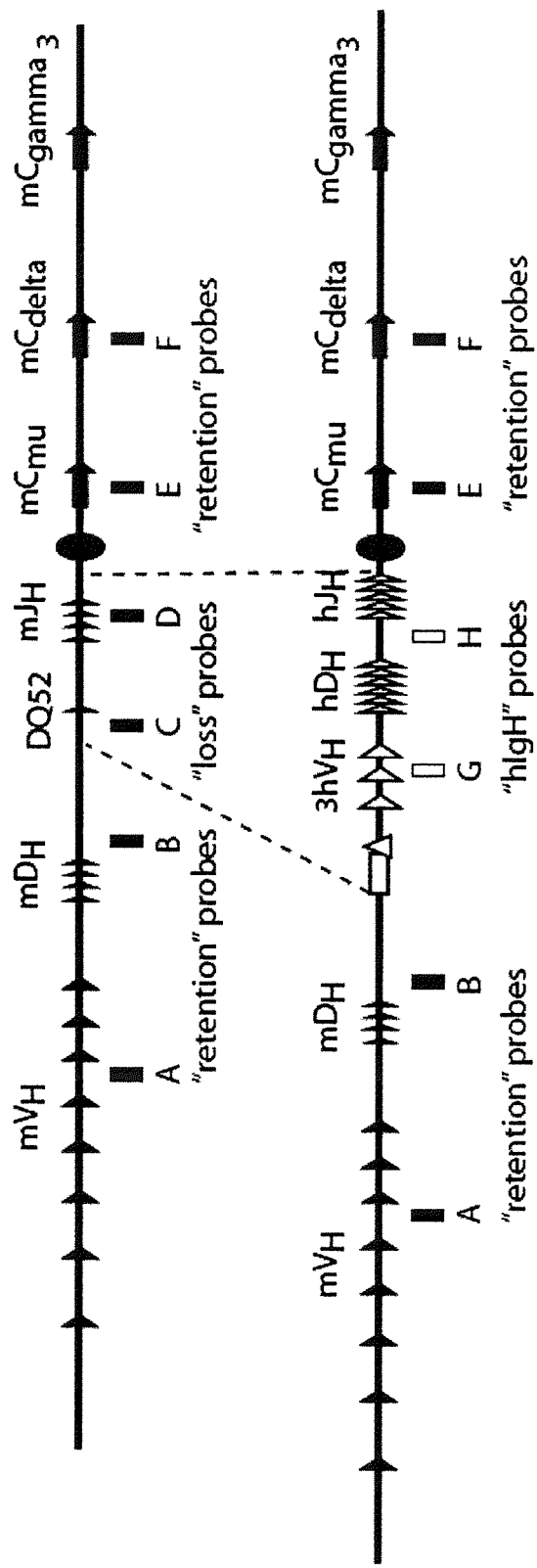
FIG. 3A shows a general illustration, not to scale, of a screening strategy including the locations of quantitative PCR (qPCR) primer/probe to detect insertion of human heavy chain gene sequences and loss of mouse heavy chain gene sequences in targeted embryonic stem (ES) cells. The screening strategy in ES cells and mice for a first human heavy gene insertion is shown with qPCR primer/probe sets for the deleted region ("loss" probes C and D), the region inserted ("hIgH" probes G and H) and flanking regions ("retention" probes A, B, E and F) on an unmodified mouse chromosome (top) and a correctly targeted chromosome (bottom).

A first insertion of human immunoglobulin DNA sequence into the mouse was achieved using 144 kb of the proximal end of the human heavy chain locus containing 3 V$_H$, all 27 D$_H$ and 9 J$_H$ human gene segments inserted into the proximal end of the mouse IgH locus, with a concomitant 16.6 kb deletion of mouse genomic sequence, using about 75 kb of mouse homology arms (Step A, FIG. 2A; Tables 1 and 3, 3hV$_H$). This large 144kb insertion and accompanying 16.6 kb deletion was performed in a single step (Step A) that occurred with a frequency of 0.2% (Table 3). Correctly targeted ES cells were scored by a loss-of-native-allele (LONA) assay (Valenzuela et at, 2003) using probes within and flanking the deleted mouse sequence and within the inserted human sequence, and the integrity of the large human insert was verified using multiple probes spanning the entire insertion (FIGS. 3A, 3B and 3C). Because many rounds of sequential ES cell targeting were anticipated, targeted ES cell clones at this, and all subsequent, steps were subjected to karyotypic analysis (supra) and only those clones showing normal karyotypes in at least 17 of 20 spreads were utilized for subsequent steps.

Targeted ES cells from Step A were re-targeted with a BACvec that produced a 19 kb deletion at the distal end of the heavy chain locus (Step B, FIG. 2A). The Step B BACvec contained a hygromycin resistance gene (hyg) in contrast to the neomycin resistance gene (neo) contained on the BACvec of Step A. The resistance genes from the two BACvecs were designed such that, upon successful targeting to the same chromosome, approximately three Mb of the mouse heavy chain variable gene locus containing all of the mouse $V_H$ gene segments other than $V_H$1-86 and all of the $D_H$ gene segments other than DQ52, as well as the two resistance genes, were flanked by loxP sites; DQ52 and all of the mouse $J_H$ chain gene segments were deleted in Step A. ES cell clones doubly targeted on the same chromosome were identified by driving the $3hV_H$ proximal cassette to homozygosity in high G418 (Mortensen, R. M. et al. (1992) Production of homozygous mutant ES cells with a single targeting construct. Mol Cell Biol 12, 2391-2395) and following the fate of the distal hyg cassette. Mouse segments up to four Mb in size, having been modified in a manner to be flanked by loxP sites, have been successfully deleted in ES cells by transient expression of CRE recombinase with high efficiencies (up to ≈11%) even in the absence of drug selection (Zheng, B. et al. (2000) Engineering mouse chromosomes with Cre-loxP: range, efficiency, and somatic applications. Mol Cell Biol 20, 648-655). In a similar manner, the inventors achieved a three Mb deletion in 8% of ES cell clones following transient CRE expression (Step C, FIG. 2A; Table 3). The deletion was scored by the LONA assay using probes at either end of the deleted mouse sequence, as well as the loss of neo and hyg and the appearance of a PCR product across the deletion point containing the sole remaining loxP site. Further, the deletion was confirmed by fluorescence in situ hybridization (data not shown).

Figure 2B:
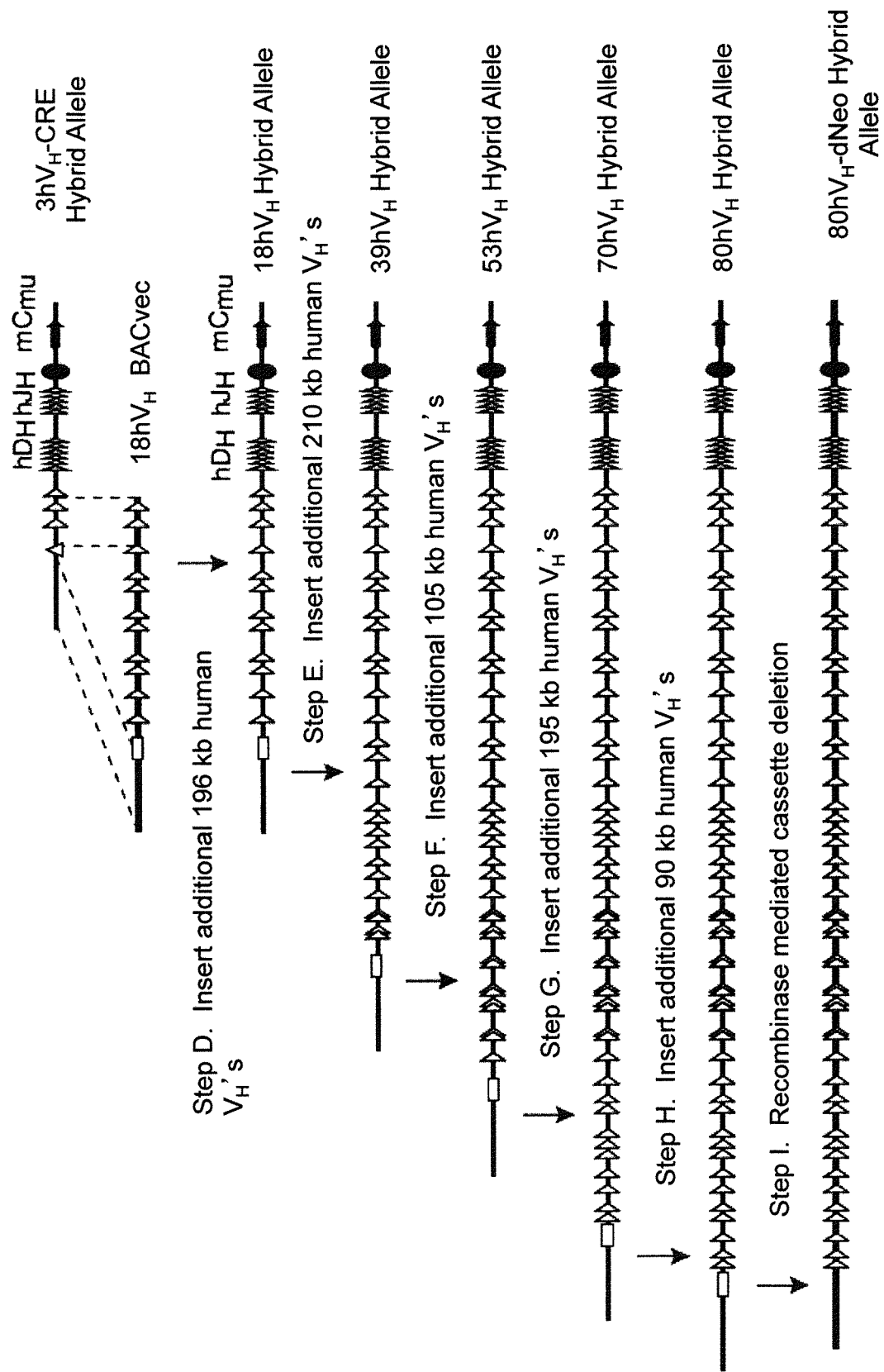
FIG. 2B shows a detailed illustration, not to scale, of six additional steps (D-I) for direct genomic replacement of a mouse immunoglobulin heavy chain variable gene locus that results in the insertion of 77 additional human $V_H$ gene segments and removal of a final selection cassette. A targeting vector for insertion of additional human $V_H$ gene segments (18hV$_H$ BACvec) to the initial insertion of human heavy chain gene segments (3hV$_H$-CRE Hybrid Allele) is shown with a 20 kb 5' mouse homology arm, a selection cassette (open rectangle), a 196 kb human genomic fragment and a 62 kb human homology arm that overlaps with the 5' end of the initial insertion of human heavy chain gene segments which is shown with a site-specific recombination site (open triangle) located 5' to the human gene segments. Human (open symbols) and mouse (closed symbols) immunoglobulin gene segments and additional selection cassettes (open rectangles) inserted by subsequent targeting vectors are shown.

The remainder of the human heavy chain variable region was added to the $3hV_H$ allele in a series of 5 steps using the VELOCIGENE® genetic engineering method (Steps E-H, FIG. 2B), with each step involving precise insertion of up to 210 kb of human gene sequences. For each step, the proximal end of each new BACvec was designed to overlap the most distal human sequences of the previous step and the distal end of each new BACvec contained the same distal region of mouse homology as used in Step A. The BACvecs of steps D, F and H contained neo selection cassettes, whereas those of steps E and G contained hyg selection cassettes, thus selections were alternated between G418 and hygromycin. Targeting in Step D was assayed by the loss of the unique PCR product across the distal loxP site of $3hV_H$ Hybrid Allele. Targeting for Steps E through I was assayed by loss of the previous selection cassette. In the final step (Step I, FIG. 2B), the neo selection cassette, flanked by Frt sites (McLeod, M. et al. (1986) Identification of the crossover site during FLP-mediated recombination in the Saccharomyces cerevisiae plasmid 2 microns circle. Mol Cell Biol 6, 3357-3367), was removed by transient FLPe expression (Buchholz, F. et al. (1998) Improved properties of FLP recombinase evolved by cycling mutagenesis. Nat Biotechnol 16, 657-662). The human sequences of the BACvecs for Steps D, E and G were derived from two parental human BACs each, whereas those from Steps F and H were from single BACs. Retention of human sequences was confirmed at every step using multiple probes spanning the inserted human sequences (as described above, e.g. FIGS. 3A, 3B and 3C). Only those clones with normal karyotype and germline potential were carried forward in each step. ES cells from the final step were still able to contribute to the germline after nine sequential manipulations (Table 3). Mice homozygous for each of the heavy chain alleles were viable, appeared healthy and demonstrated an essentially wild-type humoral immune system (see Example 3).

TABLE 3

| Hybrid Allele | Human sequence | Targeting construct | Targeting efficiency | % usage | Total $V_H$ | Functional $V_H$ |
|---|---|---|---|---|---|---|
| $3hV_H$ | 144 kb | 240 kb | 0.2% | 5 | 3 | 3 |
| $3hV_H$/DC | 144 kb | 110 kb | 0.1% | 5 | 3 | 3 |
| $3hV_H$-CRE | 144 kb | — | 8% | 5 | 3 | 3 |
| $18hV_H$ | 340 kb | 272 kb | 0.1% | 25 | 18 | 12 |
| $39hV_H$ | 550 kb | 282 kb | 0.2% | 60 | 39 | 25 |
| $53hV_H$ | 655 kb | 186 kb | 0.4% | 65 | 53 | 29 |
| $70hV_H$ | 850 kb | 238 kb | 0.5% | 90 | 70 | 39 |
| $80hV_H$ | 940 kb | 124 kb | 0.2% | 100 | 80 | 43 |
| $80hV_H$dNeo | 940 kb | — | 2.6% | 100 | 80 | 43 |

Immunoglobulin κ Light Chain Variable Gene Locus. The κ light chain variable region was humanized in eight sequential steps by the direct replacement of about three Mb of mouse sequence containing all Vκ and Jκ gene segments with about 0.5 Mb of human sequence containing the proximal human Vκ and Jκ gene segments in a manner similar to that of the heavy chain (FIG. 1B; Tables 2 and 4).

Figure 2C:
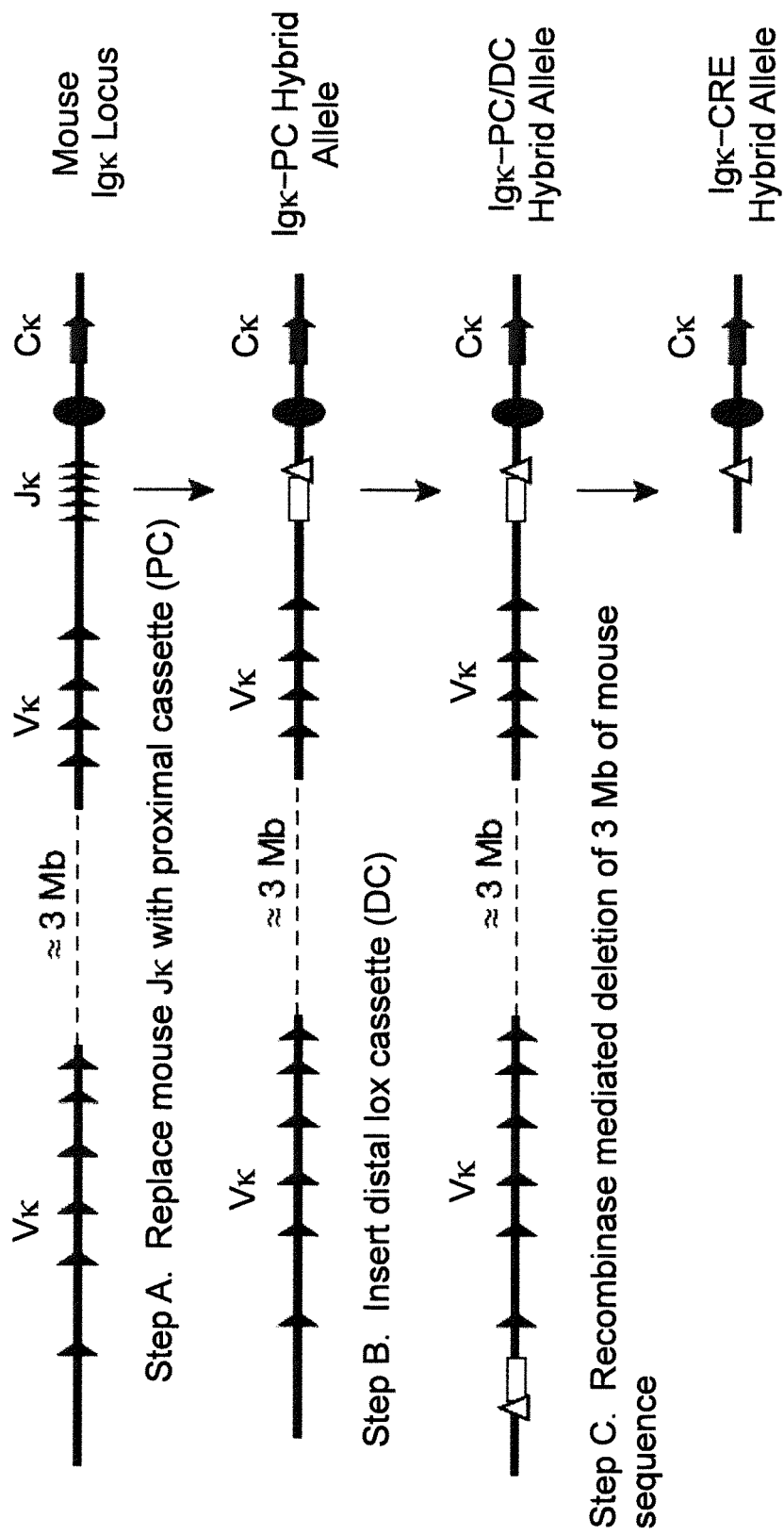
FIG. 2C shows a detailed illustration, not to scale, of three initial steps (A-C) for direct genomic replacement of a mouse immunoglobulin κ light chain variable gene locus that results in deletion of all mouse Vκ, and Jκ gene segments (Igκ-CRE Hybrid Allele). Selection cassettes (open rectangles) and site-specific recombination sites (open triangles) inserted from the targeting vectors are shown.

The variable region of the human κ light chain locus contains two nearly identical 400 kb repeats separated by a 800 kb spacer (Weichhold, G. M. et al. (1993) The human immunoglobulin kappa locus consists of two copies that are organized in opposite polarity. Genomics 16, 503-511). Because the repeats are so similar, nearly all of the locus diversity can be reproduced in mice by using the proximal repeat. Further, a natural human allele of the κ light chain locus missing the distal repeat has been reported (Schaible, G. et al. (1993) The immunoglobulin kappa locus: polymorphism and haplotypes of Caucasoid and non-Caucasoid individuals. Hum Genet 91, 261-267). The inventors replaced about three Mb of mouse κ light chain variable gene sequence with about 0.5 Mb of human κ light chain variable gene sequence to effectively replace all of the mouse Vκ and Jκ gene segments with the proximal human Vκ and all of the human Jκ gene segments (FIGS. 2C and 2D; Tables 2 and 4). In contrast to the method described in Example 1 for the heavy chain locus, the entire mouse Vκ gene region, containing all Vκ and Jλ gene segments, was deleted in a three-step process before any human sequence was added. First, a neo cassette was introduced at the proximal end of the variable region (Step A, FIG. 2C). Next, a hyg cassette was inserted at the distal end of the κ locus (Step B, FIG. 2C). LoxP sites were again situated within each selection cassette such that CRE treatment induced deletion of the remaining 3 Mb of the mouse Vκ region along with both resistance genes (Step C, FIG. 2C).

Figure 2D:
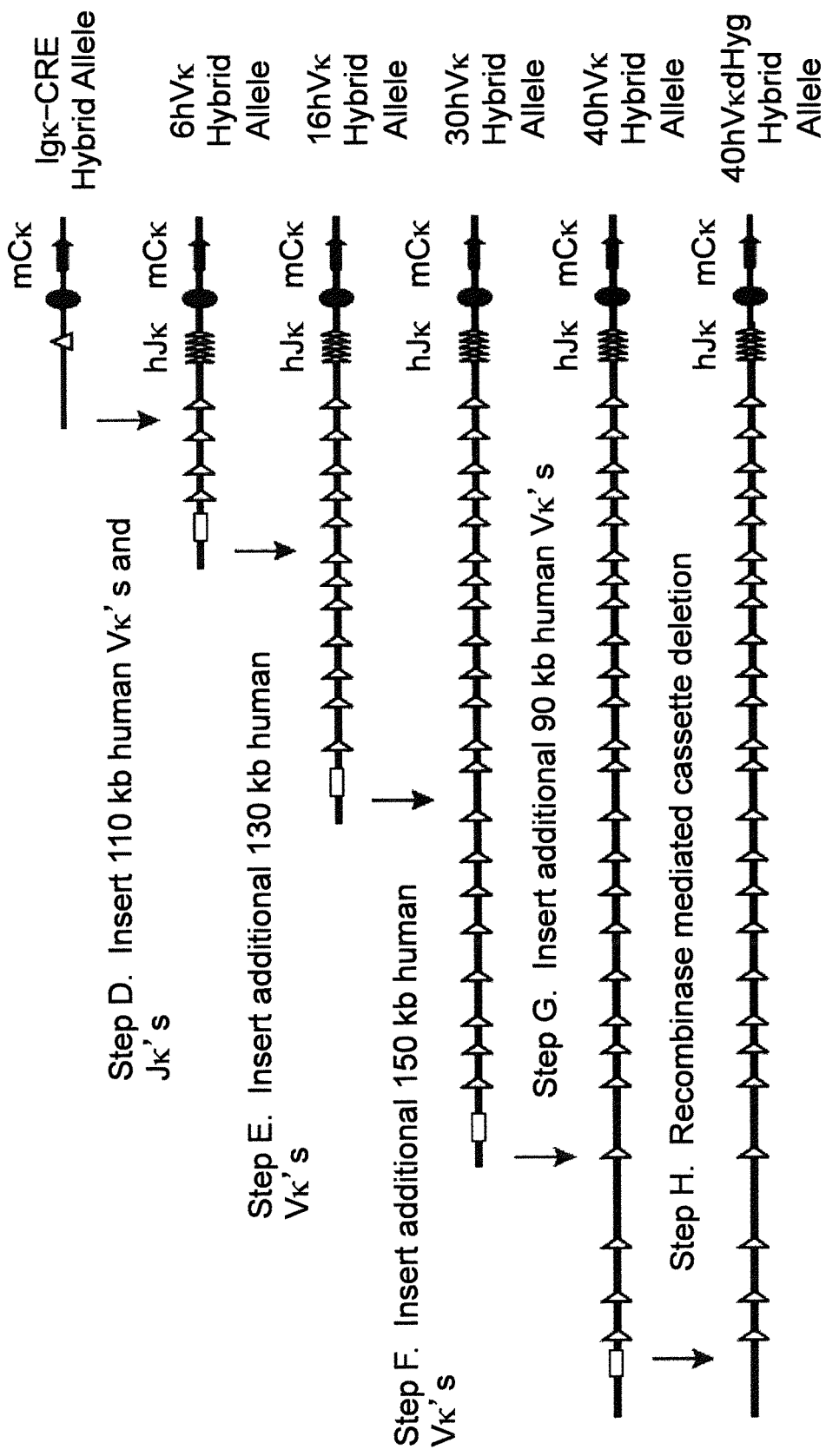
FIG. 2D shows a detailed illustration, not to scale, of five additional steps (D-H) for direct genomic replacement of a mouse immunoglobulin κ light chain variable gene locus that results in the insertion of all human Vκ and Jκ gene segments in the proximal repeat and deletion of the final selection cassette (40hVκdHyg Hybrid Allele). Human (open symbols) and mouse (closed symbols) immunoglobulin gene segments and additional selection cassettes (open rectangles) inserted by subsequent targeting vectors are shown.

A human genomic fragment of about 480 kb in size containing the entire immunoglobulin κ light chain variable region was inserted in four sequential steps (FIG. 2D; Tables 2 and 4), with up to 150 kb of human immunoglobulin κ light chain sequence inserted in a single step, using methods similar to those employed for the heavy chain (see Example 1). The final hygromycin resistance gene was removed by transient FLPe expression. As with the heavy chain, targeted ES cell clones were evaluated for integrity of the entire human insert, normal karyotype and germ-line potential after every step. Mice homozygous for each of the κ light chain chain alleles were generated and found to be healthy and of normal appearance.

TABLE 4

| Hybrid Allele | Human sequence | Targeting construct | Targeting efficiency | % usage | Total Vκ | Functional Vκ |
|---|---|---|---|---|---|---|
| Igκ-PC | 0 | 132 kb | 1.1% | — | — | — |
| Igκ-PC/DC | 0 | 90 kb | 0.4% | — | — | — |
| Igκ-CRE | 0 | — | 1% | — | — | — |
| 6hVκ | 110 kb | 122 kb | 0.3% | 14 | 6 | 4 |
| 16hVκ | 240 kb | 203 kb | 0.4% | 47 | 16 | 11 |
| 30hVκ | 390 kb | 193 kb | 0.1% | 70 | 30 | 18 |
| 40hVκ | 480 kb | 185 kb | 0.2% | 100 | 40 | 25 |
| 40hVκdHyg | 480 kb | — | 0.7% | 100 | 40 | 25 |

Example 2

Generation of Fully Humanized Mice by Combination of Multiple Humanized Immunoglobulin Alleles At several points, ES cells bearing a portion of the human immunoglobulin heavy chain or κ light chain variable repertoires as described in Example 1 were microinjected and the resulting mice bred to create multiple versions of VELOCIMMUNE® mice with progressively larger fractions of the human germline immunoglobulin repertoires (Table 5; FIGS. 5A and 5B). VELOCIMMUNE® 1 (V1) mice possess 18 human $V_H$ gene segments and all of the human $D_H$ and $J_H$ gene segments combined with 16 human Vκ gene segments and all the human Jκ gene segments. VELOCIMMUNE® 2 (V2) and VELOCIMMUNE® (V3) mice have increased variable repertoires bearing a total of 39 $V_H$ and 30 Vκ, and 80 $V_H$ and 40 Vκ, respectively. Since the genomic regions encoding the mouse $V_H$, $D_H$ and $J_H$ gene segments, and Vκ and Jλ gene segments, have been completely replaced, antibodies produced by any version of VELOCIMMUNE® mice contain human variable regions linked to mouse constant regions. The mouse λ light chain loci remain intact in all versions of the VELOCIMMUNE® mice and serve as a comparator for efficiency of expression of the various VELOCIMMUNE® κ light chain loci.

Mice doubly homozygous for both immunoglobulin heavy chain and κ light chain humanizations were generated from a subset of the alleles described in Example 1. All genotypes observed during the course of breeding to generate the doubly homozygous mice occurred in roughly Mendelian proportions. Male progeny homozygous for each of the human heavy chain alleles showed reduced fertility. Reduced fertility resulted from loss of mouse ADAM6 activity. The mouse heavy chain variable gene locus contains two embedded functional ADAM6 genes (ADAM6a and ADAM6b). During humanization of the mouse heavy chain variable gene locus, the inserted human genomic sequence contained an ADAM6 pseudogene. Mouse ADAM6 may be required for fertility, and thus lack of mouse ADAM6 genes in humanized heavy chain variable gene loci might lead to reduced fertility in these mice notwithstanding the presence of the human pseudogene. Examples 7-9 describe the precise replacement of deleted mouse ADAM6 genes back into a humanized heavy chain variable gene locus, and restoration of a wild-type level of fertility in mice with a humanized heavy chain immunoglobulin locus.

TABLE 5

| Version of VELOC-IMMUNE® Mouse | Heavy Chain | | | κ Light Chain | | |
|---|---|---|---|---|---|---|
| | Human $V_H$ | Allele | 5' $V_H$ gene | Human Vκ | Allele | 5' Vκ gene |
| V1 | 18 | 18h$V_H$ | $V_H$1-18 | 16 | 16hVκ | Vκ1-16 |
| V2 | 39 | 39h$V_H$ | $V_H$4-39 | 30 | 30hVκ | Vκ2-29 |
| V3 | 80 | 80h$V_H$ | $V_H$3-74 | 40 | 40hVκ | Vκ2-40 |

Example 3

Lymphocyte Populations in Mice with Humanized Immunoglobulin Genes

Mature B cell populations in the three different versions of VELOCIMMUNE® mice were evaluated by flow cytometry.

Briefly, cell suspensions from bone marrow, spleen and thymus were made using standard methods. Cells were resuspended at $5 \times 10^5$ cells/mL in BD Pharmingen FACS staining buffer, blocked with anti-mouse CD16/32 (BD Pharmingen), stained with the appropriate cocktail of antibodies and fixed with BD Cytofix™ all according to the manufacturer's instructions. Final cell pellets were resuspended in 0.5 mL staining buffer and analyzed using a BD FACSCALIBUR™ and BD CELLQUEST PRO™ software. All antibodies (BD Pharmingen) were prepared in a mass dilution/cocktail and added to a final concentration of 0.5 mg/$10^5$ cells. Antibody cocktails for bone marrow (A-D) staining were as follows: A: anti-mouse IgM$^b$-FITC, anti-mouse IgM$^a$-PE, anti-mouse CD45R(B220)-APC; B: anti-mouse CD43(S7)-PE, anti-mouse CD45R(B220)-APC; C: anti-mouse CD24(HSA)-PE; anti-mouse CD45R(B220)-APC; D: anti-mouse BP-1-PE, anti-mouse CD45R(B220)-APC. Antibody cocktails for spleen and inguinal lymph node (E-H) staining were as follows: E: anti-mouse IgM$^b$-FITC, anti-mouse IgM$^a$-PE, anti-mouse CD45R(B220)-APC; F: anti-mouse Ig, ⌊1, ⌊2, ⌊3 Light Chain-FITC, anti mouse Igκ Light Chain-PE, anti-mouse CD45R(B220)-APC; G: anti-mouse Ly6G/C-FITC, anti-mouse CD49b (DX5)-PE, anti-mouse CD11b-APC; H: anti-mouse CD4 (L3T4)-FITC, anti-mouse CD45R(B220)-PE, anti-mouse CD8a-APC. Results are shown in FIG. 6.

Lymphocytes isolated from spleen or lymph node of homozygous VELOCIMMUNE® mice were stained for surface expression of the markers B220 and IgM and analyzed using flow cytometry (FIG. 6). The sizes of the B220$^+$ IgM$^+$ mature B cell populations in all versions of VELOCIMMUNE® mice tested were virtually identical to those of wild type mice, regardless of the number of $V_H$ gene segments they contained. In addition, mice containing homozygous hybrid humanized immunoglobulin heavy chain loci, even those with only 3 $V_H$ gene segments but normal mouse immunoglobulin κ light chain loci or mice containing homozygous hybrid humanized κ light chain loci with normal mouse immunoglobulin heavy chain loci, also had normal numbers of B220$^+$ IgM$^+$ cells in their peripheral compartments (not shown). These results indicate that chimeric loci with human variable gene segments and mouse constant regions can fully populate the mature B cell compartment. Further, the number of variable gene segments at either the heavy chain or κ light chain loci, and thus the theoretical diversity of the antibody repertoire, does not correlate with the ability to generate wild type populations of mature B cells. In contrast, mice with randomly integrated fully-human immunoglobulin transgenes and inactivated mouse immunoglobulin loci have reduced numbers of B cells in these compartments, with the severity of the deficit depending on the number of variable gene segments included in the transgene (Green, L. L., and Jakobovits, A. (1998). Regulation of B cell development by variable gene complexity in mice reconstituted with human immunoglobulin yeast artificial chromosomes. J Exp Med 188, 483-495). This demonstrates that the "in situ genetic humanization" strategy results in a fundamentally different functional outcome than the randomly integrated transgenes achieved in the "knockout-plus-transgenic" approach.

Allelic Exclusion and Locus Choice. The ability to maintain allelic exlusion was examined in mice heterozygous for different versions of the humanized immunoglobulin heavy chain locus.

The humanization of the immunoglobulin loci was carried out in an F1 ES line (F1H4 (Valenzuela et al., 2003)), derived from 12956/SvEvTac and C57BL/6NTac heterozygous embryos. The human heavy chain germline variable gene sequences are targeted to the 129S6 allele, which carries the IgM$^a$ haplotype, whereas the unmodified mouse C576BL/6N allele bears the IgM$^b$ haplotype. These allelic forms of IgM can be distinguished by flow cytometry using antibodies specific to the polymorphisms found in the IgM$^a$ or IgM$^b$ alleles. As shown in FIG. 6 (bottom row), the B cells identified in mice heterozygous for each version of the humanized heavy chain locus only express a single allele, either IgM$^a$ (the humanized allele) or IgM$^b$ (the wild type allele). This demonstrates that the mechanisms involved in allelic exclusion are intact in VELOCIMMUNE® mice. In addition, the relative number of B cells positive for the humanized allele (IgM$^a$) is roughly proportional to the number of V$_H$ gene segments present. The humanized immunoglobulin locus is expressed in approximately 30% of the B cells in VELOCIMMUNE® 1 heterozygote mice, which have 18 human V$_H$ gene segments, and in 50% of the B cells in VELOCIMMUNE® 2 and 3 (not shown) heterozygote mice, with 39 and 80 human V$_H$ gene segments, respectively. Notably, the ratio of cells expressing the humanized versus wild type mouse allele (0.5 for VELOCIMMUNE® 1 mice and 0.9 for VELOCIMMUNE® 2 mice) is greater than the ratio of the number of variable gene segments contained in the humanized versus wild type loci (0.2 for VELOCIMMUNE® 1 mice and 0.4 for VELOCIMMUNE® 2 mice). This may indicate that the probability of allele choice is intermediate between a random choice of one or the other chromosome and a random choice of any particular V segment RSS. Further, there may be a fraction of B-cells, but not all, in which one allele becomes accessible for recombination, completes the process and shuts down recombination before the other allele becomes accessible. In addition, the even distribution of cells that have surface IgM (sIgM) derived from either the hybrid humanized heavy chain locus or the wild type mouse heavy chain locus is evidence that the hybrid locus is operating at a normal level. In contrast, randomly integrated human immunoglobulin transgenes compete poorly with wild type mouse immunoglobulin loci (Bruggemann, M. et al. (1989) A repertoire of monoclonal antibodies with human heavy chains from transgenic mice. PNAS 86, 6709-6713; Green et al., 1994; Tuaillon, N. et al. (1993) Human immunoglobulin heavy-chain minilocus recombination in transgenic mice: gene-segment use in mu and gamma transcripts. Proc Natl Acad Sci USA 90, 3720-3724). This further demonstrates the immunoglobulins produced by VELOCIMMUNE® mice are functionally different than those produced by randomly integrated transgenes in mice made by "knockout-plus-transgenic" approaches.

Polymorphisms of the Cκ regions are not available in 129S6 or C57BL/6N to examine allelic exclusion of humanized versus non-humanized κ light chain loci. However, VELOCIMMUNE® mice all possess wild type mouse λ light chain loci, therefore, it is possible to observe whether rearrangement and expression of humanized κ light chain loci can prevent mouse λ light chain expression. The ratio of the number of cells expressing the humanized κ light chain relative to the number of cells expressing mouse λ light chain was relatively unchanged in VELOCIMMUNE® mice compared with wild type mice, regardless of the number of human Vκ gene segments inserted at the κ light chain locus (FIG. 6, third row from top). In addition there was no increase in the number of double positive (κ plus λ) cells, indicating that productive recombination at the hybrid κ light chain loci results in appropriate suppression of recombination of the mouse λ light chain loci. In contrast, mice containing randomly integrated κ light chain transgenes with inactivated mouse κ light chain loci—but wild type mouse λ light chain loci—exhibit dramatically increased λ/κ ratios (Jakobovits, 1998), implying that the introduced κ light chain transgenes do not function well in such mice. This further demonstrates the different functional outcome observed in immunoglobulins made by VELOCIMMUNE® mice as compared to those made by "knockout-plus-transgenic" mice.

B cell Development. Because the mature B cell populations in VELOCIMMUNE® mice resemble those of wild type mice (described above), it is possible that defects in early B cell differentiation are compensated for by the expansion of mature B cell populations. The various stages of B cell differentiation were examined by analysis of B cell populations using flow cytometry. Table 6 sets forth the ratio of the fraction of cells in each B cell lineage defined by FACs, using specific cell surface markers, in VELOCIMMUNE® mice compared to wild type littermates.

Early B cell development occurs in the bone marrow, and different stages of B cell differentiation are characterized by changes in the types and amounts of cell surface marker expression. These differences in surface expression correlate with the molecular changes occurring at the immunoglobulin loci inside the cell. The pro-B to pre-B cell transition requires the successful rearrangement and expression of functional heavy chain protein, while transition from the pre-B to mature B stage is governed by the correct rearrangement and expression of a κ or λ light chain. Thus, inefficient transition between stages of B cell differentiation can be detected by changes in the relative populations of B cells at a given stage.

TABLE 6

| Version of VELOC-IMMUNE ® Mice | Bone Marrow | | | | Spleen | |
|---|---|---|---|---|---|---|
| | pro-B CD43$^{hi}$ B220$^{lo}$ | pre-B CD24$^{hi}$ B220$^{lo}$ | Immature B220$^{lo}$ IgM$^+$ | Mature B220$^{hi}$ IgM$^+$ | Emerging B220$^{hi}$ IgM$^+$ IgD$^+$ | Mature B220hi IgM+ |
| V1 | 1.1 | 1.0 | 0.9 | 1.0 | 1.1 | 1.0 |
| V2 | 1.0 | 1.0 | 1.0 | 1.0 | 1.0 | 1.0 |
| V3 | 1.0 | 1.0 | 1.1 | 1.0 | 1.0 | 1.1 |

No major defects were observed in B cell differentiation in any of the VELOCIMMUNE® mice. The introduction of human heavy chain gene segments does not appear to affect the pro-B to pre-B transition, and introduction of human κ light chain gene segments does not affect the pre-B to B transition in VELOCIMMUNE® mice. This demonstrates that "reverse chimeric" immunoglobulin molecules possessing human variable regions and mouse constants function normally in the context of B cell signaling and co-receptor molecules leading to appropriate B cell differentiation in a mouse environment. In contrast, the balance between the different populations during B cell differentiation are perturbed to varying extents in mice that contain randomly integrated immunoglobulin transgenes and inactivated endogenous heavy chain or κ light chain loci (Green and Jakobovits, 1998).

Example 4

Variable Gene Repertoire in Humanized Immunoglobulin Mice

Usage of human variable gene segments in the humanized antibody repertoire of VELOCIMMUNE® mice was analyzed by reverse transcriptase-polymerase chain reaction (RT-PCR) of human variable regions from multiple sources including splenocytes and hybridoma cells. Variable region sequence, gene segment usage, somatic hypermutation, and junctional diversity of rearranged variable region gene segments were determined.

Briefly, total RNA was extracted from $1 \times 10^7$-$2 \times 10^7$ splenocytes or about $10^4$-$10^5$ hybridoma cells using TRIZOL™ (Invitrogen) or Qiagen RNEASY™ Mini Kit (Qiagen) and primed with mouse constant region specific primers using the SUPERSCRIPT™ III One-Step RT-PCR system (Invitrogen). Reactions were carried out with 2-5 μL of RNA from each sample using the aforementioned 3' constant specific primers paired with pooled leader primers for each family of human variable regions for both the heavy chain and κ light chain, separately. Volumes of reagents and primers, and RT-PCR/PCR conditions were performed according to the manufacturer's instructions. Primers sequences were based upon multiple sources (Wang, X. and Stollar, B. D. (2000) Human immunoglobulin variable region gene analysis by single cell RT-PCR. J Immunol Methods 244:217-225; Ig-primer sets, Novagen). Where appropriate, nested secondary PCR reactions were carried out with pooled family-specific framework primers and the same mouse 3' immunoglobulin constant-specific primer used in the primary reaction. Aliquots (5 μL) from each reaction were analyzed by agarose electrophoresis and reaction products were purified from agarose using a MONTAGE™ Gel Extraction Kit (Millipore). Purified products were cloned using the TOPO™ TA Cloning System (Invitrogen) and transformed into DH10β E. coli cells by electroporation. Individual clones were selected from each transformation reaction and grown in 2 mL LB broth cultures with antibiotic selection overnight at 37° C. Plasmid DNA was purified from bacterial cultures by a kit-based approach (Qiagen).

Immunoglobulin Variable Gene Usage. Plasmid DNA of both heavy chain and κ light chain clones were sequenced with either T7 or M13 reverse primers on the ABI 3100 Genetic Analyzer (Applied Biosystems). Raw sequence data were imported into SEQUENCHER™ (v4.5, Gene Codes). Each sequence was assembled into contigs and aligned to human immunoglobulin sequences using IMGT V-Quest (Brochet, X., Lefranc, M. P., and Giudicelli, V. (2008). IMGT/V-QUEST: the highly customized and integrated system for IG and TR standardized V-J and V-D-J sequence analysis. Nucleic Acids Res 36, W503-508) search function to identify human $V_H$, $D_H$, $J_H$ and Vκ, Jκ segment usage. Sequences were compared to germline sequences for somatic hypermutation and recombination junction analysis.

Mice were generated from ES cells containing the initial heavy chain modification (3h$V_H$-CRE Hybrid Allele, bottom of FIG. 2A) by RAG complementation (Chen, J. et al. (1993) RAG-2-deficient blastocyst complementation: an assay of gene function in lymphocyte development. Proc Natl Acad Sci USA 90, 4528-4532), and cDNA was prepared from splenocyte RNA. The cDNA was amplified using primer sets (described above) specific for the predicted chimeric heavy chain mRNA that would arise by V(D)J recombination within the inserted human gene segments and subsequent splicing to either mouse IgM or IgG constant domains. Sequences derived from these cDNA clones (not shown) demonstrated that proper V(D)J recombination had occurred within the human variable gene sequences, that the rearranged human V(D)J gene segments were properly spliced in-frame to mouse constant domains and that class-switch recombination had occurred. Further sequence analysis of mRNA products of subsequent hybrid immunoglobulin loci was performed.

In a similar experiment, B cells from non-immunized wild type and VELOCIMMUNE® mice were separated by flow cytometry based upon surface expression of B220 and IgM or IgG. The B220$^+$IgM$^+$ or surface IgG$^+$ (sIgG$^+$) cells were pooled and $V_H$ and Vκ sequences were obtained following RT-PCR amplification and cloning (described above). Representative gene usage in a set of RT-PCR amplified cDNAs from unimmunized VELOCIMMUNE® 1 mice (Table 7) and VELOCIMMUNE® 3 mice (Table 8) was recorded (*defective RSS; †missing or pseudogene).

TABLE 7

| $V_H$ | Observed |
|---|---|
| 1-18 | 3 |
| 1-17P | 0 |
| 3-16* | 0 |
| 3-15 | 13 |
| 3-13 | 9 |
| 3-11 | 6 |
| 3-9 | 8 |
| 1-8 | 6 |
| 3-7 | 2 |
| 2-5 | 2 |
| 1-3 | 0 |
| 1-2 | 11 |
| 6-1 | 5 |

| $J_H$ | Observed |
|---|---|
| 1 | 2 |
| 2 | 1 |
| 3 | 8 |
| 4 | 33 |
| 5 | 5 |
| 6 | 16 |

| $D_H$ | Observed |
|---|---|
| 1-1 | 1 |
| 2-2 | 2 |
| 3-3 | 4 |
| 4-4 | 0 |
| 5-5 | 0 |
| 5-18 | 4 |
| 6-6 | 5 |
| 1-7 | 7 |
| 2-8 | 0 |
| 3-9 | 4 |
| 3-10 | 2 |
| 4-11 | 1 |

TABLE 7-continued

| | |
|---|---|
| 5-12 | 1 |
| 6-13 | 3 |
| 1-14 | 0 |
| 2-15 | 0 |
| 3-16 | 1 |
| 4-17 | 0 |
| 6-19 | 2 |
| 1-20 | 2 |
| 2-21 | 1 |
| 3-22 | 0 |
| 4-23 | 2 |
| 5-24 | 1 |
| 6-25 | 1 |
| 1-26 | 6 |
| 7-27 | 10 |

| Vκ | Observed |
|---|---|
| 1-16 | 2 |
| 3-15 | |
| 1-12 | 5 |
| 3-11 | 1 |
| 1-9 | 5 |
| 1-8 | 2 |
| 3-7* | 0 |
| 1-6 | 5 |
| 1-5 | 8 |
| 5-2 | 6 |
| 4-1 | 8 |

| Jκ | Observed |
|---|---|
| 1 | 12 |
| 2 | 10 |
| 3 | 5 |
| 4 | 10 |
| 5 | 0 |

TABLE 8

| $V_H$ | Observed |
|---|---|
| 7-8† | 0 |
| 3-74† | 0 |
| 3-73 | 1 |
| 3-72 | 2 |
| 2-70 | 2 |
| 1-69 | 3 |
| 3-66 | 1 |
| 3-64 | 1 |
| 4-61 | 1 |
| 4-59 | 10 |
| 1-58 | 0 |
| 3-53 | 0 |
| 5-51 | 5 |
| 3-49 | 2 |
| 3-48 | 7 |
| 1-46 | 1 |
| 1-45 | 0 |
| 3-43 | 10 |
| 4-39 | 4 |
| 3-38* | 0 |
| 3-35* | 0 |
| 4-34 | 8 |
| 3-33 | 14 |
| 4-31 | 4 |
| 3-30 | 13 |
| 4-28 | 0 |
| 2-26 | 0 |
| 1-24 | 3 |
| 3-23 | 18 |
| 3-21 | 0 |
| 3-20 | 0 |
| 1-18 | 4 |
| 1-17P | 1 |
| 3-16* | 0 |
| 3-15 | 13 |

TABLE 8-continued

| | |
|---|---|
| 3-13 | 6 |
| 3-11 | 5 |
| 3-9 | 31 |
| 1-8 | 7 |
| 3-7 | 11 |
| 2-5 | 1 |
| 1-3 | 0 |
| 1-2 | 6 |
| 6-1 | 9 |

| $D_H$ | Observed |
|---|---|
| 1-1 | 7 |
| 2-2 | 8 |
| 3-3 | 9 |
| 4-4 | 4 |
| 5-5 | 6 |
| 5-18 | 6 |
| 6-6 | 29 |
| 1-7 | 30 |
| 2-8 | 4 |
| 3-9 | 8 |
| 3-10 | 10 |
| 4-11 | 4 |
| 5-12 | 5 |
| 6-13 | 17 |
| 1-14 | 2 |
| 2-15 | 3 |
| 3-16 | 4 |
| 4-17 | 3 |
| 6-19 | 8 |
| 1-20 | 3 |
| 2-21 | 1 |
| 3-22 | 5 |
| 4-23 | 2 |
| 5-24 | 2 |
| 6-25 | 2 |
| 1-26 | 17 |
| 7-27 | 7 |

| $J_H$ | Observed |
|---|---|
| 1 | 2 |
| 2 | 8 |
| 3 | 26 |
| 4 | 95 |
| 5 | 11 |
| 6 | 58 |

| Vκ | Observed |
|---|---|
| 2-40 | |
| 1-39 | 34 |
| 1-37 | 2 |
| 1-33 | 35 |
| 2-30 | 8 |
| 2-29 | 2 |
| 2-28 | 7 |
| 1-27 | 5 |
| 2-24 | 7 |
| 6-21* | 3 |
| 3-20 | 10 |
| 1-17 | 13 |
| 1-16 | 10 |
| 3-15 | 13 |
| 1-12 | 13 |
| 3-11 | 13 |
| 1-9 | 11 |
| 1-8 | 1 |
| 3-7* | 0 |
| 1-6 | 6 |
| 1-5 | 7 |
| 5-2 | 0 |
| 4-1 | 21 |

| Jκ | Observed |
|---|---|
| 1 | 50 |
| 2 | 37 |
| 3 | 28 |

TABLE 8-continued

| | |
|---|---|
| 4 | 64 |
| 5 | 22 |

As shown in Tables 7 and 8, nearly all of the functional human $V_H$, $D_H$, $J_H$, $V\lambda$ and $J\kappa$ gene segments are utilized. Of the functional variable gene segments described but not detected in the VELOCIMMUNE® mice of this experiment, several have been reported to possess defective recombination signal sequences (RSS) and, thus, would not be expected to be expressed (Feeney, A. J. (2000) Factors that influence formation of B cell repertoire. Immunol Res 21, 195-202). Analysis of several other sets of immunoglobulin sequences from various VELOCIMMUNE® mice, isolated from both naïve and immunized repertoires, has shown usage of these gene segments, albeit at lower frequencies (data not shown). Aggregate gene usage data has shown that all functional human $V_H$, $D_H$, $J_H$, $V\kappa$, and $J\lambda$ gene segments contained in VELOCIMMUNE® mice have been observed in various naïve and immunized repertoires (data not shown). Although the human $V_H7$-81 gene segment has been identified in the analysis of human heavy chain locus sequences (Matsuda, F. et al. (1998) The complete nucleotide sequence of the human immunoglobulin heavy chain variable region locus. J Exp Med 188, 2151-2162), it is not present in the VELOCIMMUNE® mice as confirmed by re-sequencing of the entire VELOCIMMUNE® 3 mouse genome.

Sequences of heavy and light chains of antibodies are known to show exceptional variability, especially in short polypeptide segments within the rearranged variable domain. These regions, known as hypervariable regions or complementary determining regions (CDRs) create the binding site for antigen in the structure of the antibody molecule. The intervening polypeptide sequences are called framework regions (FRs). There are three CDRs (CDR1, CDR2, CDR3) and 4 FRs (FR1, FR2, FR3, FR4) in both heavy and light chains. One CDR, CDR3, is unique in that this CDR is created by recombination of both the $V_H$, $D_H$ and $J_H$ and $V\kappa$ and $J\lambda$ gene segments and generates a significant amount of repertoire diversity before antigen is encountered. This joining is imprecise due to both nucleotide deletions via exonuclease activity and non-template encoded additions via terminal deoxynucleotidyl transferase (TdT) and, thus, allows for novel sequences to result from the recombination process. Although FRs can show substantial somatic mutation due to the high mutability of the variable region as a whole, variability is not, however, distributed evenly across the variable region. CDRs are concentrated and localized regions of high variability in the surface of the antibody molecule that allow for antigen binding. Heavy chain and light chain sequences of selected antibodies from VELOCIMMUNE® mice around the CDR3 junction demonstrating junctional diversity are shown in FIGS. 7A and 7B, respectively.

As shown in FIG. 7A, non-template encoded nucleotide additions (N-additions) are observed at both the $V_H$-$D_H$ and $D_H$-$J_H$ joint in antibodies from VELOCIMMUNE® mice, indicating proper function of TdT with the human segments. The endpoints of the $V_H$, $D_H$ and $J_H$ segments relative to their germline counterparts indicate that exonuclease activity has also occurred. Unlike the heavy chain locus, the human κ light chain rearrangements exhibit little or no TdT additions at CDR3, which is formed by the recombination of the $V\kappa$ and $J\kappa$ segments (FIG. 7B). This is expected due to the lack of TdT expression in mice during light chain rearrangements at the pre-B to B cell transition. The diversity observed in the CDR3 of rearranged human $V\kappa$ regions is introduced predominantly through exonuclease activity during the recombination event.

Somatic hypermutation. Additional diversity is added to the variable regions of rearranged immunoglobulin genes during the germinal center reaction by a process termed somatic hypermutation. B cells expressing somatically mutated variable regions compete with other B cells for access to antigen presented by the follicular dendritic cells. Those B cells with higher affinity for the antigen will further expand and undergo class switching before exiting to the periphery. Thus, B cells expressing switched isotypes typically have encountered antigen and undergone germinal center reactions and will have increased numbers of mutations relative to naïve B cells. Further, variable region sequences from predominantly naïve $sIgM^+$ B cells would be expected to have relatively fewer mutations than variable sequences from $sIgG^+$ B cells which have undergone antigen selection.

Sequences from random $V_H$ or $V\kappa$ clones from $sIgM^+$ or $sIgG^+$ B cells from non-immunized VELOCIMMUNE® mice or $sIgG^+$ B cells from immunized mice were compared with their germline variable gene segments and changes relative to the germline sequence annotated. The resulting nucleotide sequences were translated in silico and mutations leading to amino acid changes also annotated. The data were collated from all the variable regions and the percent change at a given position was calculated (FIG. 8).

As shown in FIG. 8, human heavy chain variable regions derived from $sIgG^+$ B cells from non-immunized VELOCIMMUNE® mice exhibit many more nucleotides relative to $sIgM^+$ B cells from the same splenocyte pools, and heavy chain variable regions derived from immunized mice exhibit even more changes. The number of changes is increased in the complementarity-determining regions (CDRs) relative to the framework regions, indicating antigen selection. The corresponding amino acid sequences from the human heavy chain variable regions also exhibit significantly higher numbers of mutations in IgG vs IgM and even more in immunized IgG. These mutations again appear to be more frequent in the CDRs compared with the framework sequences, suggesting that the antibodies were antigen-selected in vivo. A similar increase in the number the nucleotide and amino acid mutations are seen in the $V\kappa$ sequences derived from $IgG^+$ B cells from immunized mice.

The gene usage and somatic hypermutation observed in VELOCIMMUNE® mice demonstrate that essentially all gene segments present are capable of rearrangement to form fully functionally reverse chimeric antibodies in these mice. Further, VELOCIMMUNE® antibodies fully participate within the mouse immune system to undergo affinity selection and maturation to create fully mature human antibodies that can effectively neutralize their target antigen. VELOCIMMUNE® mice are able to mount robust immune responses to multiple classes of antigens that result in usage of a wide range of human antibodies that are both high affinity and suitable for therapeutic use (data not shown).

Example 5

Analysis of Lymphoid Structure and Serum Isotypes

The gross structures of spleen, inguinal lymph nodes, Peyer's patches and thymus of tissue samples from wild type or VELOCIMMUNE® mice stained with H&E were examined by light microscopy. The levels of immunoglobulin isotypes in serum collected from wild-type and VELOCIMMUNE® mice were analyzed using LUMINEX™ technology.

Lymphoid Organ Structure. The structure and function of the lymphoid tissues are in part dependent upon the proper development of hematopoietic cells. A defect in B cell development or function may be exhibited as an alteration in the structure of the lymphoid tissues. Upon analysis of stained tissue sections, no significant difference in appearance of secondary lymphoid organs between wild type and VELOCIMMUNE® mice was identified (data not shown).

Serum Immunoglobulin Levels. The level of expression of each isotype is similar in wild type and VELOCIMMUNE® mice (FIGS. 9A, 9B and 9C). This demonstrates that humanization of the variable gene segments had no apparent adverse effect upon class switching or immunoglobulin expression and secretion and therefore apparently maintain all the endogenous mouse sequences necessary for these functions.

Example 6

Immunization and Antibody Production in Humanized Immunoglobulin Mice

Different versions of VELOCIMMUNE® mice were immunized with antigen to examine the humoral response to foreign antigen challenge.

Immunization and Hybridoma Development. VELOCIMMUNE® and wild-type mice can be immunized with an antigen in the form of protein, DNA, a combination of DNA and protein, or cells expressing the antigen. Animals are typically boosted every three weeks for a total of two to three times. Following each antigen boost, serum samples from each animal are collected and analyzed for antigen-specific antibody responses by serum titer determination. Prior to fusion, mice received a final pre-fusion boost of 5 μg protein or DNA, as desired, via intra-peritoneal and/or intravenous injections. Splenocytes are harvested and fused to Ag8.653 myeloma cells in an electrofusion chamber according to the manufacture's suggested protocol (Cyto Pulse Sciences Inc., Glen Burnie, Md.). Ten days after culture, hybridomas are screened for antigen specificity using an ELISA assay (Harlow, E. and Lane, D. (1988) Antibodies: A Laboratory Manual. Cold Spring Harbor Press, New York). Alternatively, antigen specific B cells are isolated directly from immunized VELOCIMMUNE® mice and screened using standard techniques, including those described here, to obtain human antibodies specific for an antigen of interest.

Serum Titer Determination. To monitor animal anti-antigen serum response, serum samples are collected about 10 days after each boost and the titers are determined using antigen specific ELISA. Briefly, Nunc MAXISORP™ 96 well plates are coated with 2 μg/mL antigen overnight at 4° C. and blocked with bovine serum albumin (Sigma, St. Louis, Mo.). Serum samples in a serial 3 fold dilutions are allowed to bind to the plates for one hour at room temperature. The plates are then washed with PBS containing 0.05% Tween-20 and the bound IgG are detected using HRP-conjugated goat anti-mouse Fc (Jackson Immuno Research Laboratories, Inc., West Grove, Pa.) for total IgG titer, or biotin-labeled isotype specific or light chain specific polyclonal antibodies (SouthernBiotech Inc.) for isotype specific titers, respectively. For biotin-labeled antibodies, following plate wash, HRP-conjugated streptavidin (Pierce, Rockford, Ill.) is added. All plates are developed using colorimetric substrates such as BD OPTEIA™ (BD Biosciences Pharmingen, San Diego, Calif.). After the reaction is stopped with 1 M phosphoric acid, optical absorptions at 450 nm are recorded and the data are analyzed using PRISM™ software from Graph Pad. Dilutions required to obtain two-fold of background signal are defined as titer.

In one experiment, VELOCIMMUNE® mice were immunized with human interleukin-6 receptor (hIL-6R). A representative set of serum titers for VELOCIMMUNE® and wild type mice immunized with hIL-6R is shown in FIGS. 10A and 10B.

VELOCIMMUNE® and wild-type mice mounted strong responses towards the IL-6R with similar titer ranges (FIG. 10A). Several mice from the VELOCIMMUNE® and wild-type cohorts reached a maximal response after a single antigen boost. These results indicate that the immune response strength and kinetics to this antigen were similar in the VELOCIMMUNE® and wild type mice. These antigen-specific antibody responses were further analyzed to examine the particular isotypes of the antigen-specific antibodies found in the sera. Both VELOCIMMUNE® and wild type groups predominantly elicited an IgG1 response (FIG. 10B), suggesting that class switching during the humoral response is similar in mice of each type.

Affinity Determination of Antibody Binding to Antigen in Solution. An ELISA-based solution competition assay is typically designed to determine antibody-binding affinity to the antigen.

Briefly, antibodies in conditioned medium are premixed with serial dilutions of antigen protein ranging from 0 to 10 mg/mL. The solutions of the antibody and antigen mixture are then incubated for two to four hours at room temperature to reach binding equilibria. The amounts of free antibody in the mixtures are then measured using a quantitative sandwich ELISA. Ninety-six well MAXISORB™ plates (VWR, West Chester, Pa.) are coated with 1 μg/mL antigen protein in PBS solution overnight at 4° C. followed by BSA nonspecific blocking. The antibody-antigen mixture solutions are then transferred to these plates followed by one-hour incubation. The plates are then washed with washing buffer and the plate-bound antibodies were detected with an HRP-conjugated goat anti-mouse IgG polyclonal antibody reagent (Jackson Immuno Research Lab) and developed using colorimetric substrates such as BD OPTEIA™ (BD Biosciences Pharmingen, San Diego, Calif.). After the reaction is stopped with 1 M phosphoric acid, optical absorptions at 450 nm are recorded and the data are analyzed using PRISM™ software from Graph Pad. The dependency of the signals on the concentrations of antigen in solution are analyzed with a 4 parameter fit analysis and reported as $IC_{50}$, the antigen concentration required to achieve 50% reduction of the signal from the antibody samples without the presence of antigen in solution.

In one experiment, VELOCIMMUNE® mice were immunized with hIL-6R (as described above). FIGS. 11A and 11B show a representative set of affinity measurements for anti-hIL6R antibodies from VELOCIMMUNE® and wild-type mice.

After immunized mice receive a third antigen boost, serum titers are determined by ELISA. Splenocytes are isolated from selected wild type and VELOCIMMUNE® mouse cohorts and fused with Ag8.653 myeloma cells to form hybridomas and grown under selection (as described above). Out of a total of 671 anti-IL-6R hybridomas produced, 236 were found to express antigen-specific antibodies. Media harvested from antigen positive wells was used to determine the antibody affinity of binding to antigen using a solution competition ELISA. Antibodies derived from VELOCIMMUNE® mice exhibit a wide range of affinity in binding to antigen in solution (FIG. 11A). Furthermore, 49 out of 236 anti-IL-6R hybridomas were found to block IL-6 from binding to the receptor in an in vitro bioassay (data not shown). Further, these 49 anti-IL-6R blocking antibodies exhibited a range of high solution affinities similar to that of blocking antibodies derived from the parallel immunization of wild type mice (FIG. 11B).

Example 7

Construction of a Mouse ADAM6 Targeting Vector

A targeting vector for insertion of mouse ADAM6a and ADAM6b genes into a humanized heavy chain locus was constructed using VELOCIGENE® genetic engineering technology (supra) to modify a Bacterial Artificial Chromosome (BAC) 929d24 obtained from Dr. Fred Alt (Havard University). 929d24 BAC DNA was engineered to contain genomic fragments containing the mouse ADAM6a and ADAM6b genes and a hygromycin cassette for targeted deletion of a human ADAM6 pseudogene (hADAM6ψ) located between human $V_H1$-2 and $V_H6$-1 gene segments of a humanized heavy chain locus (FIG. 12).

First, a genomic fragment containing the mouse ADAM6b gene, ~800 bp of upstream (5') sequence and ~4800 bp of downstream (3') sequence was subcloned from the 929d24 BAC clone. A second genomic fragment containing the mouse ADAM6a gene, ~300 bp of upstream (5') sequence and ~3400 bp of downstream (3') sequence, was separately subcloned from the 929d24 BAC clone. The two genomic fragments containing the mouse ADAM6b and ADAM6a genes were ligated to a hygromycin cassette flanked by Frt recombination sites to create the targeting vector (Mouse ADAM6 Targeting Vector, FIG. 20; SEQ ID NO:3). Different restriction enzyme sites were engineered onto the 5' end of the targeting vector following the mouse ADAM6b gene and onto the 3' end following the mouse ADAM6a gene (bottom of FIG. 12) for ligation into the humanized heavy chain locus.

A separate modification was made to a BAC clone containing a replacement of the mouse heavy chain locus with the human heavy chain locus, including the human ADAM6 pseudogene located between the human $V_H1$-2 and $V_H6$-1 gene segments of the humanized locus for the subsequent ligation of the mouse ADAM6 targeting vector (FIG. 13).

Briefly, a neomycin cassette flanked by /oxP recombination sites was engineered to contain homology arms containing human genomic sequence at positions 3' of the human $V_H1$-2 gene segment (5' with respect to hADAM6ψ) and 5' of human $V_H6$-1 gene segment (3' with respect to hADAM6ψ; see middle of FIG. 13). The location of the insertion site of this targeting construct was about 1.3 kb 5' and ~350 bp 3' of the human ADAM6 pseudogene. The targeting construct also included the same restriction sites as the mouse ADAM6 targeting vector to allow for subsequent BAC ligation between the modified BAC clone containing the deletion of the human ADAM6 pseudogene and the mouse ADAM6 targeting vector.

Following digestion of BAC DNA derived from both constructs, the genomic fragments were ligated together to construct an engineered BAC clone containing a humanized heavy chain locus containing an ectopically placed genomic sequence comprising mouse ADAM6a and ADAM6b nucleotide sequences. The final targeting construct for the deletion of a human ADAM6 gene within a humanized heavy chain locus and insertion of mouse ADAM6a and ADAM6b sequences in ES cells contained, from 5' to 3', a 5' genomic fragment containing ~13 kb of human genomic sequence 3' of the human $V_H1$-2 gene segment, ~800 bp of mouse genomic sequence downstream of the mouse ADAM6b gene, the mouse ADAM6b gene, ~4800 bp of genomic sequence upstream of the mouse ADAM6b gene, a 5' Frt site, a hygromycin cassette, a 3' Frt site, ~300 bp of mouse genomic sequence downstream of the mouse ADAM6a gene, the mouse ADAM6a gene, ~3400 bp of mouse genomic sequence upstream of the mouse ADAM6a gene, and a 3' genomic fragment containing ~30 kb of human genomic sequence 5' of the human $V_H6$-1 gene segment (bottom of FIG. 13).

The engineered BAC clone (described above) was used to electroporate mouse ES cells that contained a humanized heavy chain locus to created modified ES cells comprising a mouse genomic sequence ectopically placed that comprises mouse ADAM6a and ADAM6b sequences within a humanized heavy chain locus. Positive ES cells containing the ectopic mouse genomic fragment within the humanized heavy chain locus were identified by a quantitative PCR assay using TAQMAN™ probes (Lie, Y. S. and Petropoulos, C. J. (1998) Advances in quantitative PCR technology: 5'nuclease assays. Curr Opin Biotechnol 9(1):43-48). The upstream and downstream regions outside of the modified portion of the humanized heavy chain locus were confirmed by PCR using primers and probes located within the modified region to confirm the presence of the ectopic mouse genomic sequence within the humanized heavy chain locus as well as the hygromycin cassette. The nucleotide sequence across the upstream insertion point included the following, which indicates human heavy chain genomic sequence upstream of the insertion point and an I-Ceu I restriction site (contained within the parentheses below) linked contiguously to mouse genomic sequence present at the insertion point: (CCAGCTTCAT TAGTAATCGT TCATCTGTGG TAAAAAGGCA GGATTTGAAG CGATGGAAGA TGG- GAGTACG GGGCGTTGGA AGACAAAGTG CCACACAGCG CAGCCTTCGT CTAGACCCCC GGGCTAACTA TAACGGTCCT AAGGTAGCGA G) GGGATGACAG ATTCTCTGTT CAGTGCACTC AGGGTCTGCC TCCACGAGAA TCACCATGCC CTTTCTCAAG ACTGTGTTCT GTGCAGTGCC CTGTCAGTGG (SEQ ID NO:4). The nucleotide sequence across the downstream insertion point at the 3' end of the targeted region included the following, which indicates mouse genomic sequence and a PI-Sce I restriction site (contained within the parentheses below) linked contiguously with human heavy chain genomic sequence downstream of the insertion point:

```
                                          (SEQ ID NO: 5)
(AGGGGTCGAG GGGGAATTTT ACAAAGAACA AAGAAGCGGG

CATCTGCTGA CATGAGGGCC GAAGTCAGGC TCCAGGCAGC

GGGAGCTCCA CCGCGGTGGC GCCATTTCAT TACCTCTTTC

TCCGCACCCG ACATAGATAAAGCTT) ATCCCCCACC AAGCAAATCC

CCCTACCTGG GGCCGAGCTT CCCGTATGTG GGAAAATGAA

TCCCTGAGGT CGATTGCTGC ATGCAATGAA ATTCAACTAG.
```

Targeted ES cells described above were used as donor ES cells and introduced into an 8-cell stage mouse embryo by the VELOCIMOUSE® mouse engineering method (see, e.g., U.S. Pat. Nos. 7,6598,442, 7,576,259, 7,294,754). Mice bearing a humanized heavy chain locus containing an ectopic mouse genomic sequence comprising mouse ADAM6a and ADAM6b sequences were identified by genotyping using a modification of allele assay (Valenzuela et al., 2003) that detected the presence of the mouse ADAM6a and ADAM6b genes within the humanized heavy chain locus.

Mice bearing a humanized heavy chain locus that contains mouse ADAM6a and ADAM6b genes are bred to a FLPe deletor mouse strain (see, e.g., Rodriguez, C. I. et al. (2000) High-efficiency deleter mice show that FLPe is an alternative to Cre-loxP. Nature Genetics 25:139-140) in order to remove any Frt'ed hygromycin cassette introduced by the targeting vector that is not removed, e.g., at the ES cell stage or in the embryo. Optionally, the hygromycin cassette is retained in the mice.

Pups are genotyped and a pup heterozygous for a humanized heavy chain locus containing an ectopic mouse genomic fragment that comprises mouse ADAM6a and ADAM6b sequences is selected for characterizing mouse ADAM6 gene expression and fertility.

Example 8

Characterization of ADAM6 Rescue Mice

Flow Cytometry. Three mice at age 25 weeks homozygous for human heavy and human κ light chain variable gene loci (H/κ) and three mice at age 18-20 weeks homozygous for human heavy and human κ light chain having the ectopic mouse genomic fragment encoding the mouse ADAM6a and ADAM6b genes within both alleles of the human heavy chain locus (H/κ-A6) were sacrificed for identification and analysis of lymphocyte cell populations by FACs on the BD LSR II System (BD Bioscience). Lymphocytes were gated for specific cell lineages and analyzed for progression through various stages of B cell development. Tissues collected from the animals included blood, spleen and bone marrow. Blood was collected into BD microtainer tubes with EDTA (BD Biosciences). Bone marrow was collected from femurs by flushing with complete RPMI medium supplemented with fetal calf serum, sodium pyruvate, HEPES, 2-mercaptoethanol, non-essential amino acids, and gentamycin. Red blood cells from blood, spleen and bone marrow preparations were lysed with an ammonium chloride-based lysis buffer (e.g., ACK lysis buffer), followed by washing with complete RPMI medium.

For staining of cell populations, $1\times10^6$ cells from the various tissue sources were incubated with anti-mouse CD16/CD32 (2.4G2, BD Biosciences) on ice for 10 minutes, followed by labeling with one or a combination of the following antibody cocktails for 30 min on ice.

Bone marrow: anti-mouse FITC-CD43 (1B11, BioLegend), PE-ckit (2B8, BioLegend), PeCy7-IgM (II/41, eBioscience), PerCP-Cy5.5-IgD (11-26c.2a, BioLegend), APC-eFluor780-B220 (RA3-6B2, eBioscience), A700-CD19 (1D3, BD Biosciences).

Peripheral blood and spleen: anti-mouse FITC-κ (187.1, BD Biosciences), PE-λ (RML-42, BioLegend), PeCy7-IgM (II/41, eBioscience), PerCP-Cy5.5-IgD (11-26c.2a, BioLegend), APC-CD3 (145-2C11, BD), A700-CD19 (1D3, BD), APC-eFluor780-B220 (RA3-6B2, eBioscience). Following incubation with the labeled antibodies, cells were washed and fixed in 2% formaldehyde. Data acquisition was performed on an LSRII flow cytometer and analyzed with FlowJo. Results from a representative H/κ and H/κ-A6 mouse are shown in FIGS. 14-18.

The results demonstrate that B cells of H/κ-A6 mice progress through the stages of B cell development in a similar fashion to H/κ mice in the bone marrow and peripheral compartments, and show normal patterns of maturation once they enter the periphery. H/κ-A6 mice demonstrated an increased $CD43^{int}CD19^+$ cell population as compared to H/κ mice (FIG. 16B). This may indicate an accelerated IgM expression from the humanized heavy chain locus containing an ectopic mouse genomic fragment comprising the mouse ADAM6a and ADAM6b sequences in H/κ-A6 mice. In the periphery, B and T cell populations of H/κ-A6 mice appear normal and similar to H/κ mice.

Testis Morphology and Sperm Characterization. To determine if infertility in mice having humanized immunoglobulin heavy chain variable loci is due to testis and/or sperm production defects, testis morphology and sperm content of the epididymis was examined.

Briefly, testes from two groups of five mice per group (Group 1: mice homozygous for human heavy and κ light chain variable gene loci, mADAM6$^{-/-}$; Group 2: mice heterozygous for human heavy chain variable gene loci and homozygous for κ light chain variable gene loci, mADAM6$^{+/-}$) were dissected with the epididymis intact and weighed. The specimens were then fixed, embedded in paraffin, sectioned and stained with hematoxylin and eosin (HE) stain. Testis sections (2 testes per mouse, for a total of 20) were examined for defects in morphology and evidence of sperm production, while epididymis sections were examined for presence of sperm.

In this experiment, no differences in testis weight or morphology was observed between mADAM6$^{-/-}$ mice and mADAM6$^{+/-}$ mice. Sperm was observed in all genotypes, both in the testes and the epididymis. These results establish that the absence of mouse ADAM6a and ADAM6b genes does not lead to detectable changes in testis morphology, and that sperm is produced in mice in the presence and absence of these two genes. Defects in fertility of male ADAM6$^{-/-}$ mice are therefore not likely to be due to low sperm production.

Sperm Motility and Migration. Mice that lack other ADAM gene family members are infertile due to defects in sperm motility or migration. Sperm migration is defined as the ability of sperm to pass from the uterus into the oviduct, and is normally necessary for fertilization in mice. To determine if the deletion of mouse ADAM6a and ADAM6b affects this process, sperm migration was evaluated in mADAM6$^{-/-}$ mice. Sperm motility was also examined.

Briefly, sperm was obtained from testes of (1) mice heterozygous for human heavy chain variable gene loci and homozygous for human κ light chain variable gene locui (ADAM6$^{+/-}$); (2) mice homozyogous for human heavy chain variable gene loci and homozygous for human κ light chain variable gene loci (ADAM6$^{-/-}$); (3) mice homozygous for human heavy chain variable gene loci and homozygous for wild-type κ light chain (ADAM6$^{-/-}$mκ); and, (4) wild-type C57 BL/6 mice (WT). No significant abnormalities were observed in sperm count or overall sperm motility by inspection. For all mice, cumulus dispersal was observed, indicating that each sperm sample was able to penetrate the cumulus cells and bind the zona pellucida in vitro. These results establish that ADAM6$^{-/-}$ mice have sperm that are capable of penetrating the cumulus and binding the zona pellucida.

Fertilization of mouse ova in vitro (IVF) was done using sperm from mice as described above. A slightly lower number of cleaved embryos were present for ADAM6$^{-/-}$ the day following IVF, as well as a reduced number of sperm bound to the eggs. These results establish that sperm from ADAM6$^{-/-}$ mice, once exposed to an ovum, are capable of penetrating the cumulus and binding the zona pellucida.

In another experiment, the ability of sperm from ADAM6$^{-/-}$ mice to migrate from the uterus and through the oviduct was determined in a sperm migration assay.

Briefly, a first group of five superovulated female mice were set up with five ADAM6$^{-/-}$ males. A second group of five superovulated female mice were set up with five ADAM6$^{+/-}$ males. The mating pairs were observed for copulation, and five to six hours post-copulation the uterus and attached oviduct from all females were removed and flushed for analysis. Flush solutions were checked for eggs to verify ovulation and obtain a sperm count. Sperm migration was evaluated in two different ways. First, both oviducts were removed from the uterus, flushed with saline, and any sperm identified were counted. The presence of eggs was also noted as evidence of ovulation. Second, oviducts were left attached to the uterus and both tissues were fixed, embedded in paraffin, sectioned and stained (as described above). Sections were examined for presence of sperm, in both the uterus and in both oviducts.

For the five females mated with the five ADAM6$^{-/-}$ males, very little sperm was found in the flush solution from the oviduct. Flush solutions from oviducts of the five females mated with the five ADAM6$^{+/-}$ males exhibited a sperm level about 25- to 30-fold higher (avg, n=10 oviducts) than present in flush solutions from the oviducts of the five females mated with the five ADAM6$^{-/-}$ males.

Histological sections of uterus and oviduct were prepared. The sections were examined for sperm presence in the uterus and the oviduct (the colliculus tubarius). Inspection of histological sections of oviduct and uterus revealed that for female mice mated with ADAM6$^{-/-}$ mice, sperm was found in the uterus but not in the oviduct. Further, sections from females mated with ADAM6$^{-/-}$ mice revealed that sperm was not found at the uterotubal junction (UTJ). In sections from females mated with ADAM6$^{+/-}$ mice, sperm was identified in the UTJ and in the oviduct.

These results establish that mice lacking ADAM6a and ADAM6b genes make sperm that exhibit an in vivo migration defect. In all cases, sperm was observed within the uterus, indicating that copulation and sperm release apparently occur as normal, but little to no sperm was observed within the oviducts after copulation as measured either by sperm count or histological observation. These results establish that mice lacking ADAM6a and ADAM6b genes produce sperm that exhibit an inability to migrate from the uterus to the oviduct. This defect apparently leads to infertility because sperm are unable to cross the uterine-tubule junction into the oviduct, where eggs are fertilized. Taken together, all of these results converge to the support the hypothesis that mouse ADAM6 genes help direct sperm with normal motility to migrate out of the uterus, through the uterotubal junction and the oviduct, and thus approach an egg to achieve the fertilization event. The mechanism by which ADAM6 achieves this may be directly by action of the ADAM6 proteins, or through coordinate expression with other proteins, e.g., other ADAM proteins, in the sperm cell, as described below.

ADAM Gene Family Expression. A complex of ADAM proteins are known to be present as a complex on the surface of maturing sperm. Mice lacking other ADAM gene family members lose this complex as sperm mature, and exhibit a reduction of multiple ADAM proteins in mature sperm. To determine if a lack of ADAM6a and ADAM6b genes affects other ADAM proteins in a similar manner, Western blots of protein extracts from testis (immature sperm) and epididymis (maturing sperm) were analyzed to determine the expression levels of other ADAM gene family members.

In this experiment, protein extracts were analyzed from four ADAM6$^{-/-}$ and four ADAM6$^{+/-}$ mice. The results showed that expression of ADAM2 and ADAM3 were not affected in testis extracts. However, both ADAM2 and ADAM3 were dramatically reduced in epididymis extracts. This demonstrates that the absence of ADAM6a and ADAM6b in sperm of ADAM6$^{-/-}$ mice may have a direct affect on the expression and perhaps function of other ADAM proteins as sperm matures (e.g., ADAM2 and ADAM3). This suggests that ADAM6a and ADAM6b are part of an ADAM protein complex on the surface of sperm, which might be critical for proper sperm migration.

Example 9

Human Heavy Chain Variable Gene Utilization in ADAM6 Rescue Mice

Selected human heavy chain variable gene usage was determined for mice homozygous for human heavy and κ light chain variable gene loci either lacking mouse ADAM6a and ADAM6b genes (mADAM6$^{-/-}$) or containing an ectopic genomic fragment encoding for mouse ADAM6a and ADAM6b genes (ADAM6$^{+/+}$; see Example 1) by a quantitative PCR assay using TAQMAN™ probes (as described above).

Briefly, CD19$^+$ B cells were purified from the spleens of mADAM6$^{-/-}$ and ADAM6$^{+/+}$ mice using mouse CD19 Microbeads (Miltenyi Biotec) and total RNA was purified using the RNEASY™ Mini kit (Qiagen). Genomic RNA was removed using a RNase-free DNase on-column treatment (Qiagen). About 200 ng mRNA was reverse-transcribed into cDNA using the First Stand cDNA Synthesis kit (Invitrogen) and then amplified with the TAQMAN™ Universal PCR Master Mix (Applied Biosystems) using the ABI 7900 Sequence Detection System (Applied Biosystems). Relative expression of each gene was normalized to the mouse κ Constant (mCκ). Table 9 sets forth the sense/antisense/TAQMAN™ MGB probe combinations used in this experiment.

TABLE 9

| Human $V_H$ | Sequence (5'-3') | SEQ ID NOs: |
|---|---|---|
| $V_H$6-1 | Sense: CAGGTACAGCTGCAGCAGTCA | 6 |
| | Anti-sense: GGAGATGGCACAGGTGAGTGA | 7 |
| | Probe: TCCAGGACTGGTGAAGC | 8 |
| $V_H$1-2 | Sense: TAGTCCCAGTGATGAGAAAGAGAT | 9 |
| | Anti-sense: GAGAACACAGAAGTGGATGAGATC | 10 |
| | Probe: TGAGTCCAGTCCAGGGA | 11 |
| $V_H$3-23 | Sense: AAAAATTGAGTGTGAATGGATAAGAGTG | 12 |
| | Anti-sense: AACCCTGGTCAGAAACTGCCA | 13 |
| | Probe: AGAGAAACAGTGGATACGT | 14 |
| $V_H$1-69 | Sense: AACTACGCACAGAAGTTCCAGG | 15 |
| | Anti-sense: GCTCGTGGATTTGTCCGC | 16 |
| | Probe: CAGAGTCACGATTACC | 17 |

TABLE 9-continued

| Human $V_H$ | Sequence (5'-3') | SEQ ID NOs: |
|---|---|---|
| mCκ | Sense: TGAGCAGCACCCTCACGTT | 18 |
| | Anti-sense: GTGGCCTCACAGGTATAGCTGTT | 19 |
| | Probe: ACCAAGGACGAGTATGAA | 20 |

In this experiment, expression of all four human $V_H$ genes was observed in the samples analyzed. Further, the expression levels were comparable between mADAM6⁴ and ADAM6⁺/⁺ mice. These results demonstrate that human $V_H$ genes that were both distal to the modification site ($V_H$3-23 and $V_H$1-69) and proximal to the modification site ($V_H$1-2 and $V_H$6-1) were all able to recombine to form a functionally expressed human heavy chain. These results demonstrate that the ectopic genomic fragment comprising mouse ADAM6a and ADAM6b sequences inserted into a human heavy chain genomic sequence did not affect V(D)J recombination of human heavy chain gene segments within the locus, and these mice are able to recombine human heavy chain gene segments in normal fashion to produce functional heavy chain immunoglobulin proteins.

Example 10

Deletion of the Mouse Immunoglobulin Light Chain Loci

Various targeting constructs were made using VELOCI-GENE® technology (see, e.g., U.S. Pat. No. 6,586,251 and Valenzuela et al. (2003) High-throughput engineering of the mouse genome coupled with high-resolution expression analysis, *Nature Biotech.* 21(6):652-659) to modify mouse genomic Bacterial Artificial Chromosome (BAC) libraries to inactivate the mouse κ and λ light chain loci.

Deletion of the mouse light chain locus. DNA from mouse BAC clone RP23-135k15 (Invitrogen) was modified by homologous recombination to inactivate the endogenous mouse light chain locus through targeted deletion of the Vλ-Jλ-Cλ gene clusters (FIG. 20).

Briefly, the entire proximal cluster comprising Vλ1-Jλ3-Cλ3-Jλ1-Cλ1 gene segments was deleted in a single targeting event using a targeting vector comprising a neomycin cassette flanked by /oxP sites with a 5' mouse homology arm containing sequence 5' of the Vλ1 gene segment and a 3' mouse homology arm containing sequence 3' of the CM gene segment (FIG. 20, Targeting Vector 1).

A second targeting construct was prepared to precisely delete the distal endogenous mouse λ gene cluster containing Vλ2-Jλ2-Cλ2-Jλ4-Cλ4 except that the targeting construct contained a 5' mouse homology arm that contained sequence 5' of the Vλ2 gene segment and a 3' mouse homology arm that contained sequence 5' to the endogenous Cλ2 gene segment (FIG. 20, Targeting Vector 2). Thus, the second targeting construct precisely deleted Vλ2-Jλ2, while leaving Cλ2-Jλ4-Cλ4 intact at the endogenous mouse λ locus. ES cells containing an inactivated endogenous λ locus (as described above) were confirmed by karyotyping and screening methods (e.g., TAQMAN®) known in the art. DNA was then isolated from the modified ES cells and subjected to treatment with CRE recombinase thereby mediating the deletion of the proximal targeting cassette containing the neomycin marker gene, leaving only a single loxP site at the deletion point (FIG. 20, bottom).

Deletion of the mouse κ light chain locus. Several targeting constructs were made using similar methods described above to modify DNA from mouse BAC clones RP23-302g12 and RP23-254m04 (Invitrogen) by homologous recombination to inactivate the mouse κ light chain locus in a two-step process (FIG. 21).

Briefly, the Jκ gene segments (1-5) of the endogenous mouse κ light chain locus were deleted in a single targeting event using a targeting vector comprising a hygromycin-thymidine kinase (hyg-TK) cassette containing a single loxP site 3' to the hyg-TK cassette (FIG. 21, Jκ Targeting Vector). The homology arms used to make this targeting vector contained mouse genomic sequence 5' and 3' of the endogenous mouse Jκ gene segments. In a second targeting event, a second targeting vector was prepared to delete a portion of mouse genomic sequence upstream (5') to the most distal endogenous mouse Vκ gene segment (FIG. 21, Vκ Targeting Vector). This targeting vector contained an inverted lox511 site, a loxP site and a neomycin cassette. The homology arms used to make this targeting vector contained mouse genomic sequence upstream of the most distal mouse Vκ gene segment. The targeting vectors were used in a sequential fashion (i.e., Jκ then Vκ) to target DNA in ES cells. ES bearing a double-targeted chromosome (i.e., a single endogenous mouse κ locus targeted with both targeting vectors) were confirmed by karyotyping and screening methods (e.g., TAQMAN™) known in the art. DNA was then isolated from the modified ES cells and subjected to treatment with Cre recombinase thereby mediating the deletion of endogenous mouse Vκ gene segments and both selection cassettes, while leaving two juxtaposed lox sites in opposite orientation relative to one another (FIG. 21, bottom; SEQ ID NO:59).

Thus, two modified endogenous light chain loci (κ and λ) containing intact enhancer and constant regions were created for progressively inserting unrearranged human λ germline gene segments in a precise manner using targeting vectors described below.

Example 11

Replacement of Mouse Light Chain Loci with a Human λ Light Chain Mini-Locus

Multiple targeting vectors were engineered for progressive insertion of human λ gene segments into the endogenous mouse κ and λ light chain loci using similar methods as described above. Multiple independent initial modifications were made to the endogenous light chain loci each producing a chimeric light chain locus containing hVλ and Jλ gene segments operably linked to mouse light chain constant genes and enhancers.

A human λ mini-locus containing 12 human Vλ and one human Jλ gene segment. A series of initial targeting vectors were engineered to contain the first 12 consecutive human Vλ gene segments from cluster A and a hJλ1 gene segment or four hJλ gene segments using a human BAC clone named RP11-729g4 (Invitrogen). FIGS. 22A and 22B show the targeting vectors that were constructed for making an initial insertion of human λ light chain gene segments at the mouse λ and κ light chain loci, respectively.

For a first set of initial targeting vectors, a 124,125 bp DNA fragment from the 729g4 BAC clone containing 12 hVλ gene segments and a hJλ1 gene segment was engineered to contain a PI-SceI site 996 bp downstream (3') of the hJλ1 gene segment for ligation of a 3' mouse homology arm. Two different sets of homology arms were used for ligation to this human fragment; one set of homology arms contained endogenous mouse λ sequences from the 135k15 BAC clone (FIG. 22A) and another set contained endogenous κ sequence 5' and 3' of the mouse Vκ and Jκ gene segments from mouse BAC clones RP23-302g12 and RP23-254m04, respectively (FIG. 22B).

For the 12/1-λ Targeting Vector (FIG. 22A), a PI-SceI site was engineered at the 5' end of a 27,847 bp DNA fragment containing the mouse Cλ2-Jλ4-Cλ4 and enhancer 2.4 of the modified mouse λ locus described in Example 10. The ~28 kb mouse fragment was used as a 3' homology arm by ligation to the ~124 kb human λ fragment, which created a 3' junction containing, from 5' to 3', a hJλ1 gene segment, 996 bp of human λ sequence 3' of the hLλ gene segment, 1229 bp of mouse λ sequence 5' to the mouse Cλ2 gene, the mouse Cλ2 gene and the remaining portion of the ~28 kb mouse fragment. Upstream (5') from the human Vλ3-12 gene segment was an additional 1456 bp of human λ sequence before the start of the 5' mouse homology arm, which contained 23,792 bp of mouse genomic DNA corresponding to sequence 5' of the endogenous mouse λ locus. Between the 5' homology arm and the beginning of the human λ sequence was a neomycin cassette flanked by Frt sites.

Thus, the 12/1-λ Targeting Vector included, from 5' to 3', a 5' homology arm containing ~24 kb of mouse λ genomic sequence 5' of the endogenous λ locus, a 5' Frt site, a neomycin cassette, a 3' Frt site, ~123 kb of human genomic λ sequence containing the first 12 consecutive hVλ gene segments and a hJλ1 gene segment, a PI-SceI site, and a 3' homology arm containing ~28 kb of mouse genomic sequence including the endogenous Cλ2-Jλ4-Cλ4 gene segments, the mouse enhancer 2.4 sequence and additional mouse genomic sequence downstream (3') of the enhancer 2.4 (FIG. 22A).

In a similar fashion, the 12/1-κ Targeting Vector (FIG. 22B) employed the same ~124 human λ fragment with the exception that mouse homology arms containing mouse κ sequence were used such that targeting to the endogenous κ locus could be achieved by homologous recombination. Thus, the 12/1-κ Targeting Vector included, from 5' to 3', a 5' homology arm containing ~23 kb of mouse genomic sequence 5' of the endogenous κ locus, an I-CeuI site, a 5' Frt site, a neomycin cassette, a 3' Frt site, ~124 kb of human genomic λ sequence containing the first 12 consecutive hVλ gene segments and a hJλ1 gene segment, a PI-SceI site, and a 3' homology arm containing ~28 kb of mouse genomic sequence including the endogenous the mouse Cκ gene, Eκi and Eκ3' and additional mouse genomic sequence downstream (3') of Eκ3' (FIG. 22B, 12/1-κ Targeting Vector).

Homologous recombination with either of these two initial targeting vectors created a modified mouse light chain locus (κ or λ) containing 12 hVλ gene segments and a hJλ1 gene segment operably linked to the endogenous mouse light chain constant gene and enhancers (Cκ or Cλ2 and Eκi/Eκ3' or Enh 2.4/Enh 3.1) gene which, upon recombination, leads to the formation of a chimeric λ light chain.

A human λ mini-locus with 12 human Vλ and four human Jλ gene segments. In another approach to add diversity to a chimeric λ light chain locus, a third initial targeting vector was engineered to insert the first 12 consecutive human Vλ gene segments from cluster A and hJλ1, 2, 3 and 7 gene segments into the mouse κ light chain locus (FIG. 22B, 12/4-κ Targeting Vector). A DNA segment containing hJλ1, Jλ2, Jλ3 and Jλ7 gene segments was made by de novo DNA synthesis (Integrated DNA Technologies) including each Jλ gene segment and human genomic sequence of ~100 bp from both the immediate 5' and 3' regions of each Jλ gene segment. A PI-SceI site was engineered into the 3' end of this ~1 kb DNA fragment and ligated to a chloramphenicol cassette. Homology arms were PCR amplified from human λ sequence at 5' and 3' positions relative to the hJλ1 gene segment of the human BAC clone 729g4. Homologous recombination with this intermediate targeting vector was performed on a modified 729g4 BAC clone that had been previously targeted upstream (5') of the human Vλ3-12 gene segment with a neomycin cassette flanked by Frt sites, which also contained an I-CeuI site 5' to the 5' Frt site. The double-targeted 729g4 BAC clone included from 5' to 3' an I-CeuI site, a 5' Frt site, a neomycin cassette, a 3' Frt site, a ~123 kb fragment containing the first 12 hVλ gene segments, a ~1 kb fragment containing human al, 2, 3 and 7 gene segments, a PI-SceI site, and a chloramphenicol cassette. This intermediate targeting vector was digested together with I-CeuI and PI-SceI and subsequently ligated into the modified mouse BAC clone (described above) to create the third targeting vector.

This ligation resulted in a third targeting vector for insertion of human λ sequences into the endogenous κ light chain locus, which included, from 5' to 3', a 5' mouse homology arm containing ~23 kb of genomic sequence 5' of the endogenous mouse κ locus, an I-CeuI site, a 5' Frt site, a neomycin cassette, a 3' Frt site, a ~123 kb fragment containing the first 12 hVλ gene segments, a ~1 kb fragment containing hJλ1, 2, 3 and 7 gene segments, a PI-SceI site and a 3' homology arm containing ~28 kb of mouse genomic sequence including the endogenous the mouse Cκ gene, Eκi and Eκ3' and additional mouse genomic sequence downstream (3') of Eκ3' (FIG. 22B, 12/4-κ Targeting Vector). Homologous recombination with this third targeting vector created a modified mouse κ light chain locus containing 12 hVλ gene segments and four hJλ gene segments operably linked to the endogenous mouse Cκ gene which, upon recombination, leads to the formation of a chimeric human λ/mouse κ light chain.

A human λ mini-locus with an integrated human κ light chain sequence. In a similar fashion, two additional targeting vectors similar to those engineered to make an initial insertion of human λ gene segments into the endogenous κ light chain locus (FIG. 22B, 12/1-κ and 12/4-κ Targeting Vectors) were engineered to progressively insert human λ light chain gene segments using uniquely constructed targeting vectors containing contiguous human λ and κ genomic sequences. These targeting vectors were constructed to include a ~23 kb human κ genomic sequence naturally located between human Vκ4-1 and Jκ1 gene segments. This human κ genomic sequence was specifically positioned in these two additional targeting vectors between human Vλ and human Jλ gene segments (FIG. 22B, 12(κ)1-κ and 12(κ)4-κ Targeting Vectors).

Both targeting vectors containing the human κ genomic sequence were made using the modified RP11-729g4 BAC clone described above (FIG. 24). This modified BAC clone was targeted with a spectinomycin selection cassette flanked by NotI and AsiSI restriction sites (FIG. 24, top left). Homologous recombination with the spectinomycin cassette resulted in a double-targeted 729g4 BAC clone which included, from 5' to 3', an I-CeuI site, a 5' Frt site, a neomycin cassette, a 3' Frt site, a ~123 kb fragment containing the first 12 hVλ gene segments, a NotI site about 200 bp downstream (3') to the nonamer sequence of the hVλ3-1 gene segment, a spectinomycin cassette and an AsiSI site. A separate human BAC clone containing human κ sequence (CTD-2366j12) was targeted two independent times to engineer restriction sites at locations between hVκ4-1 and hJκ1 gene segments to allow for subsequent cloning of a ~23 kb fragment for ligation with the hVλ gene segments contained in the double targeted modified 729g4 BAC clone (FIG. 24, top right).

Briefly, the 2366j12 BAC clone is about 132 kb in size and contains hVκ gene segments 1-6, 1-5, 2-4, 7-3, 5-2, 4-1, human κ genomic sequence downstream of the Vκ gene segments, hJκ gene segments 1-5, the hCκ and about 20 kb of additional genomic sequence of the human κ locus. This clone was first targeted with a targeting vector containing a hygromycin cassette flanked by Frt sites and a NotI site downstream (3') of the 3' Frt site. The homology arms for this targeting vector contained human genomic sequence 5' and 3' of the Vκ gene segments within the BAC clone such that upon homologous recombination with this targeting vector, the Vκ gene segments were deleted and a NotI site was engineered ~133 bp downstream of the hVλ4-1 gene segment (FIG. 24, top right). This modified 2366j12 BAC clone was targeted independently with two targeting vectors at the 3' end to delete the hJλ gene segments with a chloramphenicol cassette that also contained either a hJλ1 gene segment, a PI-SceI site and an AsiSI site or a human λ genomic fragment containing four hJλ gene segments (supra), a PI-SceI site and an AsiSI site (FIG. 24, top right). The homology arms for these two similar targeting vectors contained sequence 5' and 3' of the hJκ gene segments. Homologous recombination with these second targeting vectors and the modified 2366j12 BAC clone yielded a double-targeted 2366j12 clone which included, from 5' to 3', a 5' Frt site, a hygromycin cassette, a 3' Frt site, a NotI site, a 22,800 bp genomic fragment of the human κ locus containing the intergenic region between the Vκ4-1 and Jκ1 gene segments, either a hJλ1 gene segment or a human λ genomic fragment containing hJλ1, Jλ2, Jλ3 and Jλ7, a PI-SceI site and a chloramphenicol cassette (FIG. 24, top right). Two final targeting vectors to make the two additional modifications were achieved by two ligation steps using the double-targeted 729g4 and 2366j12 clones.

Double targeted 729g4 and 2366j12 clones were digested with NotI and AsiSI yielding one fragment containing the neomycin cassette and hVλ gene segments and another fragment containing the ~23 kb genomic fragment of the human κ locus containing the intergenic region between the Vκ4-1 and Jκ1 gene segments, either a hJλ1 gene segment or a genomic fragment containing hJλ1, Jλ2, Jλ3 and Jλ7 gene segments, the PI-SceI site and the chloramphenicol cassette, respectively. Ligation of these fragments generated two unique BAC clones containing from 5' to 3' the hVλ gene segments, the human κ genomic sequence between the Vκ4-1 and Jκ1 gene segments, either a hJλ1 gene segment or a genomic fragment containing hJλ1, Jλ2, Jλ3 and Jλ7 gene segments, a PI-SceI site and a chloramphenicol cassette (FIG. 24, bottom). These new BAC clones were then digested with I-CeuI and PI-SceI to release the unique fragments containing the upstream neomycin cassette and the contiguous human λ and κ sequences and ligated into a modified mouse BAC clone 302g12 which contained from 5' to 3' mouse genomic sequence 5' of the endogenous κ locus, an I-CeuI site, a 5' Frt site, a neomycin cassette, a 3' Frt site, hVλ gene segments (3-12 to 3-1), a NotI site ~200 bp downstream of Vλ3-1, ~23 kb of human κ sequence naturally found between the human Vκ4-1 and Jκ1 gene segments, either a hJλ1 gene segment or a genomic fragment containing hJλ1, Jλ2, Jλ3 and Jλ7 gene segments, the mouse Eκi, the mouse Cκ gene and Eκ3' (FIG. 22, 12hVλ-VκJκ-hJλ1 and 12hVλ-VκJκ-4hJλ Targeting Vectors). Homologous recombination with both of these targeting vectors created two separate modified mouse κ light chain loci containing 12 hVλ gene segments, human κ genomic sequence, and either one or four hJλ gene segments operably linked to the endogenous mouse Cκ gene which, upon recombination, leads to the formation of a chimeric human λ/mouse κ light chain.

Example 12

Engineering Additional Human Vλ Genes Segments Into a Human λ Light Chain Mini-Locus Additional hVλ gene segments were added independently to each of the initial modifications described in Example 11 using similar targeting vectors and methods (FIG. 23A, +16-λ Targeting Vector and FIG. 23B, +16-κ Targeting Vector).

Introduction of 16 additional human Vλ gene segments. Upstream (5') homology arms used in constructing targeting vectors for adding 16 additional hVλ gene segments to the modified light chain loci described in Example 11 contained mouse genomic sequence 5' of either the endogenous κ or λ light chain loci. The 3' homology arms were the same for all targeting vectors and contained human genomic sequence overlapping with the 5' end of the human λ sequence of the modifications as described in Example 11.

Briefly, two targeting vectors were engineered for introduction of 16 additional hVλ gene segments to the modified mouse light chain loci described in Example 11 (FIGS. 23A and 5B, +16-λ or +16-κ Targeting Vector). A ~172 kb DNA fragment from human BAC clone RP11-761I13 (Invitrogen) containing 21 consecutive hVλ gene segments from cluster A was engineered with a 5' homology arm containing mouse genomic sequence 5' to either the endogenous κ or λ light chain loci and a 3' homology arm containing human genomic λ sequence. The 5' mouse κ or λ homology arms used in these targeting constructs were the same 5' homology arms described in Example 11 (FIGS. 23A and 23B). The 3' homology arm included a 53,057 bp overlap of human genomic λ sequence corresponding to the equivalent 5' end of the ~123 kb fragment of human genomic λ sequence described in Example 11. These two targeting vectors included, from 5' to 3', a 5' mouse homology arm containing either ~23 kb of genomic sequence 5' of the endogenous mouse κ light chain locus or ~24 kb of mouse genomic sequence 5' of the endogenous λ light chain locus, a 5' Frt site, a hygromycin cassette, a 3' Frt site and 171,457 bp of human genomic λ sequence containing 21 consecutive hVλ gene segments, ~53 kb of which overlaps with the 5' end of the human λ sequence described in Example 12 and serves as the 3' homology arm for this targeting construct (FIGS. 23A and 23B, +16-λ or +16-κ Targeting Vectors). Homologous recombination with these targeting vectors created independently modified mouse κ and λ light chain loci each containing 28 hVλ gene segments and a hJλ1 gene segment operably linked to endogenous mouse constant genes (Cκ or Cλ2) which, upon recombination, leads to the formation of a chimeric light chain.

In a similar fashion, the +16-κ Targeting Vector was also used to introduce the 16 additional hVλ gene segments to the other initial modifications described in Example 11 that incorporated multiple hJλ gene segments with and without an integrated human κ sequence (FIG. 22B). Homologous recombination with this targeting vector at the endogenous mouse κ locus containing the other initial modifications created mouse κ light chain loci containing 28 hVλ gene segments and hJλ1, 2, 3 and 7 gene segments with and without a human Vκ-Jκ genomic sequence operably linked to the endogenous mouse Cκ gene which, upon recombination, leads to the formation of a chimeric λ-κ light chain.

Introduction of 12 additional human Vλ gene segments. Additional hVλ gene segments were added independently to each of the modifications described above using similar targeting vectors and methods. The final locus structure resulting from homologous recombination with targeting vectors containing additional hVλ gene segments are shown in FIGS. 25A and 25B.

Briefly, a targeting vector was engineered for introduction of 12 additional hVλ gene segments to the modified mouse κ and λ light chain loci described above (FIGS. 23A and 23B, +12-λ or 12-κ Targeting Vectors). A 93,674 bp DNA fragment from human BAC clone RP11-22I18 (Invitrogen) containing 12 consecutive hVλ gene segments from cluster B was engineered with a 5' homology arm containing mouse genomic sequence 5' to either the endogenous mouse κ or λ light chain loci and a 3' homology arm containing human genomic λ sequence. The 5' homology arms used in this targeting construct were the same 5' homology arms used for the addition of 16 hVλ gene segments described above (FIGS. 23A and 23B). The 3' homology arm was made by engineering a PI-SceI site ~3431 bp 5' to the human Vλ3-29P gene segment contained in a 27,468 bp genomic fragment of human λ sequence from BAC clone RP11-761I13. This PI-SceI site served as a ligation point to join the ~94 kb fragment of additional human λ sequence to the ~27 kb fragment of human λ sequence that overlaps with the 5' end of the human λ sequence in the previous modification using the +16-λ or +16-κ Targeting Vectors (FIGS. 23A and 23B). These two targeting vectors included, from 5' to 3', a 5' homology arm containing either ~23 kb of mouse genomic sequence 5' of the endogenous κ light chain locus or ~24 kb of mouse genomic sequence 5' of the endogenous λ light chain locus, a 5' Frt site, a neomycin cassette, a 3' Frt site and 121,188 bp of human genomic λ sequence containing 16 hVλ gene segments and a PI-SceI site, ~27 kb of which overlaps with the 5' end of the human λ sequence from the insertion of 16 addition hVλ gene segments and serves as the 3' homology arm for this targeting construct (FIGS. 23A and 23B, +12-λ or 12-κ Targeting Vectors). Homologous recombination with these targeting vectors independently created modified mouse κ and λ light chain loci containing 40 hVλ gene segments and human J⌊1 operably linked to the endogenous mouse constant genes (Cκ or Cλ2) which, upon recombination, leads to the formation of a chimeric light chain (bottom of FIGS. 23A and 23B).

In a similar fashion, the +12-κ Targeting Vector was also used to introduce the 12 additional hVλ gene segments to the other initial modifications that incorporated multiple hJλ gene segments with and without an integrated human κ sequence (FIG. 22B). Homologous recombination with this targeting vector at the endogenous mouse κ locus containing the other modifications created a mouse κ light chain locus containing 40 hVλ gene segments and hJλ.1, 2, 3 and 7 gene segments with and without a human Vκ-Jκ genomic sequence operably linked to the endogenous mouse Cκ gene which, upon recombination, leads to the formation of a chimeric λ-κ light chain.

Example 13

Identification of Targeted ES Cells Bearing Human λ Light Chain Gene Segments

Targeted BAC DNA made according to the foregoing Examples was used to electroporate mouse ES cells to create modified ES cells for generating chimeric mice that express human λ light chain gene segments. ES cells containing an insertion of unrearranged human λ light chain gene segments were identified by a quantitative TAQMAN® assay. Specific primers sets and probes were design for insertion of human λ sequences and associated selection cassettes (gain of allele, GOA), loss of endogenous mouse sequences and any selection cassettes (loss of allele, LOA) and retention of flanking mouse sequences (allele retention, AR). For each additional insertion of human λ sequences, additional primer sets and probes were used to confirm the presence of the additional human λ sequences as well as the previous primer sets and probes used to confirm retention of the previously targeted human sequences. Table 10 sets forth the primers and associated probes used in the quantitative PCR assays. Table 11 sets forth the combinations used for confirming the insertion of each section of human λ light chain gene segments in ES cell clones.

ES cells bearing the human λ light chain gene segments are optionally transfected with a construct that expresses FLP in order to remove the Frt'ed neomycin cassette introduced by the insertion of the targeting construct containing human Vλ5-52-Vλ1-40 gene segments (FIGS. 23A and 23B). The neomycin cassette may optionally be removed by breeding to mice that express FLP recombinase (e.g., U.S. Pat. No. 6,774,279). Optionally, the neomycin cassette is retained in the mice.

TABLE 10

| Primer | SEQ ID NO: | Probe | SEQ ID NO: |
|---|---|---|---|
| hL2F | 60 | hL2P | 82 |
| hL2R | 61 | | |
| hL3F | 62 | hL3P | 83 |
| hL3R | 63 | | |
| NeoF | 64 | NeoP | 84 |
| NeoR | 65 | | |
| 61hJ1F | 66 | 61hJ1P | 85 |
| 61hJ1R | 67 | | |
| 67hT1F | 68 | 67hT1P | 86 |
| 67hT1R | 69 | | |
| 67hT3F | 70 | 67hT3P | 87 |
| 67hT3R | 71 | | |
| HygF | 72 | HygP | 88 |
| HygR | 73 | | |
| MKD2F | 74 | MKD2P | 89 |
| MKD2R | 75 | | |
| MKP8F | 76 | MKP8P | 90 |
| MKP8R | 77 | | |
| MKP15F | 78 | MKP15P | 91 |
| MKP15R | 79 | | |
| MK2OF | 80 | — | — |
| MKP4R | 81 | | |
| 68h2F | 92 | 68h2P | 96 |
| 68h2R | 93 | | |
| 68h5F | 94 | 68h5P | 97 |
| 68h5R | 95 | | |
| mL1F | 133 | mL1P | 141 |
| mL1R | 134 | | |
| mL2F | 135 | mL2P | 142 |
| mL2R | 136 | | |
| mL11F | 137 | mL11P | 143 |
| mL11R | 138 | | |
| mL12F | 139 | mL12P | 144 |
| mL12R | 140 | | |

TABLE 11

| Modification | Assay | Forward/Reverse Primer Set | Probe | Sequence Location |
|---|---|---|---|---|
| Insertion of 12hVλ & hJλ1 | GOA | hL2F/hL2R | hL2P | hVλ3-12- |
| | | hL3F/hL3R | hL3P | hVλ3-1 |
| | | 61hJ1F/61hJ1R | 61hJ1P | hJλ sequence |
| | | NeoF/NeoR | NeoP | Neomycin cassette |

TABLE 11-continued

| Modification | Assay | Forward/Reverse Primer Set | Probe | Sequence Location |
|---|---|---|---|---|
| | LOA | MK20F/MKP4R | | lox511/loxP sequence of inactivated κ locus |
| | | HygF/HygR | HygP | Hygromycin cassette from inactivated λ locus |
| | | mL1F/mL1R | mL1P | Mouse Vλ1-Cλ1 |
| | | mL2F/mL2R | mL2P | Cluster |
| | | mL11F/mL11R | mL11P | Mouse Vλ2-Cλ2 |
| | | mL12F/mL12R | mL12P | Cluster |
| | AR/LOA | MKD2F/MKD2R | MKD2P | Mouse sequence in 5' Vκ locus |
| | | MKP15F/MKP15R | MKP15P | Mouse sequence in 3' Vκ locus |
| Insertion of 16 hVλ | GOA | 67hT1F/67hT1R | 67hT1P | hVλ3-27- |
| | | 67hT3F/67hT3R | 67hT3P | hVλ3-12 |
| | | HygF/HygR | HygP | Hygromycin cassette |
| | | NeoF/NeoR | NeoP | Neomycin cassette |
| | LOA | mL1F/mL1R | mL1P | Mouse Vλ1-Cλ1 |
| | | mL2F/mL2R | mL2P | Cluster |
| | | mL11F/mL11R | mL11P | Mouse Vλ2-Cλ2 |
| | | mL12F/mL12R | mL12P | Cluster |
| | AR | hL2F/hL2R | hL2P | hVλ3-12- |
| | | hL3F/hL3R | hL3P | hVλ3-1 |
| | AR/LOA | MKD2F/MKD2R | MKD2P | Mouse sequence in 5' Vκ locus |
| | | MKP15F/MKP15R | MKP15P | Mouse sequence in 3' Vκ locus |
| Insertion of 12 hVλ | GOA | 68h2F/68h2R | 68h2P | hVλ5-52-hVλ1-40 |
| | | 68h5F/68h5R | 68h5P | |
| | | NeoF/NeoR | NeoP | Neomycin cassette |
| | LOA | HygF/HygR | HygP | Hygromycin cassette |
| | | mL1F/mL1R | mL1P | Mouse Vλ1-Cλ1 |
| | | mL2F/mL2R | mL2P | Cluster |
| | | mL11F/mL11R | mL11P | Mouse Vλ2-Cλ2 |
| | | mL12F/mL12R | mL12P | Cluster |
| | AR | hL2F/hL2R | hL2P | hVλ3-12- |
| | | hL3F/hL3R | hL3P | hVλ3-1 |
| | | 67hT1F/67hT1R | 67hT1P | hVλ3-27- |
| | | 67hT3F/67hT3R | 67hT3P | hVλ3-12 |
| | AR/LOA | MKD2F/MKD2R | MKD2P | Mouse sequence in 5' Vκ locus |
| | | MKP15F/MKP15R | MKP15P | Mouse sequence in 3' Vκ locus |

Example 14

Generation of Mice Expressing Human λ Light Chain from an Endogenous Light Chain Locus Targeted ES cells described above were used as donor ES cells and introduced into an 8-cell stage mouse embryo by the VELOCIMOUSE® method (see, e.g., U.S. Pat. No. 7,294,754 and Poueymirou et al. (2007) F0 generation mice that are essentially fully derived from the donor gene-targeted ES cells allowing immediate phenotypic analyses Nature Biotech. 25(1):91-99. VELOCIMICE® (F0 mice fully derived from the donor ES cell) independently bearing human λ gene segments were identified by genotyping using a modification of allele assay (Valenzuela et al., supra) that detected the presence of the unique human λ gene segments (supra).

κ:λ light chain usage of mice bearing human λ light chain gene segments. Mice homozygous for each of three successive insertions of hVλ gene segments with a single hJλ gene segment (FIG. 23B) and mice homozygous for a first insertion of hVλ gene segments with either a single hJλ gene segment or four human Jλ gene segments including a human Vκ-Jκ genomic sequence (FIG. 22B) were analyzed for κ and λ light chain expression in splenocytes using flow cytometry.

Briefly, spleens were harvested from groups of mice (ranging from three to seven animals per group) and grinded using glass slides. Following lysis of red blood cells (RBCs) with ACK lysis buffer (Lonza Walkersville), splenocytes were stained with fluorescent dye conjugated antibodies specific for mouse CD19 (Clone 1D3; BD Biosciences), mouse CD3 (17A2; Biolegend), mouse Igκ (187.1; BD Biosciences) and mouse Igλ (RML-42; Biolegend). Data was acquired using a BD™ LSR II flow cytometer (BD Biosciences) and analyzed using FLOWJO™ software (Tree Star, Inc.). Table 12 sets forth the average percent values for B cells (CD19$^+$), κ light chain (CD19$^+$Igκ$^+$Igκ$^-$), and λ light chain (CD19$^+$Igκ$^-$Igκ$^+$) expression observed in splenocytes from groups of animals bearing each genetic modification.

In a similar experiment, B cell contents of the splenic compartment from mice homozygous for a first insertion of 12 hVλ and four hJλ gene segments including a human Vκ-Jκ genomic sequence operably linked to the mouse Cκ gene (bottom of FIG. 22B) and mice homozygous for 40 hVλ and one hJλ gene segment (bottom of FIG. 23B or top of FIG. 25B) were analyzed for Igκ and Igλ expression using flow cytometry (as described above). FIG. 26A shows the Igλ and Igκ expression in CD19$^+$ B cells for a representative mouse from each group. The number of CD19$^+$ B cells per spleen was also recorded for each mouse (FIG. 26B).

In another experiment, B cell contents of the spleen and bone marrow compartments from mice homozygous for 40 hVλ and four hJλ gene segments including a human Vκ-Jκ genomic sequence operably linked to the mouse Cκ gene (bottom of FIG. 26B) were analyzed for progression through B cell development using flow cytometry of various cell surface markers.

Briefly, two groups (N=3 each, 9-12 weeks old, male and female) of wild type and mice homozygous for 40 hVλ and four hJλ gene segments including a human Vκ-Jκ genomic sequence operably linked to the mouse Cκ gene were sacrificed and spleens and bone marrow were harvested. Bone marrow was collected from femurs by flushing with complete RPMI medium (RPMI medium supplemented with fetal calf serum, sodium pyruvate, Hepes, 2-mercaptoethanol, non-essential amino acids, and gentamycin). RBCs from spleen and bone marrow preparations were lysed with ACK lysis buffer (Lonza Walkersville), followed by washing with complete RPMI medium. 1×10$^6$ cells were incubated with anti-mouse CD16/CD32 (2.4G2, BD Biosciences) on ice for 10 minutes, followed by labeling with a selected antibody panel for 30 min on ice.

Bone marrow panel: anti-mouse FITC-CD43 (1B11, BioLegend), PE-ckit (2B8, BioLegend), PeCy7-IgM (II/41, eBioscience), PerCP-Cy5.5-IgD (11-26c.2a, BioLegend), APC-B220 (RA3-662, eBioscience), APC-H7-CD19 (ID3, BD) and Pacific Blue-CD3 (17A2, BioLegend).

Bone marrow and spleen panel: anti-mouse FITC-Igκ (187.1, BD), PE-Igλ (RML-42, BioLegend), PeCy7-IgM (II/41, ebioscience), PerCP-Cy5.5-IgD (11-26c.2a, BioLegend), Pacific Blue-CD3 (17A2, BioLegend), APC-B220 (RA3-6B2, eBioscience), APC-H7-CD19 (ID3, BD).

Following staining, cells were washed and fixed in 2% formaldehyde. Data acquisition was performed on a FACSCANTOII™ flow cytometer (BD Biosciences) and analyzed with FLOWJO™ software (Tree Star, Inc.). FIGS. 27A-27D show the results for the splenic compartment of one representative mouse from each group. FIGS. 28A-28E show the results for the bone marrow compartment of one representative mouse from each group. Table 13 sets forth the average percent values for B cells (CD19$^+$), κ light chain (CD19$^+$Igκ$^+$Igλ$^-$), and λ light chain (CD19$^+$Igκ$^-$Igλ$^+$) expression observed in splenocytes from groups of animals bearing various genetic modifications. Table 14 sets forth the average percent values for B cells (CD19$^+$), mature B cells (B220$^{hi}$IgM$^+$), immature B cells (B220$^{int}$IgM$^+$), immature B cells expressing κ light chain (B220$^{int}$IgM$^+$Igκ$^+$) and immature B cells expressing λ light chain (B220$^{int}$IgM$^+$Igκ$^+$) observed in bone marrow of wild type and mice homozygous for 40 hVλ and four hJλ gene segments including a human Vκ-Jκ genomic sequence operably linked to the mouse Cκ gene. This experiment was repeated with additional groups of the mice described above and demonstrated similar results (data not shown).

TABLE 12

| Genotype | B cells | Igκ$^+$ | Igλ$^+$ |
|---|---|---|---|
| Wild Type | 46.2 | 91.0 | 3.6 |
| 12 hVλ + hJλ1 | 28.3 | 10.4 | 62.5 |
| 12 hVλ − VκJκ − hJλ1 | 12.0 | 11.0 | 67.5 |
| 12 hVλ − VκJκ − 4hJλ | 41.8 | 17.2 | 68.4 |
| 28 hVλ + hJλ1 | 22.0 | 13.3 | 51.1 |
| 40 hVλ + hJλl | 28.2 | 24.3 | 53.0 |

TABLE 13

| Genotype | B cells | Igκ$^+$ | Igλ$^+$ |
|---|---|---|---|
| Wild Type | 49.8 | 91.2 | 3.5 |
| 40 hVλ − VκJκ − 4hJλ | 33.3 | 41.6 | 43.1 |

TABLE 14

| Genotype | B cells | Mature B cells | Immature B cells | Immature Igκ$^+$ B cells | Immature Igλ$^+$ B cells |
|---|---|---|---|---|---|
| Wild Type | 62.2 | 9.2 | 12.0 | 79.0 | 8.84 |
| 40 hVλ − VκJκ − 4hJλ | 60.43 | 2.59 | 7.69 | 38.29 | 43.29 |

Human Vλ gene usage in mice bearing human λ light chain gene segments. Mice heterozygous for a first insertion of human λ sequences (hVλ3-12-hVλ3-1 and hJλ1, FIG. 23B) and homozygous for a third insertion of human) sequences (hVλ5-52-hVλ3-1 and hJλ1, FIG. 23B) were analyzed for human λ light chain gene usage by reverse-transcriptase polymerase chain reaction (RT-PCR) using RNA isolated from splenocytes.

Briefly, spleens were harvested and perfused with 10 mL RPMI-1640 (Sigma) with 5% HI-FBS in sterile disposable bags. Each bag containing a single spleen was then placed into a STOMACHER™ (Seward) and homogenized at a medium setting for 30 seconds. Homogenized spleens were filtered using a 0.7 μm cell strainer and then pelleted with a centrifuge (1000 rpm for 10 minutes) and RBCs were lysed in BD PHARM LYSE™ (BD Biosciences) for three minutes. Splenocytes were diluted with RPMI-1640 and centrifuged again, followed by resuspension in 1 mL of PBS (Irvine Scientific). RNA was isolated from pelleted splenocytes using standard techniques known in the art.

RT-PCR was performed on splenocyte RNA using primers specific for human hVλ gene segments and the mouse Cκ gene (Table 15). PCR products were gel-purified and cloned into pCR2.1-TOPO TA vector (Invitrogen) and sequenced with primers M13 Forward (GTAAAACGAC GGCCAG; SEQ ID NO:113) and M13 Reverse (CAGGAAACAG CTATGAC; SEQ ID NO:114) located within the vector at locations flanking the cloning site. Eighty-four total clones derived from the first and third insertions of human 2 sequences were sequenced to determine hVλ gene usage (Table 16). The nucleotide sequence of the hVλ-hJλ1-mCκ junction for selected RT-PCR clones is shown in FIG. 29.

In a similar fashion, mice homozygous for a third insertion of human λ light chain gene sequences (i.e. 40 hVλ gene segments and four hJλ gene segments including a human Vκ-Jκ genomic sequence, bottom of FIG. 25B) operably linked to the endogenous mouse Cκ gene were analyzed for human λ light chain gene usage by RT-PCR using RNA isolated from splenocytes (as described above). The human λ light chain gene segment usage for 26 selected RT-PCR clones are shown in Table 17. The nucleotide sequence of the hVλ-hJλ-mCκ junction for selected RT-PCR clones is shown in FIG. 30.

In a similar fashion, mice homozygous for a first insertion of human λ light chain gene segments (12 hVλ gene segments and hJλ1, FIG. 22A & FIG. 23A) operably linked to the endogenous mouse Cλ2 gene were analyzed for human λ light chain gene usage by RT-PCR using RNA isolated from splenocytes (as described above). The primers specific for hVλ gene segments (Table 15) were paired with one of two primers specific for the mouse Cλ2 gene; Cλ2-1 (SEQ ID NO:162) or Cλ2-2 (SEQ ID NO:163).

Multiple hVλ gene segments rearranged to hλ1 were observed from the RT-PCR clones from mice bearing human λ light chain gene segments at the endogenous mouse λ light chain locus. The nucleotide sequence of the hVλ-hJλ-mCλ2 junction for selected RT-PCR clones is shown in FIG. 31.

TABLE 15

| 5' hVλ Primer | Sequence (5'-3') | SEQ ID NO: |
|---|---|---|
| VLL-1 | CCTCTCCTCC TCACCCTCCT | 98 |
| VLL-1n | ATGRCCDGST YYYCTCTCCT | 99 |
| VLL-2 | CTCCTCACTC AGGGCACA | 100 |
| VLL-2n | ATGGCCTGGG CTCTGCTSCT | 101 |
| VLL-3 | ATGGCCTGGA YCSCTCTCC | 102 |
| VLL-4 | TCACCATGGC YTGGRYCYCM YTC | 103 |
| VLL-4.3 | TCACCATGGC CTGGGTCTCC TT | 104 |
| VLL-5 | TCACCATGGC CTGGAMTCYT CT | 105 |
| VLL-6 | TCACCATGGC CTGGGCTCCA CTACTT | 106 |
| VLL-7 | TCACCATGGC CTGGACTCCT | 107 |
| VLL-8 | TCACCATGGC CTGGATGATG CTT | 108 |
| VLL-9 | TAAATATGGC CTGGGCTCCT CT | 109 |
| VLL-10 | TCACCATGCC CTGGGCTCTG CT | 110 |
| VLL-11 | TCACCATGGC CCTGACTCCT CT | 111 |

| 3' Mouse Cκ Primer | Sequence (5'-3') | SEQ ID NO: |
|---|---|---|
| mIgKC3'-1 | CCCAAGCTTA CTGGATGGTG GGAAGATGGA | 112 |

TABLE 16

| hVλ | Observed No. of Clones |
|---|---|
| 3-1 | 2 |
| 4-3 | 3 |
| 2-8 | 7 |
| 3-9 | 4 |
| 3-10 | 3 |
| 2-14 | 1 |
| 3-19 | 1 |
| 2-23 | 7 |
| 3-25 | 1 |
| 1-40 | 9 |
| 7-43 | 2 |
| 1-44 | 2 |
| 5-45 | 8 |
| 7-46 | 3 |
| 9-49 | 6 |
| 1-51 | 3 |

TABLE 17

| Clone | hVλ | hJλ |
|---|---|---|
| 1-3 | 1-44 | 7 |
| 1-5 | 1-51 | 3 |
| 2-3 | 9-49 | 7 |
| 2-5 | 1-40 | 1 |
| 2-6 | 1-40 | 7 |
| 3b-5 | 3-1 | 7 |
| 4a-1 | 4-3 | 7 |
| 4a-5 | 4-3 | 7 |
| 4b-1 | 1-47 | 3 |
| 5-1 | 3-10 | 3 |
| 5-2 | 1-40 | 7 |
| 5-3 | 1-40 | 7 |
| 5-4 | 7-46 | 2 |
| 5-6 | 1-40 | 7 |
| 5-7 | 7-43 | 3 |
| 6-1 | 1-40 | 1 |
| 6-2 | 1-40 | 2 |
| 6-7 | 1-40 | 3 |
| 7a-1 | 3-10 | 7 |
| 7a-2 | 9-49 | 2 |
| 7a-7 | 3-10 | 7 |
| 7b-2 | 7-43 | 3 |
| 7b-7 | 7-46 | 7 |
| 7b-8 | 7-43 | 3 |
| 11a-1 | 5-45 | 2 |
| 11a-2 | 5-45 | 7 |

FIG. 29 shows the sequence of the hVλ-hJλ1-mCκ junction for RT-PCR clones from mice bearing a first and third insertion of hVλ gene segments with a single hJλ gene segment. The sequences shown in FIG. 29 illustrate unique rearrangements involving different hVλ gene segments with hJλ1 recombined to the mouse Cκ gene. Heterozygous mice bearing a single modified endogenous κ locus containing 12 hVλ gene segments and hJλ1 and homozygous mice bearing two modified endogenous κ loci containing 40 hVλ gene segments and hJλ1 were both able to produce human λ gene segments operably linked to the mouse Cκ gene and produce B cells that expressed human λ light chains. These rearrangements demonstrate that the chimeric loci were able to independently rearrange human λ gene segments in multiple, independent B cells in these mice. Further, these modifications to the endogenous κ light chain locus did not render any of the hVλ gene segments inoperable or prevent the chimeric locus from recombining multiple hVλ and a hJλ (Jλ1) gene segment during B cell development as evidenced by 16 different hVλ gene segments that were observed to rearrange with hJλ1 (Table 16). Further, these mice made functional antibodies containing rearranged human Vλ-Jλ gene segments operably linked to mouse Cκ genes as part of the endogenous immunoglobulin light chain repertoire.

FIG. 30 shows the sequence of the hVλ-hJλ-mCκ junction for selected RT-PCR clones from mice homozygous for 40 hVλ and four hJλ gene segments including a human Vκ-Jκ genomic sequence. The sequences shown in FIG. 30 illustrate additional unique rearrangements involving multiple different hVλ gene segments, spanning the entire chimeric locus, with multiple different hJλ gene segments rearranged and operably linked to the mouse Cκ gene. Homozygous mice bearing modified endogenous λ loci containing 40 hVλ and four hJλ gene segments were also able to produce human λ gene segments operably linked to the mouse Cκ gene and produce B cells that expressed human λ light chains. These rearrangements further demonstrate that the all stages of chimeric loci were able to independently rearrange human λ gene segments in multiple, independent B cells in these mice. Further, these additional modifications to the endogenous κ light chain locus demonstrates that each insertion of human λ gene segments did not render any of the hVλ and/or Jλ gene segments inoperable or prevent the chimeric locus from recombining the hVλ and Jλ gene segments during B cell development as evidenced by 12 different hVλ gene segments that were observed to rearrange with all four hJλ gene segments (Table 17) from the 26 selected RT-PCR clone. Further, these mice as well made functional antibodies containing human Vλ-Jλ gene segments operably linked to mouse Cκ regions as part of the endogenous immunoglobulin light chain repertoire.

FIG. 31 shows the sequence of the hVλ-hλ-mCλ2 junction for three individual RT-PCR clones from mice homozygous for 12 hVλ gene segments and hJλ1. The sequences shown in FIG. 31 illustrate additional unique rearrangements involving different hVλ gene segments, spanning the length of the first insertion, with hJλ1 rearranged and operably linked to the mouse Cλ2 gene (2D1=Vλ2-8Jλ1; 2D9=Vλ3-10Jλ1; 3E15=Vλ3-1Jλ1). One clone demonstrated a nonproductive rearrangement due to N additions at the hVλ-hJλ junction (2D1, FIG. 31). This is not uncommon in V(D)J recombination, as the joining of gene segments during recombination has been shown to be imprecise. Although this clone represents an unproductive recombinant present in the light chain repertoire of these mice, this demonstrates that the genetic mechanism that contributes to junctional diversity among antibody genes is operating normally in these mice and leading to an antibody repertoire containing light chains with greater diversity.

Homozygous mice bearing modified endogenous λ loci containing 12 hVλ gene segments and hJλ1 were also able to produce human λ gene segments operably linked to an endogenous mouse Cλ gene and produce B cells that expressed reverse chimeric λ light chains containing hVλ regions linked to mouse Cλ regions. These rearrangements further demonstrate that human λ light chain gene segments placed at the other light chain locus (i.e., the λ locus) were able to independently rearrange human λ gene segments in multiple, independent B cells in these mice. Further, the modifications to the endogenous λ light chain locus demonstrate that the insertion of human λ gene segments did not render any of the hVλ and/or hJλ1 gene segments inoperable or prevent the chimeric locus from recombining the hVλ and hJλ1 gene segments during B cell development. Further, these mice also made functional antibodies containing human Vλ-Jλ gene segments operably linked to a mouse Cλ region as part of the endogenous immunoglobulin light chain repertoire.

As shown in this Example, mice bearing human λ light chain gene segments at the endogenous κ and λ light chain loci are capable of rearranging human λ light chain gene segments and expressing them in the context of a mouse Cκ and/or Cλ region as part of the normal antibody repertoire of the mouse because a functional light chain is required at various checkpoints in B cell development in both the spleen and bone marrow. Further, early subsets of B cells (e.g., pre-, pro- and transitional B cells) demonstrate a normal phenotype in these mice as compared to wild type littermates (FIGS. 27D, 28A and 28B). A small deficit in bone marrow and peripheral B cell populations was observed, which may be attributed to a deletion of a subset of auto-reactive immature B cells and/or a suboptimal association of human λ light chain with mouse heavy chain. However, the Igκ/Igλ usage observed in these mice demonstrates a situation that is more like human light chain expression than that observed in mice.

Example 15

Breeding of Mice Expressing Human λ Light Chains from an Endogenous Light Chain Locus To optimize the usage of the human λ gene segments at an endogenous mouse light chain locus, mice bearing the unrearranged human λ gene segments are bred to another mouse containing a deletion in the opposing endogenous light chain locus (either κ or λ). For example, human λ gene segments positioned at the endogenous κ locus would be the only functional light chain gene segments present in a mouse that also carried a deletion in the endogenous λ light chain locus. In this manner, the progeny obtained would express only human λ light chains as described in the foregoing examples. Breeding is performed by standard techniques recognized in the art and, alternatively, by commercial companies, e.g., The Jackson Laboratory. Mouse strains bearing human λ light chain gene segments at the endogenous κ locus and a deletion of the endogenous λ light chain locus are screened for presence of the unique reverse-chimeric (human-mouse) λ light chains and absence of endogenous mouse λ light chains.

Mice bearing an unrearranged human λ light chain locus are also bred with mice that contain a replacement of the endogenous mouse heavy chain variable gene locus with the human heavy chain variable gene locus (see U.S. Pat. No. 6,596,541, Regeneron Pharmaceuticals, the VELOCIMMUNE® genetically engineered mouse). The VELOCIMMUNE® mouse includes, in part, having a genome comprising human heavy chain variable regions operably linked to endogenous mouse constant region loci such that the mouse produces antibodies comprising a human heavy chain variable region and a mouse heavy chain constant region in response to antigenic stimulation. The DNA encoding the variable regions of the heavy chains of the antibodies can be isolated and operably linked to DNA encoding the human heavy chain constant regions. The DNA can then be expressed in a cell capable of expressing the fully human heavy chain of the antibody. Upon a suitable breeding schedule, mice bearing a replacement of the endogenous mouse heavy chain locus with the human heavy chain locus and an unrearranged human λ light chain locus at the endogenous κ light chain locus is obtained. Antibodies containing somatically mutated human heavy chain variable regions and human λ light chain variable regions can be isolated upon immunization with an antigen of interest.

Example 16

Generation of Antibodies From Mice Expressing Human Heavy Chains and Human λ Light Chains After breeding mice that contain the unrearranged human λ light chain locus to various desired strains containing modifications and deletions of other endogenous Ig loci (as described above), selected mice are immunized with an antigen of interest.

Generally, a VELOCIMMUNE® mouse containing one of the single rearranged human germline light chain regions is challenged with an antigen, and lymphatic cells (such as B-cells) are recovered from serum of the animals. The lymphatic cells may be fused with a myeloma cell line to prepare immortal hybridoma cell lines, and such hybridoma cell lines are screened and selected to identify hybridoma cell lines that produce antibodies containing human heavy chain and human λ light chain that are specific to the antigen used for immunization. DNA encoding the variable regions of the heavy chains and the λ light chains may be isolated and linked to desirable isotypic constant regions of the heavy chain and light chain. Due to the presence of the additional hVλ gene segments as compared to the endogenous mouse λ locus, the diversity of the light chain repertoire is dramatically increased and confers higher diversity on the antigen-specific repertoire upon immunization. The resulting cloned antibody sequences may be subsequently produced in a cell, such as a CHO cell. Alternatively, DNA encoding the antigen-specific chimeric antibodies or the variable domains of the light and heavy chains may be isolated directly from antigen-specific lymphocytes (e.g., B cells).

Initially, high affinity chimeric antibodies are isolated having a human variable region and a mouse constant region. As described above, the antibodies are characterized and selected for desirable characteristics, including affinity, selectivity, epitope, etc. The mouse constant regions are replaced with a desired human constant region to generate the fully human antibody containing a somatically mutated human heavy chain and a human λ light chain derived from an unrearranged human λ light chain locus of the invention. Suitable human constant regions include, for example wild type or modified IgG1, IgG2, IgG3, or IgG4.

Example 17

Breeding of ADAM6 Mice and Human λ Variable Mice

Any of the mice described herein that comprises a modification of an endogenous ADAM6 gene or ortholog or homolog thereof, and further comprises a gene that confers ADAM6 function on the mouse, is bred with a mouse comprising a modification that comprises a human λ variable segment (e.g., a V and a J segment) operably linked to a human or mouse λ or κ constant gene. The mouse comprising the human λ variable segment can have the variable segment present at a modified endogenous λ or κ locus, or on a transgene. The mice are bred and the progeny are further interbred, if needed, and progeny are screened for fertile mice that exhibit the ADAM6 function and that also express the human λ sequence in the context of a human or mouse λ or κ constant region, as the case may be.

A mouse comprising a humanized heavy chain variable locus (human V, D, and J segments replacing all or substantially all mouse V, D, and J segments) that further comprises an ectopic ADAM6 sequence (or a sequence of an ortholog or homolog of ADAM6 that confers ADAM6 function on the mouse) is bred with a mouse that comprises a replacement of all or substantially all light chain V and J segments with human λ light chain V and J segment at the mouse λ locus and/or the mouse κ locus. Progeny are further bred as needed, and mice that express an antibody comprising a human $V_H$ fused with a heavy chain constant sequence, and a cognate human λ $V_L$ fused with a λ or a κ light chain constant sequence are identified.

The mice are exposed to an antigen of interest and allowed to generate an immune response. Antibodies specific to the antigen of interest are identified, and human $V_H$ sequences and human λ variable sequences (including human λ variable sequences linked to mouse κ constant regions) are identified and employed to make a human antibody by engineering the variable domain sequences in combination with human constant region genes.

In one instance, a mouse is created by breeding that comprises a replacement of all or substantially all mouse heavy chain V, D, and J segments with human V, D, and J segments at the endogenous mouse heavy chain locus, and that comprises a light chain allele that comprises a replacement of all or substantially all λ light chain variable sequences with one or more human λ variable sequences at an endogenous mouse λ locus operably linked to a λ constant sequence, and that comprises a light chain allele that comprises a replacement of all or substantially all κ light chain variable sequences at an endogenous κ locus with one or more human λ variable sequences. The animal is exposed to an antigen of interest and allowed to mount an immune response. Antibodies that bind the antigen of interest are identified that comprise human heavy chain variable domains cognate with human λ variable domains on a mouse λ or mouse κ constant region are identified. Nucleic acid sequences encoding the variable domains are employed to make a fully human antibody by engineering the variable sequences in combination with human constant region sequences.

Mice as described in this example comprise one or more of the Vκ-Jκ intergenic regions described in the text and the figures herein.

---

We claim:

1. A method of making a fully human immunoglobulin heavy chain or fully human immunoglobulin light chain of an antibody that specifically binds an antigen comprising the steps of:
    (a) immunizing a genetically modified mouse with an antigen, wherein the mouse:
        (i) has a germline genome that comprises:
            (1) an insertion of one or more human Vλ gene segments and one or more human Jλ gene segments upstream of a light chain constant region gene,
            (2) an insertion of one or more human $V_H$ gene segments, one or more human $D_H$ gene segments, and one or more human $J_H$ gene segments upstream of a mouse immunoglobulin heavy chain constant region gene, and
            (3) an inserted nucleotide sequence that encodes a mouse ADAM6 protein, wherein the inserted nucleotide sequence is present at the immunoglobulin heavy chain locus of the mouse, and wherein the mouse ADAM6 protein is expressed from the inserted nucleotide sequence,
        (ii) generates antibodies when immunized with the antigen, wherein the antibodies each comprise a human heavy chain variable domain operably linked to a mouse heavy chain constant domain and a human λ light chain variable domain operably linked to a light chain constant domain, and
        (iii) is fertile; and
    (b) identifying a human heavy chain variable domain or a human λ light chain variable domain of an antibody that specifically binds the antigen and that was generated by the genetically modified mouse; and
    (c) operably linking the human heavy chain variable domain or the human λ light chain variable domain to a human heavy chain constant domain or a human light chain constant domain, respectively, to form a fully human immunoglobulin heavy chain or a fully human immunoglobulin light chain.

2. The method of claim 1, wherein operably linking the human heavy chain variable domain or the human λ light chain variable domain to the human heavy chain constant domain or the human light chain constant domain, respectively, comprises operably linking a nucleotide sequence encoding the human heavy variable domain or the λ light chain variable domain to a nucleotide sequence encoding the human heavy constant domain or the human light chain constant domain, respectively.

3. The method of claim 1, wherein the genome of the mouse comprises endogenous $V_L$ gene segments and/or endogenous $J_L$ gene segments that are incapable of rearranging to form an immunoglobulin light chain in the mouse.

4. The method of claim 1, wherein the one or more human Vλ gene segments comprises at least 12 human Vλ gene segments.

5. The method of claim 1, wherein the one or more human Vλ gene segments comprises at least 28 human Vλ gene segments.

6. The method of claim 1, wherein the one or more human Vλ gene segments comprises at least 40 human Vλ gene segments.

7. The method of claim 1, wherein the inserted nucleotide sequence that encodes a mouse ADAM6 protein is positioned between two human $V_H$ gene segments.

8. The method of claim 1, wherein the inserted nucleotide sequence that encodes a mouse ADAM6 protein is positioned between a $V_H$ gene segment and a $D_H$ gene segment.

9. The method of claim 1, wherein the one or more human Jλ gene segments are selected from the group consisting of Jλ1, Jλ2, Jλ3, Jλ7, and a combination thereof.

10. The method of claim 1, wherein the one or more human Jλ gene segments comprises at least four human Jλ gene segments.

11. The method of claim 10, wherein the at least four human Jλ gene segments comprise at least Jλ1, Jλ2, Jλ3, and Jλ7.

12. The method of claim 1, wherein the immunoglobulin light chain constant region gene is a Cκ gene.

13. The method of claim 12, wherein the Cκ gene is an endogenous Cκ gene at an endogenous κ light chain locus.

14. The method of claim 13, wherein all endogenous Vκ gene segments and endogenous Jκ gene segments are replaced with the one or more human Vλ gene segments and one or more human Jλ gene segments.

15. The method of claim 1, wherein the mouse further comprises a human Vκ-Jκ intergenic region from a human κ light chain locus, wherein the human Vκ-Jκ intergenic region is contiguous with the one or more human Vλ gene segments and one or more human Jλ gene segments.

16. The method of claim 15, wherein the human Vκ-Jκ intergenic region is placed between a human Vλ gene segment and a human Jλ gene segment.

17. The method of claim 1, wherein the mouse ADAM6 protein is a mouse ADAM6a or ADAM6b protein.

18. The method of claim 1, wherein the one or more human Vλ gene segments comprise Vλ3-1, Vλ4-3, Vλ2-8, Vλ3-9, Vλ3-10, Vλ2-11, Vλ3-12 or a combination thereof.

19. The method of claim 1, wherein the one or more human Vλ gene segments comprise human Vλ2-14, Vλ3-16, Vλ2-18, Vλ3-19, Vλ3-21, Vλ3-22, Vλ2-23, Vλ3-25, Vλ3-27 or a combination thereof.

20. The method of claim 1, wherein the one or more human Vλ gene segments comprise human Vλ1-40, Vλ7-43, Vλ1-44, Vλ5-45, Vλ7-46, Vλ1-47, Vλ9-49, Vλ1-51, Vλ5-52 or a combination thereof.

21. The method of claim 1, wherein at least two λ light chain enhancers are located downstream of both the one or more human Vλ gene segments and the one or more human Jλ gene segments.

* * * * *